United States Patent
Glass et al.

(10) Patent No.: US 9,475,857 B2
(45) Date of Patent: Oct. 25, 2016

(54) METHODS AND COMPOSITIONS USING A KLOTHO-FGF23 FUSION POLYPEPTIDE

(71) Applicants: David Glass, Cortland Manor, NY (US); Shou-Ih Hu, New Providence, NJ (US)

(72) Inventors: David Glass, Cortland Manor, NY (US); Shou-Ih Hu, New Providence, NJ (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/531,620

(22) Filed: Nov. 3, 2014

(65) Prior Publication Data

US 2016/0031961 A1    Feb. 4, 2016

Related U.S. Application Data

(62) Division of application No. 13/796,711, filed on Mar. 12, 2013, now Pat. No. 8,932,589, which is a division of application No. 12/360,970, filed on Jan. 28, 2009, now Pat. No. 8,481,031.

(60) Provisional application No. 61/063,015, filed on Jan. 28, 2008.

(51) Int. Cl.

| A61K 38/18 | (2006.01) |
|---|---|
| A61K 39/395 | (2006.01) |
| C07K 14/50 | (2006.01) |
| C07K 16/00 | (2006.01) |
| C12N 1/21 | (2006.01) |
| C12N 5/10 | (2006.01) |
| C12N 15/12 | (2006.01) |
| C12N 15/63 | (2006.01) |
| C12N 9/42 | (2006.01) |
| C12N 9/00 | (2006.01) |
| C07K 14/705 | (2006.01) |
| A61K 38/00 | (2006.01) |

(52) U.S. Cl.
CPC ............ *C07K 14/50* (2013.01); *C07K 14/705* (2013.01); *C12N 9/2445* (2013.01); *C12N 9/93* (2013.01); *C12Y 302/00* (2013.01); *C12Y 302/01021* (2013.01); *C12Y 602/01003* (2013.01); *A61K 38/00* (2013.01); *C07K 2319/00* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| 5,408,038 A | 4/1995 | Smith et al. |
|---|---|---|
| 5,541,094 A | 7/1996 | Anton et al. |
| 7,060,479 B2 | 6/2006 | Dumas Milne Edwards et al. |
| 7,217,798 B2 | 5/2007 | Hinton et al. |
| 7,223,563 B2 | 5/2007 | Econs et al. |
| 7,259,248 B2 | 8/2007 | Itoh et al. |
| 7,745,406 B2 | 6/2010 | Econs et al. |
| 8,461,111 B2 | 6/2013 | Blaber et al. |
| 2006/0160181 A1 | 7/2006 | Luethy et al. |
| 2006/0281679 A1 | 12/2006 | Itoh et al. |
| 2009/0192087 A1 | 7/2009 | Glass et al. |
| 2010/0298220 A1 | 11/2010 | Blaber et al. |
| 2011/0195077 A1 | 8/2011 | Glass et al. |
| 2011/0195895 A1 | 8/2011 | Walker et al. |
| 2013/0122004 A1 | 5/2013 | Glass et al. |
| 2014/0323396 A1 | 10/2014 | Belouski et al. |
| 2016/0030585 A1 | 2/2016 | Barnes et al. |

FOREIGN PATENT DOCUMENTS

| WO | 2009/095372 A1 | 8/2009 |
|---|---|---|
| WO | 2009/117622 A2 | 9/2009 |
| WO | 2011/092234 A1 | 8/2011 |
| WO | 2015/200078 A1 | 12/2015 |

OTHER PUBLICATIONS

Ito et al., Mech. Dev., 98:115-119 (2000).
Wu et al., J. Biol. Chem., 283(48):33304-33309 (2008).
Razzuae et al., Expert Opin. Ther. Patents, 20(6):1-5 (2010).
Carpenter et al., J. Clin. Endocrinol. Metab., 95:E352-E357 (2010).
Kuro-o, Pediatr. Nephrol., 25:583-590 (2010).
Drueke et al., Nephrol Dial. Transplant., 22:1524-1526 (2007).
White et al., Kidney International, 60:2079-2086 (2001).
Yu et al., Cytokine & Growth Factor Reviews, 16:221-232 (2005).
Kurosu et al., Journal of Biological Chemistry, 281(10:6120-6123 (2006).
Tohyama et al., Journal of Biological Chemistry, 279(11):9777-9784 (2004).
Torres et al., Kidney International, 71(8):730-737 (2007).
Wu et al., Journal of Biological Chemistry, 282(40:29069-29072 (2007).
Goetz et al., Mol. and Cell. Bio., pp. 3417 (2007).

(Continued)

*Primary Examiner* — Christine J Saoud
(74) *Attorney, Agent, or Firm* — Hong-Van M. Le

(57) ABSTRACT

The present invention is directed to methods, kits and compositions for preventing or treating age-related conditions or metabolic disorders. The Klotho fusion polypeptides of the invention include at least a Klotho protein or an active fragment thereof. In one embodiment, the fusion polypeptide comprises a Klotho polypeptide, a FGF (such as FGF23) and (optionally) a modified Fc fragment. The Fc fragment can, for example, have decreased binding to Fc-gamma-receptor and increased serum half-life. The Klotho fusion proteins are useful in the treatment and prevention of a variety of age-related conditions and metabolic disorders. In another embodiment, the fusion polypeptide comprises a FGF (such as FGF23) and a modified Fc fragment.

17 Claims, 40 Drawing Sheets

(56) References Cited

OTHER PUBLICATIONS

Figure 1A:
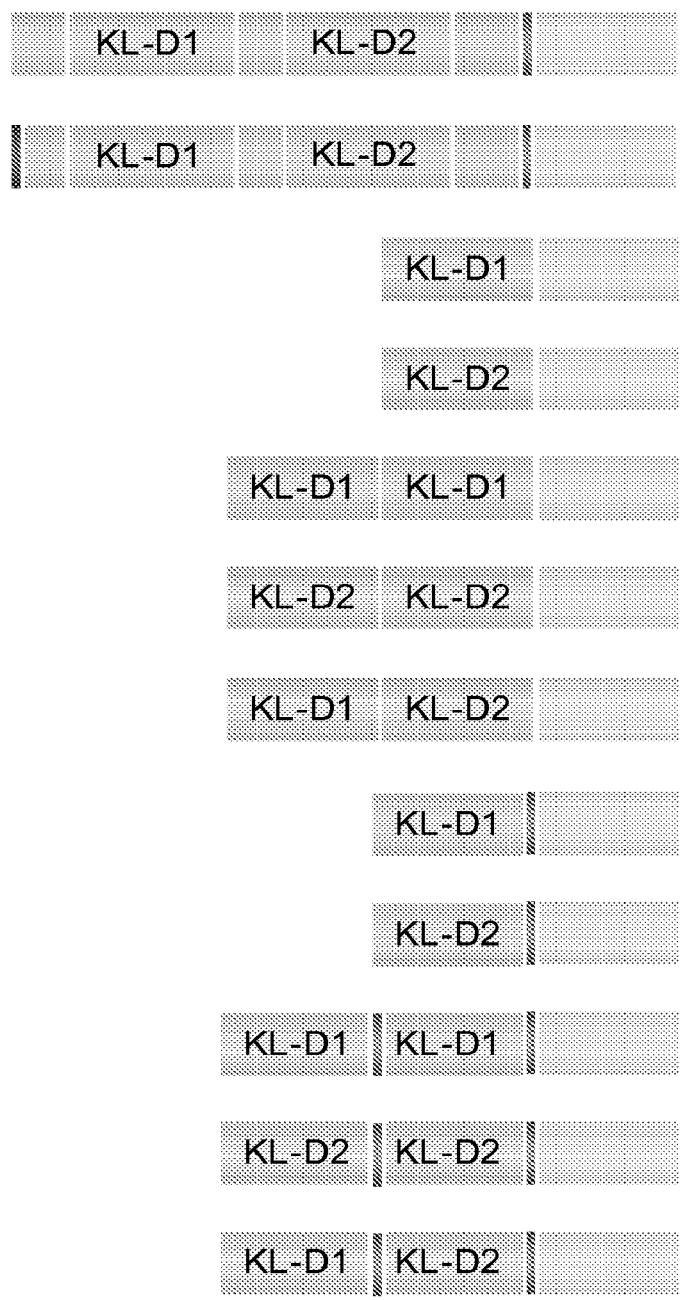

Hessell et al., Nature, 449:101 (2007).
Lode et al., Proc. Nat. Acad. Sci. USA, 95:2475 (1998).
Ray, Sci. STKE, 2006(365):tw416 (2006).
Urakawa et al., Nature, 444:770 (2006).
The ADHR Consortium, Nature Genetics, 26:345-348 (2000).
Bai et al., The Journal of Biological Chemistry, 278(11):9843-9849 (2003).
Bai et al., Endocrinology, 145(11:5269-5279 (2004).
Bai et al., Am. J. Physiol. Endorinol. Metab., 296:E79-E88 (2009).
Ben-Dov et al., The Journal of Clinical Investigation—Research Article, 117(12):4003-4008 (2007).
Berndt et al., Pflugers Arch—Eur. J. Physiol., 454:615-623 (2007).
Shimada et al., Endocrinology, 143(8):3179-3182 (2002).
Strewler, PNAS—Commentary, 98(11):5945-5946 (2001).
Gasparian et al., "Overexpression in *Escherichia coli* and Purification of Human Fibroblast Growth Factor (FGF-2)", Biochemistry, 74(2):221-225 (2009).
Beenken et al., "The Structural Biology of the FGF19 Subfamily", Adv. Exp. Med. Biol. 728:1-24 (2012).

: Klotho (extracellular domain) or active fragment of Klotho;

: FGF23 (R179Q), FGF23, FGF 19, FGF21; : linker; : IgG signal peptide.

: Klotho (extracellular domain) or active fragment of Klotho;

: FGF23 (R179Q), FGF23, FGF 19, FGF21; : linker; : IgG signal peptide.

FIGURE 2A
SEQUENCE LISTING

Human Klotho nucleic acid sequence (NM_004795) (SEQ ID NO: 1)
Protein coding region: 9-3047

```
   1 cgcgcagcat gcccgccagc gccccgccgc gccgcccgcg gccgccgccg
     ccgtcgctgt
  61 cgctgctgct ggtgctgctg ggcctgggcg gccgccgcct gcgtgcggag
     ccgggcgacg
 121 gcgcgcagac ctgggcccgt ttctcgcggc ctcctgcccc cgaggccgcg
     ggcctcttcc
 181 agggcacctt ccccgacgcc ttcctctggg ccgtgggcag cgccgcctac
     cagaccgagg
 241 gcggctggca gcagcacggc aagggtgcgt ccatctggga tacgttcacc
     caccacccc
 301 tggcaccccc gggagactcc cggaacgcca gtctgccgtt ggcgccccg
     tcgccgctgc
 361 agcccgccac cggggacgta gccagcgaca gctacaacaa cgtcttccgc
     gacacggagg
 421 cgctgcgcga gctcggggtc actcactacc gcttctccat ctcgtgggcg
     cgagtgctcc
 481 ccaatgccag cgcgggcgtc cccaaccgcg aggggctgcg ctactaccgg
     cgcctgctgg
 541 agcggctgcg ggagctggc gtgcagcccg tggtcaccct gtaccactgg
     gacctgcccc
 601 agcgcctgca ggacgcctac ggcggctggg ccaaccgcgc cctggccgac
     cacttcaggg
 661 attacgcgga gctctgcttc cgccacttcg gcggtcaggt caagtactgg
     atcaccatcg
 721 acaacccta cgtggtggcc tggcacggct acgccaccgg gcgcctggcc
     cccggcatcc
 781 ggggcagccc gcggctcggg tacctggtgg cgcacaacct cctcctggct
     catgccaaag
 841 tctggcatct ctacaatact ctttccgtc ccactcaggg aggtcaggtg
     tccattgccc
 901 taagctctca ctggatcaat cctcgaagaa tgaccgacca cagcatcaaa
     gaatgtcaaa
 961 aatctctgga ctttgtacta ggttggtttg ccaaacccgt atttattgat
     ggtgactatc
1021 ccgagagcat gaagaataac ctttcatcta ttctgcctga ttttactgaa
     tctgagaaaa
1081 agttcatcaa aggaactgct gacttttttg ctctttgctt tggacccacc
     ttgagttttc
1141 aacttttgga ccctcacatg aagttccgcc aattggaatc tcccaacctg
     aggcaactgc
1201 tttcctggat tgaccttgaa tttaaccatc ctcaaatatt tattgtggaa
     aatggctggt
1261 ttgtctcagg gaccaccaag agagatgatg ccaaatatat gtattaccte
     aaaaagttca
1321 tcatggaaac cttaaaagcc atcaagctgg atggggtgga tgtcatcggg
     tataccgcat
1381 ggtccctcat ggatggtttc gagtggcaca gaggttacag catcaggcgt
     ggactcttct
1441 atgttgactt tctaagccag gacaagatgt tgttgccaaa gtcttcagcc
     ttgttctacc
```

FIGURE 2B

```
1501 aaaagctgat agagaaaaat ggcttccctc ctttacctga aaatcagccc
ctagaaggga
1561 catttccctg tgactttgct tggggagttg ttgacaacta cattcaagta
gataccactc
1621 tgtctcagtt taccgacctg aatgtttacc tgtgggatgt ccaccacagt
aaaaggctta
1681 ttaaagtgga tggggttgtg accaagaaga ggaaatccta ctgtgttgac
tttgctgcca
1741 tccagcccca gatcgcttta ctccaggaaa tgcacgttac acattttcgc
ttctccctgg
1801 actgggccct gattctccct ctgggtaacc agtcccaggt gaaccacacc
atcctgcagt
1861 actatcgctg catggccagc gagcttgtcc gtgtcaacat caccccagtg
gtggccctgt
1921 ggcagcctat ggccccgaac caaggactgc cgcgcctcct ggccaggcag
ggcgcctggg
1981 agaacccta cactgccctg cctttgcag agtatgcccg actgtgcttt
caagagctcg
2041 gccatcacgt caagctttgg ataacgatga atgagccgta tacaaggaat
atgacataca
2101 gtgctggcca caaccttctg aaggcccatg ccctggcttg gcatgtgtac
aatgaaaagt
2161 ttaggcatgc tcagaatggg aaaatatcca tagccttgca ggctgattgg
atagaacctg
2221 cctgcccttt ctcccaaaag gacaagagg tggccgagag agttttggaa
tttgacattg
2281 gctggctggc tgagcccatt ttcggctctg gagattatcc atgggtgatg
agggactggc
2341 tgaaccaaag aaacaatttt cttcttcctt atttcactga agatgaaaaa
aagctaatcc
2401 agggtacctt tgacttttg gctttaagcc attataccac catccttgta
gactcagaaa
2461 aagaagatcc aataaaatac aatgattacc tagaagtgca agaaatgacc
gacatcacgt
2521 ggctcaactc ccccagtcag gtggcggtag tgccctgggg gttgcgcaaa
gtgctgaact
2581 ggctgaagtt caagtacgga gacctcccca tgtacataat atccaacgga
atcgatgacg
2641 ggctgcatgc tgaggacgac cagctgaggg tgtattatat gcagaattac
ataaacgaag
2701 ctctcaaagc ccacatactg gatggtatca atctttgcgg atactttgct
tattcgttta
2761 acgaccgcac agctccgagg tttggcctct atcgttatgc tgcagatcag
tttgagccca
2821 aggcatccat gaaacattac aggaaaatta ttgacagcaa tggtttcccg
ggcccagaaa
2881 ctctggaaag attttgtcca gaagaattca ccgtgtgtac tgagtgcagt
ttttttcaca
2941 cccgaaagtc tttactggct ttcatagctt ttctattttt tgcttctatt
atttctctct
3001 cccttatatt ttactactcg aagaaggca gaagaagtta caaatagttc
tgaacatttt
3061 tctattcatt cattttgaaa taattatgca gacacatcag ctgttaacca
tttgcacctc
3121 taagtgttgt gaaactgtaa atttcataca tttgacttct agaaaacatt
tttgtggctt
```

FIGURE 2C

```
    3181 atgacagagg ttttga            atcgtaaaat attgaataat
gcgaatagtg
    3241 cctgaatttg ttctcttttt gggtgattaa aaaactgaca ggcactataa
tttctgtaac
    3301 acactaacaa aagcatgaaa aataggaacc acaccaatgc aacatttgtg
cagaaatttg
    3361 aatgacaaga ttaggaatat tttcttctgc acccacttct aaatttaatg
tttttctgga
    3421 agtagtaatt gcaagagttc gaatagaaag ttatgtacca agtaaccatt
tctcagctgc
    3481 cataataatg cctagtggct tcccctctgt caaatctagt ttcctatgga
aaagaagatg
    3541 gcagatacag gagagacgac agagggtcct aggctggaat gttcctttcg
aaagcaatgc
    3601 ttctatcaaa tactagtatt aatttatgta tctggttaat gacatacttg
gagagcaaat
    3661 tatggaaatg tgtattttat atgattttg aggtcctgtc taaaccctgt
gtccctgagg
    3721 gatctgtctc actggcatct tgttgagggc cttgcacata ggaaacttt
gataagtatc
    3781 tgcggaaaaa caaacatgaa tcctgtgata ttggctctt caggaagcat
aaagcaattg
    3841 tgaaatacag tataccgcag tggctctagg tggaggaaag gaggaaaaag
tgcttattat
    3901 gtgcaacatt atgattaatc tgattataca ccatttttga gcagatcttg
gaatgaatga
    3961 catgaccttt ccctagagaa taaggatgaa ataatcactc attctatgaa
cagtgacact
    4021 actttctatt cttagctgt actgtaattt ctttcagttg atagttttac
aaattcttaa
    4081 taggttcaaa agcaatctgg tctgaataac actggatttg tttctgtgat
ctctgaggtc
    4141 tattttatgt tttgctgct acttctgtgg aagtagcttt gaactagttt
tactttgaac
    4201 tttcacgctg aaacatgcta gtgatatcta gaaagggcta attaggtctc
atcctttaat
    4261 gcccttaaa taagtcttgc tgattttcag acagggaagt ctctctatta
cactggagct
    4321 gttttataga taagtcaata ttgtatcagg caagataaac caatgtcata
acaggcattg
    4381 ccaacctcac tgacacaggg tcatagtgta taataatata ctgtactata
taatatatca
    4441 tctttagagg tatgatttt tcatgaaaga taagcttttg gtaatattca
ttttaaagtg
    4501 gacttattaa aattggatgc tagagaatca agtttatttt atgtatatat
ttttctgatt
    4561 ataagagtaa tatatgttca ttgtaaaaat ttttaaaaca cagaaactat
atgcaaagaa
    4621 aaaataaaaa ttatctataa tctcagaacc cagaaatagc cactattaac
atttcctacg
    4681 tatttatt tacatagatc atattgtata tagttagtat ctttattaat
tttattatg
    4741 aaactttcct ttgtcattat tagtcttcaa aagcatgatt tttaatagtt
gttgagtatt
    4801 ccaccacagg aatgtatcac aacttaaccg ttcccgtttg ttagactagt
ttcttattaa
```

FIGURE 2D

```
 4861 tgttgatgaa tgttgtttaa aaataatttt gttgctacat ttactttaat
ttccttgact
 4921 gtaaagagaa gtaattttgc tccttgataa agtattatat taataataaa
tctgcctgca
 4981 actttttgcc ttctttcata atc
```

Klotho amino acid sequence (NP_004786) (SEQ ID NO: 2)

```
   1 MPASAPPRRP RPPPPSLSLL LVLLGLGGRR LRAEPGDGAQ TWARFSRPPA
PEAAGLFQGT
  61 FPDGFLWAVG SAAYQTEGGW QQHGKGASIW DTFTHHPLAP PGDSRNASLP
LGAPSPLQPA
 121 TGDVASDSYN NVFRDTEALR ELGVTHYRFS ISWARVLPNG SAGVPNREGL
RYYRRLLERL
 181 RELGVQPVVT LYHWDLPQRL QDAYGGWANR ALADHFRDYA ELCFRHFGGQ
VKYWITIDNP
 241 YVVAWHGYAT GRLAPGIRGS PRLGYLVAHN LLLAHAKVWH LYNTSFRPTQ
GGQVSIALSS
 301 HWINPRRMTD HSIKECQKSL DFVLGWFAKP VFIDGDYPES MKNNLSSILP
DFTESEKKFI
 361 KGTADFFALC FGPTLSFQLL DPHMKFRQLE SPNLRQLLSW IDLEFNHPQI
FIVENGWFVS
 421 GTTKRDDAKY MYYLKKFIME TLKAIKLDGV DVIGYTAWSL MDGFEWHRGY
SIRRGLFYVD
 481 FLSQDKMLLP KSSALFYQKL IEKNGFPPLP ENQPLEGTFP CDFAWGVVDN
YIQVDTTLSQ
 541 FTDLNVYLWD VHHSKRLIKV DGVVTKKRKS YCVDFAAIQP QIALLQEMHV
THFRFSLDWA
 601 LILPLGNQSQ VNHTILQYYR CMASELVRVN ITPVVALWQP MAPNQGLPRL
LARQGAWENP
 661 YTALAFAEYA RLCFQELGHH VKLWITMNEP YTRNMTYSAG HNLLKAHALA
WHVYNEKFRH
 721 AQNGKISIAL QADWIEPACP FSQKDKEVAE RVLEFDIGWL AEPIFGSGDY
PWVMRDWLNQ
 781 RNNFLLPYFT EDEKKLIQGT FDFLALSHYT TILVDSEKED PIKYNDYLEV
QEMTDITWLN
 841 SPSQVAVVPW GLRKVLNWLK FKYGDLPMYI ISNGIDDGLH AEDDQLRVYY
MQNYINEALK
 901 AHILDGINLC GYFAYSFNDR TAPRFGLYRY AADQFEPKAS MKHYRKIIDS
NGFPGPETLE
 961 RFCPEEFTVC TECSFFHTRK SLLAFIAFLF FASIISLSLI FYYSKKGRRS YK
``` beta-Klotho nucleic acid sequence (NM_175737) (SEQ ID NO: 3)
Protein coding region: 98-3232

```
   1 atcctcagtc tcccagttca agctaatcat tgacagagct ttacaatcac
aagcttttac
  61 tgaagctttg ataagacagt ccagcagttg gtggcaaatg aagccaggct
gtgcggcagg
 121 atctccaggg aatgaatgga ttttcttcag cactgatgaa ataaccacac
gctataggaa
 181 tacaatgtcc aacgggggat gcaaagatc tgtcatcctg tcagcactta
ttctgctacg
 241 agctgttact ggattctctg gagatggaag agctatatgg tctaaaaatc
ctaattttac
```

FIGURE 2E

```
  301 tccggtaaat gaaagtcagc tgtttctcta tgacactttc cctaaaaact
ttttctgggg
  361 tattgggact ggagcattgc aagtggaagg gagttggaag aaggatggaa
aaggaccttc
  421 tatatgggat catttcatcc acacacacct taaaaatgtc agcagcacga
atggttccag
  481 tgacagttat attttctgg aaaaagactt atcagccctg gattttatag
gagtttcttt
  541 ttatcaattt tcaatttcct ggccaaggct tttccccgat ggaataqtaa
cagttgccaa
  601 cgcaaaaggt ctgcagtact acagtactct tctggacgct ctagtgctta
gaaacattga
  661 acctatagtt actttatacc actgggattt gcctttggca ctacaagaaa
aatatggggg
  721 gtggaaaaat gataccataa tagatatctt caatgactat gccacatact
gtttccagat
  781 gtttggggac cgtgtcaaat attggattac aattcacaac ccatatctag
tggcttggca
  841 tgggtatggg acaggtatgc atgccctgg agagaaggga aatttagcag
ctgtctacac
  901 tgtgggacac aacttgatca aggctcactc gaaagtttgg cataactaca
acacacattt
  961 ccgcccacat cagaagggtt ggttatcgat cacgttggga tctcattgga
tcgagccaaa
 1021 ccggtcggaa aacacgatgg atatattcaa atgtcaacaa tccatggttt
ctgtgcttgg
 1081 atggtttgcc aaccctatcc atggggatgg cgactatcca gagggatga
gaaagaagtt
 1141 gttctccgtt ctacccattt tctctgaagc agagaagcat gagatgagag
gcacagctga
 1201 tttcttqgcc ttttctttg gacccaacaa cttcaagccc ctaaacacca
tggctaaaat
 1261 gggacaaaat gtttcactta atttaagaga agcgctgaac tggattaaac
tggaatacaa
 1321 caaccctcga atcttgattg ctgagaatgg ctggttcaca gacagtcgtg
tgaaaacaga
 1381 agacaccacg gccatctaca tgatgaagaa tttcctcagc caggtgcttc
aagcaataag
 1441 gttagatgaa atacgagtgt ttggttatac tgcctggtct ctcctggatg
gctttgaatg
 1501 gcaggatgct tacaccatcc gccgaggatt attttatgtg gattttaaca
gtaaacagaa
 1561 agagcggaaa cctaagtctt cagcacacta ctacaaacag atcatacgag
aaaatggttt
 1621 ttcttaaaa gagtccacgc cagatgtgca ggccagttt ccctgtgact
tctcctgggg
 1681 tgtcactgaa tctgttctta agcccgagtc tgtggcttcg tccccacagt
tcagcgatcc
 1741 tcatctgtac gtgtggaacg ccactggcaa cagactgttg caccgagtgg
aagggtgag
 1801 gctgaaaaca cgaccgctc aatgcacaga ttttgtaaac atcaaaaaac
aacttgaqat
 1861 gttggcaaga atgaaagtca cccactaccg gtttgctctg gattggcct
cggtccttcc
 1921 cactggcaac ctgtccgcgg tgaaccgaca ggccctgagg tactacaggt
gcgtggtcag
```

FIGURE 2F

```
1981 tgaggggctg aagcttggca tctccgcgat ggtcaccctg tattatccga
cccacgccca
2041 cctaggcctc cccgagcctc tgttgcatgc cgacgggtgg ctgaacccat
cgacggccga
2101 ggccttccag gcctacgctg gctgtgctt ccaggagctg ggggacctgg
tgaagctctg
2161 gatcaccatc aacgagccta accggctaag tgacatctac aaccgctctg
gcaacgacac
2221 ctacggggcg gcgcacaacc tgctggtggc ccacgccctg gcctggcgcc
tctacgaccg
2281 gcagttcagg ccctcacagc gcggggccgt gtcgctgtcg ctgcacgcgg
actgggcgga
2341 acccgccaac ccctatgctg actcgcactg gagggcggcc gagcgcttcc
tgcagttcga
2401 gatcgcctgg ttcgccgagc cgctcttcaa gaccggggac taccccgcgg
ccatgaggga
2461 atacattgcc tccaagcacc gacggggct ttccagctcg gccctgccgc
gcctcaccga
2521 ggccgaaagg aggctgctca agggcacggt cgacttctgc gcgctcaacc
acttcaccac
2581 taggttcgtg atgcacgagc agctggccgg cagccgctac gactcggaca
gggacatcca
2641 gtttctgcag gacatcaccc gcctgagctc ccccacgcgc ctggctgtga
ttccctgggg
2701 ggtgcgcaag ctgctgcggt gggtccggag gaactacggc gacatggaca
tttacatcac
2761 cgccagtggc atcgacgacc aggctctgga ggatgaccgg ctccggaagt
actacctagg
2821 gaagtacctt caggaggtgc tgaaagcata cctgattgat aaagtcagaa
tcaaaggcta
2881 ttatgcattc aaactggctg aagagaaatc taaacccaga tttggattct
tcacatctga
2941 ttttaaagct aaatcctcaa tacaatttta caacaaagtg atcagcagca
ggggcttccc
3001 ttttgagaac agtagttcta gatgcagtca gacccaagaa aatacagagt
gcactgtctg
3061 cttattcctt gtgcagaaga aaccactgat attcctgggt tgttgcttct
tctccaccct
3121 ggttctactc ttatcaattg ccatttttca aaggcagaag agaagaaagt
tttggaaagc
3181 aaaaaactta caacacatac cattaagaa aggcaagaga gttgttagct
aaactgatct
3241 gtctgcatga tagacagttt aaaaattcat cccagttcc
``` beta-Klotho amino acid sequence (NP_783864) (SEQ ID NO: 4)

```
  1 mkpgcaagsp gnewiffstd eittryrntm sngglqrsvi lsalillrav
tgfsgdgrai
 61 wsknpnftpv nesqlflydt fpknffwgig tgalqvegsw kkdgkgpsiw
dhfihthlkn
121 vsstngsscs yiflekdlsa ldfigvsfyq fsiswprlfp dgivtvanak
glcyystlld
181 alvlrniepi vtlyhwdlpl alqekyggwk ndtiidiind yatycfqmfg
drvkywitih
241 npylvawhgy gtgmhapgek gnlaavytvg hnlikahskv whnynthfrp
hqkgwlsitl
```

FIGURE 2G

```
  301 gshwiepnrs entmdifkcq qsmvsvlgwf anpihgdgdy pegmrkklfs
vlpifseaek
  361 hemrgtadff afsfgpnnfk plntmakmgq nvslnlreal nwikleynnp
riliaengwf
  421 tdsrvktedt taiymmknfl sqvlqairld eirvfgytaw slldgfewqd
aytirrglfy
  481 vdfnskqker kpkssahyyk qiirengfsl kestpdvqgc fpcdfswgvt
esvlkpesva
  541 sspqfsdphl yvwnatgnrl lhrvegvrlk trpaqctdfv nikkqlemla
rmkvthyrfa
  601 ldwasvlptg nlsavnrqal ryyrcvvseg lklgisamvt lyypthahlg
lpepllhadg
  661 wlnpstaeaf qayaglcfqe lgdlvklwit inepnrlsdi ynrsgndtyg
aahnllvaha
  721 lawrlydrqf rpsqrgavsl slhadwaepa npyadshwra aerflqfeia
wfacplfktg
  781 dypaamreyi askhrrglss salprlteae rrllkgtvdf calnhfttrf
vmheqlagsr
  841 ydsdrdiqfl qditrlsspt rlavipwgvr kllrwvrrny gdmdiyitas
giddqaledd
  901 rlrkyylgky lqevlkayli dkvrikgyya fklaeekskp rtgfftsdfk
akssiqfynk
  961 vissrgfpfe nsssrcsqtq entectvclf lvqkkplifl gccffstlvl
llsiaifqrq
 1021 krrkfwkakn lqhiplkkck rvvs
```

Human Klotho domain 1 (KL-D1) amino acid sequence (SEQ ID NO: 5)

```
     58
qgt
   61 fpdgflwavg saayqtegcw qqhgkgasiw dtfthhplap pgdsrnaslp
lgapsplqpa
  121 tgdvasdsyn nvfrdtealr elgvthyrfs iswarvlpng sagvpnregl
ryyrrllerl
  181 relgvqpvvt lyhwdlpqrl qdayggwanr aladhfrdya elcfrhfggq
vkywitidnp
  241 yvvawhgyat grlapgircs prlgylvahn lllahakvwh lyntsfrptq
ggqvsialss
  301 hwinprrmtd hsikeccksl dfvlgwfakp vfidgdypes mknnlssilp
dftesekkfi
  361 kgtadffalc fgptlsfqll dphnkfrqle spnlrqllsw idlefnhpqi
fivengwfvs
  421 gttkrddaky myylkkfime tlkaikldgv dvigytawsl mdgfewhrgy
sirrglfyvd
  481 flsqdkmllp kssalfyqkl iekngf
```

Human Klotho domain 2 (KL-D2) amino acid sequence (SEQ ID NO: 6)

```
  517                                    gtfp cdfawgvvdn
yiqvdttlsq
  541 ftdlnvylwd vhhskrlikv dgvvtkkrks ycvdfaaiqp qiallqemhv
thfrfsldwa
  601 lilplgnqsq vnhtilcyyr cmaselvrvn itpvvalwqp mapnqglprl
larqgawenp
```

FIGURE 2H

```
    661 ytalafaeya rlcfqelghh vklwitmnep ytrnmtysag hnllkahala
whvynekfrh
    721 aqngkisial qadwiepacp fsqkdkevae rvlefdigwl aepifgsgdy
pwvmrdwlnq
    781 rnnfllpyft edekkliqgt fdflalshyt tilvdseked pikyndylev
qemtditwln
    841 spsqvavvpw glrkvlnwlk fkygdlpmyi isngiddglh aeddqlrvyy
mqnyincalk
    901 ahildginlc gyfaysfndr taprfglyry aadqfepkas mkhyrkiids ngf
```

Klotho extracellular domain (without signal peptide) amino acid sequence (SEQ ID NO: 7)

```
     28                                          epgdgac twarfsrppa
peaaglfqgt
     61 fpdgflwavg saayqteggw qqhgkgasiw dtfthhplap pgdsrnaslp
lgapsplqpa
    121 tgdvasdsyn nvfrdtealr elgvthyrfs iswarvlpng sagvpnregl
ryyrrllerl
    181 relgvqpvvt lyhwdlpqrl qdayggwanr aladhfrdya elcfrhfgqq
vkywitidnp
    241 yvvawhgyat grlapgirgs prlgylvahn llahakvwh lyntsfrptq
ggqvsialss
    301 hwinprrmtd hsikecqksl dfvlgwfakp vfidgdypes mkrnlssilp
dftesekkfi
    361 kgtadffalc fgptlsfqll dphmkfrqle spnlrqllsw idlefnhpqi
fivengwfvs
    421 gttkrddaky myylkkfime tlkaikldgv dvigytawsl mdgfewhrgy
sirrglfyvd
    481 flsqdkmllp kssalfyqkl ieknqfpplp enqpleqtfp cdfawqvvdn
yiqvdttlsq
    541 ftdlnvylwd vhhskrlikv dgvvtkkrks ycvdfaaiqp qiallqemhv
thfrfsldwa
    601 lilplgnqsq vnhtilqyyr cmaselvrvn itpvvalwqp mapnqglprl
larqgawenp
    661 ytalafaeya rlcfqelghh vklwitmnep ytrnmtysag hnllkahala
whvynekfrh
    721 aqngkisial qadwiepacp fsqkdkevae rvlefdigwl aepifgsgdy
pwvmrdwlnq
    781 rnnfllpyft edekkliqgt fdflalshyt tilvdseked pikyndylev
qemtditwln
    841 spsqvavvpw glrkvlnwlk fkygdlpmyi isngiddglh aeddqlrvyy
mqnyinealk
    901 ahildginlc gyfaysfndr taprfglyry aadqfepkas mkhyrkiids
ngfpgpetle
    961 rfcpeeftvc tecsffhtrk sl
```

Klotho signal peptide amino acid sequence (SEQ ID NO: 8)

```
      1 mpasapprrp rppppslsll lvllglggrr lra
```

IgG signal peptide amino acid sequence (SEQ ID NO: 9)

```
      1 msvltqvlal lllwltgtrc rrlra
```

FIGURE 2I

(Gly$_4$ Ser)$_3$ polypeptide linker nucleic acid sequence (SEQ ID NO: 10)

```
  1 ggaggtggag gttcaggagg tggaggttca ggaggtggag gttca
```

(Gly$_4$ Ser)$_3$ polypeptide linker amino acid sequence (SEQ ID NO: 11)

```
  1 GGGGSGGGGS GGGGS
```

(Gly$_4$ Ser) polypeptide linker amino acid sequence (SEQ ID NO: 12)

```
  1 GGGGS
```

(Gly) polypeptide linker amino acid sequence (SEQ ID NO: 13)

```
  1 G
```

(Gly Gly) polypeptide linker amino acid sequence (SEQ ID NO: 14)

```
  1 GG
```

(Gly Ser) polypeptide linker amino acid sequence (SEQ ID NO: 15)

```
  1 GS
```

(Gly$_2$ Ser) polypeptide linker amino acid sequence (SEQ ID NO: 16)

```
  1 GGS
```

(Ala) polypeptide linker amino acid sequence (SEQ ID NO: 17)

```
  1 A
```

(Ala Ala) polypeptide linker amino acid sequence (SEQ ID NO: 18)

```
  1 AA
```

Klotho signal peptide-Klotho extracellular domain-FGF23 (R179Q) amino acid sequence (SEQ ID NO: 19)

```
  1 MPASAPPRRP RPPPPSLSLL LVLLGLGGRR LRAEPGDGAQ TWARFSRPPA
 51 PEAAGLFQGT FPDGFLWAVG SAAYQTEGGW QQHGKGASIW DTFTHHPLAP
101 PGDSRNASLP LGAPSPLQPA TGDVASDSYN NVFRDTEALR ELGVTHYRFS
151 ISWARVLPNG SAGVPNREGL RYYRRLLERL RELGVQPVVT LYHWDLPQRL
201 QDAYGGWANR ALADHFRDYA ELCFRHFGGQ VKYWITIDNP YVVAWHGYAT
251 GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP
```

FIGURE 2J

```
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGTFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFTVC TECSFFHTRK SLGSGGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN TLAGGTGPEG CRPFAKFI*
```

IgG signal peptide-Klotho extracellular domain-FGF23 (R179Q) amino acid sequence (SEQ ID NO: 20)

```
   1 MSVLTQVLAL LLLWLTGLGG RRLRAEPGDG AQTWARFSRP PAPEAAGLFQ
  51 GTFPDGFLWA VGSAAYQTEG GWQQHGKGAS IWDTFTHHPL APPGDSRNAS
 101 LPLGAPSPLQ PATGDVASDS YNNVFRDTEA LRELGVTHYR FSISWARVLP
 151 NGSAGVPNRE GLRYYRRLLE RLRELGVQPV VTLYHWDLPQ RLQDAYGGWA
 201 NRALADHFRD YAELCFRHFG GQVKYWITID NPYVVAWHGY ATGRLAPGIR
 251 GSPRLGYLVA HNLLLAHAKV WHLYNTSFRP TQGGQVSIAL SSHWINPRRM
 301 TDHSIKECQK SLDFVLGWFA KPVFIDGDYP ESMKNNLSSI LPDFTESEKK
 351 FIKGTADFFA LCFGPTLSFQ LLDPHMKFRQ LESPNLRQLL SWIDLEFNHP
 401 QIFIVENGWF VSGTTKRDDA KYMYYLKKFI METLKAIKLD GVDVIGYTAW
 451 SLMDGFEWHR GYSIRRGLFY VDFLSQDKML LPKSSALFYQ KLIEKNGFPP
 501 LPENQPLEGT FPCDFAWGVV DNYIQVDTTL SQFTDLNVYL WDVHHSKRLI
 551 KVDGVVTKKR KSYCVDFAAI QPQIALLQEM HVTHFRFSLD WALILPLGNQ
 601 SQVNHTILQY YRCMASELVR VNITPVVALW QPMAPNQGLP RLLARQGAWE
 651 NPYTALAFAE YARLCFQELG HHVKLWITMN EPYTRNMTYS AGHNLLKAHA
 701 LAWHVYNEKF RHAQNGKISI ALQADWIEPA CPFSQKDKEV AERVLEFDIG
 751 WLAEPIFGSG DYPWVMRDWL NQRNNFLLPY FTEDEKKLIQ GTFDFLALSH
 801 YTTILVDSEK EDPIKYNDYL EVQEMTDITW LNSPSQVAVV PWGLRKVLNW
 851 LKFKYGDLPM YIISNGIDDG LHAEDDQLRV YYMQNYINEA LKAHILDGIN
 901 LCGYFAYSFN DRTAPRFGLY RYAADQFEPK ASMKHYRKII DSNGFPGPET
 951 LERFCPEEFT VCTECSFFHT RKSLGSGGGG SGGGGSGGGG SLKYPNASPL
1001 LGSSWGGLIH LYTATARNSY HLQIHKNGHV DGAPHQTIYS ALMIRSEDAG
1051 FVVITGVMSR RYLCMDFRGN IFGSHYFDPE NCRFQHQTLE NGYDVYHSPQ
1101 YHFLVSLGRA KRAFLPGMNP PPYSQFLSRR NEIPLIHFNT PIPRRHTQSA
1151 EDDSERDPLN VLKPRARMTP APASCSQELP SAEDNSPMAS DPLGVVRGGR
1201 VNTHAGGTGP EGCRPFAKFI *
```

KL-D1-FGF23 (R179Q) amino acid sequence (SEQ ID NO: 21)

```
   1 MPASAPPRRP RPPPPSLSLL LVLLGLGGRR LRAEPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWTTIDNP YVVAWHGYAT
```

FIGURE 2K

```
251 GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP
351 DFTESEKKFI KGTADFFALC FGPTLSFQLL DPHMKFRQLE SPNLRQLLSW
401 IDLEFNHPQI FIVENGWFVS GTTKRDDAKY MYYLKKFIME TLKAIKLDGV
451 DVIGYTAWSL MDGFEWHRGY SIRRGLFYVD FLSQDKMLLP KSSALFYQKL
501 IEKNGFPPLP ENQPLEGSGG GGSGGGGSGG GGSLKYPNAS PLLGSSWGGL
551 IHLYTATARN SYHLQIHKNG HVDGAPHQTI YSALMIRSED AGFVVITGVM
601 SRRYLCMDFR GNIFGSHYFD PENCRFQHQT LENGYDVYHS PQYHFLVSLG
651 RAKRAFLPGM NPPPYSQFLS RRNEIPLIHF NTPIPRRHTQ SAEDDSERDP
701 LNVLKPRARM TPAPASCSQE LPSAEDNSPM ASDPLGVVRG GRVNTHAGGT
751 GPEGCRPFAK FI*
```

KL-D2-FGF23 (R179Q) amino acid sequence (SEQ ID NO: 22)

```
  1 MPASAPPRRP RPPPPSLSLL LVLLGLGGRR LPLPENQPLE GTFPCDFAWG
 51 VVDNYIQVDT TLSQFTDLNV YLWDVHHSKR LIKVDGVVTK KRKSYCVDFA
101 AIQPQIALLQ EMHVTHFRFS LDWALILPLG NQSQVNHTIL QYYRCMASEL
151 VRVNITPVVA LWQPMAPNQG LPRLLARQGA WENPYTALAF AEYARLCFQE
201 LGHHVKLWIT MNEPYTRNMT YSAGHNLLKA HALAWHVYNE KFRHAQNGKI
251 SIALQADWIE PACPFSQDK EVAERVLEFD IGWLAEPIFG SGDYPWVMRD
301 WLNQRNNFLL PYFTEDEKKL IQGTFDFLAL SHYTTILVDS EKEDPIKYND
351 YLEVQEMTDI TWLNSPSQVA VVPWGLRKVL NWLKFKYGDL PMYIISNGID
401 DGLHAEDDQL RVYYMQNYIN EALKAHILDG INLCGYFAYS FNDRTAPRFG
451 LYRYAADQFE PKASMKHYRK IIDSNGFPGP ETLERFCPEE FTVCTECSFF
501 HTRKSLGSGG GGSGGGGSGG GGSLKYPNAS PLLGSSWGGL IHLYTATARN
551 SYHLQIHKNG HVDGAPHQTI YSALMIRSED AGFVVITGVM SRRYLCMDFR
601 GNIFGSHYFD PENCRFQHQT LENGYDVYHS PQYHFLVSLG RAKRAFLPGM
651 NPPPYSQFLS RRNEIPLIHF NTPIPRRHTQ SAEDDSERDP LNVLKPRARM
701 TPAPASCSQE LPSAEDNSPM ASDPLGVVRG GRVNTHAGGT GPEGCRPFAK
751 FI*
```

(KL-D1)$_2$-FGF23 (R179Q) amino acid sequence (SEQ ID NO: 23)

```
   1 MPASAPPRRP RPPPPSLSLL LVLLGLGGRR LRAEPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGSGT FPDGFLWAVG SAAYQTEGGW QQHGKGASIW
 551 DTFTHHPLAP PGDSRNASLP LGAPSPLQPA TGDVASDSYN NVFRDTEALR
 601 ELGVTHYRFS ISWARVLPNG SAGVPNREGL RYYRRLLERL RELGVQPVVT
 651 LYHWDLPQRL QDAYGGWANR ALADHFRDYA ELCFRHFGGQ VKYWITIDNP
 701 YVVAWHGYAT GRLAPGIRGS PRLGYLVAHN LLLAHAKVWH LYNTSFRPTQ
 751 GGQVSIALSS HWINPRRMTD HSIKECQKSL DFVLGWFAKP VFIDGDYPES
 801 MKNNLSSILP DFTESEKKFI KGTADFFALC FGPTLSFQLL DPHMKFRQLE
 851 SPNLRQLLSW IDLEFNHPQI FIVENGWFVS GTTKRDDAKY MYYLKKFIME
 901 TLKAIKLDGV DVIGYTAWSL MDGFEWHRGY SIRRGLFYVD FLSQDKMLLP
 951 KSSALFYQKL IEKNGFPEFG SGGGGSGGGG SGGGGSLKYP NASPLLGSSW
1001 GGLIHLYTAT ARNSYHLQIH KNGHVDGAPH QTIYSALMIR SEDAGFVVIT
1051 GVMSRRYLCM DFRGNIFGSH YFDPENCRFQ HQTLENGYDV YHSPQYHFLV
```

FIGURE 2L

```
1101 SLGRAKRAEL PGMNPPPYSQ FLSRRNEIPL IHFNTPIPRR HTQSAEDDSE
1151 RDPLNVLKPR ARMTPAPASC SQELPSAEDN SPMASDPLGV VRGGRVNTHA
1201 GGTGPEGCRP FAKFI*
```

(KL-D2)₂-FGF23 (R179Q) amino acid sequence (SEQ ID NO: 24)

```
   1 MPASAPPRRP RPPPPSLSLL LVLLGLCGRR LPLPENQPLE GTFPCDFAWG
  51 VVDNYIQVDT TLSQFTDLNV YLWDVHHSKR LIKVDGVVTK KRKSYCVDFA
 101 AIQPQIALLQ EMHVTHFRFS LDWALILPLG NQSQVNHTIL QYYRCMASEL
 151 VRVNITPVVA LWQPMAPNQG LPRLLARQGA WENPYTALAF AEYARLCFQE
 201 LGHHVKLWIT MNEPYTRNMT YSAGHNLLKA HALAWHVYNE KFRHAQNGKI
 251 SIALQADWIE PACPFSQKDK EVAERVLEFD IGWLAEPIFG SGDYPWVMRD
 301 WLNQRNNFLL PYFTEDEKKL IQGTFDFLAL SHYTTILVDS EKEDPIKYND
 351 YLEVQEMTDI TWLNSPSQVA VVPWGLRKVL NWLKFKYGDL PMYIISNGID
 401 DGLHAEDDQL RVYYMQNYIN EALKAHILDG INLCGYFAYS FNDRTAPRFG
 451 LYRYAADQFE PKASMKHYRK IIDSNGFPGP ETLERFCPEE FTVCTECSFF
 501 HTRKSLGTIP CDFAWGVVDN YIQVDTTLSQ FTDLNVYLWD VHHSKRLIKV
 551 DGVVTKKRKS YCVDFAAIQP QIALLQEMHV THFRFSLDWA LILPLGNQSQ
 601 VNIITILQYYR CMASELVRVN ITPVVALWQP MAPNQGLPRL LARQGAWENP
 651 YTALAFAEYA RLCFQELGHH VKLWITMNEP YTRNMTYSAG HNLLKAHALA
 701 WHVYNEKFRH AQNGKISIAL QADWIEPACP FSQKDKEVAE RVLEFDIGWL
 751 AEPIFGSGDY PWVMRDWLNQ RNNFLLPYFT EDEKKLIQGT FDFLALSHYT
 801 TILVDSEKED PIKYNDYLEV QEMTDITWLN SPSQVAVVPW GLRKVLNWLK
 851 FKYGDLPMYI ISNGIDDGLH AEDDQLRVYY MQNYINEALK AHILDGINLC
 901 GYFAYSFNDR TAPRFGLYRY AADQFEPKAS MKHYRKIIDS NGFGSGGGGS
 951 GGGGSGGGGS LKYPNASPLL GSSWGGLIHL YTATARNSYH LQIHKNGHVD
1001 GAPHQTIYSA LMIRSEDAGF VVITGVMSRR YLCMDFRGNI FGSHYFDPEN
1051 CRFQHQTLEN GYDVYHSPQY HFLVSLGRAK RAFLPGMNPP PYSQFLSRRN
1101 EIPLIHFNTP IPRRHTQSAE DDSERDPLNV LKPRARMTPA PASCSQELPS
1151 AEDNSPMASD PLGVVRGGRV NTHAGGTGPE GCRPFAKFI*
```

FGF23 (R179Q)-Klotho extracellular domain amino acid sequence (SEQ ID NO: 25)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IGSGGGGSGG GGSGGGGSLK EPGDGAQTWA RFSRPPAPEA AGLFQGTFPD
 301 GFLWAVGSAA YQTEGGWQQH GKGASIWDTF THHPLAPPGD SRNASLPLGA
 351 PSPLQPATGD VASDSYNNVF RDTEALRELG VTHYRFSISW ARVLPNGSAG
 401 VPNREGLRYY RRLLERLREL GVQPVVTLYH WDLPQRLQDA YGGWANRALA
 451 DHFRDYAELC FRHFGGQVKY WITIDNPYVV AWHGYATGRL APGIRGSPRL
 501 GYLVAHNLLL AHAKVWHLYN TSFRPTQGGQ VSIALSSHWI NPRRMTDHSI
 551 KECQKSLDFV LGWFAKPVFI DGDYPESMKN NLSSILPDFT ESEKKFIKGT
 601 ADFFALCFGP TLSFQLLDPH MKFRQLESPN LRQLLSWIDL EFNHPQIFIV
 651 ENGWFVSGTT KRDDAKYMYY LKKFIMETLK AIKLDGVDVI GYTAWSLMDG
 701 FEWHRGYSIR RGLFYVDFLS QDKMLLPKSS ALFYQKLIEK NGFPPLPENQ
 751 PLEGTFPCDF AWGVVDNYIQ VDTTLSQFTD LNVYLWDVHH SKRLIKVDGV
 801 VTKKRKSYCV DFAAIQPQIA LLQEMHVTHF RFSLDWALIL PLGNQSVNH
 851 TILQYYRCMA SELVRVNITP VVALWQPMAP NQGLPRLLAR QGAWENPYTA
 901 LAFAEYARLC FQELGHHVKL WITMNEPYTR NMTYSAGHNL LKAHALAWHV
 951 YNEKFRHAQN GKISIALQAD WIEPACPFSQ KDKEVAERVL EFDIGWLAEP
1001 IFGSGDYPWV MRDWLNQRNN FLLPYFTEDE KKLIQGTFDF LALSHYTTIL
```

FIGURE 2M

```
1051  VDSEKEDPIK  YNDYLEVQEM  TDITWLNSPS  QVAVVPWGLR  KVLNWLKFKY
1101  GDLPMYIISN  GIDDGLHAED  DQLRVYYMQN  YINEALKAHI  LDGINLCGYF
1151  AYSFNDRTAP  RFGLYRYAAD  QFEPKASMKH  YRKIIDSNGF  PGPETLERFC
1201  PEEFTVCTEC  SFFHTRKSL*
```

FGF23 (R179Q)-KL-D1 amino acid sequence (SEQ ID NO: 26)

```
  1  MLGARLRLWV  CALCSVCSMS  VLRAYPNASP  LLGSSWGGLI  HLYTATARNS
 51  YHLQIHKNGH  VDGAPHQTIY  SALMIRSEDA  GFVVITGVMS  RRYLCMDFRG
101  NIFGSHYFDP  ENCRFQHQTL  ENGYDVYHSP  QYHFLVSLGR  AKRAFLPGMN
151  PPPYSQFLSR  RNEIPLIHFN  TPIPRRHTQS  AEDDSERDPL  NVLKPRARMT
201  PAPASCSQEL  PSAEDNSPMA  SDPLGVVRGG  RVNTHAGGTG  PEGCRPFAKF
251  IQGTFPDGFL  WAVGSAAYQT  EGGWQQHGKG  ASIWDTFTHH  PLAPPGDSRN
301  ASLPLGAPSP  LQPATGDVAS  DSYNNVFRDT  EALRELGVTH  YRFSISWARV
351  LPNGSAGVPN  REGLRYYRRL  LERLRELGVQ  PVVTLYHWDL  PQRLQDAYGG
401  WANRALADHF  RDYAELCFRH  FGGQVKYWIT  IDNPYVVAWH  GYATGRLAPG
451  IRGSPRLGYL  VAHNLLLAHA  KVWHLYNTSF  RPTQGGQVSI  ALSSHWINPR
501  RMTDHSIKEC  QKSLDFVLGW  FAKPVFIDGD  YPESMKNNLS  SILPDFTESE
551  KKFIKGTADF  FALCFGPTLS  FQLLDPHMKF  RQLESPNLRQ  LLSWIDLEFN
601  HPQIFIVENG  WFVSGTTKRD  DAKYMYYLKK  FIMETLKAIK  LDGVDVIGYT
651  AWSLMDGFEW  HRGYSIRRGL  FYVDFLSQDK  MLLPKSSALF  YQKLIEKNGF
652  *
```

FGF23 (R179Q)-KL-D2 amino acid sequence (SEQ ID NO: 27)

```
  1  MLGARLRLWV  CALCSVCSMS  VLRAYPNASP  LLGSSWGGLI  HLYTATARNS
 51  YHLQIHKNGH  VDGAPHQTIY  SALMIRSEDA  GFVVITGVMS  RRYLCMDFRG
101  NIFGSHYFDP  ENCRFQHQTL  ENGYDVYHSP  QYHFLVSLGR  AKRAFLPGMN
151  PPPYSQFLSR  RNEIPLIHFN  TPIPRRHTQS  AEDDSERDPL  NVLKPRARMT
201  PAPASCSQEL  PSAEDNSPMA  SDPLGVVRGG  RVNTHAGGTG  PEGCRPFAKF
251  IGTFPCDFAW  GVVDNYIQVD  TTLSQFTDLN  VYLWDVHHSK  RLIKVDGVVT
301  KKRKSYCVDF  AAIQPQIALL  QEMHVTHFRF  SLDWALILPL  GNQSQVNHTI
351  LQYYRCMASE  LVRVNITPVV  ALWQPMAPNQ  GLPRLLARCG  AWENPYTALA
401  FAEYARLCFQ  ELGHHVKLWI  TMNEPYTRNM  TYSAGHNLLK  AHALAWHVYN
451  EKFRHAQNGK  ISIALQADWI  EPACPFSQKD  KEVAERVLEF  DIGWLAEPIF
501  GSGDYPWVMR  DWLNQRNNFL  LPYFTEDEKK  LIQGTFDFLA  LSHYTTILVD
551  SEKEDPIKYN  DYLEVQEMTD  ITWLNSPSQV  AVVPWGLRKV  LNWLKFKYGD
601  LPMYIISNGI  DDGLHAEDDQ  LRVYYMQNYI  NEALKAHILD  GINLCGYFAY
651  SFNDRTAPRF  GLYRYAADQF  EPKASMKHYR  KIIDSNGF*
```

FGF23 (R179Q)-(KL-D1)₂ amino acid sequence (SEQ ID NO: 28)

```
  1  MLGARLRLWV  CALCSVCSMS  VLRAYPNASP  LLGSSWGGLI  HLYTATARNS
 51  YHLQIHKNGH  VDGAPHQTIY  SALMIRSEDA  GFVVITGVMS  RRYLCMDFRG
101  NIFGSHYFDP  ENCRFQHQTL  ENGYDVYHSP  QYHFLVSLGR  AKRAFLPGMN
151  PPPYSQFLSR  RNEIPLIHFN  TPIPRRHTQS  AEDDSERDPL  NVLKPRARMT
201  PAPASCSQEL  PSAEDNSPMA  SDPLGVVRGG  RVNTHAGGTG  PEGCRPFAKF
251  IQGTFPDGFL  WAVGSAAYQT  EGGWQQHGKG  ASIWDTFTHH  PLAPPGDSRN
301  ASLPLGAPSP  LQPATGDVAS  DSYNNVFRDT  EALRELGVTH  YRFSISWARV
351  LPNGSAGVPN  REGLRYYRRL  LERLRELGVQ  PVVTLYHWDL  PQRLQDAYGG
401  WANRALADHF  RDYAELCFRH  FGGQVKYWIT  IDNPYVVAWH  GYATGRLAPG
451  IRGSPRLGYL  VAHNLLLAHA  KVWHLYNTSF  RPTQGGQVSI  ALSSHWINPR
501  RMTDHSIKEC  QKSLDFVLGW  FAKPVFIDGD  YPESMKNNLS  SILPDFTESE
551  KKFIKGTADF  FALCFGPTLS  FQLLDPHMKF  RQLESPNLRQ  LLSWIDLEFN
601  HPQIFIVENG  WFVSGTTKRD  DAKYMYYLKK  FIMETLKAIK  LDGVDVIGYT
```

FIGURE 2N

```
 651 AWSLMDGFEW HRGYSIRRGL FYVDFLSQDK MLLPKSSALF YQKLIEKNGF
 701 QGTFPDGFLW AVGSAAYQTE GGWQQHGKGA SIWDTFTHHP LAPPGDSRNA
 751 SLPLGAPSPL QPATGDVASD SYNNVFRDTE ALRELGVTHY RFSISWARVL
 801 PNGSAGVPNR EGLRYYRRLL ERLRELGVQP VVTLYHWDLP QRLQDAYGGW
 851 ANRALADHFR DYAELCFRHF GGQVKYWITI DNPYVVAWHG YATGRLAPGI
 901 RGSPRLGYLV AHNLLLAHAK VWHLYNTSFR PTQGGQVSIA LSSHWINPRR
 951 MTDHSIKECQ KSLDFVLGWF AKPVFIDGDY PESMKNNLSS ILPDFTESEK
1001 KFIKGTADFF ALCFGPTLSF QLLDPHMKFR QLESPNLRQL LSWIDLEFNH
1051 PQIFIVENGW FVSGTTKRDD AKYMYYLKKF IMETLKAIKL DGVDVIGYTA
1101 WSLMDGFEWH RGYSIRRGLF YVDFLSQDKM LLPKSSALFY QKLIEKNGF*
```

FGF23 (R179Q) -(KL-D2)$_2$ amino acid sequence (SEQ ID NO: 29)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IGTFPCDFAW GVVDNYIQVD TTLSQFTDLN VYLWDVHHSK RLIKVDGVVT
 301 KKRKSYCVDF AAIQPQIALL QEMHVTHFRF SLDWALILPL GNQSVVNHTI
 351 LQYYRCMASE LVRVNITPVV ALWQPMAPNQ GLPRLLARQG AWENPYTALA
 401 FAEYARLCFQ ELGHHVKLWI TMNEPYTRNM TYSAGHNLLK AHALAWHVYN
 451 EKFRHAQNGK ISIALQADWI EPACPFSQKD KEVAERVLEF DIGWLAEPIF
 501 GSGDYPWVMR DWLNQRNNFL LPYFTEDEKK LIQGTFDFLA LSHYTTILVD
 551 SEKEDPIKYN DYLEVQEMTD ITWLNSPSQV AVVPWGLRKV LNWLKFKYGD
 601 LPMYIISNGI DDGLHAEDDQ LRVYYMQNYI NEALKAHILD GINLCGYFAY
 651 SFNDRTAPRF GLRYAADQF EPKASMKHYR KIIDSNGFGT FPCDFAWGVV
 701 DNYIQVDTTL SQFTDLNVYL WDVHHSKRLI KVDGVVTKKR KSYCVDFAAI
 751 QPQIALLQEM HVTHFRFSLD WALILPLGNQ SQVNHTILQY YRCMASELVR
 801 VNITPVVALW QPMAPNQGLP RLLARQGAWE NPYTALAFAE YARLCFQELG
 851 HHVKLWTTMN EPYTRNMTYS AGHNLLKAHA LAWHVYNEKF RHAQNGKTST
 901 ALQADWIEPA CPFSQKDKEV AERVLEFDIG WLAEPIFGSG DYPWVMRDWL
 951 NQRNNFLLPY FTEDEKKLIQ GTFDFLALSH YTTILVDSEK EDPIKYNDYL
1001 EVQEMTDITW LNSPSQVAVV PWGLRKVLNW LKFKYGDLPM YIISNGIDDG
1051 LHAEDDQLRV YYMQNYINEA LKAHILDGIN LCGYFAYSFN DRTAPRFGLY
1101 RYAADQFEPK ASMKHYRKII DSNGF*
```

FGF19 nucleic acid sequence (NM_005117) (SEQ ID NO: 30)
Protein coding region (464-1114)

```
    1 gctcccagcc aagaacctcg gggccgctgc gcggtgggga ggagttcccc
gaaacccggc
   61 cgctaagcga ggcctcctcc tcccgcagat ccgaacggcc tgggcggggt
caccccggct
  121 gggacaagaa gccgccgcct gcctgcccgg gccggggag gggctgggg
ctggggccgg
  181 aggcggggtg tgagtgggtg tgtgcggggg cggaggcttg atgcaatcc
cgataagaaa
  241 tgctcgggtg tcttgggcac ctacccgtgg ggcccgtaag gcgctactat
ataaggctgc
  301 cggcccggag ccgccgcgcc gtcagagcag gagcgctgcg tccaggatct
agggccacga
  361 ccatcccaac ccggcactca cagccccgca gcgcatcccg gtcgccgccc
agcctcccgc
```

FIGURE 2O

```
 421 accccatcg ccggagctgc gccgagagcc ccagggaggt gccatgcgga
gcgggtgtgt
 481 ggtggtccac gtatggatcc tggccggcct ctggctggcc gtggccgggc
gcccctcgc
 541 cttctcggac gcgggcccc acgtgcacta cggctgggc gacccatcc
gcctgcggca
 601 cctgtacacc tccggccccc acgggctctc cagctgcttc ctgcgcatcc
gtgccgacgg
 661 cgtcgtggac tgcgcgcggg ccagagcgc gcacagtttg ctggagatca
aggcagtcgc
 721 tctgcggacc gtggccatca agggcgtgca cagcgtgcgg tacctctgca
tgggcgccga
 781 cggcaagatg cagggctgc ttcagtactc ggaggaagac tgtgctttcg
aggaggagat
 841 ccgcccagat ggctacaatg tgtaccgatc cgagaagcac cgcctccgg
tctccctgag
 901 cagtgccaaa cagcggcagc tgtacaagaa cagaggcttt cttccactct
ctcatttcct
 961 gcccatgctg cccatggtcc cagaggagcc tgaggacctc agggccact
tggaatctga
1021 catgttctct tcgcccctgg agaccgacag catggaccca tttgggcttg
tcaccggact
1081 ggaggccgtg aggagtccca gctttgagaa gtaactgaga ccatgcccgg
gcctcttcac
1141 tgctgccagg ggctgtggta cctgcagcgt gggggacgtg cttctacaag
aacagtcctg
1201 agtccacgtt ctgtttagct ttaggaagaa acatctagaa gttgtacata
ttcagagttt
1261 tccattggca gtgccagttt ctagccaata gacttgtctg atcataacat
tgtaagcctg
1321 tagcttgccc agctgctgcc tgggccccca ttctgctccc tcgaggttgc
tggacaagct
1381 gctgcactgt ctcagttctg cttgaatacc tccatcgatg gggaactcac
ttcctttgga
1441 aaaattctta tgtcaagctg aaattctcta attttttctc atcacttccc
caggagcagc
1501 cagaagacag gcagtagttt taatttcagg aacaggtgat ccactctgta
aaacagcagg
1561 taaatttcac tcaaccccat gtgggaattg atctatatct ctacttccag
ggaccatttg
1621 cccttcccaa atccctccag gccagaactg actggagcag gcatggccca
ccaggcttca
1681 ggagtagggg aagcctggag ccccactcca gccctgggac aacttgagaa
ttccccctga
1741 ggccagttct gtcatggatg ctgtcctgag aataacttgc tgtcccggtg
tcacctgctt
1801 ccatctccca gcccaccagc cctctgccca cctcacatgc ctccccatgg
attggggcct
1861 cccaggcccc ccaccttatg tcaacctgca cttcttgttc aaaaatcagg
aaaagaaaag
1921 atttgaagac cccaagtctt gtcaataact tgctgtgtgg aagcagcggg
ggaagaccta
1981 gaacccttc cccagcactt ggttttccaa catgatattt atgagtaatt
tattttgata
2041 tgtacatctc ttattttctt acattattta tgcccccaaa ttatatttat
gtatgtaagt
2101 gaggtttgtt ttgtatatta aatggagtt tgtttgtaaa aaaaaaaaa aaaaaaa
```

FIGURE 2P

FGF19 amino acid sequence (NP_005108) (SEQ ID NO: 31)

```
  1 MRSGCVVVHV WILAGLWLAV AGRPLAFSDA GPHVHYGWGD PIRLRHLYTS
GPHGLSSCFL
 61 RIRADGVVDC ARGQSAHSLL EIKAVALRTV AIKGVHSVRY LCMGADGKMQ
GLLQYSEEDC
121 AFEEEIRPDG YNVYRSEKHR LPVSLSSAKQ RQLYKNRGFL PLSHFLPMLP
MVPEEPEDLR
181 GHLESDMFSS PLETDSMDPF GLVTGLEAVR SPSFEK
```

FGF21 nucleic acid sequence (NM_019113 ) (SEQ ID NO: 32)
Protein coding region 151-780

```
  1 CTGTCAGCTG AGGATCCAGC CGAAAGAGGA GCCAGGCACT CAGGCCACCT
GAGTCTACTC
 61 ACCTGGACAA CTGGAATCTG CACCAATTC TAAACCACTC AGCTTCTCCG
AGCTCACACC
121 CCGGAGATCA CCTGAGGACC CGAGCCATTG ATGGACTCGG ACGAGACCGG
GTTCGAGCAC
181 TCAGGACTGT GGGTTTCTGT GCTGGCTGGT CTTCTGCTGG GAGCCTGCCA
GGCACACCCC
241 ATCCCTGACT CCAGTCCTCT CCTGCAATTC GGGGGCCAAG TCCGGCAGCG
GTACCTCTAC
301 ACAGATGATG CCCAGCAGAC AGAAGCCCAC CTGGAGATCA GGGAGGATGG
GACGGTGGGG
361 GGCGCTGCTG ACCAGAGCCC CGAAAGTCTC CTGCAGCTGA AAGCCTTGAA
GCCGGGAGTT
421 ATTCAAATCT TGGGAGTCAA GACATCCAGG TTCCTGTGCC AGCGGCCAGA
TGGGGCCCTG
481 TATGGATCGC TCCACTTTGA CCCTGAGGCC TGCAGCTTCC GGGAGCTGCT
TCTTGAGGAC
541 GGATACAATG TTTACCAGTC CGAAGCCCAC GGCCTCCCGC TGCACCTGCC
AGGGAACAAG
601 TCCCCACACC GGGACCCTGC ACCCCGAGGA CCAGCTCGCT TCCTGCCACT
ACCAGGCCTG
661 CCCCCCGCAC TCCCGGAGCC ACCCGGAATC CTGGCCCCCC AGCCCCCCGA
TGTGGGCTCC
721 TCGGACCCTC TGAGCATGGT GGGACCTTCC CAGGGCCGAA GCCCCAGCTA
CGCTTCCTGA
781 AGCCAGAGGC TGTTTACTAT GACATCTCCT CTTTATTTAT TAGGTTATTT
ATCTTATTTA
841 TTTTTTTATT TTTCTTACTT GAGATAATAA AGAGTTCCAG AGGAGAAAAA
AAAAAAAAA
901 AAAAAAAAAA AAAAAAAAA AAAAAAAAA AAAAAAAAA
```

FGF21 amino acid sequence (NP_061986) (SEQ ID NO: 33)

```
  1 MDSDETGFEH SGLWVSVLAG LLLGACQAHP IPDSSPLLQF GGQVRQRYLY
TDDAQQTEAH
 61 LEIREDGTVG GAADQSPESL LQLKALKPGV IQILGVKTSR FLCQRPDGAL
YGSLHFDPEA
121 CSFRELLLED GYNVYQSEAH GLPLHLPGNK SPHRDPAPRG PARFLPLPGL
PPALPEPPGI
181 LAPQPPDVGS SDPLSMVGPS QGRSPSYAS
```

FIGURE 2Q

FGF23 nucleic acid sequence (NM_020638) (SEQ ID NO: 34)
Protein coding region 147-902

```
   1 cggcaaaaag agggaatcc agtctaggat cctcacacca gctacttgca agggagaagg
  61 aaaaggccag taaggcctgc gccaggagag tcccgacagg agtgtcaggt ttcaatctca
 121 gcaccagcca ctcagagcag ggcacgatgt tgggggcccg cctcaggctc tgggtctgtg
 181 ccttgtgcag cgtctgcagc atgagcgtcc tcagagccta tcccaatgcc tccccactgc
 241 tcggctccag ctgggtggc ctgatccacc tgtacacagc cacagccagg aacagctacc
 301 acctgcagat ccacaagaat ggccatgtgg atggcgcacc catcagacc atctacagtg
 361 ccctgatgat cagatcagac gatgctggct ttgtggtgat tacaggtgtg atgagcagaa
 421 gatacctctg catggatttc agaggcaaca ttttggatc acactatttc gacccggaga
 481 actgcaggtt ccaacaccag acgctggaaa acgggtacga cgtctaccac tctcctcagt
 541 atcacttcct ggtcagtctg ggccgggcga agagagcctt cctgccaggc atgaacccac
 601 ccccgtactc ccagttcctg tccggagga acgagatccc cctaattcac ttcaacaccc
 661 ccataccacg gcggcacacc cggagcgccg aggacgactc ggagcgggac cccctgaacg
 721 tgctgaagcc ccgggcccgg atgacccggg ccccggcctc ctgttcacag gagctcccga
 781 gcgccgagga caacagcccc atggccagtg accattagg ggtggtcagg ggcggtcgag
 841 tgaacacgca cgctggggga acgggcccgg aaggctgccg ccccttcgcc aagttcatct
 901 agggtcgctg gaagggcacc ctctttaacc catccctcag caaacgcagc tcttcccaag
 961 gaccaggtcc cttgacgttc cgaggatggg aaaggtgaca ggggcatgta tggaatttgc
1021 tgcttctctg gggtcccttc cacaggaggt cctgtgagaa ccaacctttg aggcccaagt
1081 catggggttt caccgccttc ctcactccat atagaacacc ttcccaata ggaaacccca
1141 acaggtaaac tagaaatttc cccttcatga aggtagagag aagggtctc tcccaacata
1201 tttctcttcc ttgtgcctct cctctttatc acttttaagc ataaaaaaaa aaaaaaaaa
1261 aaaaaaaaaa aaaagcagtc ggttcctgag ctcaagactt tgaaggtgta gggaagagga
1321 aatcggagat cccagaagct tctccactgc cctatgcatt tatgttagat gccccgatcc
1381 cactggcatt tgagtgtgca aaccttgaca ttaacagctg aatggggcaa gttgatgaaa
1441 acactacttt caagccttcg ttcttccttg agcatctctg gggaagagct gtcaaaagac
1501 tggtggtagg ctggtgaaaa cttgacagct agacttgatg cttgctgaaa tgaggcagga
```

FIGURE 2R

```
1561 atcataatag aaaactcagc ctccctacag ggtgagcacc ttctgtctcg ctgtctccct
1621 ctgtgcagcc acagccagac ggcccagaat ggccccactc tgttcccaag cagttcatga
1681 tacagcctca ccttttggcc ccatctctgg ttttt gaaaa tttggtctaa ggaataaata
1741 gcttttacac tggctcacga aaatctgccc tgctagaatt tgcttttcaa aatgcaaata
1801 aattccaact ctcctaagac gcatttaatt aaggctctac ttccaggttg agtacgaatc
1861 cattctgaac aaactacaaa aatgtgactg ggaaggggc tttgagagac tgggactgct
1921 ctgggttagg ttttctgtgc actgaaaaat cgtgtccttt tctctaaatg aagtcggcatc
1981 aaggactcag ggggaaagaa atcagggcac atgttataga agttatgaaa agacaaccac
2041 atggtcaggc tcttgtctgt ggtctctagg gctctgcagc agcagtggct cttccgattag
2101 ttaaaactct cctaggctga cacatctggg tctcaatccc cttggaaatt cttggtgcat
2161 taaatgaagc cttaccccat tactgcggtt cttcctgtaa ggggctcca ttttcctccc
2221 tctctttaaa tgaccaccta aaggacagta tattaacaag caaagtcgat tcaacaacag
2281 cttcttccca gtcactttt tttttctcac tgccatcaca tactaacctt atactttgat
2341 ctattctttt tggttatgag agaaatgttg ggcaactgtt tttacctgat ggttttaagc
2401 tgaacttgaa ggactggttc ctattctgaa acagtaaaac tatgtataat agtatatagc
2461 catgcatggc aaatatttta atatttctgt tttcatttcc tgttggaaat attatcctgc
2521 ataatagcta ttggaggctc ctcagtgaaa gatcccaaaa ggatttggt ggaaaactag
2581 ttgtaatctc acaaactcaa cactaccatc aggggtttc tttatggcaa agccaaaata
2641 gctcctacaa tttcttatat ccctcgtcat gtggcagtat ttattttattt atttcgaagt
2701 ttgcctatcc ttctatattt atagatattt ataaaaatgt aacccctttt tccttctttc
2761 tgtttaaaat aaaataaaa tttatctcag cttctgttag cttatcctct ttgtagtact
2821 acttaaaagc atgtcggaat ataagaataa aaaggattat gggagggaa cattagggaa
2881 atccagagaa ggcaaaattg aaaaaagat tttagaattt taaaattttc aaagatttct
2941 tccattcata aggagactca atgattttaa ttgatctaga cagaattatt taagtttttat
3001 caatattgga tttctggt
```

FGF23 amino acid sequence (NP_065689) (SEQ ID NO: 35)

```
  1 MLGARLRLWV CALCSVCSMS VLRAYPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
```

FIGURE 2S
```
    121 ENGYDVYHSP QYHFLVSLGR AKRAFLPGMN PPPYSQFLSR RNEIPLIHFN
TPIPRRHTRS
    181 AEDDSERDPL NVLKPRARMT PAPASCSQEL PSAEDNSPMA SDPLGVVRGG
RVNTHAGGTG
    241 PEGCRPFAKF I
```

FGF23 (R179Q) amino acid sequence (SEQ ID NO: 36)

```
      1 MLGARLRLWV CALCSVCSMS VLRAYPNASP LLGSSWGGLI HLYTATARNS
YHLQIHKNGH
     61 VDGAPHQTIY SALMIRSEDA GFVVITGVMS RRYLCMDFRG NIFGSHYFDP
ENCRFQHQTL
    121 ENGYDVYHSP QYHFLVSLGR AKRAFLPGMN PPPYSQFLSR RNEIPLIHFN
TPIPRRHTQS
    181 AEDDSERDPL NVLKPRARMT PAPASCSQEL PSAEDNSPMA SDPLGVVRGG
RVNTHAGGTG
    241 PEGCRPFAKF I
```

Human beta-Klotho domain 1 (b-KL-D1) amino acid sequence (SEQ ID NO: 37)

```
     77                    ydt fpknffwgig tgalqvegsw kkdgkgpsiw
dhfihthlkn
    121 vsstngsscs yiflekdlsa ldfigvsfyq fsiswprlfp dgivtvanak
glqyystlld
    181 alvlrniepi vtlyhwdlpl alqekyggwk ndtiidifnd yatycfqmfg
drvkywitih
    241 npylvawhgy gtgmhapgek gnlaavytvg hnlikahskv whnynthfrp
hqkgwlsitl
    301 gshwiepnrs entmdifkcq qsmvsvlgwf anpihgdgdy pegmrkklfs
vlpifseaek
    361 hemrgtadff afsfgpnnfk plntmakmgq nvslnlreal nwikleynnp
riliaengwf
    421 tdsrvktedt taiymmknfl sqvlqairld eirvfqytaw slldqfewqd
aytirrglfy
    481 vdfnskqker kpkssahyyk qiirengf
```

Human beta-Klotho domain 2 (b-KL-D2) amino acid sequence (SEQ ID NO: 38)

```
    571                     trpaqctdfv nikkqlemla
rmkvthyrfa
    601 ldwasvlptg nlsavnrqal ryyrcvvseg lklgisamvt lyypthahlg
lpepllhadg
    661 wlnpstaeaf qayaglcfqe lgdlvklwit inepnrlsdi ynrsgndtyg
aannllvaha
    721 lawrlydrqf rpsqrgavsl slhadwaepa npyadshwra aerflqfeia
wfaeplfktg
    781 dypaamreyi askhrrglss salprlteae rrllkgtvdf calnhfttrf
vmheqlagsr
    841 ydsdrciqfl qditrlsspt rlavipwgvr kllrwvrrny gdmdiyitas
giddqaledd
    901 rlrkyylgky lqevlkayli dkvrikgyya fklaeekskp rfgfftsdfk
akssiqfynk
    961 vissrgf
```

FIGURE 2T

Beta-Klotho extracellular domain (without signal peptide) amino acid sequence (SEQ ID NO: 39)

```
     52 gfsgdgrai
     61 wsknpnttpv nesqlflydt fpknftwgig tgalqvegsw kkdgkgpsiw
dhfihthlkn
    121 vsstngssds yiflekdlsa ldfigvsfyq fsiswprlfp dgivtvanak
glqyystlld
    181 alvlrniepi vtlyhwdlpl alqekyggwk ndtiidifnd yatycfqmfg
drvkywitih
    241 npylvawhgy gtgmhapgek gnlaavytvg hnlikahskv whrynthfrp
hqkgwlsitl
    301 qshwiepnrs entmdifkcq qsmvsvlgwf anpihgdgdy pegmrkklfs
vlpifseaek
    361 hcmrgtadff afsfgpnnfk plrtmakmgq nvslnlrcal nwiklcynnp
riliaengwf
    421 tdsrvktedt taiymmknfl sqvlqairld eirvfgytaw slldgfewqd
aytirrglfy
    481 vdfnskqker kpkssahyyk qiirengfsl kestpdvqgq fpcdfswgvt
esvlkpesva
    541 sspqfsdphl yvwnatgnrl lhrvegvrlk trpaqctdfv nikkqlemla
rmkvthyrfa
    601 ldwasvlptg nlsavnrqal ryyrcvvseg lklgisamvt lyypthahlg
lpepllhadg
    661 wlnpstaeaf qayaglcfqe lgdlvklwit inepnrlsdi ynrsgndtyg
aahnllvaha
    721 lawrlydrqf rpsqrgavsl slnadwaepa npyadshwra aertlqteia
wfaeplfktg
    781 dypaamreyi askhrrglss salprlteae rrllkgtvdf calnhfttrf
vmheqlagsr
    841 ydsdrdiqfl qditrlsspt rlavipwgvr kllrwvrrny gdmdiyitas
giddqaledd
    901 rlrkyylgky lqevlkayli dkvrikgyya fklaeekskp rfgfftsdfk
akssiqfynk
    961 vissrgfpfe nsssrcsqtq entectvclf lvqkkpl
``` sKlotho without signal peptide – FGF23 amino acid sequence (without signal peptide) (SEQ ID NO: 40)

```
                                          EPGDGAQ TWARFSRPPA
     51 PEAAGLFQGT FPDGFLWAVG SAAYQTEGGW QQHGKGASIW DTFTHHPLAP
    101 PGDSRNASLP LGAPSPLQPA TGDVASDSYN NVFRDTEALR ELGVTHYRFS
    151 ISWARVLPNG SAGVPNREGL RYYRRLLERL RELGVQPVVT LYHWDLPQRL
    201 QDAYGGWANR ALADHFRDYA ELCFRHFGGQ VKYWITIDNP YVVAWHGYAT
    251 GRLAPGIRGS PRLGYLVAHN LLLAHAKVWH LYNTSFRPTQ GGQVSIALSS
    301 HWINPRRMTD HSIKECQKSL DFVLGWFAKP VFIDGDYPES MKNNLSSILP
    351 DFTESEKKFI KGTADFFALC FGPTLSFQLL DPHMKFRQLE SPNLRQLLSW
    401 IDLEFNHPQI FIVENGWFVS GTTKRDDAKY MYYLKKFIME TLKAIKLDGV
    451 DVIGYTAWSL MDGFEWHRGY SIRRGLFYVD FLSQDKMLLP KSSALFYQKL
    501 IEKNGFPPLP ENQPLEGTFP CDFAWGVVDN YIQVDTTLSQ FTDLNVYLWD
    551 VHHSKRLIKV DGVVTKKRKS YCVDFAAIQP QIALLQEMHV THFRFSLDWA
    601 LILPLGNQSQ VNHTILQYYR CMASELVRVN ITPVVALWQP MAPNQGLPRL
    651 LARQGAWENP YTALAFAEYA RLCFQELGHH VKLWITMNEP YTRNMTYSAG
```

FIGURE 2U

```
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFIVC TECSFFHTRK SLGSGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTRSAED DSERDPLNVL KPRARMTPAP ASCSQELPSA EDNSPMASDP
1201 LGVVRGGRVN THAGGTGPEG CRPFAKFI*
``` sKlotho without signal peptide -FGF23 (R179Q) (without signal peptide) amino acid sequence (SEQ ID NO: 41)

```
                                          EPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFIESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGIFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFIVC TECSFFHTRK SLGSGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN THAGGTGPEG CRPFAKFI*
```

FGF23 without signal peptide (SEQ ID NO:42)

```
                         YPNASP LLGSSWGGLI HLYTATARNS YHLQIHKNGH
   61 VDGAPHQTIY SALMIRSEDA GFVVITGVMS RRYLCMDFRG NIFGSHYFDP ENCRFQHQTL
  121 ENGYDVYHSP QYHFLVSLGR AKRAFLPGMN PPPYSQFLSR RNEIPLIHFN TPIPRRHTRS
  181 AEDDSERDPL NVLKPRARMT PAPASCSQEL PSAEDNSPMA SDPLGVVRGG RVNTHAGGTG
  241 PEGCRPFAKF I
```

FIGURE 2V

FGF23(R179Q) without signal peptide (SEQ ID NO:43)

```
                                YPNASP LLGSSWGGLI HLYTATARNS YHLQIHKNGH
     61 VDGAPHQTIY SALMIRSEDA GFVVITGVMS RRYLCMDFRG NIFGSHYFDP ENCRFQHQTL
    121 ENGYDVYHSP QYHFLVSLGR AKRAFLPGMN PPPYSQFLSR RNEIPLIHFN TPIPRRHTQS
    181 AEDDSERDPL NVLKPRARMT PAPASCSQEL PSAEDNSPMA SDPLGVVRGG RVNTHAGGTG
    241 PEGCRPFAKF T
``` sKlotho with Klotho signal peptide (SEQ ID NO:44)

```
      1 MPASAPPRRP RPPPPSLSLL LVLLGLGGRR LRAEPGDGAQ TWARFSRPPA
     51 PEAAGLFQGT FPDGFLWAVG SAAYQTEGGW QQHGKGASIW DTFTHHPLAP
    101 PGDSRNASLP LGAPSPLQPA TGDVASDSYN NVFRDTEALR ELGVTHYRFS
    151 ISWARVLPNG SAGVPNREGL RYYRRLLERL RELGVQPVVT LYHWDLPQRL
    201 QDAYGGWANR ALADHFRDYA ELCFRHFGGQ VKYWITIDNP YVVAWHGYAT
    251 GRLAPGIRGS PRLGYLVAHN LLLAHAKVWH LYNTSFRPTQ GGQVSIALSS
    301 HWINPRRMTD HSIKECQKSL DFVLGWFAKP VFIDGDYPES MKNNLSSILP
    351 DFTESEKKFI KGTADFFALC FGPTLSFQLL DPHMKFRQLE SPNLRQILSW
    401 IDLEFNHPQI FIVENGWFVS GTTKRDDAKY MYYLKKFIME TLKAIKLDGV
    451 DVIGYTAWSL MDGFEWHRGY SIRRGLFYVD FLSQDKMLIP KSSALFYQKL
    501 IEKNGFPPLP ENQPLEGTFP CDFAWGVVDN YIQVDTTLSQ FTDLNVYLWD
    551 VHHSKRLIKV DGVVTKKRKS YCVDFAAIQP QIALLQEMHV THFRFSLDWA
    601 LLLPLGNQSQ VNHTILQYYR CMASELVRVN ITPVVALWQP MAPNQGLPRL
    651 LARQGAWENP YTALAFAEYA RLCFQELGHH VKLWTTMNEP YTRNMTYSAG
    701 HNLLKAHALA WHVYNEKFRH AQNGKISIAL QADWIEPACP FSQKDKEVAE
    751 RVLEFDIGWL AEPIFGSGDY PWVMRDWLNQ RNNFLLPYFT EDEKKLIQGT
    801 FDFLALSHYT TILVDSEKED PIKYNDYLEV QEMTDITWLN SPSQVAVVPW
    851 GLRKVLNWLK FKYGDLPMYI ISNGIDDGLH AEDDQLRVYY MQNYINEALK
    901 AHILDGINLC GYFAYSFNDR TAPRFGLYRY AADQFEPKAS MKHYRKIIDS
    951 NGFPGPETLE RFCPEEFTVC TECSFFHTRK SL
``` sKlotho with IgG Signal peptide (SEQ ID NO:45)

```
      1 MSVLTQVLAL LLLWLTGLGG RRLRAEPGDG AQTWARFSRP PAPEAAGLFQ
     51 GTFPDGFLWA VGSAAYQTEG GWQQHGKGAS IWDTFTHHPL APPGDSRNAS
    101 LPLGAPSPLQ PATGDVASDS YNNVFRDTEA LRELGVTHYR FSISWARVLP
    151 NGSAGVPNRE GLRYYRRLLE RLRELGVQPV VTLYHWDLPQ RLQDAYGGWA
    201 NRALADHFRD YAELCFRHFG GQVKYWITID NPYVVAWHGY ATGRLAPGIR
    251 GSPRLGYLVA HNLLLAHAKV WHLYNTSFRP TQGGQVSIAL SSHWINPRRM
    301 TDHSIKECQK SLDFVLGWFA KPVFIDGDYP ESMKNNLSSI LPDFTESEKK
    351 FIKGTADFFA LCFGPTLSFQ LLDPHMKFRQ LESPNLRQLL SWIDLEFNHP
    401 QIFIVENGWF VSGTTKRDDA KYMYYLKKFI METLKAIKLD GVDVIGYTAW
    451 SLMDGFEWHR GYSIRRGLFY VDFLSQDKML LPKSSALFYQ KLIEKNGFPP
    501 LPENQPLEGT FPCDFAWGVV DNYIQVDTTL SQFTDLNVYL WDVHHSKRLI
    551 KVDGVVTKKR KSYCVDFAAI QPQIALLQEM HVTHFRFSLD WALILPLGNQ
```

FIGURE 2W

```
601 SQVNHTILQY YRCMASELVR VNITPVVALW QPMAPNQGLP RLLARQGAWE
651 NPYTALAFAE YARLCFQELG HHVKLWITMN EPYTRNMTYS AGHNLLKAHA
701 LAWHVYNEKF RHAQNGKIST ALQADWIEPA CPFSQKDKFV AERVLEFDIG
751 WLAEPIFGSG DYPWVMRDWL NQRNNFLLPY FTEDEKKLIQ GTFDFLALSH
801 YTTILVDSEK EDPIKYNDYL EVQEMTDITW LNSPSQVAVV PWGLRKVLNW
851 LKFKYGDLPM YIISNGIDDG LHAEDDQLRV YYMQNYINEA LKAHILDGIN
901 LCGYFAYSFN DRTAPRFGLY RYAADQFEPK ASMKHYRKII DSNGFPGPET
951 LERFCPEEFT VCTECSFFHT RKSL*
``` sKlotho-FGF23-FcLALA v1 (SEQ ID NO: 46)

```
   1 ATGCCCGCCA GCGCCCCGCC GCGCCGCCCG CGGCCGCCGC CGCCGTCGCT
     GTCGCTGCTG
  61 CTGGTGCTGC TGGGCCTGGG CGGCCGCCGC CTGCGTGCGG AGCCGGGCGA
     CGGCGCGCAG
 121 ACCTGGGCCC GTTTCTCGCG GCCTCCTGCC CCGAGGCCG CGGGCCTCTT
     CCAGGGCACC
 181 TTCCCCGACG GCTTCCTCTG GGCCGTGGGC AGCGCCGCCT ACCAGACCGA
     GGGCGGCTGG
 241 CAGCAGCACG GCAAGGGTGC GTCCATCTGG GATACGTTCA CCCACCACCC
     CCTGGCACCC
 301 CCGGGAGACT CCCGGAACGC CAGTCTGCCG TTGGCGCCC CGTCGCCGCT
     GCAGCCCGCC
 361 ACCGGGGACG TAGCCAGCGA CAGCTACAAC AACGTCTTCC GCGACACGGA
     GGCGCTGCGC
 421 GAGCTCGGGG TCACTCACTA CCGCTTCTCC ATCTCGTGGG CGCGAGTGCT
     CCCCAATGGC
 481 AGCGCGGGCG TCCCCAACCG CGAGGGGCTG CGCTACTACC GCGCCTGCT
     GGAGCGGCTG
 541 CGGGAGCTGG GCGTGCAGCC CGTGGTCACC CTGTACCACT GGGACCTGCC
     CCAGCGCCTG
 601 CAGGACGCCT ACGGCGGCTG GGCCAACCGC GCCCTGGCCG ACCACTTCAG
     GGATTACGCG
 661 GAGCTCTGCT TCCGCCACTT CGGCGGTCAG GTCAAGTACT GGATCACCAT
     CGACAACCCC
 721 TACGTGGTGG CCTGGCACGG CTACGCCACC GGGCGCCTGG CCCCCGGCAT
     CCGGGGCAGC
 781 CCGCGGCTCG GGTACCTGGT GGCGCACAAC CTCCTCCTGG CTCATGCCAA
     AGTCTGGCAT
 841 CTCTACAATA CTTCTTTCCG TCCCACTCAG GGAGGTCAGG TGTCCATTGC
     CCTAAGCTCT
 901 CACTGGATCA ATCCTCGAAG AATGACCGAC CACAGCATCA AGAATGTCA
     AAAATCTCTG
 961 GACTTTGTAC TAGGTTGGTT TGCCAAACCC GTATTTATTG ATGGTGACTA
     TCCCGAGAGC
1021 ATGAAGAATA ACCTTTCATC TATTCTGCCT GATTTACTG AATCTGAGAA
     AAAGTTCATC
1081 AAAGGAACTG CTGACTTTTT TGCTCTTTGC TTTGGACCCA CCTTGAGTTT
     CAACTTTTG
1141 CACCCTCACA TGAAGTTCCC CCAATTGGAA TCTCCCAACC TCAGCCAACT
     GCTTTCCTGG
1201 ATTGACCTTG AATTTAACCA TCCTCAAATA TTATTGTGG AAAATGGCTG
     GTTTGTCTCA
```

FIGURE 2X

```
1261 GGGACCACCA AGAGAGATGA TGCCAAATAT ATGTATTACC TCAAAAAGTT
     CATCATGGAA
1321 ACCTTAAAAG CCATCAAGCT GGATGGGGTG GATGTCATCG GGTATACCGC
     ATGGTCCCTC
1381 ATGGATGGTT TCGAGTGGCA CAGAGGTTAC AGCATCAGGC GTGGACTCTT
     CTATGTTGAC
1441 TTTCTAAGCC AGGACAAGAT GTTGTTGCCA AAGTCTTCAG CCTTGTTCTA
     CCAAAAGCTG
1501 ATAGAGAAAA ATGGCTTCCC TCCTTTACCT GAAAATCAGC CCCTAGAAGG
     GACATTTCCC
1561 TGTGACTTTG CTTGGGGAGT TGTTGACAAC TACATTCAAG TAGATACCAC
     TCTGTCTCAG
1621 TTTACCGACC TGAATGTTTA CCTGTGGGAT GTCCACCACA GTAAAAGGCT
     TATTAAAGTG
1681 GATGGGGTTG TGACCAAGAA GAGGAAATCC TACTGTGTTG ACTTTGCTGC
     CATCCAGCCC
1741 CAGATCGCTT TACTCCAGGA AATGCACGTT ACACATTTTC GCTTCTCCCT
     GGACTGGGCC
1801 CTGATTCTCC CTCTGGGTAA CCAGTCCCAG GTGAACCACA CCATCCTGCA
     GTACTATCGC
1861 TGCATGGCCA GCGAGCTTGT CCGTGTCAAC ATCACCCCAG TGGTGGCCCT
     GTGGCAGCCT
1921 ATGGCCCCGA ACCAAGGACT GCCGCGCCTC CTGGCCAGGC AGGGCGCCTG
     GGAGAACCCC
1981 TACACTGCCC TGGCCTTTGC AGAGTATGCC CGACTGTGCT TCAAGAGCT
     CGGCCATCAC
2041 GTCAAGCTTT GGATAACGAT GAATGAGCCG TATACAAGGA ATATGACATA
     CAGTGCTGGC
2101 CACAACCTTC TGAACGCCCA TGCCCTGCCT TGCCATCTCT ACAATCAAAA
     GTTTAGGCAT
2161 GCTCAGAATG GGAAAATATC CATAGCCTTG CAGGCTGATT GGATAGAACC
     TGCCTGCCCT
2221 TTCTCCCAAA AGGACAAAGA GGTGGCCGAG AGAGTTTTGG AATTTGACAT
     TGGCTGGCTG
2281 GCTGAGCCCA TTTTCGGCTC TGGAGATTAT CCATGGGTGA TGAGGGACTG
     GCTGAACCAA
2341 AGAAACAATT TTCTTCTTCC TTATTTCACT GAAGATGAAA AAAAGCTAAT
     CCAGGGTACC
2401 TTTGACTTTT TGGCTTTAAG CCATTATACC ACCATCCTTG TAGACTCAGA
     AAAAGAAGAT
2461 CCAATAAAAT ACAATGATTA CCTAGAAGTG CAAGAAATGA CCGACATCAC
     GTGGCTCAAC
2521 TCCCCCAGTC AGGTGGCGGT AGTGCCCTGG GGGTTGCGCA AGTGCTGAA
     CTGGCTGAAG
2581 TTCAAGTACG GAGACCTCCC CATGTACATA ATATCCAACG GAATCGATGA
     CGGGCTGCAT
2641 GCTGAGGACG ACCAGCTGAG GGTGTATTAT ATGCAGAATT ACATAAACGA
     AGCTCTCAAA
2701 GCCCACATAC TGGATGGTAT CAATCTTTGC GGATACTTTG CTTATTCGTT
     TAACGACCGC
2761 ACAGCTCCGA GGTTTGGCCT CTATCGTTAT GCTGCAGATC AGTTTGAGCC
     CAAGGCATCC
2821 ATGAAACATT ACAGGAAAAT TATTGACAGC AATGGTTTCC CGGGCCCAGA
     AACTCTGGAA
2881 AGATTTTGTC CAGAAGAATT CACCGTGTGT ACTGAGTGCA GTTTTTTTCA
     CACCCGAAAG
```

FIGURE 2Y

```
2941 TCTTTAGGAT CCGGAGGTGG AGGTTCAGGA GGTGGAGGTT CAGGAGGTGG
     AGGTTCACTT
3001 AAGTATCCCA ATGCCTCCCC ACTGCTCGGC TCCAGCTGGG GTGGCCTGAT
     CCACCTGTAC
3061 ACAGCCACAG CCAGGAACAG CTACCACCTG CAGATCCACA AGAATGGCCA
     TGTGGATGGC
3121 GCACCCCATC AGACCATCTA CAGTGCCCTG ATGATCAGAT CAGAGGATGC
     TGGCTTTGTG
3181 GTGATTACAG GTGTGATGAG CAGAAGATAC CTCTGCATGG ATTTCAGAGG
     CAACATTTTT
3241 GGATCACACT ATTTCGACCC GGAGAACTGC AGGTTCCAAC ACCAGACGCT
     GGAAAACGGG
3301 TACGACGTCT ACCACTCTCC TCAGTATCAC TTCCTGGTCA GTCTGGGCCG
     GCGAAGAGA
3361 GCCTTCCTGC CAGGCATGAA CCCACCCCCG TACTCCCAGT TCCTGTCCCG
     GAGGAACGAG
3421 ATCCCCCTAA TTCACTTCAA CACCCCCATA CCACGGCGGC ACACCCAGAG
     CGCCGAGGAC
3481 GACTCGGAGC GGGACCCCCT GAACGTGCTG AAGCCCCGGG CCCGGATGAC
     CCCGGCCCCG
3541 GCCTCCTGTT CACAGGAGCT CCCGAGCGCC GAGGACAACA GCCCGATGGC
     CAGTGACCCA
3601 TTAGGGGTGG TCAGGGGCGG TCGAGTGAAC ACGCACGCTG GGGGAACGGG
     CCCGGAAGGC
3661 TGCCGCCCCT TCGCCAAGTT CATCGGAGGT GGAGGTTCAA AAACCCACAC
     GTGTCCTCCT
3721 TGTCCTGCCC CAGAAGCAGC AGGTGGTCCA TCAGTTTTTC TTTTCCCTCC
     CAAACCCAAG
3781 GATACGCTGA TGATCTCTCG CACGCCTGAG GTGACATGCG TCGTAGTAGA
     CGTGAGCCAC
3841 GAAGATCCCG AGGTGAAGTT CAATTGGTAT GTGGACGGAG TAGAAGTGCA
     TAACGCGAAA
3901 ACTAAGCCGC GCGAGGAACA ATATAACAGT ACTTACAGGG TGGTATCCGT
     GCTCACAGTC
3961 CTGCACCAGG ACTGGCTGAA CGGTAAGGAA TACAAGTGCA AAGTAAGCAA
     CAAGGCACTT
4021 CCCGCGCCTA TTGAGAAAAC AATCTCCAAG GCGAAGGGAC AACCAAGAGA
     ACCTCAGGTT
4081 TACACTCTCC CGCCTTCCAG GGAAGAGATG ACCAAAAATC AAGTTTCCCT
     GACTTGCCTC
4141 GTCAAAGGAT TCTACCCTTC CGACATTGCT GTTGAATGGG AAAGCAATGG
     ACAACCAGAG
4201 AACAACTACA AGACAACACC CCCGGTGCTG GATAGTGACG GATCTTTCTT
     TCTCTACTCA
4261 AAGCTGACCG TGGATAAGTC CAGGTGGCAG CAGGGAAACG TGTTTTCCTG
     CTCTGTCATG
4321 CATGAAGCGC TGCATAATCA CTATACCCAG AAGTCTCTGA GCTTGAGCCC
     AGGCAAGTAA
``` sKlotho-FGF23-FcLALA v1 (SEQ ID NO: 47)

```
  1 MPASAPPRRP RPPPPSLSLL LVLLGLGGRR LRAEPGDGAQ TWARFSRPPA
 51 PEAAGLFQGT FPDGFLWAVG SAAYQTEGGW QQHGKGASIW DTFTHHPLAP
101 PGDSRNASLP LGAPSPLQPA TGDVASDSYN NVFRDTEALR ELGVTHYRFS
151 ISWARVLPNG SAGVPNREGL RYYRRLLERL RELGVQPVVT LYHWDLPQRL
```

FIGURE 2Z

```
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGTFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFTVC TECSFFHTRK SLGSGGGGSG GGCSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN THAGGTGPEG CRPFAKFIGG GGSKTHTCPP CPAPEAAGGP
1251 SVFLFPPKPK DTLMISRTPE VTCVVVDVSH EDPEVKFNWY VDGVEVHNAK
1301 TKPREEQYNS TYRVVSVLTV LHQDWLNGKE YKCKVSNKAL PAPIEKTISK
1351 AKGQPREPQV YTLPPSREEM TKNQVSLTCL VKGFYPSDIA VEWESNGQPE
1401 NNYKTTPPVL DSDGSFFLYS KLTVDKSRWQ QGNVFSCSVM HEALHNHYTQ
1451 KSLSLSPGK*
``` sKlotho-FGF23-FcLALA v2 (SEQ ID NO: 48)

```
   1 ATGCCCGCCA GCGCCCCGCC GCGCCGCCCG CGGCCGCCGC CGCCGTCGCT
     GTCGCTGCTG
  61 CTGGTGCTGC TGGGCCTGGG CGGCCGCCGC CTGCGTGCGG AGCCGGGCGA
     CGGCGCGCAG
 121 ACCTGGGCCC GTTTCTCGCG GCCTCCTGCC CCCGAGGCCG CGGGCCTCTT
     CCAGGGCACC
 181 TTCCCCGACG GCTTCCTCTG GGCCGTGGGC AGCGCCGCCT ACCAGACCGA
     GGGCGGCTGG
 241 CAGCAGCACG GCAAGGGTGC GTCCATCTGG GATACGTTCA CCCACCACCC
     CCTGGCACCC
 301 CCGGGAGACT CCCGGAACGC CAGTCTGCCG TTGGGCGCCC CGTCGCCGCT
     GCAGCCCGCC
 361 ACCGGGGACG TAGCCAGCGA CAGCTACAAC AACGTCTTCC GCGACACGGA
     GGCGCTGCGC
 421 GAGCTCGGGG TCACTCACTA CCGCTTCTCC ATCTCGTGGG CGCGAGTGCT
     CCCCAATGGC
 481 AGCCCCGCCC TCCCCAACCG CGACGGCCTG CCCTACTACC GCCCCCTGCT
     GGAGCGGCTG
 541 CGGGAGCTGG GCGTGCAGCC CGTGGTCACC CTGTACCACT GGGACCTGCC
     CCAGCGCCTG
 601 CAGGACGCCT ACGGCGGCTG GGCCAACCGC GCCCTGGCCG ACCACTTCAG
     GGATTACGCG
 661 GAGCTCTGCT TCCGCCACTT CGGCGGTCAG GTCAAGTACT GGATCACCAT
     CGACAACCCC
 721 TACGTGGTGG CCTGGCACGG CTACGCCACC GGGCGCCTGG CCCCCGGCAT
     CCGGGGCAGC
```

Figure 2Z - a

```
 731 CCGCGGCTCG GGTACCTGGT GGCGCACAAC CTCCTCCTGG CTCATGCCAA
     AGTCTGGCAT
 841 CTCTACAATA CTTCTTTCCG TCCCACTCAG GGAGGTCAGG TGTCCATTGC
     CCTAAGCTCT
 901 CACTGGATCA ATCCTCGAAG AATGACCGAC CACAGCATCA AGAATGTCA
     AAAATCTCTG
 961 GACTTTGTAC TAGGTTGGTT TGCCAAACCC GTATTTATTG ATGGTGACTA
     TCCCGAGAGC
1021 ATGAAGAATA ACCTTTCATC TATTCTGCCT GATTTTACTG AATCTGAGAA
     AAAGTTCATC
1081 AAAGGAACTG CTGACTTTTT TGCTCTTTGC TTTGGACCCA CCTTGAGTTT
     TCAACTTTTG
1141 GACCCTCACA TGAAGTTCCG CCAATTGGAA TCTCCCAACC TGAGGCAACT
     GCTTTCCTGG
1201 ATTGACCTTG AATTTAACCA TCCTCAAATA TTTATTGTGG AAAATGGCTG
     GTTTGTCTCA
1261 GGGACCACCA AGAGAGATGA TGCCAAATAT ATGTATTACC TCAAAAAGTT
     CATCATGGAA
1321 ACCTTAAAAG CCATCAAGCT GGATGGGGTG GATGTCATCG GGTATACCGC
     ATGGTCCCTC
1331 ATGGATGGTT TCGAGTGGCA CAGAGGTTAC AGCATCAGGC GTGGACTCTT
     CTATGTTGAC
1441 TTTCTAAGCC AGGACAAGAT GTTGTTGCCA AAGTCTTCAG CCTTGTTCTA
     CCAAAAGCTG
1501 ATAGAGAAAA ATGGCTTCCC TCCTTTACCT GAAAATCAGC CCCTAGAAGG
     GACATTTCCC
1561 TGTGACTTTG CTTGGGGAGT TGTTGACAAC TACATTCAAG TAGATACCAC
     TCTGTCTCAG
1621 TTTACCGACC TGAATGTTTA CCTGTGGGAT GTCCACCACA GTAAAAGGCT
     TATTAAAGTG
1631 GATGGGGTTG TGACCAAGAA GAGGAAATCC TACTGTGTTG ACTTTGCTGC
     CATCCAGCCC
1741 CAGATCGCTT TACTCCAGGA AATGCACGTT ACACATTTTC GCTTCTCCCT
     GGACTGGGCC
1801 CTGATTCTCC CTCTGGGTAA CCAGTCCCAG GTGAACCACA CCATCCTGCA
     GTACTATCGC
1861 TGCATGGCCA GCGAGCTTGT CCGTGTCAAC ATCACCCCAG TGGTGGCCCT
     GTGGCAGCCT
1921 ATGGCCCCGA ACCAAGGACT GCCGCGCCTC CTGGCCAGGC AGGGCGCCTG
     GGAGAACCCC
1981 TACACTGCCC TGGCCTTTGC AGAGTATGCC CGACTGTGCT TTCAAGAGCT
     CGGCCATCAC
2041 GTCAAGCTTT GGATAACGAT GAATGAGCCG TATACAAGGA ATATGACATA
     CAGTGCTGGC
2101 CACAACCTTC TGAAGGCCCA TGCCCTGGCT TGGCATGTGT ACAATGAAAA
     GTTTAGGCAT
2161 GCTCAGAATG GGAAAATATC CATAGCCTTG CAGGCTGATT GGATAGAACC
     TGCCTGCCCT
2221 TTCTCCCAAA AGGACAAAGA GGTGGCCGAG AGAGTTTTGG AATTTGACAT
     TGGCTGGCTG
2231 GCTGAGCCCA TTTTCGGCTC TGGAGATTAT CCATGGGTGA TGAGGGACTG
     GCTGAACCAA
2341 AGAAACAATT TTCTTCTTCC TTATTTCACT GAAGATGAAA AAAAGCTAAT
     CCAGCCTACC
2401 TTTGACTTTT TGGCTTTAAG CCATTATACC ACCATCCTTG TAGACTCAGA
     AAAAGAAGAT
```

FIGURE 2Z - b

```
2461 CCAATAAAAT ACAATGATTA CCTAGAAGTG CAAGAAATGA CCGACATCAC
     GTGGCTCAAC
2521 TCCCCCAGTC AGGTGGCGGT AGTGCCCTGG GGGTTGCGCA AAGTGCTGAA
     CTGGCTGAAG
2581 TTCAAGTACG GAGACCTCCC CATGTACATA ATATCCAACG GAATCGATGA
     CGGGCTGCAT
2641 GCTGAGGACG ACCAGCTGAG GGTGTATTAT ATGCAGAATT ACATAAACGA
     AGCTCTCAAA
2701 GCCCACATAC TGGATGGTAT CAATCTTTGC GGATACTTTG CTTATTCGTT
     TAACGACCGC
2761 ACAGCTCCGA GGTTTGGCCT CTATCGTTAT GCTGCAGATC AGTTTGAGCC
     CAAGGCATCC
2821 ATGAAACATT ACAGGAAAAT TATTGACAGC AATGGTTTCC CGGGCCCAGA
     AACTCTGGAA
2881 AGATTTTGTC CAGAAGAATT CACCGTGTGT ACTGAGTGCA GTTTTTTTCA
     CACCCGAAAG
2941 TCTTTAGGAT CCGGAGGTGG AGGTTCAGGA GGTGGAGGTT CAGGAGGTGG
     AGGTTCACTT
3001 AAGTATCCCA ATGCCTCCCC ACTGCTCGGC TCCAGCTGGG GTGGCCTGAT
     CCACCTGTAC
3061 ACAGCCACAG CCAGGAACAG CTACCACCTG CAGATCCACA AGAATGGCCA
     TGTGGATGGC
3121 GCACCCCATC AGACCATCTA CAGTGCCCTG ATGATCAGAT CAGAGGATGC
     TGGCTTTGTG
3181 GTGATTACAG GTGTGATGAG CAGAAGATAC CTCTGCATGG ATTTCAGAGG
     CAACATTTTT
3241 GGATCACACT ATTTCGACCC GGAGAACTGC AGGTTCCAAC ACCAGACGCT
     GGAAAACGGG
3301 TACGACGTCT ACCACTCTCC TCAGTATCAC TTCCTGGTCA GTCTGGGCCG
     GGCGTTGAGA
3361 GCC CTGC CAGGCATGAA CCCACCCCCG TACTCCCAGT TCCTGTCCCG
     GAGG  CGAG
3421 ATCCCCCTAA TTCACTTCAA CACCCCCATA CCACGGCGGC ACACCCAGAG
     CGCCGAGGAC
3481 GACTCGGAGC GGGACCCCCT GAACGTGCTG AAGCCCCGGG CCCGGATGAC
     CCCGGCCCCG
3541 GCCTCCTGTT CACAGGAGCT CCCGAGCGCC GAGGACAACA GCCCGATGGC
     CAGTGACCCA
3601 TTAGGGGTGG TCAGGGGCGG TCGAGTGAAC ACGCACGCTG GGGAACGGG
     CCCGGAAGGC
3661 TGCCGCCCCT TCGCCAAGTT CATCGGAGGT GGAGGTTCAG CCCCAGAAGC
     AGCAGGTGGT
3721 CCATCAGTTT TTCTTTTCCC TCCCAAACCC AAGGATACGC TGATGATCTC
     TCGCACGCCT
3781 GAGGTGACAT GCGTCGTAGT AGACGTGAGC CACGAAGATC CCGAGGTGAA
     GTTCAATTGG
3841 TATGTGGACG GAGTAGAAGT GCATAACGCG AAAACTAAGC CGCGCGAGGA
     ACAATATAAC
3901 AGTACTTACA GGGTGGTATC CGTGCTCACA GTCCTGCACC AGGACTGGCT
     GAACGGTAAG
3961 GAATACAAGT GCAAAGTAAG CAACAAGGCA CTTCCCGCGC CTATTGAGAA
     AACAATCTCC
4021 AAGGCAAGG GACAACCAAG AGAACCTCAG GTTTACACTC TCCCGCCTTC
     CAGGGAAGAG
4081 ATGACCAAAA ATCAAGTTTC CCTGACTTGC CTCGTCAAAG GATTCTACCC
     TTCCGACATT
```

FIGURE 2Z - c

```
4141 GCTGTTGAAT GGGAAAGCAA TGGACAACCA GAGAACAACT ACAAGACAAC
     ACCCCCGGTG
4201 CTGGATAGTG ACGGATCTTT CTTTCTCTAC TCAAAGCTGA CCGTGGATAA
     GTCCAGGTGG
4261 CAGCAGGGAA ACGTGTTTTC CTGCTCTGTC ATGCATGAAG CGCTGCATAA
     TCACTATACC
4321 CAGAAGTCTC TGAGCTTGAG CCCAGGCAAG TAA
``` sKlotho-FGF23-FcLALA v2 (SEQ ID NO: 49)

```
   1 MPASAPPRRP RPPPPSLSLL LVLLGLGGRR LRAEPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGTRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVTGYTAWSL MDGFEWHRGY STRRGLFYVD FLSQDKMLLP KSSALFYQKL
 501 IEKNGFPPLP ENQPLEGTFP CDFAWGVVDN YIQVDTTLSQ FTDLNVYLWD
 551 VHHSKRLIKV DGVVTKKRKS YCVDFAATQR QTALLQFMHV THFREFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFTVC TECSFFHTRK SLGSGGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN THAGGTGPEG CRPFAKFIGG GGSAPEAAGG PSVFLFPPKP
1251 KDTLMISRTP EVTCVVVDVS HEDPEVKFNW YVDGVEVHNA KTKPREEQYN
1301 STYRVVSVLT VLHQDWLNGK EYKCKVSNKA LPAPIEKTIS KAKGQPREPQ
1351 VYTLPPSREE MTKNQVSLTC LVKGFYPSDI AVEWESNGQP ENNYKTTPPV
1401 LDSDGSFFLY SKLTVDKSRW QQGNVFSCSV MHEALHNHYT QKSLSLSPGK
1451 *
```

FGF23-FcLALA v1 (SEQ ID NO: 50)

```
   1 ATGTTGCCCC CCCGCCTCAG CCTCTGGGTC TGTCCCTTGT CCACCGTCTG
     CAGCATGAGC
  61 GTCCTCACAG CCTATCCCAA TGCCTCCCCA CTCCTCGGCT CCACCTGGGG
     TGGCCTGATC
 121 CACCTGTACA CAGCCACAGC CAGGAACAGC TACCACCTGC AGATCCACAA
     GAATGGCCAT
 181 GTGGATGGCG CACCCCATCA GACCATCTAC AGTGCCCTGA TGATCAGATC
     AGAGGATGCT
 241 GGCTTTGTGG TGATTACAGG TGTGATGAGC AGAAGATACC TCTGCATGGA
     TTTCAGAGGC
```

FIGURE 2Z - d

```
 301 AACATTTTTG GATCACACTA TTTCGACCCG GAGAACTGCA GGTTCCAACA
     CCAGACGCTG
 361 GAAAACGGGT ACGACGTCTA CCACTCTCCT CAGTATCACT TCCTGGTCAG
     TCTGGGCCGG
 421 GCGAAGAGAG CCTTCCTGCC AGGCATGAAC CCACCCCCGT ACTCCCAGTT
     CCTGTCCCGG
 481 AGGAACGAGA TCCCCCTAAT TCACTTCAAC ACCCCCATAC ACGGCGGCA
     CACCCAGAGC
 541 GCCGAGGACG ACTCGGAGCG GGACCCCCTG AACGTGCTGA AGCCCCGGGC
     CCGGATGACC
 601 CCGGCCCCGG CCTCCTGTTC ACAGGAGCTC CCGAGCGCCG AGGACAACAG
     CCCGATGGCC
 661 AGTGACCCAT TAGGGGTGGT CAGGGGCGGT CGAGTGAACA CGCACGCTGG
     GGGAACGGGC
 721 CCGGAAGCCT GCCGCCCCTT CCCCAAGTTC ATCGGACCTG GAGGTTCAAA
     AACCCACACG
 781 TGTCCTCCTT GTCCTGCCCC AGAAGCAGCA GGTGGTCCAT CAGTTTTTCT
     TTTCCCTCCC
 841 AAACCCAAGG ATACGCTGAT GATCTCTCGC ACGCCTGAGG TGACATGCGT
     CGTAGTAGAC
 901 GTGAGCCACG AAGATCCCGA GGTGAAGTTC AATTGGTATG TGGACGGAGT
     AGAAGTGCAT
 961 AACGCGAAAA CTAAGCCGCG CGAGGAACAA TATAACAGTA CTTACAGGGT
     GGTATCCGTG
1021 CTCACAGTCC TGCACCAGGA CTGGCTGAAC GGTAAGGAAT ACAAGTGCAA
     AGTAAGCAAC
1081 AAGGCACTTC CCGCGCCTAT TGAGAAAACA ATCTCCAAGG CGAAGGGACA
     ACCAAGAGAA
1141 CCTCAGGTTT ACACTCTCCC GCCTTCCAGG GAAGAGATGA CCAAAAATCA
     AGTTTCCCTG
1201 ACTTGCCTCG TCAAAGGATT CTACCCTTCC GACATTGCTG TTGAATGGGA
     AAGCAATGGA
1261 CAACCAGAGA ACAACTACAA GACAACACCC CGGTGCTGG ATAGTGACGG
     ATCTTTCTTT
1321 CTCTACTCAA AGCTGACCGT GGATAAGTCC AGTGGCAGC AGGGAAACGT
     GTTTTCCTGC
1381 TCTGTCATGC ATGAAGCGCT GCATAATCAC TATACCCAGA AGTCTCTGAG
     CTTGAGCCCA
1441 GGCAAGTAA
```

FGF23(R179Q)-FcLALAv1 (SEQ ID NO: 51)

```
  1 MLGARLRLWV CALCSVCSMS VLRAYPNASP LLGSSWGGLI HLYTATARNS
 51 YHLQIHKNGH VDGAPHQTIY SALMIRSEDA GFVVITGVMS RRYLCMDFRG
101 NIFGSHYFDP ENCRFQHQTL ENGYDVYHSP QYHFLVSLGR AKRAFLPGMN
151 PPPYSQFLSR RNEIPLIHFN TPIPRRHTQS AEDDSERDPL NVLKPRARMT
201 PAPASCSQEL PSAEDNSPMA SDPLGVVRGG RVNTHAGGTG PEGCRPFAKF
251 IGGGGSKTHT CPPCPAPEAA GGPSVFLFPP KPKDTLMISR TPEVTCVVVD
301 VSHEDPEVKF NWYVDGVEVH NAKTKPREEQ YNSTYRVVSV LTVLHQDWLN
351 GKEYKCKVSN KALPAPIEKT ISKAKGQPRE PQVYTLPPSR EEMTKNQVSL
401 TCLVKGFYPS DIAVEWESNG QPENNYKTTP PVLDSDGSFF LYSKLTVDKS
451 RWQQGNVFSC SVMHEALHNH YTQKSLSLSP GK*
```

FGF23-FcLALA v2 (SEQ ID NO: 52)

FIGURE 2Z - e

```
   1 ATGTTGGGGG CCCGCCTCAG GCTCTGGGTC TGTGCCTTGT GCAGCGTCTG
     CAGCATGAGC
  61 GTCCTCAGAG CCTATCCCAA TGCCTCCCCA CTGCTCGGCT CCAGCTGGGG
     TGGCCTGATC
 121 CACCTGTACA CAGCCACAGC CAGGAACAGC TACCACCTGC AGATCCACAA
     GAATGGCCAT
 181 GTGGATGGCG CACCCCATCA GACCATCTAC AGTGCCCTGA TGATCAGATC
     AGAGGATGCT
 241 GGCTTTGTGG TGATTACAGG TGTGATGAGC AGAAGATACC TCTGCATGGA
     TTTCAGAGGC
 301 AACATTTTTG GATCACACTA TTTCGACCCG GAGAACTGCA GGTTCCAACA
     CCAGACGCTG
 361 GAAAACGGGT ACGACGTCTA CCACTCTCCT CAGTATCACT TCCTGGTCAG
     TCTGGGCCGG
 421 GCGAAGAGAG CCTTCCTGCC AGGCATGAAC CCACCCCCGT ACTCCCAGTT
     CCTGTCCCGG
 481 AGGAACGAGA TCCCCCTAAT TCACTTCAAC ACCCCCATAC ACGGCGGCA
     CACCCAGAGC
 541 GCCGAGGACG ACTCGGAGCG GGACCCCCTG AACGTGCTGA AGCCCCGGGC
     CCGGATGACC
 601 CCGGCCCCGG CCTCCTGTTC ACAGGAGCTC CCGAGCGCCG AGGACAACAG
     CCCGATGGCC
 661 AGTGACCCAT TAGGGGTGGT CAGGGGCGGT CGAGTGAACA CGCACGCTGG
     GGGAACGGGC
 721 CCGGAAGGCT GCCGCCCCTT CGCCAAGTTC ATCGGAGGTG GAGGTTCAGC
     CCCAGAAGCA
 781 GCAGGTGGTC CATCAGTTTT CTTTTTCCCT CCCAAACCCA AGGATACGCT
     GATGATCTCT
 841 CGCACGCCTG AGGTGACATG CGTCGTAGTA GACGTGAGCC ACGAAGATCC
     CGAGGTGAAG
 901 TTCAATTGGT ATGTGGACGG AGTAGAAGTG CATAACGCGA AAACTAAGCC
     GCGCGAGGAA
 961 CAATATAACA GTACTTACAG GGTGGTATCC GTGCTCACAG TCCTGCACCA
     GGACTGGCTG
1021 AACGGTAAGG AATACAAGTG CAAAGTAAGC AACAAGGCAC TTCCCGCGCC
     TATTGAGAAA
1081 ACAATCTCCA AGGCGAAGGG ACAACCAAGA GAACCTCAGG TTTACACTCT
     CCCGCCTTCC
1141 AGGGAAGAGA TGACCAAAAA TCAAGTTTCC CTGACTTGCC TCGTCAAAGG
     ATTCTACCCT
1201 TCCGACATTG CTGTTGAATG GGAAAGCAAT GGACAACCAG AGAACAACTA
     CAAGACAACA
1261 CCCCCGGTGC TGGATAGTGA CGGATCTTTC TTTCTCTACT CAAAGCTGAC
     CGTGGATAAG
1321 TCCAGGTGGC AGCAGGGAAA CGTGTTTTCC TGCTCTGTCA TGCATGAAGC
     GCTGCATAAT
1381 CACTATACCC AGAAGTCTCT GAGCTTGAGC CCAGGCAAGT AA
```

FGF23(R179Q)-FcLALAv2 (SEQ ID NO: 53)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRITQS AEDDSERDPL NVLKPRARMT
 201 PAPASCSQEL PSAEDNSPMA SDPLGVVRGG RVNTHAGGTG PEGCRPFAKF
```

FIGURE 2Z - f

```
251 IGGGGSAPEA AGGPSVFLFP PKPKDTLMIS RTPEVTCVVV DVSHEDPEVK
301 FNWYVDGVEV HNAKTKPREE QYNSTYRVVS VLTVLHQDWL NGKEYKCKVS
351 NKALPAPIEK TISKAKGQPR EPQVYTLPPS REEMTKNQVS LTCLVKGFYP
401 SDIAVEWESN GQPENNYKTT PPVLDSDGSF FLYSKLTVDK SRWQQGNVFS
451 CSVMHEALHN HYTQKSLSLS PGK*
``` lane 1, Ctrl; lane 2, FGF23; lane 3, sKlotho; lanes 4-6, sKlotho-FGF23 lane 1, Ctrl; lane 2, FGF23; lane 3, sKlotho; lanes 4-6, sKlotho-FGF23 lane 1, purified sKlotho-FGF23-6xHis; lane 2, molecular weight marker

SEQUENCE LISTING

<160> NUMBER OF SEQ ID NOS: 53

<210> SEQ ID NO 1
<211> LENGTH: 5003
<212> TYPE: DNA
<213> ORGANISM: Homo sapiens

<400> SEQUENCE: 1

```
cgcgcagcat gcccgccagc gccccgccgc ccgcccgcg gccgccgccg ccgtcgctgt     60
cgctgctgct ggtgctgctg ggcctgggcg gcgccgcct gctgtgcggag ccgggcgacg    120 gcgcgcagac ctgggcccgt tctcgcggc ctcctgcccc cgaggccgcg ggcctcttcc    180
agggcacctt ccccgacggc ttcctctggg ccgtgggcag cgccgcctac cagaccgagg    240
gcggctggca gcagcacggc aagggtgcgt ccatctggga tacgttcacc caccaccccc    300
tggcaccccc gggagactcc cggaacgcca gtctgccgtt gggcgccccg tcgccgctgc    360
agcccgccac cggggacgta gccagcgaca gctacaacaa cgtcttccgc gacacggagg    420
cgctgcgcga gctcggggtc actcactacc gcttctccat ctcgtgggcg cgagtgctcc    480
ccaatggcag cgcgggcgtc cccaaccgcg aggggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac acttcaggg    660 attacgcgga gctctgcttc cgccacttcg gcggtcaggt caagtactgg atcaccatcg    720
acaaccccta cgtggtggcc tggcacgct acgccaccgg gcgcctggcc ccggcatcc    780 ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggtttg ccaaacccgt atttattgat ggtgactatc   1020
ccgagagcat gaagaataac ctttcatcta ttctgcctga ttttactgaa tctgagaaaa   1080
agttcatcaa ggaactgct gactttttg ctctttgctt tggacccacc ttgagttttc   1140
aacttttgga ccctcacatg aagttccgcc aattggaatc tcccaacctg aggcaactgc   1200 ttcctggat tgaccttgaa tttaaccatc tcaaatatt tattgtgaa atggctggt   1260 ttgtctcagg gaccaccaag agagatgatg ccaaatatat gtattacctc aaaaagttca   1320
```

```
tcatggaaac cttaaaagcc atcaagctgg atggggtgga tgtcatcggg tataccgcat    1380
ggtccctcat ggatggtttc gagtggcaca gaggttacag catcaggcgt ggactcttct    1440
atgttgactt tctaagccag acaagatgt tgttgccaaa gtcttcagcc ttgttctacc     1500
aaaagctgat agagaaaaat ggcttccctc ctttacctga aaatcagccc ctagaaggga    1560
catttccctg tgactttgct tggggagttg ttgacaacta cattcaagta gataccactc    1620
tgtctcagtt taccgacctg aatgtttacc tgtgggatgt ccaccacagt aaaaggctta    1680
ttaaagtgga tggggttgtg accaagaaga ggaaatccta ctgtgttgac tttgctgcca    1740
tccagcccca gatcgcttta ctccaggaaa tgcacgttac acattttcgc ttctccctgg    1800
actgggccct gattctccct ctgggtaacc agtcccaggt gaaccacacc atcctgcagt    1860
actatcgctg catggccagc gagcttgtcc gtgtcaacat cacccagtg gtggccctgt    1920 ggcagcctat ggccccgaac caaggactgc cgcgcctcct ggccaggcag ggcgcctggg    1980
agaaccccta cactgccctg cctttgcag agtatgcccg actgtgcttt caagagctcg     2040
gccatcacgt caagctttgg ataacgatga atgagccgta tacaaggaat atgacataca    2100
gtgctggcca caaccttctg aaggcccatg ccctggcttg gcatgtgtac aatgaaaagt    2160
ttaggcatgc tcagaatggg aaaatatcca tagccttgca ggctgattgg atagaacctg    2220
cctgcccttt ctcccaaaag gacaaagagg tggccgagag agttttggaa tttgacattg    2280
gctggctggc tgagcccatt tcggctctg gagattatcc atgggtgatg agggactggc     2340
tgaaccaaag aaacaatttt cttcttcctt atttcactga agatgaaaaa aagctaatcc    2400
agggtacctt tgactttttg gctttaagcc attataccac catccttgta gactcagaaa    2460
aagaagatcc aataaaatac aatgattacc tagaagtgca agaaatgacc gacatcacgt    2520
ggctcaactc ccccagtcag gtggcggtag tgccctgggg gttgcgcaaa gtgctgaact    2580
ggctgaagtt caagtacgga gacctcccca tgtacataat atccaacgga atcgatgacg    2640
ggctgcatgc tgaggacgac cagctgaggg tgtattatat gcagaattac ataaacgaag    2700
ctctcaaagc ccacatactg gatggtatca atctttgcgg atactttgct tattcgtttta   2760 acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag attttgtcca gaagaattca ccgtgtgtac tgagtgcagt tttttcaca     2940 cccgaaagtc tttactggct ttcatagctt ttctattttt tgcttctatt atttctctct    3000 ccctatatt ttactactcg aagaaggca gaagaagtta caaatagttc tgaacatttt      3060
tctattcatt catttgaaa taattatgca gacacatcag ctgttaacca tttgcacctc     3120
taagtgttgt gaaactgtaa atttcataca tttgacttct agaaaacatt tttgtggctt    3180
atgacagagg tttttgaaatg gcataggtg atcgtaaaat attgaataat gcgaatagtg    3240
cctgaatttg ttctctttt gggtgattaa aaaactgaca ggcactataa tttctgtaac     3300
acactaacaa aagcatgaaa ataggaacc acaccaatgc aacatttgtg cagaaatttg     3360
aatgacaaga ttaggaatat ttcttctgc acccacttct aaatttaatg ttttttctgga    3420 agtagtaatt gcaagagttc gaatagaaag ttatgtacca agtaaccatt tctcagctgc    3480
cataataatg cctagtggct tcccctctgt caaatctagt ttcctatgga aagaagatg     3540 gcagatacag gagagacgac agagggtcct aggctggaat gttcctttcg aaagcaatgc    3600
ttctatcaaa tactagtatt aatttatgta tctggttaat gacatacttg gagagcaaat    3660
```

-continued

```
tatggaaatg tgtattttat atgattttg aggtcctgtc taaaccctgt gtccctgagg    3720
gatctgtctc actggcatct tgttgagggc cttgcacata ggaaactttt gataagtatc    3780
tgcggaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccattttga gcagatcttg aatgaatga     3960 catgaccttt ccctagagaa taaggatgaa ataatcactc attctatgaa cagtgacact    4020
actttctatt ctttagctgt actgtaattt ctttgagttg atagttttac aaattcttaa    4080
taggttcaaa agcaatctgg tctgaataac actggatttg tttctgtgat ctctgaggtc    4140
tattttatgt ttttgctgct acttctgtgg aagtagcttt gaactagttt tactttgaac    4200
tttcacgctg aaacatgcta gtgatatcta gaaagggcta attaggtctc atcctttaat    4260
gccccttaaa taagtcttgc tgattttcag acagggaagt ctctctatta cactggagct    4320
gttttataga taagtcaata ttgtatcagg caagataaac caatgtcata acaggcattg    4380
ccaacctcac tgacacaggg tcatagtgta taataatata ctgtactata taatatatca    4440
tctttagagg tatgattttt tcatgaaaga taagcttttg gtaatattca ttttaaagtg    4500
gacttattaa aattggatgc tagagaatca agtttatttt atgtatatat ttttctgatt    4560
ataagagtaa tatatgttca ttgtaaaaat ttttaaaaca cagaaactat atgcaaagaa    4620
aaaataaaaa ttatctataa tctcagaacc cagaaatagc cactattaac atttcctacg    4680
tattttattt tacatagatc atattgtata tagttagtat ctttattaat ttttattatg    4740
aaactttcct ttgtcattat tagtcttcaa aagcatgatt tttaatagtt gttgagtatt    4800
ccaccacagg aatgtatcac aacttaaccg ttcccgtttg ttagactagt ttcttattaa    4860
tgttgatgaa tgttgtttaa aaataatttt gttgctacat ttactttaat ttccttgact    4920
gtaaagagaa gtaattttgc tccttgataa agtattatat taataataaa tctgcctgca    4980 acttttttgcc ttctttcata atc                                            5003
```

<210> SEQ ID NO 2
<211> LENGTH: 1012
<212> TYPE: PRT
<213> ORGANISM: Homo sapiens

<400> SEQUENCE: 2

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
```

```
            130                 135                 140
Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
                370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560
```

```
Asp Gly Val Val Thr Lys Lys Arg Lys Ser Tyr Cys Val Asp Phe Ala
            565                 570                 575

Ala Ile Gln Pro Gln Ile Ala Leu Leu Gln Glu Met His Val Thr His
        580                 585                 590

Phe Arg Phe Ser Leu Asp Trp Ala Leu Ile Leu Pro Leu Gly Asn Gln
    595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
        770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
        850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
        930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975
```

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
            995                 1000                1005

Arg Ser  Tyr Lys
    1010

<210> SEQ ID NO 3
<211> LENGTH: 3279
<212> TYPE: DNA
<213> ORGANISM: Homo sapiens

<400> SEQUENCE: 3

| | | | | | |
|---|---|---|---|---|---|
| atcctcagtc | tcccagttca | agctaatcat | tgacagagct | ttacaatcac | aagcttttac | 60 |
| tgaagctttg | ataagacagt | ccagcagttg | gtggcaaatg | aagccaggct | gtgcggcagg | 120 |
| atctccaggg | aatgaatgga | ttttcttcag | cactgatgaa | ataaccacac | gctataggaa | 180 |
| tacaatgtcc | aacgggggat | tgcaaagatc | tgtcatcctg | tcagcactta | ttctgctacg | 240 |
| agctgttact | ggattctctg | gagatggaag | agctatatgg | tctaaaaatc | ctaattttac | 300 |
| tccggtaaat | gaaagtcagc | tgtttctcta | tgacactttc | cctaaaaact | ttttctgggg | 360 |
| tattgggact | ggagcattgc | aagtggaagg | gagttggaag | aaggatggaa | aaggaccttc | 420 |
| tatatgggat | catttcatcc | acacacacct | taaaaatgtc | agcagcacga | atggttccag | 480 |
| tgacagttat | attttctgg | aaaaagactt | atcagccctg | gattttatag | gagtttcttt | 540 |
| ttatcaattt | tcaatttcct | ggccaaggct | tttccccgat | ggaatagtaa | cagttgccaa | 600 |
| cgcaaaaggt | ctgcagtact | acagtactct | tctggacgct | ctagtgctta | gaaacattga | 660 |
| acctatagtt | actttatacc | actgggattt | gcctttggca | ctacaagaaa | atatgggggg | 720 |
| gtggaaaaat | gataccataa | tagatatctt | caatgactat | gccacatact | gtttccagat | 780 |
| gtttggggac | cgtgtcaaat | attggattac | aattcacaac | ccatatctag | tggcttggca | 840 |
| tgggtatggg | acaggtatgc | atgcccctgg | agagaaggga | aatttagcag | ctgtctacac | 900 |
| tgtgggacac | aacttgatca | aggctcactc | gaaagtttgg | cataactaca | acacacattt | 960 |
| ccgcccacat | cagaagggtt | ggttatcgat | cacgttggga | tctcattgga | tcgagccaaa | 1020 |
| ccggtcggaa | aacacgatgg | atatattcaa | atgtcaacaa | tccatggttt | ctgtgcttgg | 1080 |
| atggtttgcc | aacccatcc | atggggatgg | cgactatcca | gaggggatga | aaagaagtt | 1140 |
| gttctccgtt | ctaccccattt | tctctgaagc | agagaagcat | gagatgagag | gcacagctga | 1200 |
| tttctttgcc | ttttctttg | gacccaacaa | cttcaagccc | ctaaacacca | tggctaaaat | 1260 |
| gggacaaaat | gtttcactta | atttaagaga | agcgctgaac | tggattaaac | tggaatacaa | 1320 |
| caaccctcga | atcttgattg | ctgagaatgg | ctggttcaca | gacagtcgtg | tgaaaacaga | 1380 |
| agacaccacg | gccatctaca | tgatgaagaa | tttcctcagc | caggtgcttc | aagcaataag | 1440 |
| gttagatgaa | atacgagtgt | ttggttatac | tgcctggtct | ctcctggatg | gctttgaatg | 1500 |
| gcaggatgct | tacaccatcc | gccgaggatt | attttatgtg | gattttaaca | gtaaacagaa | 1560 |
| agagcggaaa | cctaagtctt | cagcacacta | ctacaaacag | atcatacgag | aaaatggttt | 1620 |
| ttctttaaaa | gagtccacgc | cagatgtgca | gggccagttt | ccctgtgact | ctcctgggg | 1680 |
| tgtcactgaa | tctgttctta | agcccgagtc | tgtggcttcg | tccccacagt | tcagcgatcc | 1740 |
| tcatctgtac | gtgtggaacg | ccactggcaa | cagactgttg | caccgagtgg | aaggggtgag | 1800 |
| gctgaaaaca | cgacccgctc | aatgcacaga | ttttgtaaac | atcaaaaaac | aacttgagat | 1860 |

```
gttggcaaga atgaaagtca cccactaccg gtttgctctg gattgggcct cggtccttcc    1920
cactggcaac ctgtccgcgg tgaaccgaca ggccctgagg tactacaggt gcgtggtcag    1980
tgagggctg aagcttggca tctccgcgat ggtcaccctg tattatccga cccacgccca     2040
cctaggcctc cccgagcctc tgttgcatgc cgacgggtgg ctgaacccat cgacggccga    2100
ggccttccag gcctacgctg ggctgtgctt ccaggagctg ggggacctgg tgaagctctg    2160
gatcaccatc aacgagccta accggctaag tgacatctac aaccgctctg caacgacac     2220
ctacggggcg gcgcacaacc tgctggtggc ccacgccctg gcctggcgcc tctacgaccg    2280
gcagttcagg ccctcacagc gcggggccgt gtcgctgtcg ctgcacgcgg actgggcgga    2340
acccgccaac ccctatgctg actcgcactg gagggcggcc gagcgcttcc tgcagttcga    2400
gatcgcctgg ttcgccgagc cgctcttcaa gaccggggac taccccgcgg ccatgaggga    2460
atacattgcc tccaagcacc gacgggggct ttccagctcg gccctgccgc gcctcaccga    2520
ggccgaaagg aggctgctca agggcacggt cgacttctgc gcgctcaacc acttcaccac    2580
taggttcgtg atgcacgagc agctggccgg cagccgctac gactcggaca gggacatcca    2640
gtttctgcag gacatcaccc gcctgagctc ccccacgcgc ctggctgtga ttccctgggg    2700
ggtgcgcaag ctgctgcggt gggtccggag gaactacggc gacatggaca tttacatcac    2760
cgccagtggc atcgacgacc aggctctgga ggatgaccgg ctccggaagt actacctagg    2820
gaagtacctt caggaggtgc tgaaagcata cctgattgat aaagtcagaa tcaaaggcta    2880
ttatgcattc aaactggctg aagagaaatc taaacccaga tttggattct tcacatctga    2940
tttttaaagct aaatcctcaa tacaatttta caacaaagtg atcagcagca ggggcttccc    3000
ttttgagaac agtagttcta gatgcagtca gacccaagaa atacagagt gcactgtctg     3060
cttattcctt gtgcagaaga aaccactgat attcctgggt tgttgcttct tctccaccct    3120
ggttctactc ttatcaattg ccatttttca aaggcagaag agaagaaagt tttggaaagc    3180
aaaaaactta caacacatac cattaaagaa aggcaagaga gttgttagct aaactgatct    3240
gtctgcatga tagacagttt aaaaattcat cccagttcc                          3279
```

<210> SEQ ID NO 4
<211> LENGTH: 1044
<212> TYPE: PRT
<213> ORGANISM: Homo sapiens

<400> SEQUENCE: 4

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125
```

```
Asp Ser Tyr Ile Phe Leu Glu Lys Asp Leu Ser Ala Leu Asp Phe Ile
        130                 135                 140
Gly Val Ser Phe Tyr Gln Phe Ser Ile Ser Trp Pro Arg Leu Phe Pro
145                 150                 155                 160
Asp Gly Ile Val Thr Val Ala Asn Ala Lys Gly Leu Gln Tyr Tyr Ser
                    165                 170                 175
Thr Leu Leu Asp Ala Leu Val Leu Arg Asn Ile Glu Pro Ile Val Thr
                180                 185                 190
Leu Tyr His Trp Asp Leu Pro Leu Ala Leu Gln Glu Lys Tyr Gly Gly
            195                 200                 205
Trp Lys Asn Asp Thr Ile Ile Asp Ile Phe Asn Asp Tyr Ala Thr Tyr
210                 215                 220
Cys Phe Gln Met Phe Gly Asp Arg Val Lys Tyr Trp Ile Thr Ile His
225                 230                 235                 240
Asn Pro Tyr Leu Val Ala Trp His Gly Tyr Gly Thr Gly Met His Ala
                245                 250                 255
Pro Gly Glu Lys Gly Asn Leu Ala Ala Val Tyr Thr Val Gly His Asn
                260                 265                 270
Leu Ile Lys Ala His Ser Lys Val Trp His Asn Tyr Asn Thr His Phe
            275                 280                 285
Arg Pro His Gln Lys Gly Trp Leu Ser Ile Thr Leu Gly Ser His Trp
290                 295                 300
Ile Glu Pro Asn Arg Ser Glu Asn Thr Met Asp Ile Phe Lys Cys Gln
305                 310                 315                 320
Gln Ser Met Val Ser Val Leu Gly Trp Phe Ala Asn Pro Ile His Gly
                325                 330                 335
Asp Gly Asp Tyr Pro Glu Gly Met Arg Lys Lys Leu Phe Ser Val Leu
                340                 345                 350
Pro Ile Phe Ser Glu Ala Glu Lys His Glu Met Arg Gly Thr Ala Asp
            355                 360                 365
Phe Phe Ala Phe Ser Phe Gly Pro Asn Asn Phe Lys Pro Leu Asn Thr
370                 375                 380
Met Ala Lys Met Gly Gln Asn Val Ser Leu Asn Leu Arg Glu Ala Leu
385                 390                 395                 400
Asn Trp Ile Lys Leu Glu Tyr Asn Asn Pro Arg Ile Leu Ile Ala Glu
                405                 410                 415
Asn Gly Trp Phe Thr Asp Ser Arg Val Lys Thr Glu Asp Thr Thr Ala
                420                 425                 430
Ile Tyr Met Met Lys Asn Phe Leu Ser Gln Val Leu Gln Ala Ile Arg
            435                 440                 445
Leu Asp Glu Ile Arg Val Phe Gly Tyr Thr Ala Trp Ser Leu Leu Asp
450                 455                 460
Gly Phe Glu Trp Gln Asp Ala Tyr Thr Ile Arg Arg Gly Leu Phe Tyr
465                 470                 475                 480
Val Asp Phe Asn Ser Lys Gln Lys Glu Arg Lys Pro Lys Ser Ser Ala
                485                 490                 495
His Tyr Tyr Lys Gln Ile Ile Arg Glu Asn Gly Phe Ser Leu Lys Glu
                500                 505                 510
Ser Thr Pro Asp Val Gln Gly Gln Phe Pro Cys Asp Phe Ser Trp Gly
            515                 520                 525
Val Thr Glu Ser Val Leu Lys Pro Glu Ser Val Ala Ser Ser Pro Gln
530                 535                 540
```

```
Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
            565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
        610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
        690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
            755                 760                 765

Ile Ala Trp Phe Ala Glu Pro Leu Phe Lys Thr Gly Asp Tyr Pro Ala
        770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
            835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
```

```
                        965                 970                 975
Ser Gln Thr Gln Glu Asn Thr Glu Cys Thr Val Cys Leu Phe Leu Val
                    980                 985                 990

Gln Lys Lys Pro Leu Ile Phe Leu Gly Cys Cys Phe Phe Ser Thr Leu
                995                 1000                1005

Val Leu Leu Leu Ser Ile Ala Ile Phe Gln Arg Gln Lys Arg Arg
            1010                1015                1020

Lys Phe Trp Lys Ala Lys Asn Leu Gln His Ile Pro Leu Lys Lys
        1025                1030                1035

Gly Lys Arg Val Val Ser
    1040

<210> SEQ ID NO 5
<211> LENGTH: 449
<212> TYPE: PRT
<213> ORGANISM: Homo sapiens

<400> SEQUENCE: 5

Gln Gly Thr Phe Pro Asp Gly Phe Leu Trp Ala Val Gly Ser Ala Ala
 1               5                  10                  15

Tyr Gln Thr Glu Gly Gly Trp Gln Gln His Gly Lys Gly Ala Ser Ile
            20                  25                  30

Trp Asp Thr Phe Thr His His Pro Leu Ala Pro Pro Gly Asp Ser Arg
        35                  40                  45

Asn Ala Ser Leu Pro Leu Gly Ala Pro Ser Pro Leu Gln Pro Ala Thr
    50                  55                  60

Gly Asp Val Ala Ser Asp Ser Tyr Asn Asn Val Phe Arg Asp Thr Glu
65                  70                  75                  80

Ala Leu Arg Glu Leu Gly Val Thr His Tyr Arg Phe Ser Ile Ser Trp
                85                  90                  95

Ala Arg Val Leu Pro Asn Gly Ser Ala Gly Val Pro Asn Arg Glu Gly
            100                 105                 110

Leu Arg Tyr Tyr Arg Arg Leu Leu Glu Arg Leu Arg Glu Leu Gly Val
        115                 120                 125

Gln Pro Val Val Thr Leu Tyr His Trp Asp Leu Pro Gln Arg Leu Gln
    130                 135                 140

Asp Ala Tyr Gly Gly Trp Ala Asn Arg Ala Leu Ala Asp His Phe Arg
145                 150                 155                 160

Asp Tyr Ala Glu Leu Cys Phe Arg His Phe Gly Gly Gln Val Lys Tyr
                165                 170                 175

Trp Ile Thr Ile Asp Asn Pro Tyr Val Val Ala Trp His Gly Tyr Ala
            180                 185                 190

Thr Gly Arg Leu Ala Pro Gly Ile Arg Gly Ser Pro Arg Leu Gly Tyr
        195                 200                 205

Leu Val Ala His Asn Leu Leu Leu Ala His Ala Lys Val Trp His Leu
    210                 215                 220

Tyr Asn Thr Ser Phe Arg Pro Thr Gln Gly Gly Gln Val Ser Ile Ala
225                 230                 235                 240

Leu Ser Ser His Trp Ile Asn Pro Arg Arg Met Thr Asp His Ser Ile
                245                 250                 255

Lys Glu Cys Gln Lys Ser Leu Asp Phe Val Leu Gly Trp Phe Ala Lys
            260                 265                 270

Pro Val Phe Ile Asp Gly Asp Tyr Pro Glu Ser Met Lys Asn Asn Leu
        275                 280                 285
```

```
Ser Ser Ile Leu Pro Asp Phe Thr Glu Ser Glu Lys Lys Phe Ile Lys
    290                 295                 300
Gly Thr Ala Asp Phe Phe Ala Leu Cys Phe Gly Pro Thr Leu Ser Phe
305                 310                 315                 320
Gln Leu Leu Asp Pro His Met Lys Phe Arg Gln Leu Glu Ser Pro Asn
                    325                 330                 335
Leu Arg Gln Leu Leu Ser Trp Ile Asp Leu Glu Phe Asn His Pro Gln
                340                 345                 350
Ile Phe Ile Val Glu Asn Gly Trp Phe Val Ser Gly Thr Thr Lys Arg
            355                 360                 365
Asp Asp Ala Lys Tyr Met Tyr Tyr Leu Lys Lys Phe Ile Met Glu Thr
370                 375                 380
Leu Lys Ala Ile Lys Leu Asp Gly Val Asp Val Ile Gly Tyr Thr Ala
385                 390                 395                 400
Trp Ser Leu Met Asp Gly Phe Glu Trp His Arg Gly Tyr Ser Ile Arg
                    405                 410                 415
Arg Gly Leu Phe Tyr Val Asp Phe Leu Ser Gln Asp Lys Met Leu Leu
                420                 425                 430
Pro Lys Ser Ser Ala Leu Phe Tyr Gln Lys Leu Ile Glu Lys Asn Gly
                435                 440                 445
Phe
```

<210> SEQ ID NO 6
<211> LENGTH: 437
<212> TYPE: PRT
<213> ORGANISM: Homo sapiens

<400> SEQUENCE: 6

```
Gly Thr Phe Pro Cys Asp Phe Ala Trp Gly Val Val Asp Asn Tyr Ile
1               5                   10                  15
Gln Val Asp Thr Thr Leu Ser Gln Phe Thr Asp Leu Asn Val Tyr Leu
                20                  25                  30
Trp Asp Val His His Ser Lys Arg Leu Ile Lys Val Asp Gly Val Val
            35                  40                  45
Thr Lys Lys Arg Lys Ser Tyr Cys Val Asp Phe Ala Ala Ile Gln Pro
    50                  55                  60
Gln Ile Ala Leu Leu Gln Glu Met His Val Thr His Phe Arg Phe Ser
65                  70                  75                  80
Leu Asp Trp Ala Leu Ile Leu Pro Leu Gly Asn Gln Ser Gln Val Asn
                85                  90                  95
His Thr Ile Leu Gln Tyr Tyr Arg Cys Met Ala Ser Glu Leu Val Arg
            100                 105                 110
Val Asn Ile Thr Pro Val Val Ala Leu Trp Gln Pro Met Ala Pro Asn
    115                 120                 125
Gln Gly Leu Pro Arg Leu Leu Ala Arg Gln Gly Ala Trp Glu Asn Pro
130                 135                 140
Tyr Thr Ala Leu Ala Phe Ala Glu Tyr Ala Arg Leu Cys Phe Gln Glu
145                 150                 155                 160
Leu Gly His His Val Lys Leu Trp Ile Thr Met Asn Glu Pro Tyr Thr
                165                 170                 175
Arg Asn Met Thr Tyr Ser Ala Gly His Asn Leu Leu Lys Ala His Ala
            180                 185                 190
Leu Ala Trp His Val Tyr Asn Glu Lys Phe Arg His Ala Gln Asn Gly
        195                 200                 205
```

-continued

```
Lys Ile Ser Ile Ala Leu Gln Ala Asp Trp Ile Glu Pro Ala Cys Pro
    210                 215                 220

Phe Ser Gln Lys Asp Lys Glu Val Ala Glu Arg Val Leu Glu Phe Asp
225                 230                 235                 240

Ile Gly Trp Leu Ala Glu Pro Ile Phe Gly Ser Gly Asp Tyr Pro Trp
                245                 250                 255

Val Met Arg Asp Trp Leu Asn Gln Arg Asn Asn Phe Leu Leu Pro Tyr
            260                 265                 270

Phe Thr Glu Asp Glu Lys Lys Leu Ile Gln Gly Thr Phe Asp Phe Leu
        275                 280                 285

Ala Leu Ser His Tyr Thr Thr Ile Leu Val Asp Ser Glu Lys Glu Asp
290                 295                 300

Pro Ile Lys Tyr Asn Asp Tyr Leu Glu Val Gln Glu Met Thr Asp Ile
305                 310                 315                 320

Thr Trp Leu Asn Ser Pro Ser Gln Val Ala Val Pro Trp Gly Leu
                325                 330                 335

Arg Lys Val Leu Asn Trp Leu Lys Phe Lys Tyr Gly Asp Leu Pro Met
                340                 345                 350

Tyr Ile Ile Ser Asn Gly Ile Asp Asp Gly Leu His Ala Glu Asp Asp
            355                 360                 365

Gln Leu Arg Val Tyr Tyr Met Gln Asn Tyr Ile Asn Glu Ala Leu Lys
370                 375                 380

Ala His Ile Leu Asp Gly Ile Asn Leu Cys Gly Tyr Phe Ala Tyr Ser
385                 390                 395                 400

Phe Asn Asp Arg Thr Ala Pro Arg Phe Gly Leu Tyr Arg Tyr Ala Ala
                405                 410                 415

Asp Gln Phe Glu Pro Lys Ala Ser Met Lys His Tyr Arg Lys Ile Ile
            420                 425                 430

Asp Ser Asn Gly Phe
            435

<210> SEQ ID NO 7
<211> LENGTH: 949
<212> TYPE: PRT
<213> ORGANISM: Homo sapiens

<400> SEQUENCE: 7

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140
```

-continued

Glu Arg Leu Arg Glu Leu Gly Val Gln Pro Val Thr Leu Tyr His
145                 150                 155                 160

Trp Asp Leu Pro Gln Arg Leu Gln Asp Ala Tyr Gly Gly Trp Ala Asn
            165                 170                 175

Arg Ala Leu Ala Asp His Phe Arg Asp Tyr Ala Glu Leu Cys Phe Arg
        180                 185                 190

His Phe Gly Gly Gln Val Lys Tyr Trp Ile Thr Ile Asp Asn Pro Tyr
    195                 200                 205

Val Val Ala Trp His Gly Tyr Ala Thr Gly Arg Leu Ala Pro Gly Ile
210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
            245                 250                 255

Gln Gly Gly Gln Val Ser Ile Ala Leu Ser Ser His Trp Ile Asn Pro
        260                 265                 270

Arg Arg Met Thr Asp His Ser Ile Lys Glu Cys Gln Lys Ser Leu Asp
    275                 280                 285

Phe Val Leu Gly Trp Phe Ala Lys Pro Val Phe Ile Asp Gly Asp Tyr
290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
            325                 330                 335

Cys Phe Gly Pro Thr Leu Ser Phe Gln Leu Leu Asp Pro His Met Lys
        340                 345                 350

Phe Arg Gln Leu Glu Ser Pro Asn Leu Arg Gln Leu Leu Ser Trp Ile
    355                 360                 365

Asp Leu Glu Phe Asn His Pro Gln Ile Phe Ile Val Glu Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
            405                 410                 415

Val Asp Val Ile Gly Tyr Thr Ala Trp Ser Leu Met Asp Gly Phe Glu
        420                 425                 430

Trp His Arg Gly Tyr Ser Ile Arg Arg Gly Leu Phe Tyr Val Asp Phe
    435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
            485                 490                 495

Asn Tyr Ile Gln Val Asp Thr Thr Leu Ser Gln Phe Thr Asp Leu Asn
        500                 505                 510

Val Tyr Leu Trp Asp Val His His Ser Lys Arg Leu Ile Lys Val Asp
    515                 520                 525

Gly Val Val Thr Lys Lys Arg Lys Ser Tyr Cys Val Asp Phe Ala Ala
530                 535                 540

Ile Gln Pro Gln Ile Ala Leu Leu Gln Glu Met His Val Thr His Phe
545                 550                 555                 560

```
Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu
945

<210> SEQ ID NO 8
<211> LENGTH: 33
<212> TYPE: PRT
```

<213> ORGANISM: Homo sapiens

<400> SEQUENCE: 8

Met Pro Ala Ser Ala Pro Pro Arg Arg Pro Arg Pro Pro Pro Ser
1               5                   10                  15
Leu Ser Leu Leu Leu Val Leu Leu Gly Leu Gly Gly Arg Arg Leu Arg
            20                  25                  30
Ala

<210> SEQ ID NO 9
<211> LENGTH: 25
<212> TYPE: PRT
<213> ORGANISM: Homo sapiens

<400> SEQUENCE: 9

Met Ser Val Leu Thr Gln Val Leu Ala Leu Leu Leu Leu Trp Leu Thr
1               5                   10                  15
Gly Thr Arg Cys Arg Arg Leu Arg Ala
            20                  25

<210> SEQ ID NO 10
<211> LENGTH: 45
<212> TYPE: DNA
<213> ORGANISM: Artificial
<220> FEATURE:
<223> OTHER INFORMATION: linker

<400> SEQUENCE: 10
ggaggtggag gttcaggagg tggaggttca ggaggtggag gttca          45

<210> SEQ ID NO 11
<211> LENGTH: 15
<212> TYPE: PRT
<213> ORGANISM: Artificial
<220> FEATURE:
<223> OTHER INFORMATION: linker

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 5
<212> TYPE: PRT
<213> ORGANISM: Artificial
<220> FEATURE:
<223> OTHER INFORMATION: linker

<400> SEQUENCE: 12

Gly Gly Gly Gly Ser
1               5

<210> SEQ ID NO 13
<211> LENGTH: 1
<212> TYPE: PRT
<213> ORGANISM: Artificial
<220> FEATURE:
<223> OTHER INFORMATION: linker

<400> SEQUENCE: 13

Gly
1

<210> SEQ ID NO 14

```
<211> LENGTH: 2
<212> TYPE: PRT
<213> ORGANISM: Artificial
<220> FEATURE:
<223> OTHER INFORMATION: linker

<400> SEQUENCE: 14

Gly Gly
1

<210> SEQ ID NO 15
<211> LENGTH: 2
<212> TYPE: PRT
<213> ORGANISM: Artificial
<220> FEATURE:
<223> OTHER INFORMATION: linker

<400> SEQUENCE: 15

Gly Ser
1

<210> SEQ ID NO 16
<211> LENGTH: 3
<212> TYPE: PRT
<213> ORGANISM: Artificial
<220> FEATURE:
<223> OTHER INFORMATION: linker

<400> SEQUENCE: 16

Gly Gly Ser
1

<210> SEQ ID NO 17
<211> LENGTH: 1
<212> TYPE: PRT
<213> ORGANISM: Artificial
<220> FEATURE:
<223> OTHER INFORMATION: linker

<400> SEQUENCE: 17

Ala
1

<210> SEQ ID NO 18
<211> LENGTH: 2
<212> TYPE: PRT
<213> ORGANISM: Artificial
<220> FEATURE:
<223> OTHER INFORMATION: linker

<400> SEQUENCE: 18

Ala Ala
1

<210> SEQ ID NO 19
<211> LENGTH: 1228
<212> TYPE: PRT
<213> ORGANISM: Artificial
<220> FEATURE:
<223> OTHER INFORMATION: fusion polypeptide

<400> SEQUENCE: 19

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30
```

Ala Glu Pro Gly Asp Gly Ala Gln Thr Trp Ala Arg Phe Ser Arg Pro
         35                  40                  45

Pro Ala Pro Glu Ala Ala Gly Leu Phe Gln Gly Thr Phe Pro Asp Gly
 50                  55                  60

Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
                115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
                210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
                290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe

```
            450                 455                 460
Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
            530                 535                 540

Asn Val Tyr Leu Trp Asp Val His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
        770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
                850                 855                 860

Asp Leu Pro Met Tyr Ile Ile Ser Asn Gly Ile Asp Asp Gly Leu His
865                 870                 875                 880
```

```
Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
        900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Cys Arg Pro Phe Ala Lys Phe Ile
    1220                1225

<210> SEQ ID NO 20
<211> LENGTH: 1220
<212> TYPE: PRT
<213> ORGANISM: Artificial
<220> FEATURE:
<223> OTHER INFORMATION: fusion polypeptide

<400> SEQUENCE: 20
```

```
Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Ala Pro Glu Ala Ala Gly Leu
            35                  40                  45

Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65              70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
                100                 105                 110

Thr Gly Asp Val Ala Ser Asp Ser Tyr Asn Asn Val Phe Arg Asp Thr
            115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
                180                 185                 190

Gln Asp Ala Tyr Gly Gly Trp Ala Asn Arg Ala Leu Ala Asp His Phe
            195                 200                 205

Arg Asp Tyr Ala Glu Leu Cys Phe Arg His Phe Gly Gly Gln Val Lys
210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
                260                 265                 270

Leu Tyr Asn Thr Ser Phe Arg Pro Thr Gln Gly Gly Gln Val Ser Ile
    275                 280                 285

Ala Leu Ser Ser His Trp Ile Asn Pro Arg Arg Met Thr Asp His Ser
    290                 295                 300

Ile Lys Glu Cys Gln Lys Ser Leu Asp Phe Val Leu Gly Trp Phe Ala
305                 310                 315                 320

Lys Pro Val Phe Ile Asp Gly Asp Tyr Pro Glu Ser Met Lys Asn Asn
                325                 330                 335

Leu Ser Ser Ile Leu Pro Asp Phe Thr Glu Ser Glu Lys Lys Phe Ile
            340                 345                 350

Lys Gly Thr Ala Asp Phe Phe Ala Leu Cys Phe Gly Pro Thr Leu Ser
            355                 360                 365

Phe Gln Leu Leu Asp Pro His Met Lys Phe Arg Gln Leu Glu Ser Pro
    370                 375                 380

Asn Leu Arg Gln Leu Leu Ser Trp Ile Asp Leu Glu Phe Asn His Pro
385                 390                 395                 400

Gln Ile Phe Ile Val Glu Asn Gly Trp Phe Val Ser Gly Thr Thr Lys
                405                 410                 415
```

```
Arg Asp Asp Ala Lys Tyr Met Tyr Tyr Leu Lys Lys Phe Ile Met Glu
                420                 425                 430

Thr Leu Lys Ala Ile Lys Leu Asp Gly Val Asp Val Ile Gly Tyr Thr
        435                 440                 445

Ala Trp Ser Leu Met Asp Gly Phe Glu Trp His Arg Gly Tyr Ser Ile
    450                 455                 460

Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
            500                 505                 510

Cys Asp Phe Ala Trp Gly Val Val Asp Asn Tyr Ile Gln Val Asp Thr
            515                 520                 525

Thr Leu Ser Gln Phe Thr Asp Leu Asn Val Tyr Leu Trp Asp Val His
        530                 535                 540

His Ser Lys Arg Leu Ile Lys Val Asp Gly Val Val Thr Lys Lys Arg
545                 550                 555                 560

Lys Ser Tyr Cys Val Asp Phe Ala Ala Ile Gln Pro Gln Ile Ala Leu
                565                 570                 575

Leu Gln Glu Met His Val Thr His Phe Arg Phe Ser Leu Asp Trp Ala
            580                 585                 590

Leu Ile Leu Pro Leu Gly Asn Gln Ser Gln Val Asn His Thr Ile Leu
        595                 600                 605

Gln Tyr Tyr Arg Cys Met Ala Ser Glu Leu Val Arg Val Asn Ile Thr
610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
                645                 650                 655

Ala Phe Ala Glu Tyr Ala Arg Leu Cys Phe Gln Glu Leu Gly His His
            660                 665                 670

Val Lys Leu Trp Ile Thr Met Asn Glu Pro Tyr Thr Arg Asn Met Thr
        675                 680                 685

Tyr Ser Ala Gly His Asn Leu Leu Lys Ala His Ala Leu Ala Trp His
    690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
                725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
        755                 760                 765

Trp Leu Asn Gln Arg Asn Asn Phe Leu Leu Pro Tyr Phe Thr Glu Asp
    770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
            820                 825                 830

Ser Pro Ser Gln Val Ala Val Val Pro Trp Gly Leu Arg Lys Val Leu
```

```
                    835                 840                 845
Asn Trp Leu Lys Phe Lys Tyr Gly Asp Leu Pro Met Tyr Ile Ile Ser
850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
                    885                 890                 895

Asp Gly Ile Asn Leu Cys Gly Tyr Phe Ala Tyr Ser Phe Asn Asp Arg
                900                 905                 910

Thr Ala Pro Arg Phe Gly Leu Tyr Arg Tyr Ala Ala Asp Gln Phe Glu
                915                 920                 925

Pro Lys Ala Ser Met Lys His Tyr Arg Lys Ile Ile Asp Ser Asn Gly
930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu Gly Ser
                965                 970                 975

Gly Gly Gly Gly Ser Gly Gly Gly Ser Gly Gly Gly Ser Leu
                980                 985                 990

Lys Tyr Pro Asn Ala Ser Pro Leu Leu Gly Ser Ser Trp Gly Gly Leu
                995                 1000                1005

Ile His Leu Tyr Thr Ala Thr Ala Arg Asn Ser Tyr His Leu Gln
        1010                1015                1020

Ile His Lys Asn Gly His Val Asp Gly Ala Pro His Gln Thr Ile
        1025                1030                1035

Tyr Ser Ala Leu Met Ile Arg Ser Glu Asp Ala Gly Phe Val Val
        1040                1045                1050

Ile Thr Gly Val Met Ser Arg Arg Tyr Leu Cys Met Asp Phe Arg
        1055                1060                1065

Gly Asn Ile Phe Gly Ser His Tyr Phe Asp Pro Glu Asn Cys Arg
        1070                1075                1080

Phe Gln His Gln Thr Leu Glu Asn Gly Tyr Asp Val Tyr His Ser
        1085                1090                1095

Pro Gln Tyr His Phe Leu Val Ser Leu Gly Arg Ala Lys Arg Ala
        1100                1105                1110

Phe Leu Pro Gly Met Asn Pro Pro Tyr Ser Gln Phe Leu Ser
        1115                1120                1125

Arg Arg Asn Glu Ile Pro Leu Ile His Phe Asn Thr Pro Ile Pro
        1130                1135                1140

Arg Arg His Thr Gln Ser Ala Glu Asp Asp Ser Glu Arg Asp Pro
        1145                1150                1155

Leu Asn Val Leu Lys Pro Arg Ala Arg Met Thr Pro Ala Pro Ala
        1160                1165                1170

Ser Cys Ser Gln Glu Leu Pro Ser Ala Glu Asp Asn Ser Pro Met
        1175                1180                1185

Ala Ser Asp Pro Leu Gly Val Val Arg Gly Gly Arg Val Asn Thr
        1190                1195                1200

His Ala Gly Gly Thr Gly Pro Glu Gly Cys Arg Pro Phe Ala Lys
        1205                1210                1215

Phe Ile
        1220

<210> SEQ ID NO 21
```

```
<211> LENGTH: 762
<212> TYPE: PRT
<213> ORGANISM: Artificial
<220> FEATURE:
<223> OTHER INFORMATION: fusion polypeptide

<400> SEQUENCE: 21
```

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

```
Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
            405                 410                 415

Trp Phe Val Ser Gly Thr Thr Lys Arg Asp Asp Ala Lys Tyr Met Tyr
        420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
            485                 490                 495

Tyr Gln Lys Leu Ile Glu Lys Asn Gly Phe Pro Pro Leu Pro Glu Asn
        500                 505                 510

Gln Pro Leu Glu Gly Ser Gly Gly Gly Ser Gly Gly Gly Ser
            515                 520                 525

Gly Gly Gly Gly Ser Leu Lys Tyr Pro Asn Ala Ser Pro Leu Leu Gly
530                 535                 540

Ser Ser Trp Gly Gly Leu Ile His Leu Tyr Thr Ala Thr Ala Arg Asn
545                 550                 555                 560

Ser Tyr His Leu Gln Ile His Lys Asn Gly His Val Asp Gly Ala Pro
            565                 570                 575

His Gln Thr Ile Tyr Ser Ala Leu Met Ile Arg Ser Glu Asp Ala Gly
        580                 585                 590

Phe Val Val Ile Thr Gly Val Met Ser Arg Arg Tyr Leu Cys Met Asp
        595                 600                 605

Phe Arg Gly Asn Ile Phe Gly Ser His Tyr Phe Asp Pro Glu Asn Cys
        610                 615                 620

Arg Phe Gln His Gln Thr Leu Glu Asn Gly Tyr Asp Val Tyr His Ser
625                 630                 635                 640

Pro Gln Tyr His Phe Leu Val Ser Leu Gly Arg Ala Lys Arg Ala Phe
            645                 650                 655

Leu Pro Gly Met Asn Pro Pro Tyr Ser Gln Phe Leu Ser Arg Arg
        660                 665                 670

Asn Glu Ile Pro Leu Ile His Phe Asn Thr Pro Ile Pro Arg Arg His
            675                 680                 685

Thr Gln Ser Ala Glu Asp Asp Ser Glu Arg Asp Pro Leu Asn Val Leu
        690                 695                 700

Lys Pro Arg Ala Arg Met Thr Pro Ala Pro Ala Ser Cys Ser Gln Glu
705                 710                 715                 720

Leu Pro Ser Ala Glu Asp Asn Ser Pro Met Ala Ser Asp Pro Leu Gly
            725                 730                 735

Val Val Arg Gly Gly Arg Val Asn Thr His Ala Gly Gly Thr Gly Pro
            740                 745                 750

Glu Gly Cys Arg Pro Phe Ala Lys Phe Ile
        755                 760

<210> SEQ ID NO 22
<211> LENGTH: 752
<212> TYPE: PRT
<213> ORGANISM: Artificial
<220> FEATURE:
```

<223> OTHER INFORMATION: fusion polypeptide

<400> SEQUENCE: 22

```
Met Pro Ala Ser Ala Pro Pro Arg Arg Pro Arg Pro Pro Ser
1               5                   10                  15
Leu Ser Leu Leu Leu Val Leu Leu Gly Leu Gly Gly Arg Arg Leu Pro
            20                  25                  30
Leu Pro Glu Asn Gln Pro Leu Glu Gly Thr Phe Pro Cys Asp Phe Ala
        35                  40                  45
Trp Gly Val Val Asp Asn Tyr Ile Gln Val Asp Thr Thr Leu Ser Gln
    50                  55                  60
Phe Thr Asp Leu Asn Val Tyr Leu Trp Asp Val His His Ser Lys Arg
65                  70                  75                  80
Leu Ile Lys Val Asp Gly Val Val Thr Lys Lys Arg Lys Ser Tyr Cys
            85                  90                  95
Val Asp Phe Ala Ala Ile Gln Pro Gln Ile Ala Leu Leu Gln Glu Met
        100                 105                 110
His Val Thr His Phe Arg Phe Ser Leu Asp Trp Ala Leu Ile Leu Pro
    115                 120                 125
Leu Gly Asn Gln Ser Gln Val Asn His Thr Ile Leu Gln Tyr Tyr Arg
    130                 135                 140
Cys Met Ala Ser Glu Leu Val Arg Val Asn Ile Thr Pro Val Val Ala
145                 150                 155                 160
Leu Trp Gln Pro Met Ala Pro Asn Gln Gly Leu Pro Arg Leu Leu Ala
            165                 170                 175
Arg Gln Gly Ala Trp Glu Asn Pro Tyr Thr Ala Leu Ala Phe Ala Glu
        180                 185                 190
Tyr Ala Arg Leu Cys Phe Gln Glu Leu Gly His His Val Lys Leu Trp
    195                 200                 205
Ile Thr Met Asn Glu Pro Tyr Thr Arg Asn Met Thr Tyr Ser Ala Gly
    210                 215                 220
His Asn Leu Leu Lys Ala His Ala Leu Ala Trp His Val Tyr Asn Glu
225                 230                 235                 240
Lys Phe Arg His Ala Gln Asn Gly Lys Ile Ser Ile Ala Leu Gln Ala
            245                 250                 255
Asp Trp Ile Glu Pro Ala Cys Pro Phe Ser Gln Lys Asp Lys Glu Val
        260                 265                 270
Ala Glu Arg Val Leu Glu Phe Asp Ile Gly Trp Leu Ala Glu Pro Ile
    275                 280                 285
Phe Gly Ser Gly Asp Tyr Pro Trp Val Met Arg Asp Trp Leu Asn Gln
    290                 295                 300
Arg Asn Asn Phe Leu Leu Pro Tyr Phe Thr Glu Asp Glu Lys Lys Leu
305                 310                 315                 320
Ile Gln Gly Thr Phe Asp Phe Leu Ala Leu Ser His Tyr Thr Thr Ile
            325                 330                 335
Leu Val Asp Ser Glu Lys Glu Asp Pro Ile Lys Tyr Asn Asp Tyr Leu
        340                 345                 350
Glu Val Gln Glu Met Thr Asp Ile Thr Trp Leu Asn Ser Pro Ser Gln
    355                 360                 365
Val Ala Val Val Pro Trp Gly Leu Arg Lys Val Leu Asn Trp Leu Lys
    370                 375                 380
Phe Lys Tyr Gly Asp Leu Pro Met Tyr Ile Ile Ser Asn Gly Ile Asp
385                 390                 395                 400
```

```
Asp Gly Leu His Ala Glu Asp Gln Leu Arg Val Tyr Tyr Met Gln
            405                 410                 415

Asn Tyr Ile Asn Glu Ala Leu Lys Ala His Ile Leu Asp Gly Ile Asn
        420                 425                 430

Leu Cys Gly Tyr Phe Ala Tyr Ser Phe Asn Asp Arg Thr Ala Pro Arg
        435                 440                 445

Phe Gly Leu Tyr Arg Tyr Ala Ala Asp Gln Phe Glu Pro Lys Ala Ser
        450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
            485                 490                 495

Cys Ser Phe Phe His Thr Arg Lys Ser Leu Gly Ser Gly Gly Gly Gly
            500                 505                 510

Ser Gly Gly Gly Gly Ser Gly Gly Gly Gly Ser Leu Lys Tyr Pro Asn
        515                 520                 525

Ala Ser Pro Leu Leu Gly Ser Ser Trp Gly Gly Leu Ile His Leu Tyr
        530                 535                 540

Thr Ala Thr Ala Arg Asn Ser Tyr His Leu Gln Ile His Lys Asn Gly
545                 550                 555                 560

His Val Asp Gly Ala Pro His Gln Thr Ile Tyr Ser Ala Leu Met Ile
            565                 570                 575

Arg Ser Glu Asp Ala Gly Phe Val Val Ile Thr Gly Val Met Ser Arg
            580                 585                 590

Arg Tyr Leu Cys Met Asp Phe Arg Gly Asn Ile Phe Gly Ser His Tyr
        595                 600                 605

Phe Asp Pro Glu Asn Cys Arg Phe Gln His Gln Thr Leu Glu Asn Gly
        610                 615                 620

Tyr Asp Val Tyr His Ser Pro Gln Tyr His Phe Leu Val Ser Leu Gly
625                 630                 635                 640

Arg Ala Lys Arg Ala Phe Leu Pro Gly Met Asn Pro Pro Pro Tyr Ser
            645                 650                 655

Gln Phe Leu Ser Arg Arg Asn Glu Ile Pro Leu Ile His Phe Asn Thr
            660                 665                 670

Pro Ile Pro Arg Arg His Thr Gln Ser Ala Glu Asp Asp Ser Glu Arg
        675                 680                 685

Asp Pro Leu Asn Val Leu Lys Pro Arg Ala Arg Met Thr Pro Ala Pro
        690                 695                 700

Ala Ser Cys Ser Gln Glu Leu Pro Ser Ala Glu Asp Asn Ser Pro Met
705                 710                 715                 720

Ala Ser Asp Pro Leu Gly Val Val Arg Gly Gly Arg Val Asn Thr His
            725                 730                 735

Ala Gly Gly Thr Gly Pro Glu Gly Cys Arg Pro Phe Ala Lys Phe Ile
            740                 745                 750

<210> SEQ ID NO 23
<211> LENGTH: 1215
<212> TYPE: PRT
<213> ORGANISM: Artificial
<220> FEATURE:
<223> OTHER INFORMATION: fusion polypeptide

<400> SEQUENCE: 23

Met Pro Ala Ser Ala Pro Pro Arg Arg Pro Arg Pro Pro Pro Pro Ser
1               5                   10                  15
```

```
Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
```

```
            435                 440                 445
Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Ser Gly Thr Phe Pro Asp Gly Phe Leu Trp Ala
                515                 520                 525

Val Gly Ser Ala Ala Tyr Gln Thr Glu Gly Gly Trp Gln Gln His Gly
530                 535                 540

Lys Gly Ala Ser Ile Trp Asp Thr Phe Thr His Pro Leu Ala Pro
545                 550                 555                 560

Pro Gly Asp Ser Arg Asn Ala Ser Leu Pro Leu Gly Ala Pro Ser Pro
                565                 570                 575

Leu Gln Pro Ala Thr Gly Asp Val Ala Ser Asp Ser Tyr Asn Asn Val
                580                 585                 590

Phe Arg Asp Thr Glu Ala Leu Arg Glu Leu Gly Val Thr His Tyr Arg
                595                 600                 605

Phe Ser Ile Ser Trp Ala Arg Val Leu Pro Asn Gly Ser Ala Gly Val
610                 615                 620

Pro Asn Arg Glu Gly Leu Arg Tyr Tyr Arg Arg Leu Leu Glu Arg Leu
625                 630                 635                 640

Arg Glu Leu Gly Val Gln Pro Val Val Thr Leu Tyr His Trp Asp Leu
                645                 650                 655

Pro Gln Arg Leu Gln Asp Ala Tyr Gly Gly Trp Ala Asn Arg Ala Leu
                660                 665                 670

Ala Asp His Phe Arg Asp Tyr Ala Glu Leu Cys Phe Arg His Phe Gly
                675                 680                 685

Gly Gln Val Lys Tyr Trp Ile Thr Ile Asp Asn Pro Tyr Val Val Ala
690                 695                 700

Trp His Gly Tyr Ala Thr Gly Arg Leu Ala Pro Gly Ile Arg Gly Ser
705                 710                 715                 720

Pro Arg Leu Gly Tyr Leu Val Ala His Asn Leu Leu Leu Ala His Ala
                725                 730                 735

Lys Val Trp His Leu Tyr Asn Thr Ser Phe Arg Pro Thr Gln Gly Gly
                740                 745                 750

Gln Val Ser Ile Ala Leu Ser Ser His Trp Ile Asn Pro Arg Arg Met
                755                 760                 765

Thr Asp His Ser Ile Lys Glu Cys Gln Lys Ser Leu Asp Phe Val Leu
                770                 775                 780

Gly Trp Phe Ala Lys Pro Val Phe Ile Asp Gly Asp Tyr Pro Glu Ser
785                 790                 795                 800

Met Lys Asn Asn Leu Ser Ser Ile Leu Pro Asp Phe Thr Glu Ser Glu
                805                 810                 815

Lys Lys Phe Ile Lys Gly Thr Ala Asp Phe Phe Ala Leu Cys Phe Gly
                820                 825                 830

Pro Thr Leu Ser Phe Gln Leu Leu Asp Pro His Met Lys Phe Arg Gln
                835                 840                 845

Leu Glu Ser Pro Asn Leu Arg Gln Leu Leu Ser Trp Ile Asp Leu Glu
                850                 855                 860
```

Phe Asn His Pro Gln Ile Phe Ile Val Glu Asn Gly Trp Phe Val Ser
865                 870                 875                 880

Gly Thr Thr Lys Arg Asp Asp Ala Lys Tyr Met Tyr Leu Lys Lys
        885                 890                 895

Phe Ile Met Glu Thr Leu Lys Ala Ile Lys Leu Asp Gly Val Asp Val
            900                 905                 910

Ile Gly Tyr Thr Ala Trp Ser Leu Met Asp Gly Phe Glu Trp His Arg
        915                 920                 925

Gly Tyr Ser Ile Arg Arg Gly Leu Phe Tyr Val Asp Phe Leu Ser Gln
930                 935                 940

Asp Lys Met Leu Leu Pro Lys Ser Ser Ala Leu Phe Tyr Gln Lys Leu
945                 950                 955                 960

Ile Glu Lys Asn Gly Phe Pro Glu Phe Ser Gly Gly Gly Ser
            965                 970                 975

Gly Gly Gly Gly Ser Gly Gly Gly Ser Leu Lys Tyr Pro Asn Ala
            980                 985                 990

Ser Pro Leu Leu Gly Ser Ser Trp Gly Gly Leu Ile His Leu Tyr Thr
        995                 1000                1005

Ala Thr Ala Arg Asn Ser Tyr His Leu Gln Ile His Lys Asn Gly
    1010                1015                1020

His Val Asp Gly Ala Pro His Gln Thr Ile Tyr Ser Ala Leu Met
    1025                1030                1035

Ile Arg Ser Glu Asp Ala Gly Phe Val Val Ile Thr Gly Val Met
    1040                1045                1050

Ser Arg Arg Tyr Leu Cys Met Asp Phe Arg Gly Asn Ile Phe Gly
    1055                1060                1065

Ser His Tyr Phe Asp Pro Glu Asn Cys Arg Phe Gln His Gln Thr
    1070                1075                1080

Leu Glu Asn Gly Tyr Asp Val Tyr His Ser Pro Gln Tyr His Phe
    1085                1090                1095

Leu Val Ser Leu Gly Arg Ala Lys Arg Ala Phe Leu Pro Gly Met
    1100                1105                1110

Asn Pro Pro Pro Tyr Ser Gln Phe Leu Ser Arg Arg Asn Glu Ile
    1115                1120                1125

Pro Leu Ile His Phe Asn Thr Pro Ile Pro Arg Arg His Thr Gln
    1130                1135                1140

Ser Ala Glu Asp Asp Ser Glu Arg Asp Pro Leu Asn Val Leu Lys
    1145                1150                1155

Pro Arg Ala Arg Met Thr Pro Ala Pro Ala Ser Cys Ser Gln Glu
    1160                1165                1170

Leu Pro Ser Ala Glu Asp Asn Ser Pro Met Ala Ser Asp Pro Leu
    1175                1180                1185

Gly Val Val Arg Gly Gly Arg Val Asn Thr His Ala Gly Gly Thr
    1190                1195                1200

Gly Pro Glu Gly Cys Arg Pro Phe Ala Lys Phe Ile
    1205                1210                1215

<210> SEQ ID NO 24
<211> LENGTH: 1189
<212> TYPE: PRT
<213> ORGANISM: Artificial
<220> FEATURE:
<223> OTHER INFORMATION: fusion polypeptide

<400> SEQUENCE: 24

```
Met Pro Ala Ser Ala Pro Pro Arg Arg Pro Pro Pro Pro Pro Ser
1               5                   10                  15

Leu Ser Leu Leu Leu Val Leu Leu Gly Leu Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Arg Lys Ser Tyr Cys
            85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
            115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
                180                 185                 190

Tyr Ala Arg Leu Cys Phe Gln Glu Leu Gly His His Val Lys Leu Trp
            195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
                260                 265                 270

Ala Glu Arg Val Leu Glu Phe Asp Ile Gly Trp Leu Ala Glu Pro Ile
            275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
            355                 360                 365

Val Ala Val Val Pro Trp Gly Leu Arg Lys Val Leu Asn Trp Leu Lys
    370                 375                 380

Phe Lys Tyr Gly Asp Leu Pro Met Tyr Ile Ile Ser Asn Gly Ile Asp
385                 390                 395                 400

Asp Gly Leu His Ala Glu Asp Asp Gln Leu Arg Val Tyr Tyr Met Gln
            405                 410                 415
```

```
Asn Tyr Ile Asn Glu Ala Leu Lys Ala His Ile Leu Asp Gly Ile Asn
                420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
        450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
                485                 490                 495

Cys Ser Phe Phe His Thr Arg Lys Ser Leu Gly Thr Phe Pro Cys Asp
                500                 505                 510

Phe Ala Trp Gly Val Val Asp Asn Tyr Ile Gln Val Asp Thr Thr Leu
            515                 520                 525

Ser Gln Phe Thr Asp Leu Asn Val Tyr Leu Trp Asp Val His His Ser
        530                 535                 540

Lys Arg Leu Ile Lys Val Asp Gly Val Val Thr Lys Lys Arg Lys Ser
545                 550                 555                 560

Tyr Cys Val Asp Phe Ala Ala Ile Gln Pro Gln Ile Ala Leu Leu Gln
                565                 570                 575

Glu Met His Val Thr His Phe Arg Phe Ser Leu Asp Trp Ala Leu Ile
                580                 585                 590

Leu Pro Leu Gly Asn Gln Ser Gln Val Asn His Thr Ile Leu Gln Tyr
            595                 600                 605

Tyr Arg Cys Met Ala Ser Glu Leu Val Arg Val Asn Ile Thr Pro Val
        610                 615                 620

Val Ala Leu Trp Gln Pro Met Ala Pro Asn Gln Gly Leu Pro Arg Leu
625                 630                 635                 640

Leu Ala Arg Gln Gly Ala Trp Glu Asn Pro Tyr Thr Ala Leu Ala Phe
                645                 650                 655

Ala Glu Tyr Ala Arg Leu Cys Phe Gln Glu Leu Gly His His Val Lys
                660                 665                 670

Leu Trp Ile Thr Met Asn Glu Pro Tyr Thr Arg Asn Met Thr Tyr Ser
            675                 680                 685

Ala Gly His Asn Leu Leu Lys Ala His Ala Leu Ala Trp His Val Tyr
        690                 695                 700

Asn Glu Lys Phe Arg His Ala Gln Asn Gly Lys Ile Ser Ile Ala Leu
705                 710                 715                 720

Gln Ala Asp Trp Ile Glu Pro Ala Cys Pro Phe Ser Gln Lys Asp Lys
                725                 730                 735

Glu Val Ala Glu Arg Val Leu Glu Phe Asp Ile Gly Trp Leu Ala Glu
                740                 745                 750

Pro Ile Phe Gly Ser Gly Asp Tyr Pro Trp Val Met Arg Asp Trp Leu
            755                 760                 765

Asn Gln Arg Asn Asn Phe Leu Leu Pro Tyr Phe Thr Glu Asp Glu Lys
        770                 775                 780

Lys Leu Ile Gln Gly Thr Phe Asp Phe Leu Ala Leu Ser His Tyr Thr
785                 790                 795                 800

Thr Ile Leu Val Asp Ser Glu Lys Glu Asp Pro Ile Lys Tyr Asn Asp
                805                 810                 815

Tyr Leu Glu Val Gln Glu Met Thr Asp Ile Thr Trp Leu Asn Ser Pro
                820                 825                 830

Ser Gln Val Ala Val Val Pro Trp Gly Leu Arg Lys Val Leu Asn Trp
```

```
                         835                 840                 845
Leu Lys Phe Lys Tyr Gly Asp Leu Pro Met Tyr Ile Ile Ser Asn Gly
        850                 855                 860

Ile Asp Asp Gly Leu His Ala Glu Asp Gln Leu Arg Val Tyr Tyr
865                 870                 875                 880

Met Gln Asn Tyr Ile Asn Glu Ala Leu Lys Ala His Ile Leu Asp Gly
                    885                 890                 895

Ile Asn Leu Cys Gly Tyr Phe Ala Tyr Ser Phe Asn Asp Arg Thr Ala
        900                 905                 910

Pro Arg Phe Gly Leu Tyr Arg Tyr Ala Ala Asp Gln Phe Glu Pro Lys
            915                 920                 925

Ala Ser Met Lys His Tyr Arg Lys Ile Ile Asp Ser Asn Gly Phe Gly
        930                 935                 940

Ser Gly Gly Gly Gly Ser Gly Gly Gly Ser Gly Gly Gly Gly Ser
945                 950                 955                 960

Leu Lys Tyr Pro Asn Ala Ser Pro Leu Leu Gly Ser Ser Trp Gly Gly
                965                 970                 975

Leu Ile His Leu Tyr Thr Ala Thr Ala Arg Asn Ser Tyr His Leu Gln
        980                 985                 990

Ile His Lys Asn Gly His Val Asp Gly Ala Pro His Gln Thr Ile Tyr
            995                 1000                1005

Ser Ala Leu Met Ile Arg Ser Glu Asp Ala Gly Phe Val Val Ile
        1010                1015                1020

Thr Gly Val Met Ser Arg Arg Tyr Leu Cys Met Asp Phe Arg Gly
        1025                1030                1035

Asn Ile Phe Gly Ser His Tyr Phe Asp Pro Glu Asn Cys Arg Phe
        1040                1045                1050

Gln His Gln Thr Leu Glu Asn Gly Tyr Asp Val Tyr His Ser Pro
        1055                1060                1065

Gln Tyr His Phe Leu Val Ser Leu Gly Arg Ala Lys Arg Ala Phe
        1070                1075                1080

Leu Pro Gly Met Asn Pro Pro Tyr Ser Gln Phe Leu Ser Arg
        1085                1090                1095

Arg Asn Glu Ile Pro Leu Ile His Phe Asn Thr Pro Ile Pro Arg
        1100                1105                1110

Arg His Thr Gln Ser Ala Glu Asp Asp Ser Glu Arg Asp Pro Leu
        1115                1120                1125

Asn Val Leu Lys Pro Arg Ala Arg Met Thr Pro Ala Pro Ala Ser
        1130                1135                1140

Cys Ser Gln Glu Leu Pro Ser Ala Glu Asp Asn Ser Pro Met Ala
        1145                1150                1155

Ser Asp Pro Leu Gly Val Val Arg Gly Gly Arg Val Asn Thr His
        1160                1165                1170

Ala Gly Gly Thr Gly Pro Glu Gly Cys Arg Pro Phe Ala Lys Phe
        1175                1180                1185

Ile
```

<210> SEQ ID NO 25
<211> LENGTH: 1219
<212> TYPE: PRT
<213> ORGANISM: Artificial
<220> FEATURE:
<223> OTHER INFORMATION: fusion polypeptide

<400> SEQUENCE: 25

-continued

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Ser Gly Gly Gly
                245                 250                 255

Gly Ser Gly Gly Gly Ser Gly Gly Gly Ser Leu Lys Glu Pro
            260                 265                 270

Gly Asp Gly Ala Gln Thr Trp Ala Arg Phe Ser Arg Pro Pro Ala Pro
        275                 280                 285

Glu Ala Ala Gly Leu Phe Gln Gly Thr Phe Pro Asp Gly Phe Leu Trp
290                 295                 300

Ala Val Gly Ser Ala Ala Tyr Gln Thr Glu Gly Gly Trp Gln Gln His
305                 310                 315                 320

Gly Lys Gly Ala Ser Ile Trp Asp Thr Phe Thr His His Pro Leu Ala
                325                 330                 335

Pro Pro Gly Asp Ser Arg Asn Ala Ser Leu Pro Leu Gly Ala Pro Ser
            340                 345                 350

Pro Leu Gln Pro Ala Thr Gly Asp Val Ala Ser Asp Ser Tyr Asn Asn
        355                 360                 365

Val Phe Arg Asp Thr Glu Ala Leu Arg Glu Leu Gly Val Thr His Tyr
    370                 375                 380

Arg Phe Ser Ile Ser Trp Ala Arg Val Leu Pro Asn Gly Ser Ala Gly
385                 390                 395                 400

Val Pro Asn Arg Glu Gly Leu Arg Tyr Tyr Arg Arg Leu Leu Glu Arg
                405                 410                 415
```

-continued

```
Leu Arg Glu Leu Gly Val Gln Pro Val Thr Leu Tyr His Trp Asp
            420                 425                 430

Leu Pro Gln Arg Leu Gln Asp Ala Tyr Gly Gly Trp Ala Asn Arg Ala
        435                 440                 445

Leu Ala Asp His Phe Arg Asp Tyr Ala Glu Leu Cys Phe Arg His Phe
    450                 455                 460

Gly Gly Gln Val Lys Tyr Trp Ile Thr Ile Asp Asn Pro Tyr Val Val
465                 470                 475                 480

Ala Trp His Gly Tyr Ala Thr Gly Arg Leu Ala Pro Gly Ile Arg Gly
                485                 490                 495

Ser Pro Arg Leu Gly Tyr Leu Val Ala His Asn Leu Leu Leu Ala His
            500                 505                 510

Ala Lys Val Trp His Leu Tyr Asn Thr Ser Phe Arg Pro Thr Gln Gly
        515                 520                 525

Gly Gln Val Ser Ile Ala Leu Ser Ser His Trp Ile Asn Pro Arg Arg
    530                 535                 540

Met Thr Asp His Ser Ile Lys Glu Cys Gln Lys Ser Leu Asp Phe Val
545                 550                 555                 560

Leu Gly Trp Phe Ala Lys Pro Val Phe Ile Asp Gly Asp Tyr Pro Glu
                565                 570                 575

Ser Met Lys Asn Asn Leu Ser Ser Ile Leu Pro Asp Phe Thr Glu Ser
            580                 585                 590

Glu Lys Lys Phe Ile Lys Gly Thr Ala Asp Phe Phe Ala Leu Cys Phe
        595                 600                 605

Gly Pro Thr Leu Ser Phe Gln Leu Leu Asp Pro His Met Lys Phe Arg
    610                 615                 620

Gln Leu Glu Ser Pro Asn Leu Arg Gln Leu Leu Ser Trp Ile Asp Leu
625                 630                 635                 640

Glu Phe Asn His Pro Gln Ile Phe Ile Val Glu Asn Gly Trp Phe Val
                645                 650                 655

Ser Gly Thr Thr Lys Arg Asp Asp Ala Lys Tyr Met Tyr Tyr Leu Lys
            660                 665                 670

Lys Phe Ile Met Glu Thr Leu Lys Ala Ile Lys Leu Asp Gly Val Asp
        675                 680                 685

Val Ile Gly Tyr Thr Ala Trp Ser Leu Met Asp Gly Phe Glu Trp His
    690                 695                 700

Arg Gly Tyr Ser Ile Arg Arg Gly Leu Phe Tyr Val Asp Phe Leu Ser
705                 710                 715                 720

Gln Asp Lys Met Leu Leu Pro Lys Ser Ser Ala Leu Phe Tyr Gln Lys
                725                 730                 735

Leu Ile Glu Lys Asn Gly Phe Pro Pro Leu Pro Glu Asn Gln Pro Leu
            740                 745                 750

Glu Gly Thr Phe Pro Cys Asp Phe Ala Trp Gly Val Val Asp Asn Tyr
        755                 760                 765

Ile Gln Val Asp Thr Thr Leu Ser Gln Phe Thr Asp Leu Asn Val Tyr
    770                 775                 780

Leu Trp Asp Val His His Ser Lys Arg Leu Ile Lys Val Asp Gly Val
785                 790                 795                 800

Val Thr Lys Lys Arg Lys Ser Tyr Cys Val Asp Phe Ala Ala Ile Gln
                805                 810                 815

Pro Gln Ile Ala Leu Leu Gln Glu Met His Val Thr His Phe Arg Phe
            820                 825                 830

Ser Leu Asp Trp Ala Leu Ile Leu Pro Leu Gly Asn Gln Ser Gln Val
```

```
                    835                 840                 845
Asn His Thr Ile Leu Gln Tyr Tyr Arg Cys Met Ala Ser Glu Leu Val
                    850                 855                 860

Arg Val Asn Ile Thr Pro Val Val Ala Leu Trp Gln Pro Met Ala Pro
865                 870                 875                 880

Asn Gln Gly Leu Pro Arg Leu Leu Ala Arg Gln Gly Ala Trp Glu Asn
                    885                 890                 895

Pro Tyr Thr Ala Leu Ala Phe Ala Glu Tyr Ala Arg Leu Cys Phe Gln
                    900                 905                 910

Glu Leu Gly His His Val Lys Leu Trp Ile Thr Met Asn Glu Pro Tyr
                    915                 920                 925

Thr Arg Asn Met Thr Tyr Ser Ala Gly His Asn Leu Leu Lys Ala His
930                 935                 940

Ala Leu Ala Trp His Val Tyr Asn Glu Lys Phe Arg His Ala Gln Asn
945                 950                 955                 960

Gly Lys Ile Ser Ile Ala Leu Gln Ala Asp Trp Ile Glu Pro Ala Cys
                    965                 970                 975

Pro Phe Ser Gln Lys Asp Lys Glu Val Ala Glu Arg Val Leu Glu Phe
                    980                 985                 990

Asp Ile Gly Trp Leu Ala Glu Pro Ile Phe Gly Ser Gly Asp Tyr Pro
                    995                 1000                1005

Trp Val Met Arg Asp Trp Leu Asn Gln Arg Asn Asn Phe Leu Leu
                1010                1015                1020

Pro Tyr Phe Thr Glu Asp Glu Lys Lys Leu Ile Gln Gly Thr Phe
                1025                1030                1035

Asp Phe Leu Ala Leu Ser His Tyr Thr Thr Ile Leu Val Asp Ser
                1040                1045                1050

Glu Lys Glu Asp Pro Ile Lys Tyr Asn Asp Tyr Leu Glu Val Gln
                1055                1060                1065

Glu Met Thr Asp Ile Thr Trp Leu Asn Ser Pro Ser Gln Val Ala
                1070                1075                1080

Val Val Pro Trp Gly Leu Arg Lys Val Leu Asn Trp Leu Lys Phe
                1085                1090                1095

Lys Tyr Gly Asp Leu Pro Met Tyr Ile Ile Ser Asn Gly Ile Asp
                1100                1105                1110

Asp Gly Leu His Ala Glu Asp Gln Leu Arg Val Tyr Tyr Met
                1115                1120                1125

Gln Asn Tyr Ile Asn Glu Ala Leu Lys Ala His Ile Leu Asp Gly
                1130                1135                1140

Ile Asn Leu Cys Gly Tyr Phe Ala Tyr Ser Phe Asn Asp Arg Thr
                1145                1150                1155

Ala Pro Arg Phe Gly Leu Tyr Arg Tyr Ala Ala Asp Gln Phe Glu
                1160                1165                1170

Pro Lys Ala Ser Met Lys His Tyr Arg Lys Ile Ile Asp Ser Asn
                1175                1180                1185

Gly Phe Pro Gly Pro Glu Thr Leu Glu Arg Phe Cys Pro Glu Glu
                1190                1195                1200

Phe Thr Val Cys Thr Glu Cys Ser Phe Phe His Thr Arg Lys Ser
                1205                1210                1215

Leu

<210> SEQ ID NO 26
<211> LENGTH: 700
```

```
<212> TYPE: PRT
<213> ORGANISM: Artificial
<220> FEATURE:
<223> OTHER INFORMATION: fusion polypeptide

<400> SEQUENCE: 26

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
        355                 360                 365

Arg Leu Leu Glu Arg Leu Arg Glu Leu Gly Val Gln Pro Val Val Thr
    370                 375                 380
```

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
            405                 410                 415

Cys Phe Arg His Phe Gly Gly Gln Val Lys Tyr Trp Ile Thr Ile Asp
            420                 425                 430

Asn Pro Tyr Val Val Ala Trp His Gly Tyr Ala Thr Gly Arg Leu Ala
            435                 440                 445

Pro Gly Ile Arg Gly Ser Pro Arg Leu Gly Tyr Leu Val Ala His Asn
450                 455                 460

Leu Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
            485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
            515                 520                 525

Gly Asp Tyr Pro Glu Ser Met Lys Asn Asn Leu Ser Ser Ile Leu Pro
530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
            565                 570                 575

His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
            595                 600                 605

Asn Gly Trp Phe Val Ser Gly Thr Thr Lys Arg Asp Asp Ala Lys Tyr
            610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
            645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
            675                 680                 685

Leu Phe Tyr Gln Lys Leu Ile Glu Lys Asn Gly Phe
690                 695                 700

<210> SEQ ID NO 27
<211> LENGTH: 688
<212> TYPE: PRT
<213> ORGANISM: Artificial
<220> FEATURE:
<223> OTHER INFORMATION: fusion polypeptide

<400> SEQUENCE: 27

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

```
Asn Ser Tyr His Leu Gln Ile His Lys Asn Gly His Val Asp Gly Ala
 50                  55                  60
Pro His Gln Thr Ile Tyr Ser Ala Leu Met Ile Arg Ser Glu Asp Ala
 65                  70                  75                  80
Gly Phe Val Val Ile Thr Gly Val Met Ser Arg Arg Tyr Leu Cys Met
                     85                  90                  95
Asp Phe Arg Gly Asn Ile Phe Gly Ser His Tyr Phe Asp Pro Glu Asn
                 100                 105                 110
Cys Arg Phe Gln His Gln Thr Leu Glu Asn Gly Tyr Asp Val Tyr His
             115                 120                 125
Ser Pro Gln Tyr His Phe Leu Val Ser Leu Gly Arg Ala Lys Arg Ala
 130                 135                 140
Phe Leu Pro Gly Met Asn Pro Pro Tyr Ser Gln Phe Leu Ser Arg
 145                 150                 155                 160
Arg Asn Glu Ile Pro Leu Ile His Phe Asn Thr Pro Ile Pro Arg Arg
                 165                 170                 175
His Thr Gln Ser Ala Glu Asp Ser Glu Arg Asp Pro Leu Asn Val
             180                 185                 190
Leu Lys Pro Arg Ala Arg Met Thr Pro Ala Pro Ala Ser Cys Ser Gln
         195                 200                 205
Glu Leu Pro Ser Ala Glu Asp Asn Ser Pro Met Ala Ser Asp Pro Leu
 210                 215                 220
Gly Val Val Arg Gly Arg Val Asn Thr His Ala Gly Gly Thr Gly
 225                 230                 235                 240
Pro Glu Gly Cys Arg Pro Phe Ala Lys Phe Ile Gly Thr Phe Pro Cys
                 245                 250                 255
Asp Phe Ala Trp Gly Val Val Asp Asn Tyr Ile Gln Val Asp Thr Thr
             260                 265                 270
Leu Ser Gln Phe Thr Asp Leu Asn Val Tyr Leu Trp Asp Val His His
         275                 280                 285
Ser Lys Arg Leu Ile Lys Val Asp Gly Val Val Thr Lys Lys Arg Lys
 290                 295                 300
Ser Tyr Cys Val Asp Phe Ala Ala Ile Gln Pro Gln Ile Ala Leu Leu
 305                 310                 315                 320
Gln Glu Met His Val Thr His Phe Arg Phe Ser Leu Asp Trp Ala Leu
                 325                 330                 335
Ile Leu Pro Leu Gly Asn Gln Ser Gln Val Asn His Thr Ile Leu Gln
             340                 345                 350
Tyr Tyr Arg Cys Met Ala Ser Glu Leu Val Arg Val Asn Ile Thr Pro
         355                 360                 365
Val Val Ala Leu Trp Gln Pro Met Ala Pro Asn Gln Gly Leu Pro Arg
 370                 375                 380
Leu Leu Ala Arg Gln Gly Ala Trp Glu Asn Pro Tyr Thr Ala Leu Ala
 385                 390                 395                 400
Phe Ala Glu Tyr Ala Arg Leu Cys Phe Gln Glu Leu Gly His His Val
                 405                 410                 415
Lys Leu Trp Ile Thr Met Asn Glu Pro Tyr Thr Arg Asn Met Thr Tyr
             420                 425                 430
Ser Ala Gly His Asn Leu Leu Lys Ala His Ala Leu Ala Trp His Val
         435                 440                 445
Tyr Asn Glu Lys Phe Arg His Ala Gln Asn Gly Lys Ile Ser Ile Ala
 450                 455                 460
Leu Gln Ala Asp Trp Ile Glu Pro Ala Cys Pro Phe Ser Gln Lys Asp
```

```
            465                 470                 475                 480
Lys Glu Val Ala Glu Arg Val Leu Glu Phe Asp Ile Gly Trp Leu Ala
                    485                 490                 495
Glu Pro Ile Phe Gly Ser Gly Asp Tyr Pro Trp Val Met Arg Asp Trp
                500                 505                 510
Leu Asn Gln Arg Asn Asn Phe Leu Pro Tyr Phe Thr Glu Asp Glu
                515                 520                 525
Lys Lys Leu Ile Gln Gly Thr Phe Asp Phe Leu Ala Leu Ser His Tyr
            530                 535                 540
Thr Thr Ile Leu Val Asp Ser Glu Lys Glu Asp Pro Ile Lys Tyr Asn
545                 550                 555                 560
Asp Tyr Leu Glu Val Gln Glu Met Thr Asp Ile Thr Trp Leu Asn Ser
                565                 570                 575
Pro Ser Gln Val Ala Val Val Pro Trp Gly Leu Arg Lys Val Leu Asn
                580                 585                 590
Trp Leu Lys Phe Lys Tyr Gly Asp Leu Pro Met Tyr Ile Ile Ser Asn
            595                 600                 605
Gly Ile Asp Asp Gly Leu His Ala Glu Asp Asp Gln Leu Arg Val Tyr
            610                 615                 620
Tyr Met Gln Asn Tyr Ile Asn Glu Ala Leu Lys Ala His Ile Leu Asp
625                 630                 635                 640
Gly Ile Asn Leu Cys Gly Tyr Phe Ala Tyr Ser Phe Asn Asp Arg Thr
                645                 650                 655
Ala Pro Arg Phe Gly Leu Tyr Arg Tyr Ala Ala Asp Gln Phe Glu Pro
                660                 665                 670
Lys Ala Ser Met Lys His Tyr Arg Lys Ile Ile Asp Ser Asn Gly Phe
                675                 680                 685

<210> SEQ ID NO 28
<211> LENGTH: 1149
<212> TYPE: PRT
<213> ORGANISM: Artificial
<220> FEATURE:
<223> OTHER INFORMATION: fusion polypeptide

<400> SEQUENCE: 28

Met Leu Gly Ala Arg Leu Arg Leu Trp Val Cys Ala Leu Cys Ser Val
1               5                   10                  15
Cys Ser Met Ser Val Leu Arg Ala Tyr Pro Asn Ala Ser Pro Leu Leu
                20                  25                  30
Gly Ser Ser Trp Gly Gly Leu Ile His Leu Tyr Thr Ala Thr Ala Arg
            35                  40                  45
Asn Ser Tyr His Leu Gln Ile His Lys Asn Gly His Val Asp Gly Ala
        50                  55                  60
Pro His Gln Thr Ile Tyr Ser Ala Leu Met Ile Arg Ser Glu Asp Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asp Pro Glu Asn
                100                 105                 110
Cys Arg Phe Gln His Gln Thr Leu Glu Asn Gly Tyr Asp Val Tyr His
            115                 120                 125
Ser Pro Gln Tyr His Phe Leu Val Ser Leu Gly Arg Ala Lys Arg Ala
        130                 135                 140
Phe Leu Pro Gly Met Asn Pro Pro Tyr Ser Gln Phe Leu Ser Arg
```

```
            145                 150                 155                 160
Arg Asn Glu Ile Pro Leu Ile His Phe Asn Thr Pro Ile Pro Arg Arg
                    165                 170                 175

His Thr Gln Ser Ala Glu Asp Asp Ser Glu Arg Asp Pro Leu Asn Val
                    180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
            210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
                260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
        290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
                340                 345                 350

Asn Gly Ser Ala Gly Val Pro Asn Arg Glu Gly Leu Arg Tyr Tyr Arg
            355                 360                 365

Arg Leu Leu Glu Arg Leu Arg Glu Leu Gly Val Gln Pro Val Val Thr
        370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
            420                 425                 430

Asn Pro Tyr Val Val Ala Trp His Gly Tyr Ala Thr Gly Arg Leu Ala
            435                 440                 445

Pro Gly Ile Arg Gly Ser Pro Arg Leu Gly Tyr Leu Val Ala His Asn
        450                 455                 460

Leu Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
                485                 490                 495

Ile Asn Pro Arg Arg Met Thr Asp His Ser Ile Lys Glu Cys Gln Lys
                500                 505                 510

Ser Leu Asp Phe Val Leu Gly Trp Phe Ala Lys Pro Val Phe Ile Asp
            515                 520                 525

Gly Asp Tyr Pro Glu Ser Met Lys Asn Asn Leu Ser Ser Ile Leu Pro
        530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
                565                 570                 575
```

-continued

His Met Lys Phe Arg Gln Leu Glu Ser Pro Asn Leu Arg Gln Leu Leu
                580                 585                 590

Ser Trp Ile Asp Leu Glu Phe Asn His Pro Gln Ile Phe Ile Val Glu
            595                 600                 605

Asn Gly Trp Phe Val Ser Gly Thr Thr Lys Arg Asp Asp Ala Lys Tyr
        610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
        675                 680                 685

Leu Phe Tyr Gln Lys Leu Ile Glu Lys Asn Gly Phe Gln Gly Thr Phe
    690                 695                 700

Pro Asp Gly Phe Leu Trp Ala Val Gly Ser Ala Ala Tyr Gln Thr Glu
705                 710                 715                 720

Gly Gly Trp Gln Gln His Gly Lys Gly Ala Ser Ile Trp Asp Thr Phe
                725                 730                 735

Thr His His Pro Leu Ala Pro Pro Gly Asp Ser Arg Asn Ala Ser Leu
            740                 745                 750

Pro Leu Gly Ala Pro Ser Pro Leu Gln Pro Ala Thr Gly Asp Val Ala
        755                 760                 765

Ser Asp Ser Tyr Asn Asn Val Phe Arg Asp Thr Glu Ala Leu Arg Glu
770                 775                 780

Leu Gly Val Thr His Tyr Arg Phe Ser Ile Ser Trp Ala Arg Val Leu
785                 790                 795                 800

Pro Asn Gly Ser Ala Gly Val Pro Asn Arg Glu Gly Leu Arg Tyr Tyr
                805                 810                 815

Arg Arg Leu Leu Glu Arg Leu Arg Glu Leu Gly Val Gln Pro Val Val
            820                 825                 830

Thr Leu Tyr His Trp Asp Leu Pro Gln Arg Leu Gln Asp Ala Tyr Gly
        835                 840                 845

Gly Trp Ala Asn Arg Ala Leu Ala Asp His Phe Arg Asp Tyr Ala Glu
    850                 855                 860

Leu Cys Phe Arg His Phe Gly Gly Gln Val Lys Tyr Trp Ile Thr Ile
865                 870                 875                 880

Asp Asn Pro Tyr Val Val Ala Trp His Gly Tyr Ala Thr Gly Arg Leu
                885                 890                 895

Ala Pro Gly Ile Arg Gly Ser Pro Arg Leu Gly Tyr Leu Val Ala His
            900                 905                 910

Asn Leu Leu Leu Ala His Ala Lys Val Trp His Leu Tyr Asn Thr Ser
        915                 920                 925

Phe Arg Pro Thr Gln Gly Gly Gln Val Ser Ile Ala Leu Ser Ser His
    930                 935                 940

Trp Ile Asn Pro Arg Arg Met Thr Asp His Ser Ile Lys Glu Cys Gln
945                 950                 955                 960

Lys Ser Leu Asp Phe Val Leu Gly Trp Phe Ala Lys Pro Val Phe Ile
                965                 970                 975

Asp Gly Asp Tyr Pro Glu Ser Met Lys Asn Asn Leu Ser Ser Ile Leu
            980                 985                 990

```
Pro Asp Phe Thr Glu Ser Glu Lys Lys Phe Ile Lys Gly Thr Ala Asp
        995                 1000                1005

Phe Phe Ala Leu Cys Phe Gly Pro Thr Leu Ser Phe Gln Leu Leu
    1010                1015                1020

Asp Pro His Met Lys Phe Arg Gln Leu Glu Ser Pro Asn Leu Arg
    1025                1030                1035

Gln Leu Leu Ser Trp Ile Asp Leu Glu Phe Asn His Pro Gln Ile
    1040                1045                1050

Phe Ile Val Glu Asn Gly Trp Phe Val Ser Gly Thr Thr Lys Arg
    1055                1060                1065

Asp Asp Ala Lys Tyr Met Tyr Tyr Leu Lys Lys Phe Ile Met Glu
    1070                1075                1080

Thr Leu Lys Ala Ile Lys Leu Asp Gly Val Asp Val Ile Gly Tyr
    1085                1090                1095

Thr Ala Trp Ser Leu Met Asp Gly Phe Glu Trp His Arg Gly Tyr
    1100                1105                1110

Ser Ile Arg Arg Gly Leu Phe Tyr Val Asp Phe Leu Ser Gln Asp
    1115                1120                1125

Lys Met Leu Leu Pro Lys Ser Ser Ala Leu Phe Tyr Gln Lys Leu
    1130                1135                1140

Ile Glu Lys Asn Gly Phe
    1145

<210> SEQ ID NO 29
<211> LENGTH: 1125
<212> TYPE: PRT
<213> ORGANISM: Artificial
<220> FEATURE:
<223> OTHER INFORMATION: fusion polypeptide

<400> SEQUENCE: 29

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190
```

-continued

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                245                 250                 255

Asp Phe Ala Trp Gly Val Val Asp Asn Tyr Ile Gln Val Asp Thr Thr
            260                 265                 270

Leu Ser Gln Phe Thr Asp Leu Asn Val Tyr Leu Trp Asp Val His His
    275                 280                 285

Ser Lys Arg Leu Ile Lys Val Asp Gly Val Val Thr Lys Lys Arg Lys
290                 295                 300

Ser Tyr Cys Val Asp Phe Ala Ala Ile Gln Pro Gln Ile Ala Leu Leu
305                 310                 315                 320

Gln Glu Met His Val Thr His Phe Arg Phe Ser Leu Asp Trp Ala Leu
                325                 330                 335

Ile Leu Pro Leu Gly Asn Gln Ser Gln Val Asn His Thr Ile Leu Gln
            340                 345                 350

Tyr Tyr Arg Cys Met Ala Ser Glu Leu Val Arg Val Asn Ile Thr Pro
    355                 360                 365

Val Val Ala Leu Trp Gln Pro Met Ala Pro Asn Gln Gly Leu Pro Arg
370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                405                 410                 415

Lys Leu Trp Ile Thr Met Asn Glu Pro Tyr Thr Arg Asn Met Thr Tyr
            420                 425                 430

Ser Ala Gly His Asn Leu Leu Lys Ala His Ala Leu Ala Trp His Val
    435                 440                 445

Tyr Asn Glu Lys Phe Arg His Ala Gln Asn Gly Lys Ile Ser Ile Ala
450                 455                 460

Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                485                 490                 495

Glu Pro Ile Phe Gly Ser Gly Asp Tyr Pro Trp Val Met Arg Asp Trp
            500                 505                 510

Leu Asn Gln Arg Asn Asn Phe Leu Leu Pro Tyr Phe Thr Glu Asp Glu
    515                 520                 525

Lys Lys Leu Ile Gln Gly Thr Phe Asp Phe Leu Ala Leu Ser His Tyr
530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Pro Trp Gly Leu Arg Lys Val Leu Asn
            580                 585                 590

Trp Leu Lys Phe Lys Tyr Gly Asp Leu Pro Met Tyr Ile Ile Ser Asn
    595                 600                 605

Gly Ile Asp Asp Gly Leu His Ala Glu Asp Asp Gln Leu Arg Val Tyr

-continued

```
            610                 615                 620
Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                645                 650                 655

Ala Pro Arg Phe Gly Leu Tyr Arg Tyr Ala Ala Asp Gln Phe Glu Pro
            660                 665                 670

Lys Ala Ser Met Lys His Tyr Arg Lys Ile Ile Asp Ser Asn Gly Phe
            675                 680                 685

Gly Thr Phe Pro Cys Asp Phe Ala Trp Gly Val Val Asp Asn Tyr Ile
            690                 695                 700

Gln Val Asp Thr Thr Leu Ser Gln Phe Thr Asp Leu Asn Val Tyr Leu
705                 710                 715                 720

Trp Asp Val His His Ser Lys Arg Leu Ile Lys Val Asp Gly Val Val
                725                 730                 735

Thr Lys Lys Arg Lys Ser Tyr Cys Val Asp Phe Ala Ala Ile Gln Pro
            740                 745                 750

Gln Ile Ala Leu Leu Gln Glu Met His Val Thr His Phe Arg Phe Ser
            755                 760                 765

Leu Asp Trp Ala Leu Ile Leu Pro Leu Gly Asn Gln Ser Gln Val Asn
770                 775                 780

His Thr Ile Leu Gln Tyr Tyr Arg Cys Met Ala Ser Glu Leu Val Arg
785                 790                 795                 800

Val Asn Ile Thr Pro Val Val Ala Leu Trp Gln Pro Met Ala Pro Asn
            805                 810                 815

Gln Gly Leu Pro Arg Leu Leu Ala Arg Gln Gly Ala Trp Glu Asn Pro
            820                 825                 830

Tyr Thr Ala Leu Ala Phe Ala Glu Tyr Ala Arg Leu Cys Phe Gln Glu
            835                 840                 845

Leu Gly His His Val Lys Leu Trp Ile Thr Met Asn Glu Pro Tyr Thr
            850                 855                 860

Arg Asn Met Thr Tyr Ser Ala Gly His Asn Leu Leu Lys Ala His Ala
865                 870                 875                 880

Leu Ala Trp His Val Tyr Asn Glu Lys Phe Arg His Ala Gln Asn Gly
                885                 890                 895

Lys Ile Ser Ile Ala Leu Gln Ala Asp Trp Ile Glu Pro Ala Cys Pro
            900                 905                 910

Phe Ser Gln Lys Asp Lys Glu Val Ala Glu Arg Val Leu Glu Phe Asp
            915                 920                 925

Ile Gly Trp Leu Ala Glu Pro Ile Phe Gly Ser Gly Asp Tyr Pro Trp
            930                 935                 940

Val Met Arg Asp Trp Leu Asn Gln Arg Asn Asn Phe Leu Leu Pro Tyr
945                 950                 955                 960

Phe Thr Glu Asp Glu Lys Lys Leu Ile Gln Gly Thr Phe Asp Phe Leu
            965                 970                 975

Ala Leu Ser His Tyr Thr Thr Ile Leu Val Asp Ser Glu Lys Glu Asp
                980                 985                 990

Pro Ile Lys Tyr Asn Asp Tyr Leu Glu Val Gln Glu Met Thr Asp Ile
            995                 1000                1005

Thr Trp Leu Asn Ser Pro Ser Gln Val Ala Val Val Pro Trp Gly
            1010                1015                1020

Leu Arg Lys Val Leu Asn Trp Leu Lys Phe Lys Tyr Gly Asp Leu
            1025                1030                1035
```

```
Pro Met Tyr Ile Ile Ser Asn Gly Ile Asp Asp Gly Leu His Ala
    1040            1045                1050

Glu Asp Asp Gln Leu Arg Val Tyr Tyr Met Gln Asn Tyr Ile Asn
    1055            1060                1065

Glu Ala Leu Lys Ala His Ile Leu Asp Gly Ile Asn Leu Cys Gly
    1070            1075                1080

Tyr Phe Ala Tyr Ser Phe Asn Asp Arg Thr Ala Pro Arg Phe Gly
    1085            1090                1095

Leu Tyr Arg Tyr Ala Ala Asp Gln Phe Glu Pro Lys Ala Ser Met
    1100            1105                1110

Lys His Tyr Arg Lys Ile Ile Asp Ser Asn Gly Phe
    1115            1120                1125

<210> SEQ ID NO 30
<211> LENGTH: 2157
<212> TYPE: DNA
<213> ORGANISM: Homo sapiens

<400> SEQUENCE: 30
gctcccagcc aagaacctcg gggccgctgc gcggtgggga ggagttcccc gaaacccggc      60
cgctaagcga ggcctcctcc tcccgcagat ccgaacggcc tgggcggggt caccccggct     120
gggacaagaa gccgccgcct gcctgccagg gccggggag ggggctgggg ctggggccgg      180
aggcggggtg tgagtgggtg tgtgcggggg gcggaggctt gatgcaatcc cgataagaaa    240
tgctcgggtc tcttgggcac ctacccgtgg ggcccgtaag gcgctactat ataaggctgc    300
cggcccggag ccgccgcgcc gtcagagcag gagcgctgcg tccaggatct agggccacga    360
ccatcccaac ccggcactca cagccccgca gcgcatcccg gtcgccgccc agcctcccgc    420 accccatcg ccggagctgc gccgagagcc ccagggaggt gccatgcgga gcgggtgtgt      480
ggtggtccac gtatggatcc tggccggcct ctggctggcc gtggccgggc gcccctcgc     540 cttctcggac gcggggcccc acgtgcacta cggctggggc gaccccatcc gcctgcggca    600
cctgtacacc tccggccccc acgggctctc cagctgcttc ctgcgcatcc gtgccgacgg    660
cgtcgtggac tgcgcgcggg gccagagcgc gcacagtttg ctggagatca aggcagtcgc    720
tctgcggacc gtggccatca agggcgtgca cagcgtgcgg tacctctgca tgggcgccga    780
cggcaagatg caggggctgc ttcagtactc ggaggaagac tgtgctttcg aggaggagat    840
ccgcccagat ggctacaatg tgtaccgatc cgagaagcac cgcctcccgg tctccctgag    900
cagtgccaaa cagcggcagc tgtacaagaa cagaggcttt cttccactct ctcatttcct    960
gcccatgctg cccatggtcc cagaggagcc tgaggacctc aggggccact ggaatctga   1020 catgttctct tcgcccctgg agaccgacag catggaccca tttgggcttg tcaccggact   1080
ggaggccgtg aggagtccca gctttgagaa gtaactgaga ccatgcccgg gcctcttcac   1140
tgctgccagg gctgtggta cctgcagcgt ggggacgtg cttctacaag aacagtcctg     1200
agtccacgtt ctgtttagct ttaggaagaa acatctagaa gttgtacata ttcagagttt    1260
tccattggca gtgccagttt ctagccaata gacttgtctg atcataacat tgtaagcctg    1320
tagcttgccc agctgctgcc tgggccccca ttctgctccc tcgaggttgc tggacaagct    1380
gctgcactgt ctcagttctg cttgaatacc tccatcgatg gggaactcac ttcctttgga   1440
aaaattctta tgtcaagctg aaattctcta atttttctc atcacttccc caggagcagc    1500
cagaagacag gcagtagttt taatttcagg aacaggtgat ccactctgta aaacagcagg   1560
```

```
taaatttcac tcaaccccat gtgggaattg atctatatct ctacttccag ggaccatttg    1620
cccttcccaa atccctccag gccagaactg actggagcag gcatggccca ccaggcttca    1680
ggagtagggg aagcctggag ccccactcca gccctgggac aacttgagaa ttccccctga    1740
ggccagttct gtcatggatg ctgtcctgag aataacttgc tgtcccggtg tcacctgctt    1800
ccatctccca gcccaccagc cctctgccca cctcacatgc ctccccatgg attggggcct    1860
cccaggcccc ccaccttatg tcaacctgca cttcttgttc aaaaatcagg aaaagaaaag    1920
atttgaagac cccaagtctt gtcaataact tgctgtgtgg aagcagcggg ggaagaccta    1980 gaacccttc cccagcactt ggttttccaa catgatattt atgagtaatt tattttgata    2040
tgtacatctc ttattttctt acattattta tgcccccaaa ttatatttat gtatgtaagt    2100
gaggtttgtt ttgtatatta aatggagtt tgtttgtaaa aaaaaaaaaa aaaaaaa       2157
```

<210> SEQ ID NO 31
<211> LENGTH: 216
<212> TYPE: PRT
<213> ORGANISM: Homo sapiens

<400> SEQUENCE: 31

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 32
<211> LENGTH: 940
<212> TYPE: DNA
<213> ORGANISM: Homo sapiens

<400> SEQUENCE: 32

```
ctgtcagctg aggatccagc cgaaagagga gccaggcact caggccacct gagtctactc    60
```

```
acctggacaa ctggaatctg gcaccaattc taaaccactc agcttctccg agctcacacc    120
ccggagatca cctgaggacc cgagccattg atggactcgg acgagaccgg gttcgagcac    180
tcaggactgt gggtttctgt gctggctggt cttctgctgg gagcctgcca ggcacacccc    240
atccctgact ccagtcctct cctgcaattc gggggccaag tccggcagcg gtacctctac    300
acagatgatg cccagcagac agaagcccac ctggagatca gggaggatgg gacggtgggg    360
ggcgctgctg accagagccc cgaaagtctc ctgcagctga aagccttgaa gccgggagtt    420
attcaaatct tgggagtcaa gacatccagg ttcctgtgcc agcggccaga tggggccctg    480
tatggatcgc tccactttga ccctgaggcc tgcagcttcc gggagctgct tcttgaggac    540
ggatacaatg tttaccagtc cgaagcccac ggcctcccgc tgcacctgcc agggaacaag    600
tccccacacc gggaccctgc acccgagga ccagctcgct tcctgccact accaggcctg     660 cccccgcac tcccggagcc accggaatc ctggccccc agcccccga tgtgggctcc         720 tcggacctc tgagcatggt gggaccttcc cagggccgaa gccccagcta cgcttcctga    780
agccagaggc tgtttactat gacatctcct ctttatttat taggttattt atcttattta    840
tttttttatt tttcttactt gagataataa agagttccag aggagaaaaa aaaaaaaaa     900 aaaaaaaaa aaaaaaaaa aaaaaaaaa aaaaaaaaa                               940
```

<210> SEQ ID NO 33
<211> LENGTH: 209
<212> TYPE: PRT
<213> ORGANISM: Homo sapiens

<400> SEQUENCE: 33

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 34
<211> LENGTH: 3018
<212> TYPE: DNA
<213> ORGANISM: Homo sapiens

<400> SEQUENCE: 34

```
cggcaaaaag gagggaatcc agtctaggat cctcacacca gctacttgca agggagaagg      60
aaaaggccag taaggcctgg gccaggagag tcccgacagg agtgtcaggt ttcaatctca     120
gcaccagcca ctcagagcag ggcacgatgt tgggggcccg cctcaggctc tgggtctgtg     180
ccttgtgcag cgtctgcagc atgagcgtcc tcagagccta tcccaatgcc tccccactgc     240
tcggctccag ctggggtggc ctgatccacc tgtacacagc cacagccagg aacagctacc     300
acctgcagat ccacaagaat ggccatgtgg atggcgcacc ccatcagacc atctacagtg     360
ccctgatgat cagatcagag gatgctggct tgtggtgat acaggtgtg atgagcagaa       420
gatacctctg catggatttc agaggcaaca ttttttggatc acactatttc gacccggaga     480
actgcaggtt ccaacaccag acgctggaaa acgggtacga cgtctaccac tctcctcagt     540
atcacttcct ggtcagtctg gccgggcga agagagcctt cctgccaggc atgaacccac     600
ccccgtactc ccagttcctg tcccggagga acgagatccc cctaattcac ttcaacaccc     660
ccataccacg gcggcacacc cggagcgcgc aggacgactc ggagcgggac ccctgaacg      720
tgctgaagcc ccgggcccgg atgacccgg ccccggcctc ctgttcacag gagctcccga     780
gcgccgagga caacagcccg atggccagtg acccattagg ggtggtcagg ggcggtcgag     840
tgaacacgca cgctggggga acgggcccgg aaggctgccg ccccttcgcc aagttcatct     900
agggtcgctg gaagggcacc ctctttaacc catccctcag caaacgcagc tcttcccaag     960
gaccaggtcc cttgacgttc cgaggatggg aaaggtgaca ggggcatgta tggaatttgc    1020
tgcttctctg gggtccttc cacaggaggt cctgtgagaa ccaacctttg aggcccaagt    1080
catggggttt caccgccttc ctcactccat atagaacacc tttcccaata ggaaacccca    1140
acaggtaaac tagaaatttc cccttcatga aggtagagag aagggggtctc tcccaacata    1200
tttctcttcc ttgtgcctct cctctttatc acttttaagc ataaaaaaaa aaaaaaaaa    1260
aaaaaaaaa aaaagcagtg ggttcctgag ctcaagactt tgaaggtgta gggaagagga    1320
aatcggagat cccagaagct tctccactgc cctatgcatt tatgttagat gccccgatcc    1380
cactggcatt tgagtgtgca aaccttgaca ttaacagctg aatggggcaa gttgatgaaa    1440
acactacttt caagccttcg ttcttccttg agcatctctg ggaagagct gtcaaaagac    1500
tggtggtagg ctggtgaaaa cttgacagct agacttgatg cttgctgaaa tgaggcagga    1560
atcataatag aaaactcagc ctccctacag ggtgagcacc ttctgtctcg ctgtctccct    1620
ctgtgcagcc acagccagag ggccagaat ggccccactc tgttcccaag cagttcatga    1680
tacagcctca cctttggcc ccatctctgg tttttgaaaa tttggtctaa ggaataaata    1740
gcttttacac tggctcacga aaatctgccc tgctagaatt gcttttcaa aatgggaaata    1800
aattccaact ctcctaagag gcatttaatt aaggctctac ttccaggttg agtaggaatc    1860
cattctgaac aaactacaaa aatgtgactg ggaaggggc tttgagagac tgggactgct    1920
ctggggttagg ttttctgtgg actgaaaaat cgtgtccttt tctctaaatg aagtggcatc    1980
aaggactcag ggggaaagaa atcaggggac atgttataga agttatgaaa agacaaccac    2040
atggtcaggc tcttgtctgt ggtctctagg gctctgcagc agcagtggct cttcgattag    2100
```

```
ttaaaactct cctaggctga cacatctggg tctcaatccc cttggaaatt cttggtgcat    2160
taaatgaagc cttaccccat tactgcggtt cttcctgtaa gggggctcca ttttcctccc    2220 tctcttttaaa tgaccaccta aggacagta tattaacaag caaagtcgat tcaacaacag    2280
cttcttccca gtcactttt tttttctcac tgccatcaca tactaacctt atactttgat    2340
ctattctttt tggttatgag agaaatgttg ggcaactgtt tttacctgat ggttttaagc    2400
tgaacttgaa ggactggttc ctattctgaa acagtaaaac tatgtataat agtatatagc    2460
catgcatggc aaatatttta atatttctgt tttcatttcc tgttggaaat attatcctgc    2520
ataatagcta ttggaggctc ctcagtgaaa gatcccaaaa ggattttggt ggaaaactag    2580
ttgtaatctc acaaactcaa cactaccatc agggg ttttc tttatggcaa agccaaaata    2640
gctcctacaa tttcttatat ccctcgtcat gtggcagtat ttatttattt atttggaagt    2700
ttgcctatcc ttctatattt atagatattt ataaaaatgt aaccccttt t cctttcttc    2760 tgtttaaaat aaaaataaaa tttatctcag cttctgttag cttatcctct ttgtagtact    2820
acttaaaagc atgtcggaat ataagaataa aaaggattat gggaggggaa cattagggaa    2880
atccagagaa ggcaaaattg aaaaaaagat tttagaattt taaaattttc aaagatttct    2940
tccattcata aggagactca atgattttaa ttgatctaga cagaattatt taagttttat    3000
caatattgga tttctggt                                                  3018
```

<210> SEQ ID NO 35
<211> LENGTH: 251
<212> TYPE: PRT
<213> ORGANISM: Homo sapiens

<400> SEQUENCE: 35

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205
```

```
Glu Leu Pro Ser Ala Glu Asp Asn Ser Pro Met Ala Ser Asp Pro Leu
        210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 36
<211> LENGTH: 251
<212> TYPE: PRT
<213> ORGANISM: Artificial
<220> FEATURE:
<223> OTHER INFORMATION: fusion polypeptide

<400> SEQUENCE: 36

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 37
<211> LENGTH: 431
<212> TYPE: PRT
<213> ORGANISM: Homo sapiens

<400> SEQUENCE: 37

Tyr Asp Thr Phe Pro Lys Asn Phe Phe Trp Gly Ile Gly Thr Gly Ala
1               5                   10                  15

Leu Gln Val Glu Gly Ser Trp Lys Lys Asp Gly Lys Gly Pro Ser Ile
```

```
                     20                  25                  30
Trp Asp His Phe Ile His Thr His Leu Lys Asn Val Ser Ser Thr Asn
                 35                  40                  45
Gly Ser Ser Asp Ser Tyr Ile Phe Leu Glu Lys Asp Leu Ser Ala Leu
             50                  55                  60
Asp Phe Ile Gly Val Ser Phe Tyr Gln Phe Ser Ile Ser Trp Pro Arg
 65                  70                  75                  80
Leu Phe Pro Asp Gly Ile Val Thr Val Ala Asn Ala Lys Gly Leu Gln
                 85                  90                  95
Tyr Tyr Ser Thr Leu Leu Asp Ala Leu Val Leu Arg Asn Ile Glu Pro
            100                 105                 110
Ile Val Thr Leu Tyr His Trp Asp Leu Pro Leu Ala Leu Gln Glu Lys
            115                 120                 125
Tyr Gly Gly Trp Lys Asn Asp Thr Ile Ile Asp Ile Phe Asn Asp Tyr
            130                 135                 140
Ala Thr Tyr Cys Phe Gln Met Phe Gly Asp Arg Val Lys Tyr Trp Ile
145                 150                 155                 160
Thr Ile His Asn Pro Tyr Leu Val Ala Trp His Gly Tyr Gly Thr Gly
                165                 170                 175
Met His Ala Pro Gly Glu Lys Gly Asn Leu Ala Ala Val Tyr Thr Val
            180                 185                 190
Gly His Asn Leu Ile Lys Ala His Ser Lys Val Trp His Asn Tyr Asn
            195                 200                 205
Thr His Phe Arg Pro His Gln Lys Gly Trp Leu Ser Ile Thr Leu Gly
            210                 215                 220
Ser His Trp Ile Glu Pro Asn Arg Ser Glu Asn Thr Met Asp Ile Phe
225                 230                 235                 240
Lys Cys Gln Gln Ser Met Val Ser Val Leu Gly Trp Phe Ala Asn Pro
                245                 250                 255
Ile His Gly Asp Gly Asp Tyr Pro Glu Gly Met Arg Lys Lys Leu Phe
            260                 265                 270
Ser Val Leu Pro Ile Phe Ser Glu Ala Glu Lys His Glu Met Arg Gly
            275                 280                 285
Thr Ala Asp Phe Phe Ala Phe Ser Phe Gly Pro Asn Asn Phe Lys Pro
            290                 295                 300
Leu Asn Thr Met Ala Lys Met Gly Gln Asn Val Ser Leu Asn Leu Arg
305                 310                 315                 320
Glu Ala Leu Asn Trp Ile Lys Leu Glu Tyr Asn Asn Pro Arg Ile Leu
                325                 330                 335
Ile Ala Glu Asn Gly Trp Phe Thr Asp Ser Arg Val Lys Thr Glu Asp
            340                 345                 350
Thr Thr Ala Ile Tyr Met Met Lys Asn Phe Leu Ser Gln Val Leu Gln
            355                 360                 365
Ala Ile Arg Leu Asp Glu Ile Arg Val Phe Gly Tyr Thr Ala Trp Ser
            370                 375                 380
Leu Leu Asp Gly Phe Glu Trp Gln Asp Ala Tyr Thr Ile Arg Arg Gly
385                 390                 395                 400
Leu Phe Tyr Val Asp Phe Asn Ser Lys Gln Lys Glu Arg Lys Pro Lys
                405                 410                 415
Ser Ser Ala His Tyr Tyr Lys Gln Ile Ile Arg Glu Asn Gly Phe
            420                 425                 430

<210> SEQ ID NO 38
```

```
<211> LENGTH: 397
<212> TYPE: PRT
<213> ORGANISM: Homo sapiens

<400> SEQUENCE: 38

Thr Arg Pro Ala Gln Cys Thr Asp Phe Val Asn Ile Lys Lys Gln Leu
1               5                   10                  15

Glu Met Leu Ala Arg Met Lys Val Thr His Tyr Arg Phe Ala Leu Asp
            20                  25                  30

Trp Ala Ser Val Leu Pro Thr Gly Asn Leu Ser Ala Val Asn Arg Gln
        35                  40                  45

Ala Leu Arg Tyr Tyr Arg Cys Val Val Ser Glu Gly Leu Lys Leu Gly
    50                  55                  60

Ile Ser Ala Met Val Thr Leu Tyr Tyr Pro Thr His Ala His Leu Gly
65                  70                  75                  80

Leu Pro Glu Pro Leu Leu His Ala Asp Gly Trp Leu Asn Pro Ser Thr
                85                  90                  95

Ala Glu Ala Phe Gln Ala Tyr Ala Gly Leu Cys Phe Gln Glu Leu Gly
            100                 105                 110

Asp Leu Val Lys Leu Trp Ile Thr Ile Asn Glu Pro Asn Arg Leu Ser
        115                 120                 125

Asp Ile Tyr Asn Arg Ser Gly Asn Asp Thr Tyr Gly Ala Ala His Asn
    130                 135                 140

Leu Leu Val Ala His Ala Leu Ala Trp Arg Leu Tyr Asp Arg Gln Phe
145                 150                 155                 160

Arg Pro Ser Gln Arg Gly Ala Val Ser Leu Ser Leu His Ala Asp Trp
                165                 170                 175

Ala Glu Pro Ala Asn Pro Tyr Ala Asp Ser His Trp Arg Ala Ala Glu
            180                 185                 190

Arg Phe Leu Gln Phe Glu Ile Ala Trp Phe Ala Glu Pro Leu Phe Lys
        195                 200                 205

Thr Gly Asp Tyr Pro Ala Ala Met Arg Glu Tyr Ile Ala Ser Lys His
    210                 215                 220

Arg Arg Gly Leu Ser Ser Ser Ala Leu Pro Arg Leu Thr Glu Ala Glu
225                 230                 235                 240

Arg Arg Leu Leu Lys Gly Thr Val Asp Phe Cys Ala Leu Asn His Phe
                245                 250                 255

Thr Thr Arg Phe Val Met His Glu Gln Leu Ala Gly Ser Arg Tyr Asp
            260                 265                 270

Ser Asp Arg Asp Ile Gln Phe Leu Gln Asp Ile Thr Arg Leu Ser Ser
        275                 280                 285

Pro Thr Arg Leu Ala Val Ile Pro Trp Gly Val Arg Lys Leu Leu Arg
    290                 295                 300

Trp Val Arg Arg Asn Tyr Gly Asp Met Asp Ile Tyr Ile Thr Ala Ser
305                 310                 315                 320

Gly Ile Asp Asp Gln Ala Leu Glu Asp Asp Arg Leu Arg Lys Tyr Tyr
                325                 330                 335

Leu Gly Lys Tyr Leu Gln Glu Val Leu Lys Ala Tyr Leu Ile Asp Lys
            340                 345                 350

Val Arg Ile Lys Gly Tyr Tyr Ala Phe Lys Leu Ala Glu Glu Lys Ser
        355                 360                 365

Lys Pro Arg Phe Gly Phe Phe Thr Ser Asp Phe Lys Ala Lys Ser Ser
    370                 375                 380

Ile Gln Phe Tyr Asn Lys Val Ile Ser Ser Arg Gly Phe
```

```
385                 390                 395
```

<210> SEQ ID NO 39
<211> LENGTH: 946
<212> TYPE: PRT
<213> ORGANISM: Homo sapiens

<400> SEQUENCE: 39

```
Gly Phe Ser Gly Asp Gly Arg Ala Ile Trp Ser Lys Asn Pro Asn Phe
1               5                   10                  15

Thr Pro Val Asn Glu Ser Gln Leu Phe Leu Tyr Asp Thr Phe Pro Lys
            20                  25                  30

Asn Phe Phe Trp Gly Ile Gly Thr Gly Ala Leu Gln Val Glu Gly Ser
        35                  40                  45

Trp Lys Lys Asp Gly Lys Gly Pro Ser Ile Trp Asp His Phe Ile His
    50                  55                  60

Thr His Leu Lys Asn Val Ser Ser Thr Asn Gly Ser Ser Asp Ser Tyr
65                  70                  75                  80

Ile Phe Leu Glu Lys Asp Leu Ser Ala Leu Asp Phe Ile Gly Val Ser
                85                  90                  95

Phe Tyr Gln Phe Ser Ile Ser Trp Pro Arg Leu Phe Pro Asp Gly Ile
            100                 105                 110

Val Thr Val Ala Asn Ala Lys Gly Leu Gln Tyr Tyr Ser Thr Leu Leu
        115                 120                 125

Asp Ala Leu Val Leu Arg Asn Ile Glu Pro Ile Val Thr Leu Tyr His
    130                 135                 140

Trp Asp Leu Pro Leu Ala Leu Gln Glu Lys Tyr Gly Gly Trp Lys Asn
145                 150                 155                 160

Asp Thr Ile Ile Asp Ile Phe Asn Asp Tyr Ala Thr Tyr Cys Phe Gln
                165                 170                 175

Met Phe Gly Asp Arg Val Lys Tyr Trp Ile Thr Ile His Asn Pro Tyr
            180                 185                 190

Leu Val Ala Trp His Gly Tyr Gly Thr Gly Met His Ala Pro Gly Glu
        195                 200                 205

Lys Gly Asn Leu Ala Ala Val Tyr Thr Val Gly His Asn Leu Ile Lys
    210                 215                 220

Ala His Ser Lys Val Trp His Asn Tyr Asn Thr His Phe Arg Pro His
225                 230                 235                 240

Gln Lys Gly Trp Leu Ser Ile Thr Leu Gly Ser His Trp Ile Glu Pro
                245                 250                 255

Asn Arg Ser Glu Asn Thr Met Asp Ile Phe Lys Cys Gln Gln Ser Met
            260                 265                 270

Val Ser Val Leu Gly Trp Phe Ala Asn Pro Ile His Gly Asp Gly Asp
        275                 280                 285

Tyr Pro Glu Gly Met Arg Lys Lys Leu Phe Ser Val Leu Pro Ile Phe
    290                 295                 300

Ser Glu Ala Glu Lys His Glu Met Arg Gly Thr Ala Asp Phe Phe Ala
305                 310                 315                 320

Phe Ser Phe Gly Pro Asn Asn Phe Lys Pro Leu Asn Thr Met Ala Lys
                325                 330                 335

Met Gly Gln Asn Val Ser Leu Asn Leu Arg Glu Ala Leu Asn Trp Ile
            340                 345                 350

Lys Leu Glu Tyr Asn Asn Pro Arg Ile Leu Ile Ala Gly Asn Gly Trp
        355                 360                 365
```

```
Phe Thr Asp Ser Arg Val Lys Thr Glu Asp Thr Thr Ala Ile Tyr Met
    370             375                 380

Met Lys Asn Phe Leu Ser Gln Val Leu Gln Ala Ile Arg Leu Asp Glu
385             390                 395                 400

Ile Arg Val Phe Gly Tyr Thr Ala Trp Ser Leu Leu Asp Gly Phe Glu
            405                 410                 415

Trp Gln Asp Ala Tyr Thr Ile Arg Arg Gly Leu Phe Tyr Val Asp Phe
            420                 425                 430

Asn Ser Lys Gln Lys Glu Arg Pro Lys Ser Ser Ala His Tyr Tyr
        435                 440                 445

Lys Gln Ile Ile Arg Glu Asn Gly Phe Ser Leu Lys Glu Ser Thr Pro
450                 455                 460

Asp Val Gln Gly Gln Phe Pro Cys Asp Phe Ser Trp Gly Val Thr Glu
465                 470                 475                 480

Ser Val Leu Lys Pro Glu Ser Val Ala Ser Pro Gln Phe Ser Asp
                485                 490                 495

Pro His Leu Tyr Val Trp Asn Ala Thr Gly Asn Arg Leu Leu His Arg
            500                 505                 510

Val Glu Gly Val Arg Leu Lys Thr Arg Pro Ala Gln Cys Thr Asp Phe
            515                 520                 525

Val Asn Ile Lys Lys Gln Leu Glu Met Leu Ala Arg Met Lys Val Thr
        530                 535                 540

His Tyr Arg Phe Ala Leu Asp Trp Ala Ser Val Leu Pro Thr Gly Asn
545                 550                 555                 560

Leu Ser Ala Val Asn Arg Gln Ala Leu Arg Tyr Tyr Arg Cys Val Val
                565                 570                 575

Ser Glu Gly Leu Lys Leu Gly Ile Ser Ala Met Val Thr Leu Tyr Tyr
            580                 585                 590

Pro Thr His Ala His Leu Gly Leu Pro Glu Pro Leu Leu His Ala Asp
        595                 600                 605

Gly Trp Leu Asn Pro Ser Thr Ala Glu Ala Phe Gln Ala Tyr Ala Gly
    610                 615                 620

Leu Cys Phe Gln Glu Leu Gly Asp Leu Val Lys Leu Trp Ile Thr Ile
625                 630                 635                 640

Asn Glu Pro Asn Arg Leu Ser Asp Ile Tyr Asn Arg Ser Gly Asn Asp
                645                 650                 655

Thr Tyr Gly Ala Ala His Asn Leu Leu Val Ala His Ala Leu Ala Trp
            660                 665                 670

Arg Leu Tyr Asp Arg Gln Phe Arg Pro Ser Gln Arg Gly Ala Val Ser
        675                 680                 685

Leu Ser Leu His Ala Asp Trp Ala Glu Pro Ala Asn Pro Tyr Ala Asp
690                 695                 700

Ser His Trp Arg Ala Ala Glu Arg Phe Leu Gln Phe Glu Ile Ala Trp
705                 710                 715                 720

Phe Ala Glu Pro Leu Phe Lys Thr Gly Asp Tyr Pro Ala Ala Met Arg
                725                 730                 735

Glu Tyr Ile Ala Ser Lys His Arg Arg Gly Leu Ser Ser Ser Ala Leu
            740                 745                 750

Pro Arg Leu Thr Glu Ala Glu Arg Leu Leu Lys Gly Thr Val Asp
        755                 760                 765

Phe Cys Ala Leu Asn His Phe Thr Thr Arg Phe Val Met His Glu Gln
770                 775                 780

Leu Ala Gly Ser Arg Tyr Asp Ser Asp Arg Asp Ile Gln Phe Leu Gln
```

```
                785                 790                 795                 800
Asp Ile Thr Arg Leu Ser Ser Pro Thr Arg Leu Ala Val Ile Pro Trp
                    805                 810                 815

Gly Val Arg Lys Leu Leu Arg Trp Val Arg Asn Tyr Gly Asp Met
                820                 825                 830

Asp Ile Tyr Ile Thr Ala Ser Gly Ile Asp Asp Gln Ala Leu Glu Asp
                    835                 840                 845

Asp Arg Leu Arg Lys Tyr Tyr Leu Gly Lys Tyr Leu Gln Glu Val Leu
                850                 855                 860

Lys Ala Tyr Leu Ile Asp Lys Val Arg Ile Lys Gly Tyr Tyr Ala Phe
865                 870                 875                 880

Lys Leu Ala Glu Glu Lys Ser Lys Pro Arg Phe Gly Phe Phe Thr Ser
                    885                 890                 895

Asp Phe Lys Ala Lys Ser Ser Ile Gln Phe Tyr Asn Lys Val Ile Ser
                900                 905                 910

Ser Arg Gly Phe Pro Phe Glu Asn Ser Ser Arg Cys Ser Gln Thr
                    915                 920                 925

Gln Glu Asn Thr Glu Cys Thr Val Cys Leu Phe Leu Val Gln Lys Lys
                930                 935                 940

Pro Leu
945

<210> SEQ ID NO 40
<211> LENGTH: 1195
<212> TYPE: PRT
<213> ORGANISM: Artificial
<220> FEATURE:
<223> OTHER INFORMATION: fusion polypeptide

<400> SEQUENCE: 40

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
                20                  25                  30

Leu Trp Ala Val Gly Ser Ala Ala Tyr Gln Thr Glu Gly Gly Trp Gln
            35                  40                  45

Gln His Gly Lys Gly Ala Ser Ile Trp Asp Thr Phe Thr His His Pro
        50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
        130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
                180                 185                 190

His Phe Gly Gly Gln Val Lys Tyr Trp Ile Thr Ile Asp Asn Pro Tyr
```

-continued

```
            195                 200                 205
Val Val Ala Trp His Gly Tyr Ala Thr Gly Arg Leu Ala Pro Gly Ile
210                 215                 220
Arg Gly Ser Pro Arg Leu Gly Tyr Leu Val Ala His Asn Leu Leu Leu
225                 230                 235                 240
Ala His Ala Lys Val Trp His Leu Tyr Asn Thr Ser Phe Arg Pro Thr
                245                 250                 255
Gln Gly Gly Gln Val Ser Ile Ala Leu Ser Ser His Trp Ile Asn Pro
                260                 265                 270
Arg Arg Met Thr Asp His Ser Ile Lys Glu Cys Gln Lys Ser Leu Asp
                275                 280                 285
Phe Val Leu Gly Trp Phe Ala Lys Pro Val Phe Ile Asp Gly Asp Tyr
290                 295                 300
Pro Glu Ser Met Lys Asn Asn Leu Ser Ser Ile Leu Pro Asp Phe Thr
305                 310                 315                 320
Glu Ser Glu Lys Lys Phe Ile Lys Gly Thr Ala Asp Phe Phe Ala Leu
                325                 330                 335
Cys Phe Gly Pro Thr Leu Ser Phe Gln Leu Leu Asp Pro His Met Lys
                340                 345                 350
Phe Arg Gln Leu Glu Ser Pro Asn Leu Arg Gln Leu Leu Ser Trp Ile
                355                 360                 365
Asp Leu Glu Phe Asn His Pro Gln Ile Phe Ile Val Glu Asn Gly Trp
                370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                405                 410                 415
Val Asp Val Ile Gly Tyr Thr Ala Trp Ser Leu Met Asp Gly Phe Glu
                420                 425                 430
Trp His Arg Gly Tyr Ser Ile Arg Arg Gly Leu Phe Tyr Val Asp Phe
                435                 440                 445
Leu Ser Gln Asp Lys Met Leu Leu Pro Lys Ser Ser Ala Leu Phe Tyr
450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                485                 490                 495
Asn Tyr Ile Gln Val Asp Thr Thr Leu Ser Gln Phe Thr Asp Leu Asn
                500                 505                 510
Val Tyr Leu Trp Asp Val His His Ser Lys Arg Leu Ile Lys Val Asp
                515                 520                 525
Gly Val Val Thr Lys Lys Arg Lys Ser Tyr Cys Val Asp Phe Ala Ala
                530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
                565                 570                 575
Gln Val Asn His Thr Ile Leu Gln Tyr Tyr Arg Cys Met Ala Ser Glu
                580                 585                 590
Leu Val Arg Val Asn Ile Thr Pro Val Val Ala Leu Trp Gln Pro Met
                595                 600                 605
Ala Pro Asn Gln Gly Leu Pro Arg Leu Leu Ala Arg Gln Gly Ala Trp
                610                 615                 620
```

```
Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
            645                 650                 655

Pro Tyr Thr Arg Asn Met Thr Tyr Ser Ala Gly His Asn Leu Leu Lys
        660                 665                 670

Ala His Ala Leu Ala Trp His Val Tyr Asn Glu Lys Phe Arg His Ala
    675                 680                 685

Gln Asn Gly Lys Ile Ser Ile Ala Leu Gln Ala Asp Trp Ile Glu Pro
690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gly Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu Gly Ser Gly Gly Gly Ser Gly Gly Gly Gly
945                 950                 955                 960

Ser Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
        995                 1000                1005

Pro His  Gln Thr Ile Tyr Ser  Ala Leu Met Ile Arg  Ser Glu Asp
    1010                1015                1020

Ala Gly  Phe Val Val Ile Thr  Gly Val Met Ser Arg  Arg Tyr Leu
    1025                1030                1035
```

Cys Met Asp Phe Arg Gly Asn Ile Phe Gly Ser His Tyr Phe Asp
    1040                1045                1050

Pro Glu Asn Cys Arg Phe Gln His Gln Thr Leu Glu Asn Gly Tyr
    1055                1060                1065

Asp Val Tyr His Ser Pro Gln Tyr His Phe Leu Val Ser Leu Gly
    1070                1075                1080

Arg Ala Lys Arg Ala Phe Leu Pro Gly Met Asn Pro Pro Pro Tyr
    1085                1090                1095

Ser Gln Phe Leu Ser Arg Arg Asn Glu Ile Pro Leu Ile His Phe
    1100                1105                1110

Asn Thr Pro Ile Pro Arg Arg His Thr Arg Ser Ala Glu Asp Asp
    1115                1120                1125

Ser Glu Arg Asp Pro Leu Asn Val Leu Lys Pro Arg Ala Arg Met
    1130                1135                1140

Thr Pro Ala Pro Ala Ser Cys Ser Gln Glu Leu Pro Ser Ala Glu
    1145                1150                1155

Asp Asn Ser Pro Met Ala Ser Asp Pro Leu Gly Val Val Arg Gly
    1160                1165                1170

Gly Arg Val Asn Thr His Ala Gly Gly Thr Gly Pro Glu Gly Cys
    1175                1180                1185

Arg Pro Phe Ala Lys Phe Ile
    1190                1195

<210> SEQ ID NO 41
<211> LENGTH: 1195
<212> TYPE: PRT
<213> ORGANISM: Artificial
<220> FEATURE:
<223> OTHER INFORMATION: fusion polypeptide

<400> SEQUENCE: 41

Glu Pro Gly Asp Gly Ala Gln Thr Trp Ala Arg Phe Ser Arg Pro
1               5                   10                  15

Ala Pro Glu Ala Ala Gly Leu Phe Gln Gly Thr Phe Pro Asp Gly Phe
                20                  25                  30

Leu Trp Ala Val Gly Ser Ala Ala Tyr Gln Thr Glu Gly Gly Trp Gln
            35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
                180                 185                 190

-continued

His Phe Gly Gly Gln Val Lys Tyr Trp Ile Thr Ile Asp Asn Pro Tyr
            195                 200                 205

Val Val Ala Trp His Gly Tyr Ala Thr Gly Arg Leu Ala Pro Gly Ile
210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
            275                 280                 285

Phe Val Leu Gly Trp Phe Ala Lys Pro Val Phe Ile Asp Gly Asp Tyr
            290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
            355                 360                 365

Asp Leu Glu Phe Asn His Pro Gln Ile Phe Ile Val Glu Asn Gly Trp
            370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
            485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
            515                 520                 525

Gly Val Val Thr Lys Lys Arg Lys Ser Tyr Cys Val Asp Phe Ala Ala
            530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
            595                 600                 605

Ala Pro Asn Gln Gly Leu Pro Arg Leu Leu Ala Arg Gln Gly Ala Trp

```
              610                 615                 620
Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                    645                 650                 655

Pro Tyr Thr Arg Asn Met Thr Tyr Ser Ala Gly His Asn Leu Leu Lys
                660                 665                 670

Ala His Ala Leu Ala Trp His Val Tyr Asn Glu Lys Phe Arg His Ala
            675                 680                 685

Gln Asn Gly Lys Ile Ser Ile Ala Leu Gln Ala Asp Trp Ile Glu Pro
        690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                    725                 730                 735

Tyr Pro Trp Val Met Arg Asp Trp Leu Asn Gln Arg Asn Asn Phe Leu
                740                 745                 750

Leu Pro Tyr Phe Thr Glu Asp Glu Lys Lys Leu Ile Gln Gly Thr Phe
            755                 760                 765

Asp Phe Leu Ala Leu Ser His Tyr Thr Thr Ile Leu Val Asp Ser Glu
        770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                    805                 810                 815

Trp Gly Leu Arg Lys Val Leu Asn Trp Leu Lys Phe Lys Tyr Gly Asp
                820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gln Asn Tyr Ile Asn Glu
        850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                    885                 890                 895

Tyr Ala Ala Asp Gln Phe Glu Pro Lys Ala Ser Met Lys His Tyr Arg
                900                 905                 910

Lys Ile Ile Asp Ser Asn Gly Phe Pro Gly Pro Glu Thr Leu Glu Arg
            915                 920                 925

Phe Cys Pro Glu Glu Phe Thr Val Cys Thr Glu Cys Ser Phe Phe His
        930                 935                 940

Thr Arg Lys Ser Leu Gly Ser Gly Gly Gly Ser Gly Gly Gly Gly
945                 950                 955                 960

Ser Gly Gly Gly Ser Leu Lys Tyr Pro Asn Ala Ser Pro Leu Leu
                    965                 970                 975

Gly Ser Ser Trp Gly Gly Leu Ile His Leu Tyr Thr Ala Thr Ala Arg
                980                 985                 990

Asn Ser Tyr His Leu Gln Ile His  Lys Asn Gly His Val  Asp Gly Ala
            995                 1000                 1005

Pro His  Gln Thr Ile Tyr Ser  Ala Leu Met Ile Arg  Ser Glu Asp
        1010                 1015                 1020

Ala Gly  Phe Val Val Ile Thr  Gly Val Met Ser Arg  Arg Tyr Leu
        1025                 1030                 1035
```

```
Cys Met Asp Phe Arg Gly Asn Ile Phe Gly Ser His Tyr Phe Asp
    1040                1045                1050

Pro Glu Asn Cys Arg Phe Gln His Gln Thr Leu Glu Asn Gly Tyr
    1055                1060                1065

Asp Val Tyr His Ser Pro Gln Tyr His Phe Leu Val Ser Leu Gly
    1070                1075                1080

Arg Ala Lys Arg Ala Phe Leu Pro Gly Met Asn Pro Pro Pro Tyr
    1085                1090                1095

Ser Gln Phe Leu Ser Arg Arg Asn Glu Ile Pro Leu Ile His Phe
    1100                1105                1110

Asn Thr Pro Ile Pro Arg Arg His Thr Gln Ser Ala Glu Asp Asp
    1115                1120                1125

Ser Glu Arg Asp Pro Leu Asn Val Leu Lys Pro Arg Ala Arg Met
    1130                1135                1140

Thr Pro Ala Pro Ala Ser Cys Ser Gln Glu Leu Pro Ser Ala Glu
    1145                1150                1155

Asp Asn Ser Pro Met Ala Ser Asp Pro Leu Gly Val Val Arg Gly
    1160                1165                1170

Gly Arg Val Asn Thr His Ala Gly Gly Thr Gly Pro Glu Gly Cys
    1175                1180                1185

Arg Pro Phe Ala Lys Phe Ile
    1190                1195

<210> SEQ ID NO 42
<211> LENGTH: 227
<212> TYPE: PRT
<213> ORGANISM: Artificial
<220> FEATURE:
<223> OTHER INFORMATION: fusion polypeptide

<400> SEQUENCE: 42

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
                20                  25                  30

Lys Asn Gly His Val Asp Gly Ala Pro His Gln Thr Ile Tyr Ser Ala
            35                  40                  45

Leu Met Ile Arg Ser Glu Asp Ala Gly Phe Val Val Ile Thr Gly Val
        50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
                100                 105                 110

Ser Leu Gly Arg Ala Lys Arg Ala Phe Leu Pro Gly Met Asn Pro Pro
            115                 120                 125

Pro Tyr Ser Gln Phe Leu Ser Arg Arg Asn Glu Ile Pro Leu Ile His
        130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
                180                 185                 190
```

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
        210                 215                 220

Lys Phe Ile
225

<210> SEQ ID NO 43
<211> LENGTH: 227
<212> TYPE: PRT
<213> ORGANISM: Artificial
<220> FEATURE:
<223> OTHER INFORMATION: fusion polypeptide

<400> SEQUENCE: 43

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
        20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Gln Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
        210                 215                 220

Lys Phe Ile
225

<210> SEQ ID NO 44
<211> LENGTH: 982
<212> TYPE: PRT
<213> ORGANISM: Artificial
<220> FEATURE:
<223> OTHER INFORMATION: fusion polypeptide

<400> SEQUENCE: 44

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg

```
                20                  25                  30
Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445
```

-continued

```
Gly Val Asp Val Ile Gly Tyr Thr Ala Trp Ser Leu Met Asp Gly Phe
            450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
            485                 490                 495
Tyr Gln Lys Leu Ile Glu Lys Asn Gly Phe Pro Pro Leu Pro Glu Asn
            500                 505                 510
Gln Pro Leu Glu Gly Thr Phe Pro Cys Asp Phe Ala Trp Gly Val Val
            515                 520                 525
Asp Asn Tyr Ile Gln Val Asp Thr Thr Leu Ser Gln Phe Thr Asp Leu
            530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
            595                 600                 605
Ser Gln Val Asn His Thr Ile Leu Gln Tyr Tyr Arg Cys Met Ala Ser
            610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
                660                 665                 670
Cys Phe Gln Glu Leu Gly His His Val Lys Leu Trp Ile Thr Met Asn
            675                 680                 685
Glu Pro Tyr Thr Arg Asn Met Thr Tyr Ser Ala Gly His Asn Leu Leu
            690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
                740                 745                 750
Leu Glu Phe Asp Ile Gly Trp Leu Ala Glu Pro Ile Phe Gly Ser Gly
            755                 760                 765
Asp Tyr Pro Trp Val Met Arg Asp Trp Leu Asn Gln Arg Asn Asn Phe
            770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
            820                 825                 830
Met Thr Asp Ile Thr Trp Leu Asn Ser Pro Ser Gln Val Ala Val Val
            835                 840                 845
Pro Trp Gly Leu Arg Lys Val Leu Asn Trp Leu Lys Phe Lys Tyr Gly
            850                 855                 860
```

```
Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu
                980
```

```
<210> SEQ ID NO 45
<211> LENGTH: 974
<212> TYPE: PRT
<213> ORGANISM: Artificial
<220> FEATURE:
<223> OTHER INFORMATION: fusion polypeptide

<400> SEQUENCE: 45

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
                20                  25                  30

Thr Trp Ala Arg Phe Ser Arg Pro Pro Ala Pro Glu Ala Ala Gly Leu
            35                  40                  45

Phe Gln Gly Thr Phe Pro Asp Gly Phe Leu Trp Ala Val Gly Ser Ala
        50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
                100                 105                 110

Thr Gly Asp Val Ala Ser Asp Ser Tyr Asn Asn Val Phe Arg Asp Thr
            115                 120                 125

Glu Ala Leu Arg Glu Leu Gly Val Thr His Tyr Arg Phe Ser Ile Ser
        130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
                180                 185                 190

Gln Asp Ala Tyr Gly Gly Trp Ala Asn Arg Ala Leu Ala Asp His Phe
            195                 200                 205

Arg Asp Tyr Ala Glu Leu Cys Phe Arg His Phe Gly Gly Gln Val Lys
        210                 215                 220

Tyr Trp Ile Thr Ile Asp Asn Pro Tyr Val Val Ala Trp His Gly Tyr
225                 230                 235                 240
```

```
Ala Thr Gly Arg Leu Ala Pro Gly Ile Arg Gly Ser Pro Arg Leu Gly
            245                 250                 255
Tyr Leu Val Ala His Asn Leu Leu Ala His Ala Lys Val Trp His
        260                 265                 270
Leu Tyr Asn Thr Ser Phe Arg Pro Thr Gln Gly Gly Gln Val Ser Ile
        275                 280                 285
Ala Leu Ser Ser His Trp Ile Asn Pro Arg Arg Met Thr Asp His Ser
        290                 295                 300
Ile Lys Glu Cys Gln Lys Ser Leu Asp Phe Val Leu Gly Trp Phe Ala
305                 310                 315                 320
Lys Pro Val Phe Ile Asp Gly Asp Tyr Pro Glu Ser Met Lys Asn Asn
                325                 330                 335
Leu Ser Ser Ile Leu Pro Asp Phe Thr Glu Ser Glu Lys Lys Phe Ile
            340                 345                 350
Lys Gly Thr Ala Asp Phe Phe Ala Leu Cys Phe Gly Pro Thr Leu Ser
            355                 360                 365
Phe Gln Leu Leu Asp Pro His Met Lys Phe Arg Gln Leu Glu Ser Pro
        370                 375                 380
Asn Leu Arg Gln Leu Leu Ser Trp Ile Asp Leu Glu Phe Asn His Pro
385                 390                 395                 400
Gln Ile Phe Ile Val Glu Asn Gly Trp Phe Val Ser Gly Thr Thr Lys
                405                 410                 415
Arg Asp Asp Ala Lys Tyr Met Tyr Tyr Leu Lys Lys Phe Ile Met Glu
                420                 425                 430
Thr Leu Lys Ala Ile Lys Leu Asp Gly Val Asp Val Ile Gly Tyr Thr
            435                 440                 445
Ala Trp Ser Leu Met Asp Gly Phe Glu Trp His Arg Gly Tyr Ser Ile
        450                 455                 460
Arg Arg Gly Leu Phe Tyr Val Asp Phe Leu Ser Gln Asp Lys Met Leu
465                 470                 475                 480
Leu Pro Lys Ser Ser Ala Leu Phe Tyr Gln Lys Leu Ile Glu Lys Asn
                485                 490                 495
Gly Phe Pro Pro Leu Pro Glu Asn Gln Pro Leu Glu Gly Thr Phe Pro
            500                 505                 510
Cys Asp Phe Ala Trp Gly Val Val Asp Asn Tyr Ile Gln Val Asp Thr
        515                 520                 525
Thr Leu Ser Gln Phe Thr Asp Leu Asn Val Tyr Leu Trp Asp Val His
        530                 535                 540
His Ser Lys Arg Leu Ile Lys Val Asp Gly Val Val Thr Lys Lys Arg
545                 550                 555                 560
Lys Ser Tyr Cys Val Asp Phe Ala Ala Ile Gln Pro Gln Ile Ala Leu
                565                 570                 575
Leu Gln Glu Met His Val Thr His Phe Arg Phe Ser Leu Asp Trp Ala
            580                 585                 590
Leu Ile Leu Pro Leu Gly Asn Gln Ser Gln Val Asn His Thr Ile Leu
        595                 600                 605
Gln Tyr Tyr Arg Cys Met Ala Ser Glu Leu Val Arg Val Asn Ile Thr
        610                 615                 620
Pro Val Val Ala Leu Trp Gln Pro Met Ala Pro Asn Gln Gly Leu Pro
625                 630                 635                 640
Arg Leu Leu Ala Arg Gln Gly Ala Trp Glu Asn Pro Tyr Thr Ala Leu
                645                 650                 655
Ala Phe Ala Glu Tyr Ala Arg Leu Cys Phe Gln Glu Leu Gly His His
```

```
                  660                 665                 670
Val Lys Leu Trp Ile Thr Met Asn Glu Pro Tyr Thr Arg Asn Met Thr
                675                 680                 685

Tyr Ser Ala Gly His Asn Leu Leu Lys Ala His Ala Leu Ala Trp His
            690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
                725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
            755                 760                 765

Trp Leu Asn Gln Arg Asn Asn Phe Leu Leu Pro Tyr Phe Thr Glu Asp
            770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
            820                 825                 830

Ser Pro Ser Gln Val Ala Val Pro Trp Gly Leu Arg Lys Val Leu
            835                 840                 845

Asn Trp Leu Lys Phe Lys Tyr Gly Asp Leu Pro Met Tyr Ile Ile Ser
850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
                885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
            915                 920                 925

Pro Lys Ala Ser Met Lys His Tyr Arg Lys Ile Ile Asp Ser Asn Gly
            930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu
                965                 970

<210> SEQ ID NO 46
<211> LENGTH: 4380
<212> TYPE: PRT
<213> ORGANISM: Artificial
<220> FEATURE:
<223> OTHER INFORMATION: fusion peptide derived from human

<400> SEQUENCE: 46

Ala Thr Gly Cys Cys Gly Cys Cys Ala Gly Cys Gly Cys Cys Cys
1               5                   10                  15

Cys Gly Cys Cys Gly Cys Gly Cys Gly Cys Cys Gly Cys Gly
                20                  25                  30

Gly Cys Cys Gly Cys Cys Gly Cys Cys Gly Cys Cys Gly Thr Cys Gly
            35                  40                  45

Cys Thr Gly Thr Cys Gly Cys Thr Gly Cys Thr Gly Cys Thr Gly Gly
```

-continued

```
    50                  55                  60

Thr Gly Cys Thr Gly Cys Thr Gly Gly Gly Cys Cys Thr Gly Gly Gly
65                  70                  75                  80

Cys Gly Gly Cys Cys Gly Cys Cys Gly Cys Cys Thr Gly Cys Gly Thr
                85                  90                  95

Gly Cys Gly Gly Ala Gly Cys Cys Gly Gly Gly Cys Gly Ala Cys Gly
            100                 105                 110

Gly Cys Gly Cys Gly Cys Ala Gly Ala Cys Cys Thr Gly Gly Gly Cys
        115                 120                 125

Cys Cys Gly Thr Thr Thr Cys Thr Cys Gly Cys Gly Gly Cys Cys Thr
    130                 135                 140

Cys Cys Thr Gly Cys Cys Cys Cys Cys Gly Ala Gly Gly Cys Cys Gly
145                 150                 155                 160

Cys Gly Gly Gly Cys Cys Thr Cys Thr Thr Cys Cys Ala Gly Gly Gly
                165                 170                 175

Cys Ala Cys Cys Thr Thr Cys Cys Cys Cys Gly Ala Cys Gly Gly Cys
            180                 185                 190

Thr Thr Cys Cys Thr Cys Thr Gly Gly Gly Cys Cys Gly Thr Gly Gly
        195                 200                 205

Gly Cys Ala Gly Cys Gly Cys Cys Gly Cys Cys Thr Ala Cys Cys Ala
    210                 215                 220

Gly Ala Cys Cys Gly Ala Gly Gly Gly Cys Gly Gly Cys Thr Gly Gly
225                 230                 235                 240

Cys Ala Gly Cys Ala Gly Cys Ala Cys Gly Gly Cys Ala Ala Gly Gly
                245                 250                 255

Gly Thr Gly Cys Gly Thr Cys Cys Ala Thr Cys Thr Gly Gly Gly Ala
            260                 265                 270

Thr Ala Cys Gly Thr Thr Cys Ala Cys Cys Cys Ala Cys Cys Ala Cys
        275                 280                 285

Cys Cys Cys Cys Thr Gly Gly Cys Ala Cys Cys Cys Cys Cys Gly Gly
    290                 295                 300

Gly Ala Gly Ala Cys Thr Cys Cys Cys Gly Gly Ala Ala Cys Gly Cys
305                 310                 315                 320

Cys Ala Gly Thr Cys Thr Gly Cys Cys Gly Thr Thr Gly Gly Gly Cys
                325                 330                 335

Gly Cys Cys Cys Cys Gly Thr Cys Gly Cys Cys Gly Cys Thr Gly Cys
            340                 345                 350

Ala Gly Cys Cys Cys Gly Cys Cys Ala Cys Cys Gly Gly Gly Gly Ala
        355                 360                 365

Cys Gly Thr Ala Gly Cys Cys Ala Gly Cys Gly Ala Cys Ala Gly Cys
    370                 375                 380

Thr Ala Cys Ala Ala Cys Ala Ala Cys Gly Thr Cys Thr Thr Cys Cys
385                 390                 395                 400

Gly Cys Gly Ala Cys Ala Cys Gly Gly Ala Gly Gly Cys Gly Cys Thr
                405                 410                 415

Gly Cys Gly Cys Gly Ala Gly Cys Thr Cys Gly Gly Gly Gly Thr Cys
            420                 425                 430

Ala Cys Thr Cys Ala Cys Thr Ala Cys Cys Gly Cys Thr Thr Cys Thr
        435                 440                 445

Cys Cys Ala Thr Cys Thr Cys Gly Thr Gly Gly Gly Cys Gly Cys Gly
    450                 455                 460

Ala Gly Thr Gly Cys Thr Cys Cys Cys Cys Ala Ala Thr Gly Gly Cys
465                 470                 475                 480
```

-continued

```
Ala Gly Cys Gly Cys Gly Gly Cys Gly Thr Cys Cys Cys Ala
            485                 490                 495

Ala Cys Cys Gly Cys Gly Ala Gly Gly Gly Cys Thr Gly Cys Gly
            500                 505                 510

Cys Thr Ala Cys Thr Ala Cys Cys Gly Cys Gly Cys Cys Thr Gly
            515                 520                 525

Cys Thr Gly Gly Ala Gly Cys Gly Gly Cys Thr Gly Cys Gly Gly
            530                 535                 540

Ala Gly Cys Thr Gly Gly Cys Gly Thr Gly Cys Ala Gly Cys Cys
545                 550                 555                 560

Cys Gly Thr Gly Gly Thr Cys Ala Cys Cys Thr Gly Thr Ala Cys
            565                 570                 575

Cys Ala Cys Thr Gly Gly Ala Cys Cys Thr Gly Cys Cys Cys
            580                 585                 590

Ala Gly Cys Gly Cys Cys Thr Gly Cys Ala Gly Gly Ala Cys Gly Cys
            595                 600                 605

Cys Thr Ala Cys Gly Gly Cys Gly Gly Cys Thr Gly Gly Gly Cys Cys
            610                 615                 620

Ala Ala Cys Cys Gly Cys Gly Cys Cys Cys Thr Gly Gly Cys Cys Gly
625                 630                 635                 640

Ala Cys Cys Ala Cys Thr Thr Cys Ala Gly Gly Ala Thr Thr Ala
            645                 650                 655

Cys Gly Cys Gly Gly Ala Gly Cys Thr Cys Thr Gly Cys Thr Thr Cys
            660                 665                 670

Cys Gly Cys Cys Ala Cys Thr Cys Gly Gly Cys Gly Gly Thr Cys
            675                 680                 685

Ala Gly Gly Thr Cys Ala Ala Gly Thr Ala Cys Thr Gly Gly Ala Thr
            690                 695                 700

Cys Ala Cys Cys Ala Thr Cys Gly Ala Cys Ala Ala Cys Cys Cys
705                 710                 715                 720

Thr Ala Cys Gly Thr Gly Gly Thr Gly Gly Cys Cys Thr Gly Gly Cys
            725                 730                 735

Ala Cys Gly Gly Cys Thr Ala Cys Gly Cys Ala Cys Cys Gly Gly
            740                 745                 750

Gly Cys Gly Cys Cys Thr Gly Gly Cys Cys Cys Cys Gly Gly Cys
            755                 760                 765

Ala Thr Cys Cys Gly Gly Gly Cys Ala Gly Cys Cys Cys Gly Cys
            770                 775                 780

Gly Gly Cys Thr Cys Gly Gly Thr Ala Cys Cys Thr Gly Gly Thr
785                 790                 795                 800

Gly Gly Cys Gly Cys Ala Cys Ala Ala Cys Cys Thr Cys Cys Thr Cys
            805                 810                 815

Cys Thr Gly Gly Cys Thr Cys Ala Thr Gly Cys Cys Ala Ala Ala Gly
            820                 825                 830

Thr Cys Thr Gly Gly Cys Ala Thr Cys Thr Cys Thr Ala Cys Ala Ala
            835                 840                 845

Thr Ala Cys Thr Thr Cys Thr Thr Cys Cys Gly Thr Cys Cys Cys
            850                 855                 860

Ala Cys Thr Cys Ala Gly Gly Ala Gly Gly Thr Cys Ala Gly Gly
865                 870                 875                 880

Thr Gly Thr Cys Cys Ala Thr Gly Cys Cys Thr Ala Ala Gly
            885                 890                 895
```

Cys Thr Cys Thr Cys Ala Cys Thr Gly Gly Ala Thr Cys Ala Ala Thr
                900                 905                 910

Cys Cys Thr Cys Gly Ala Ala Gly Ala Ala Thr Gly Ala Cys Cys Gly
        915                 920                 925

Ala Cys Cys Ala Cys Ala Gly Cys Ala Thr Cys Ala Ala Ala Gly Ala
    930                 935                 940

Ala Thr Gly Thr Cys Ala Ala Ala Ala Thr Cys Thr Cys Thr Gly
945                 950                 955                 960

Gly Ala Cys Thr Thr Thr Gly Thr Ala Cys Thr Ala Gly Gly Thr Thr
            965                 970                 975

Gly Gly Thr Thr Thr Gly Cys Cys Ala Ala Cys Cys Cys Gly Thr
        980                 985                 990

Ala Thr Thr Thr Ala Thr Thr Gly Ala Thr Gly Gly Thr Gly Ala Cys
        995                 1000                1005

Thr Ala Thr Cys Cys Cys Gly Ala Gly Ala Gly Cys Ala Thr Gly
    1010                1015                1020

Ala Ala Gly Ala Ala Thr Ala Ala Cys Cys Thr Thr Thr Cys Ala
    1025                1030                1035

Thr Cys Thr Ala Thr Thr Cys Thr Gly Cys Cys Thr Gly Ala Thr
    1040                1045                1050

Thr Thr Thr Ala Cys Thr Gly Ala Ala Thr Cys Thr Gly Ala Gly
    1055                1060                1065

Ala Ala Ala Ala Ala Gly Thr Thr Cys Ala Thr Cys Ala Ala Ala
    1070                1075                1080

Gly Gly Ala Ala Cys Thr Gly Cys Thr Gly Ala Cys Thr Thr Thr
    1085                1090                1095

Thr Thr Thr Gly Cys Thr Cys Thr Thr Thr Gly Cys Thr Thr Thr
    1100                1105                1110

Gly Gly Ala Cys Cys Cys Ala Cys Cys Thr Thr Gly Ala Gly Thr
    1115                1120                1125

Thr Thr Thr Cys Ala Ala Cys Thr Thr Thr Thr Gly Gly Ala Cys
    1130                1135                1140

Cys Cys Thr Cys Ala Cys Ala Thr Gly Ala Ala Gly Thr Thr Cys
    1145                1150                1155

Cys Gly Cys Cys Ala Ala Thr Thr Gly Gly Ala Ala Thr Cys Thr
    1160                1165                1170

Cys Cys Cys Ala Ala Cys Cys Thr Gly Ala Gly Gly Cys Ala Ala
    1175                1180                1185

Cys Thr Gly Cys Thr Thr Thr Cys Cys Thr Gly Gly Ala Thr Thr
    1190                1195                1200

Gly Ala Cys Cys Thr Thr Gly Ala Ala Thr Thr Thr Ala Ala Cys
    1205                1210                1215

Cys Ala Thr Cys Cys Thr Cys Ala Ala Ala Thr Ala Thr Thr Thr
    1220                1225                1230

Ala Thr Thr Gly Thr Gly Gly Ala Ala Ala Ala Thr Gly Gly Cys
    1235                1240                1245

Thr Gly Gly Thr Thr Thr Gly Thr Cys Thr Cys Ala Gly Gly Gly
    1250                1255                1260

Ala Cys Cys Ala Cys Cys Ala Ala Gly Ala Gly Ala Gly Ala Thr
    1265                1270                1275

Gly Ala Thr Gly Cys Cys Ala Ala Ala Thr Ala Thr Ala Thr Gly
    1280                1285                1290

Thr Ala Thr Thr Ala Cys Cys Thr Cys Ala Ala Ala Ala Ala Gly

```
    1295                1300                1305

Thr Thr  Cys Ala Thr Cys Ala  Thr Gly Gly Ala Ala  Ala Cys Cys
    1310                1315                1320

Thr Thr  Ala Ala Ala Ala Gly  Cys Cys Ala Thr Cys  Ala Ala Gly
    1325                1330                1335

Cys Thr  Gly Gly Ala Thr Gly  Gly Gly Gly Thr Gly  Gly Ala Thr
    1340                1345                1350

Gly Thr  Cys Ala Thr Cys Gly  Gly Gly Thr Ala Thr  Ala Cys Cys
    1355                1360                1365

Gly Cys  Ala Thr Gly Gly Thr  Cys Cys Cys Thr Cys  Ala Thr Gly
    1370                1375                1380

Gly Ala  Thr Gly Gly Thr Thr  Thr Cys Gly Ala Gly  Thr Gly Gly
    1385                1390                1395

Cys Ala  Cys Ala Gly Ala Gly  Gly Thr Thr Ala Cys  Ala Gly Cys
    1400                1405                1410

Ala Thr  Cys Ala Gly Gly Cys  Gly Thr Gly Gly Ala  Cys Thr Cys
    1415                1420                1425

Thr Thr  Cys Thr Ala Thr Gly  Thr Thr Gly Ala Cys  Thr Thr Thr
    1430                1435                1440

Cys Thr  Ala Ala Gly Cys Cys  Ala Gly Gly Ala Cys  Ala Ala Gly
    1445                1450                1455

Ala Thr  Gly Thr Thr Gly Thr  Thr Gly Cys Cys Ala  Ala Ala Gly
    1460                1465                1470

Thr Cys  Thr Thr Cys Ala Gly  Cys Cys Thr Thr Gly  Thr Thr Cys
    1475                1480                1485

Thr Ala  Cys Cys Ala Ala Ala  Ala Gly Cys Thr Gly  Ala Thr Ala
    1490                1495                1500

Gly Ala  Gly Ala Ala Ala Ala  Ala Thr Gly Gly Cys  Thr Thr Cys
    1505                1510                1515

Cys Cys  Thr Cys Cys Thr Thr  Thr Ala Cys Cys Thr  Gly Ala Ala
    1520                1525                1530

Ala Ala  Thr Cys Ala Gly Cys  Cys Cys Cys Thr Ala  Gly Ala Ala
    1535                1540                1545

Gly Gly  Gly Ala Cys Ala Thr  Thr Thr Cys Cys Cys  Thr Gly Thr
    1550                1555                1560

Gly Ala  Cys Thr Thr Thr Gly  Cys Thr Thr Gly Gly  Gly Gly Ala
    1565                1570                1575

Gly Thr  Thr Gly Thr Thr Gly  Ala Cys Ala Ala Cys  Thr Ala Cys
    1580                1585                1590

Ala Thr  Thr Cys Ala Ala Gly  Thr Ala Gly Ala Thr  Ala Cys Cys
    1595                1600                1605

Ala Cys  Thr Cys Thr Gly Thr  Cys Thr Cys Ala Gly  Thr Thr Thr
    1610                1615                1620

Ala Cys  Cys Gly Ala Cys Cys  Thr Gly Ala Ala Thr  Gly Thr Thr
    1625                1630                1635

Thr Ala  Cys Cys Thr Gly Thr  Gly Gly Gly Ala Thr  Gly Thr Cys
    1640                1645                1650

Cys Ala  Cys Cys Ala Cys Ala  Gly Thr Ala Ala Ala  Ala Gly Gly
    1655                1660                1665

Cys Thr  Thr Ala Thr Thr Ala  Ala Ala Gly Thr Gly  Gly Ala Thr
    1670                1675                1680

Gly Gly  Gly Gly Thr Thr Gly  Thr Gly Ala Cys Cys  Ala Ala Gly
    1685                1690                1695
```

-continued

```
Ala Ala Gly Ala Gly Gly Ala Ala Thr Cys Cys Thr Ala Cys
1700                1705                1710

Thr Gly Thr Gly Thr Thr Gly Ala Cys Thr Thr Gly Cys Thr
    1715                1720                1725

Gly Cys Cys Ala Thr Cys Cys Ala Gly Cys Cys Cys Cys Ala Gly
        1730                1735                1740

Ala Thr Cys Gly Cys Thr Thr Ala Cys Thr Cys Cys Ala Gly
    1745                1750                1755

Gly Ala Ala Ala Thr Gly Cys Ala Cys Gly Thr Thr Ala Cys Ala
    1760                1765                1770

Cys Ala Thr Thr Thr Thr Cys Gly Cys Thr Thr Cys Thr Cys Cys
    1775                1780                1785

Cys Thr Gly Gly Ala Cys Thr Gly Gly Gly Cys Cys Cys Thr Gly
    1790                1795                1800

Ala Thr Thr Cys Thr Cys Cys Thr Cys Thr Gly Gly Gly Thr
    1805                1810                1815

Ala Ala Cys Cys Ala Gly Thr Cys Cys Cys Ala Gly Gly Thr Gly
    1820                1825                1830

Ala Ala Cys Cys Ala Cys Ala Cys Cys Ala Thr Cys Cys Thr Gly
    1835                1840                1845

Cys Ala Gly Thr Ala Cys Thr Ala Thr Cys Gly Cys Thr Gly Cys
    1850                1855                1860

Ala Thr Gly Gly Cys Cys Ala Gly Cys Gly Ala Gly Cys Thr Thr
    1865                1870                1875

Gly Thr Cys Cys Gly Thr Gly Thr Cys Ala Ala Cys Ala Thr Cys
    1880                1885                1890

Ala Cys Cys Cys Cys Ala Gly Thr Gly Thr Gly Gly Cys Cys
    1895                1900                1905

Cys Thr Gly Thr Gly Gly Cys Ala Gly Cys Cys Thr Ala Thr Gly
    1910                1915                1920

Gly Cys Cys Cys Cys Gly Ala Ala Cys Cys Ala Ala Gly Gly Ala
    1925                1930                1935

Cys Thr Gly Cys Cys Gly Cys Gly Cys Cys Thr Cys Cys Thr Gly
    1940                1945                1950

Gly Cys Cys Ala Gly Gly Cys Ala Gly Gly Cys Gly Cys Cys
    1955                1960                1965

Thr Gly Gly Gly Ala Gly Ala Ala Cys Cys Cys Thr Ala Cys
    1970                1975                1980

Ala Cys Thr Gly Cys Cys Cys Thr Gly Gly Cys Cys Thr Thr Thr
    1985                1990                1995

Gly Cys Ala Gly Ala Gly Thr Ala Thr Gly Cys Cys Cys Gly Ala
    2000                2005                2010

Cys Thr Gly Thr Gly Cys Thr Thr Cys Ala Ala Gly Ala Gly
    2015                2020                2025

Cys Thr Cys Gly Gly Cys Cys Ala Thr Cys Ala Cys Gly Thr Cys
    2030                2035                2040

Ala Ala Gly Cys Thr Thr Thr Gly Gly Ala Thr Ala Ala Cys Gly
    2045                2050                2055

Ala Thr Gly Ala Ala Thr Gly Ala Gly Cys Cys Gly Thr Ala Thr
    2060                2065                2070

Ala Cys Ala Ala Gly Gly Ala Ala Thr Ala Thr Gly Ala Cys Ala
    2075                2080                2085
```

```
Thr Ala  Cys Ala Gly Thr Gly  Cys Thr Gly Gly Cys  Cys Ala Cys
    2090                 2095                 2100

Ala Ala  Cys Cys Thr Thr Cys  Thr Gly Ala Ala Gly  Gly Cys Cys
    2105                 2110                 2115

Cys Ala  Thr Gly Cys Cys Cys  Thr Gly Gly Cys Thr  Thr Gly Gly
    2120                 2125                 2130

Cys Ala  Thr Gly Thr Gly Thr  Ala Cys Ala Ala Thr  Gly Ala Ala
    2135                 2140                 2145

Ala Ala  Gly Thr Thr Thr Ala  Gly Gly Cys Ala Thr  Gly Cys Thr
    2150                 2155                 2160

Cys Ala  Gly Ala Ala Thr Gly  Gly Gly Ala Ala Ala  Ala Thr Ala
    2165                 2170                 2175

Thr Cys  Cys Ala Thr Ala Gly  Cys Cys Thr Thr Gly  Cys Ala Gly
    2180                 2185                 2190

Gly Cys  Thr Gly Ala Thr Thr  Gly Gly Ala Thr Ala  Gly Ala Ala
    2195                 2200                 2205

Cys Cys  Thr Gly Cys Cys Thr  Gly Cys Cys Cys Thr  Thr Thr Cys
    2210                 2215                 2220

Thr Cys  Cys Cys Ala Ala Ala  Ala Gly Gly Ala Cys  Ala Ala Ala
    2225                 2230                 2235

Gly Ala  Gly Gly Thr Gly Gly  Cys Cys Gly Ala Gly  Ala Gly Ala
    2240                 2245                 2250

Gly Thr  Thr Thr Thr Gly Gly  Ala Ala Thr Thr Thr  Gly Ala Cys
    2255                 2260                 2265

Ala Thr  Thr Gly Gly Cys Thr  Gly Gly Cys Thr Gly  Gly Cys Thr
    2270                 2275                 2280

Gly Ala  Gly Cys Cys Cys Ala  Thr Thr Thr Thr Cys  Gly Gly Cys
    2285                 2290                 2295

Thr Cys  Thr Gly Gly Ala Gly  Ala Thr Thr Ala Thr  Cys Cys Ala
    2300                 2305                 2310

Thr Gly  Gly Gly Thr Gly Ala  Thr Gly Ala Gly Gly  Gly Ala Cys
    2315                 2320                 2325

Thr Gly  Gly Cys Thr Gly Ala  Ala Cys Cys Ala Ala  Ala Gly Ala
    2330                 2335                 2340

Ala Ala  Cys Ala Ala Thr Thr  Thr Thr Cys Thr Thr  Cys Thr Thr
    2345                 2350                 2355

Cys Cys  Thr Thr Ala Thr Thr  Thr Cys Ala Cys Thr  Gly Ala Ala
    2360                 2365                 2370

Gly Ala  Thr Gly Ala Ala Ala  Ala Ala Ala Ala Gly  Cys Thr Ala
    2375                 2380                 2385

Ala Thr  Cys Cys Ala Gly Gly  Gly Thr Ala Cys Cys  Thr Thr Thr
    2390                 2395                 2400

Gly Ala  Cys Thr Thr Thr Thr  Thr Gly Gly Cys Thr  Thr Thr Ala
    2405                 2410                 2415

Ala Gly  Cys Cys Ala Thr Thr  Ala Thr Ala Cys Cys  Ala Cys Cys
    2420                 2425                 2430

Ala Thr  Cys Cys Thr Thr Gly  Thr Ala Gly Ala Cys  Thr Cys Ala
    2435                 2440                 2445

Gly Ala  Ala Ala Ala Ala Gly  Ala Ala Gly Ala Thr  Cys Cys Ala
    2450                 2455                 2460

Ala Thr  Ala Ala Ala Ala Thr  Ala Cys Ala Ala Thr  Gly Ala Thr
    2465                 2470                 2475

Thr Ala  Cys Cys Thr Ala Gly  Ala Ala Gly Thr Gly  Cys Ala Ala
```

```
    2480                2485                2490

Gly Ala  Ala Ala Thr Gly Ala  Cys Cys Gly Ala Cys  Ala Thr Cys
    2495                2500                2505

Ala Cys  Gly Thr Gly Gly Cys  Thr Cys Ala Ala Cys  Thr Cys Cys
    2510                2515                2520

Cys Cys  Cys Ala Gly Thr Cys  Ala Gly Gly Thr Gly  Gly Cys Gly
    2525                2530                2535

Gly Thr  Ala Gly Thr Gly Cys  Cys Cys Thr Gly Gly  Gly Gly Gly
    2540                2545                2550

Thr Thr  Gly Cys Gly Cys Ala  Ala Ala Gly Thr Gly  Cys Thr Gly
    2555                2560                2565

Ala Ala  Cys Thr Gly Gly Cys  Thr Gly Ala Ala Gly  Thr Thr Cys
    2570                2575                2580

Ala Ala  Gly Thr Ala Cys Gly  Gly Ala Gly Ala Cys  Cys Thr Cys
    2585                2590                2595

Cys Cys  Cys Ala Thr Gly Thr  Ala Cys Ala Thr Ala  Ala Thr Ala
    2600                2605                2610

Thr Cys  Cys Ala Ala Cys Gly  Gly Ala Ala Thr Cys  Gly Ala Thr
    2615                2620                2625

Gly Ala  Cys Gly Gly Gly Cys  Thr Gly Cys Ala Thr  Gly Cys Thr
    2630                2635                2640

Gly Ala  Gly Gly Ala Cys Gly  Ala Cys Cys Ala Gly  Cys Thr Gly
    2645                2650                2655

Ala Gly  Gly Gly Thr Gly Thr  Ala Thr Thr Ala Thr  Ala Thr Gly
    2660                2665                2670

Cys Ala  Gly Ala Ala Thr Thr  Ala Cys Ala Thr Ala  Ala Ala Cys
    2675                2680                2685

Gly Ala  Ala Gly Cys Thr Cys  Thr Cys Ala Ala Ala  Gly Cys Cys
    2690                2695                2700

Cys Ala  Cys Ala Thr Ala Cys  Thr Gly Gly Ala Thr  Gly Gly Thr
    2705                2710                2715

Ala Thr  Cys Ala Ala Thr Cys  Thr Thr Thr Gly Cys  Gly Gly Ala
    2720                2725                2730

Thr Ala  Cys Thr Thr Thr Gly  Cys Thr Thr Ala Thr  Thr Cys Gly
    2735                2740                2745

Thr Thr  Thr Ala Ala Cys Gly  Ala Cys Cys Gly Cys  Ala Cys Ala
    2750                2755                2760

Gly Cys  Thr Cys Cys Gly Ala  Gly Gly Thr Thr Thr  Gly Gly Cys
    2765                2770                2775

Cys Thr  Cys Thr Ala Thr Cys  Gly Thr Thr Ala Thr  Gly Cys Thr
    2780                2785                2790

Gly Cys  Ala Gly Ala Thr Cys  Ala Gly Thr Thr Thr  Gly Ala Gly
    2795                2800                2805

Cys Cys  Cys Ala Ala Gly Gly  Cys Ala Thr Cys Cys  Ala Thr Gly
    2810                2815                2820

Ala Ala  Ala Cys Ala Thr Thr  Ala Cys Ala Gly Gly  Ala Ala Ala
    2825                2830                2835

Ala Thr  Thr Ala Thr Thr Gly  Ala Cys Ala Gly Cys  Ala Ala Thr
    2840                2845                2850

Gly Gly  Thr Thr Thr Cys Cys  Cys Gly Gly Gly Cys  Cys Cys Ala
    2855                2860                2865

Gly Ala  Ala Ala Cys Thr Cys  Thr Gly Gly Ala Ala  Ala Gly Ala
    2870                2875                2880
```

-continued

```
Thr Thr Thr Thr Gly Thr Cys Cys Ala Gly Ala Ala  Gly Ala Ala
    2885            2890            2895

Thr Thr Cys Ala Cys Cys Gly Thr Gly Thr Gly Thr  Ala Cys Thr
    2900            2905            2910

Gly Ala Gly Thr Gly Cys Ala Gly Thr Thr Thr Thr  Thr Thr Thr
    2915            2920            2925

Cys Ala Cys Ala Cys Cys Cys Gly Ala Ala Ala Gly  Thr Cys Thr
    2930            2935            2940

Thr Thr Ala Gly Gly Ala Thr Cys Cys Gly Gly Ala  Gly Gly Thr
    2945            2950            2955

Gly Gly Ala Gly Gly Thr Thr Cys Ala Gly Gly Ala  Gly Gly Thr
    2960            2965            2970

Gly Gly Ala Gly Gly Thr Thr Cys Ala Gly Gly Ala  Gly Gly Thr
    2975            2980            2985

Gly Gly Ala Gly Gly Thr Thr Cys Ala Cys Thr Thr  Ala Ala Gly
    2990            2995            3000

Thr Ala Thr Cys Cys Cys Ala Ala Thr Gly Cys Cys  Thr Cys Cys
    3005            3010            3015

Cys Cys Ala Cys Thr Gly Cys Thr Cys Gly Gly Cys  Thr Cys Cys
    3020            3025            3030

Ala Gly Cys Thr Gly Gly Gly Thr Gly Gly Cys  Cys Thr Gly
    3035            3040            3045

Ala Thr Cys Cys Ala Cys Cys Thr Gly Thr Ala Cys  Ala Cys Ala
    3050            3055            3060

Gly Cys Cys Ala Cys Ala Gly Cys Cys Ala Gly Gly  Ala Ala Cys
    3065            3070            3075

Ala Gly Cys Thr Ala Cys Cys Ala Cys Cys Thr Gly  Cys Ala Gly
    3080            3085            3090

Ala Thr Cys Cys Ala Cys Ala Ala Gly Ala Ala Thr  Gly Gly Cys
    3095            3100            3105

Cys Ala Thr Gly Thr Gly Gly Ala Thr Gly Gly Cys  Gly Cys Ala
    3110            3115            3120

Cys Cys Cys Cys Ala Thr Cys Ala Gly Ala Cys Cys  Ala Thr Cys
    3125            3130            3135

Thr Ala Cys Ala Gly Thr Gly Cys Cys Cys Thr Gly  Ala Thr Gly
    3140            3145            3150

Ala Thr Cys Ala Gly Ala Thr Cys Ala Gly Ala Gly  Gly Ala Thr
    3155            3160            3165

Gly Cys Thr Gly Gly Cys Thr Thr Thr Gly Thr Gly  Gly Thr Gly
    3170            3175            3180

Ala Thr Thr Ala Cys Ala Gly Gly Thr Gly Thr Gly  Ala Thr Gly
    3185            3190            3195

Ala Gly Cys Ala Gly Ala Ala Gly Ala Thr Ala Cys  Cys Thr Cys
    3200            3205            3210

Thr Gly Cys Ala Thr Gly Gly Ala Thr Thr Thr Cys  Ala Gly Ala
    3215            3220            3225

Gly Gly Cys Ala Ala Cys Ala Thr Thr Thr Thr Thr  Gly Gly Ala
    3230            3235            3240

Thr Cys Ala Cys Ala Cys Thr Ala Thr Thr Thr Cys  Gly Ala Cys
    3245            3250            3255

Cys Cys Gly Gly Ala Gly Ala Ala Cys Thr Gly Cys  Ala Gly Gly
    3260            3265            3270
```

Thr Thr Cys Cys Ala Ala Cys Ala Cys Ala Gly Ala Cys Gly
3275            3280            3285

Cys Thr Gly Gly Ala Ala Ala Ala Cys Gly Gly Gly Thr Ala Cys
3290            3295            3300

Gly Ala Cys Gly Thr Cys Thr Ala Cys Cys Ala Cys Thr Cys Thr
3305            3310            3315

Cys Cys Thr Cys Ala Gly Thr Ala Thr Cys Ala Cys Thr Thr Cys
3320            3325            3330

Cys Thr Gly Gly Thr Cys Ala Gly Thr Cys Thr Gly Gly Gly Cys
3335            3340            3345

Cys Gly Gly Gly Cys Gly Ala Ala Gly Ala Gly Ala Gly Cys Cys
3350            3355            3360

Thr Thr Cys Cys Thr Gly Cys Cys Ala Gly Gly Cys Ala Thr Gly
3365            3370            3375

Ala Ala Cys Cys Cys Ala Cys Cys Cys Cys Cys Gly Thr Ala Cys
3380            3385            3390

Thr Cys Cys Ala Gly Thr Thr Cys Cys Thr Gly Thr Cys Cys
3395            3400            3405

Cys Gly Gly Ala Gly Gly Ala Ala Cys Gly Ala Gly Ala Thr Cys
3410            3415            3420

Cys Cys Cys Cys Thr Ala Ala Thr Thr Cys Ala Cys Thr Thr Cys
3425            3430            3435

Ala Ala Cys Ala Cys Cys Cys Cys Ala Thr Ala Cys Cys Ala
3440            3445            3450

Cys Gly Gly Cys Gly Gly Cys Ala Cys Ala Cys Cys Ala Gly
3455            3460            3465

Ala Gly Cys Gly Cys Cys Gly Ala Gly Gly Ala Cys Gly Ala Cys
3470            3475            3480

Thr Cys Gly Gly Ala Gly Cys Gly Gly Ala Cys Cys Cys Cys
3485            3490            3495

Cys Thr Gly Ala Ala Cys Gly Thr Gly Cys Thr Gly Ala Ala Gly
3500            3505            3510

Cys Cys Cys Cys Gly Gly Gly Cys Cys Cys Gly Gly Ala Thr Gly
3515            3520            3525

Ala Cys Cys Cys Cys Gly Gly Cys Cys Cys Cys Gly Gly Cys Cys
3530            3535            3540

Thr Cys Cys Thr Gly Thr Thr Cys Ala Cys Ala Gly Gly Ala Gly
3545            3550            3555

Cys Thr Cys Cys Cys Gly Ala Gly Cys Gly Cys Cys Gly Ala Gly
3560            3565            3570

Gly Ala Cys Ala Ala Cys Ala Gly Cys Cys Cys Gly Ala Thr Gly
3575            3580            3585

Gly Cys Cys Ala Gly Thr Gly Ala Cys Cys Cys Ala Thr Thr Ala
3590            3595            3600

Gly Gly Gly Gly Thr Gly Gly Thr Cys Ala Gly Gly Gly Cys
3605            3610            3615

Gly Gly Thr Cys Gly Ala Gly Thr Gly Ala Ala Cys Ala Cys Gly
3620            3625            3630

Cys Ala Cys Gly Cys Thr Gly Gly Gly Gly Ala Ala Cys Gly
3635            3640            3645

Gly Gly Cys Cys Cys Gly Gly Ala Ala Gly Gly Cys Thr Gly Cys
3650            3655            3660

Cys Gly Cys Cys Cys Cys Thr Thr Cys Gly Cys Cys Ala Ala Gly

-continued

```
                3665                3670                3675
Thr Thr Cys Ala Thr Cys Gly Gly Ala Gly Gly Thr Gly Gly Ala
            3680                3685                3690
Gly Gly Thr Thr Cys Ala Ala Ala Ala Cys Cys Cys Ala Cys
            3695                3700            3705
Ala Cys Gly Thr Gly Thr Cys Cys Thr Cys Cys Thr Thr Gly Thr
            3710                3715                3720
Cys Cys Thr Gly Cys Cys Cys Ala Gly Ala Ala  Gly Cys Ala
            3725                3730            3735
Gly Cys Ala Gly Gly Thr Gly Gly Thr Cys Cys Ala Thr Cys Ala
            3740                3745                3750
Gly Thr Thr Thr Thr Thr Cys Thr Thr Thr Cys Cys Cys Thr
            3755                3760            3765
Cys Cys Cys Ala Ala Ala Cys Cys Cys Ala Ala Gly Gly Ala Thr
            3770                3775                3780
Ala Cys Gly Cys Thr Gly Ala Thr Gly Ala Thr Cys Thr Cys Thr
            3785                3790                3795
Cys Gly Cys Ala Cys Gly Cys Cys Thr Gly Ala Gly Gly Thr Gly
            3800                3805            3810
Ala Cys Ala Thr Gly Cys Gly Thr Cys Gly Thr Ala  Gly Thr Ala
            3815                3820                3825
Gly Ala Cys Gly Thr Gly Ala Gly Cys Cys Ala Cys Gly Ala Ala
            3830                3835                3840
Gly Ala Thr Cys Cys Gly Ala Gly Gly Thr Gly Ala Ala Gly
            3845                3850            3855
Thr Thr Cys Ala Ala Thr Thr Gly Gly Thr Ala Thr Gly Thr Gly
            3860                3865                3870
Gly Ala Cys Gly Gly Ala Gly Thr Ala Gly Ala Ala Gly Thr Gly
            3875                3880                3885
Cys Ala Thr Ala Ala Cys Gly Cys Gly Ala Ala Ala Cys Thr
            3890                3895            3900
Ala Ala Gly Cys Cys Gly Cys Gly Cys Gly Ala Gly Gly Ala Ala
            3905                3910            3915
Cys Ala Ala Thr Ala Thr Ala Ala Cys Ala Gly Thr Ala Cys Thr
            3920                3925                3930
Thr Ala Cys Ala Gly Gly Gly Thr Gly Gly Thr Ala Thr Cys Cys
            3935                3940            3945
Gly Thr Gly Cys Thr Cys Ala Cys Ala Gly Thr Cys Cys Thr Gly
            3950                3955                3960
Cys Ala Cys Cys Ala Gly Gly Ala Cys Thr Gly Cys Thr Gly
            3965                3970            3975
Ala Ala Cys Gly Gly Thr Ala Ala Gly Gly Ala Ala Thr Ala Cys
            3980                3985                3990
Ala Ala Gly Thr Gly Cys Ala Ala Ala Gly Thr Ala Ala Gly Cys
            3995                4000            4005
Ala Ala Cys Ala Ala Gly Gly Cys Ala Cys Thr Thr Cys Cys Cys
            4010                4015                4020
Gly Cys Gly Cys Cys Thr Ala Thr Thr Gly Ala Gly Ala Ala Ala
            4025                4030            4035
Ala Cys Ala Ala Thr Cys Thr Cys Cys Ala Ala Gly Gly Cys Gly
            4040                4045            4050
Ala Ala Gly Gly Gly Ala Cys Ala Ala Cys Cys Ala Ala Gly Ala
            4055                4060            4065
```

Gly Ala Ala Cys Cys Thr Cys Ala Gly Thr Thr Thr Ala Cys
                4070              4075              4080

Ala Cys Thr Cys Thr Cys Cys Gly Cys Cys Thr Thr Cys Cys
                4085              4090              4095

Ala Gly Gly Gly Ala Ala Gly Ala Gly Ala Thr Gly Ala Cys Cys
                4100              4105              4110

Ala Ala Ala Ala Ala Thr Cys Ala Ala Gly Thr Thr Thr Cys Cys
                4115              4120              4125

Cys Thr Gly Ala Cys Thr Thr Gly Cys Cys Thr Cys Gly Thr Cys
                4130              4135              4140

Ala Ala Ala Gly Gly Ala Thr Thr Cys Thr Ala Cys Cys Cys Thr
                4145              4150              4155

Thr Cys Cys Gly Ala Cys Ala Thr Thr Gly Cys Thr Gly Thr Thr
                4160              4165              4170

Gly Ala Ala Thr Gly Gly Gly Ala Ala Ala Gly Cys Ala Ala Thr
                4175              4180              4185

Gly Gly Ala Cys Ala Ala Cys Cys Ala Gly Ala Gly Ala Ala Cys
                4190              4195              4200

Ala Ala Cys Thr Ala Cys Ala Ala Gly Ala Cys Ala Ala Cys Ala
                4205              4210              4215

Cys Cys Cys Cys Cys Gly Gly Thr Gly Cys Thr Gly Gly Ala Thr
                4220              4225              4230

Ala Gly Thr Gly Ala Cys Gly Gly Ala Thr Cys Thr Thr Thr Cys
                4235              4240              4245

Thr Thr Thr Cys Thr Cys Thr Ala Cys Thr Cys Ala Ala Ala Gly
                4250              4255              4260

Cys Thr Gly Ala Cys Cys Gly Thr Gly Gly Ala Thr Ala Ala Gly
                4265              4270              4275

Thr Cys Cys Ala Gly Gly Thr Gly Gly Cys Ala Gly Cys Ala Gly
                4280              4285              4290

Gly Gly Ala Ala Ala Cys Gly Thr Gly Thr Thr Thr Cys Cys
                4295              4300              4305

Thr Gly Cys Thr Cys Thr Gly Thr Cys Ala Thr Gly Cys Ala Thr
                4310              4315              4320

Gly Ala Ala Gly Cys Gly Cys Thr Gly Cys Ala Thr Ala Ala Thr
                4325              4330              4335

Cys Ala Cys Thr Ala Thr Ala Cys Cys Cys Ala Gly Ala Ala Gly
                4340              4345              4350

Thr Cys Thr Cys Thr Gly Ala Gly Cys Thr Thr Gly Ala Gly Cys
                4355              4360              4365

Cys Cys Ala Gly Gly Cys Ala Ala Gly Thr Ala Ala
                4370              4375              4380

<210> SEQ ID NO 47
<211> LENGTH: 1459
<212> TYPE: PRT
<213> ORGANISM: Artificial
<220> FEATURE:
<223> OTHER INFORMATION: fusion peptide derived from human

<400> SEQUENCE: 47

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

```
Ala Glu Pro Gly Asp Gly Ala Gln Thr Trp Ala Arg Phe Ser Arg Pro
         35                  40                  45

Pro Ala Pro Glu Ala Ala Gly Leu Phe Gln Gly Thr Phe Pro Asp Gly
     50                  55                  60

Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445
```

```
Gly Val Asp Val Ile Gly Tyr Thr Ala Trp Ser Leu Met Asp Gly Phe
450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
                500                 505                 510
Gln Pro Leu Glu Gly Thr Phe Pro Cys Asp Phe Ala Trp Gly Val Val
            515                 520                 525
Asn Asn Tyr Ile Gln Val Asp Thr Thr Leu Ser Gln Phe Thr Asp Leu
530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
        595                 600                 605
Ser Gln Val Asn His Thr Ile Leu Gln Tyr Tyr Arg Cys Met Ala Ser
    610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
            660                 665                 670
Cys Phe Gln Glu Leu Gly His His Val Lys Leu Trp Ile Thr Met Asn
        675                 680                 685
Glu Pro Tyr Thr Arg Asn Met Thr Tyr Ser Ala Gly His Asn Leu Leu
    690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
        755                 760                 765
Asp Tyr Pro Trp Val Met Arg Asp Trp Leu Asn Gln Arg Asn Asn Phe
    770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
            820                 825                 830
Met Thr Asp Ile Thr Trp Leu Asn Ser Pro Ser Gln Val Ala Val Val
        835                 840                 845
Pro Trp Gly Leu Arg Lys Val Leu Asn Trp Leu Lys Phe Lys Tyr Gly
    850                 855                 860
Asp Leu Pro Met Tyr Ile Ile Ser Asn Gly Ile Asp Asp Gly Leu His
```

```
                865                 870                 875                 880
Ala Glu Asp Asp Gln Leu Arg Val Tyr Tyr Met Gln Asn Tyr Ile Asn
                    885                 890                 895
Glu Ala Leu Lys Ala His Ile Leu Asp Gly Ile Asn Leu Cys Gly Tyr
            900                 905                 910
Phe Ala Tyr Ser Phe Asn Asp Arg Thr Ala Pro Arg Phe Gly Leu Tyr
        915                 920                 925
Arg Tyr Ala Ala Asp Gln Phe Glu Pro Lys Ala Ser Met Lys His Tyr
    930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                965                 970                 975
His Thr Arg Lys Ser Leu Gly Ser Gly Gly Gly Ser Gly Gly Gly
                    980                 985                 990
Gly Ser Gly Gly Gly Gly Ser Leu Lys Tyr Pro Asn Ala Ser Pro Leu
            995                 1000                1005
Leu Gly Ser Ser Trp Gly Gly Leu Ile His Leu Tyr Thr Ala Thr
    1010                1015                1020
Ala Arg Asn Ser Tyr His Leu Gln Ile His Lys Asn Gly His Val
    1025                1030                1035
Asp Gly Ala Pro His Gln Thr Ile Tyr Ser Ala Leu Met Ile Arg
    1040                1045                1050
Ser Glu Asp Ala Gly Phe Val Val Ile Thr Gly Val Met Ser Arg
    1055                1060                1065
Arg Tyr Leu Cys Met Asp Phe Arg Gly Asn Ile Phe Gly Ser His
    1070                1075                1080
Tyr Phe Asp Pro Glu Asn Cys Arg Phe Gln His Gln Thr Leu Glu
    1085                1090                1095
Asn Gly Tyr Asp Val Tyr His Ser Pro Gln Tyr His Phe Leu Val
    1100                1105                1110
Ser Leu Gly Arg Ala Lys Arg Ala Phe Leu Pro Gly Met Asn Pro
    1115                1120                1125
Pro Pro Tyr Ser Gln Phe Leu Ser Arg Arg Asn Glu Ile Pro Leu
    1130                1135                1140
Ile His Phe Asn Thr Pro Ile Pro Arg Arg His Thr Gln Ser Ala
    1145                1150                1155
Glu Asp Asp Ser Glu Arg Asp Pro Leu Asn Val Leu Lys Pro Arg
    1160                1165                1170
Ala Arg Met Thr Pro Ala Pro Ala Ser Cys Ser Gln Glu Leu Pro
    1175                1180                1185
Ser Ala Glu Asp Asn Ser Pro Met Ala Ser Asp Pro Leu Gly Val
    1190                1195                1200
Val Arg Gly Gly Arg Val Asn Thr His Ala Gly Gly Thr Gly Pro
    1205                1210                1215
Glu Gly Cys Arg Pro Phe Ala Lys Phe Ile Gly Gly Gly Ser
    1220                1225                1230
Lys Thr His Thr Cys Pro Pro Cys Pro Ala Pro Glu Ala Ala Gly
    1235                1240                1245
Gly Pro Ser Val Phe Leu Phe Pro Pro Lys Pro Lys Asp Thr Leu
    1250                1255                1260
Met Ile Ser Arg Thr Pro Glu Val Thr Cys Val Val Val Asp Val
    1265                1270                1275
```

Ser His Glu Asp Pro Glu Val Lys Phe Asn Trp Tyr Val Asp Gly
    1280                1285                1290

Val Glu Val His Asn Ala Lys Thr Lys Pro Arg Glu Glu Gln Tyr
    1295                1300                1305

Asn Ser Thr Tyr Arg Val Val Ser Val Leu Thr Val Leu His Gln
    1310                1315                1320

Asp Trp Leu Asn Gly Lys Glu Tyr Lys Cys Lys Val Ser Asn Lys
    1325                1330                1335

Ala Leu Pro Ala Pro Ile Glu Lys Thr Ile Ser Lys Ala Lys Gly
    1340                1345                1350

Gln Pro Arg Glu Pro Gln Val Tyr Thr Leu Pro Pro Ser Arg Glu
    1355                1360                1365

Glu Met Thr Lys Asn Gln Val Ser Leu Thr Cys Leu Val Lys Gly
    1370                1375                1380

Phe Tyr Pro Ser Asp Ile Ala Val Glu Trp Glu Ser Asn Gly Gln
    1385                1390                1395

Pro Glu Asn Asn Tyr Lys Thr Thr Pro Pro Val Leu Asp Ser Asp
    1400                1405                1410

Gly Ser Phe Phe Leu Tyr Ser Lys Leu Thr Val Asp Lys Ser Arg
    1415                1420                1425

Trp Gln Gln Gly Asn Val Phe Ser Cys Ser Val Met His Glu Ala
    1430                1435                1440

Leu His Asn His Tyr Thr Gln Lys Ser Leu Ser Leu Ser Pro Gly
    1445                1450                1455

Lys

<210> SEQ ID NO 48
<211> LENGTH: 4353
<212> TYPE: PRT
<213> ORGANISM: Artificial
<220> FEATURE:
<223> OTHER INFORMATION: fusion peptide derived from human

<400> SEQUENCE: 48

Ala Thr Gly Cys Cys Gly Cys Cys Ala Gly Cys Gly Cys Cys Cys
1               5                   10                  15

Cys Gly Cys Cys Gly Cys Gly Cys Cys Gly Cys Cys Gly Cys Gly
                20                  25                  30

Gly Cys Cys Gly Cys Gly Cys Cys Gly Cys Cys Gly Thr Cys Gly
            35                  40                  45

Cys Thr Gly Thr Cys Gly Cys Thr Gly Cys Thr Gly Cys Gly Gly
        50                  55                  60

Thr Gly Cys Thr Gly Cys Thr Gly Gly Gly Cys Cys Thr Gly Gly
65                  70                  75                  80

Cys Gly Gly Cys Cys Gly Cys Cys Gly Cys Thr Gly Cys Gly Thr
                85                  90                  95

Gly Cys Gly Gly Ala Gly Cys Cys Gly Gly Cys Gly Ala Cys Gly
                100                 105                 110

Gly Cys Gly Cys Gly Cys Ala Gly Ala Cys Cys Thr Gly Gly Cys
                115                 120                 125

Cys Cys Gly Thr Thr Thr Cys Thr Gly Cys Gly Gly Cys Cys Thr
            130                 135                 140

Cys Cys Thr Gly Cys Cys Cys Cys Gly Ala Gly Gly Cys Cys Gly
145                 150                 155                 160

```
Cys Gly Gly Gly Cys Thr Cys Thr Thr Cys Cys Ala Gly Gly
            165                 170                 175
Cys Ala Cys Cys Thr Thr Cys Cys Cys Cys Gly Ala Cys Gly Gly Cys
        180                 185                 190
Thr Thr Cys Cys Thr Cys Thr Gly Gly Gly Cys Cys Gly Thr Gly Gly
            195                 200                 205
Gly Cys Ala Gly Cys Gly Cys Cys Cys Thr Ala Cys Cys Ala
210                 215                 220
Gly Ala Cys Cys Gly Ala Gly Gly Gly Cys Thr Gly Gly
225                 230                 235                 240
Cys Ala Gly Cys Ala Gly Cys Ala Cys Gly Gly Cys Ala Ala Gly Gly
            245                 250                 255
Gly Thr Gly Cys Gly Thr Cys Cys Ala Thr Cys Thr Gly Gly Gly Ala
            260                 265                 270
Thr Ala Cys Gly Thr Thr Cys Ala Cys Cys Ala Cys Ala Cys
        275                 280                 285
Cys Cys Cys Cys Thr Gly Gly Cys Ala Cys Cys Cys Cys Gly Gly
            290                 295                 300
Gly Ala Gly Ala Cys Thr Cys Cys Cys Gly Gly Ala Ala Cys Gly Cys
305                 310                 315                 320
Cys Ala Gly Thr Cys Thr Gly Cys Cys Gly Thr Thr Gly Gly Gly Cys
                325                 330                 335
Gly Cys Cys Cys Cys Gly Thr Cys Gly Cys Cys Gly Cys Thr Gly Cys
            340                 345                 350
Ala Gly Cys Cys Gly Cys Cys Ala Cys Cys Gly Gly Gly Ala
            355                 360                 365
Cys Gly Thr Ala Gly Cys Cys Ala Gly Cys Gly Ala Cys Ala Gly Cys
            370                 375                 380
Thr Ala Cys Ala Ala Cys Ala Ala Cys Gly Thr Cys Thr Thr Cys Cys
385                 390                 395                 400
Gly Cys Gly Ala Cys Ala Cys Gly Gly Ala Gly Gly Cys Gly Cys Thr
            405                 410                 415
Gly Cys Gly Cys Gly Ala Gly Cys Thr Cys Gly Gly Gly Thr Cys
            420                 425                 430
Ala Cys Thr Cys Ala Cys Thr Ala Cys Cys Gly Cys Thr Thr Cys Thr
            435                 440                 445
Cys Cys Ala Thr Cys Thr Cys Gly Thr Gly Gly Cys Gly Cys Gly
        450                 455                 460
Ala Gly Thr Gly Cys Thr Cys Cys Cys Ala Ala Thr Gly Gly Cys
465                 470                 475                 480
Ala Gly Cys Gly Cys Gly Gly Gly Cys Gly Thr Cys Cys Cys Ala
            485                 490                 495
Ala Cys Cys Gly Cys Gly Ala Gly Gly Gly Cys Thr Gly Cys Gly
        500                 505                 510
Cys Thr Ala Cys Thr Ala Cys Cys Gly Cys Gly Cys Cys Thr Gly
            515                 520                 525
Cys Thr Gly Gly Ala Gly Cys Gly Gly Cys Thr Gly Cys Gly Gly Gly
            530                 535                 540
Ala Gly Cys Thr Gly Gly Cys Gly Thr Cys Ala Gly Cys Cys
545                 550                 555                 560
Cys Gly Thr Gly Gly Thr Cys Ala Cys Cys Thr Gly Thr Ala Cys
            565                 570                 575
Cys Ala Cys Thr Gly Gly Gly Ala Cys Cys Thr Gly Cys Cys Cys Cys
```

```
            580                 585                 590

Ala Gly Cys Gly Cys Cys Thr Gly Cys Ala Gly Gly Ala Cys Gly Cys
        595                 600                 605

Cys Thr Ala Cys Gly Gly Cys Gly Gly Cys Thr Gly Gly Gly Cys Cys
    610                 615                 620

Ala Ala Cys Cys Gly Cys Gly Cys Cys Cys Thr Gly Gly Cys Cys Gly
625                 630                 635                 640

Ala Cys Cys Ala Cys Thr Thr Cys Ala Gly Gly Gly Ala Thr Thr Ala
                645                 650                 655

Cys Gly Cys Gly Gly Ala Gly Cys Thr Cys Thr Gly Cys Thr Thr Cys
            660                 665                 670

Cys Gly Cys Cys Ala Cys Thr Thr Cys Gly Gly Cys Gly Gly Thr Cys
        675                 680                 685

Ala Gly Gly Thr Cys Ala Ala Gly Thr Ala Cys Thr Gly Gly Ala Thr
    690                 695                 700

Cys Ala Cys Cys Ala Thr Cys Gly Ala Cys Ala Ala Cys Cys Cys Cys
705                 710                 715                 720

Thr Ala Cys Gly Thr Gly Gly Thr Gly Gly Cys Cys Thr Gly Gly Cys
                725                 730                 735

Ala Cys Gly Gly Cys Thr Ala Cys Gly Cys Cys Ala Cys Cys Gly Gly
            740                 745                 750

Gly Cys Gly Cys Cys Thr Gly Gly Cys Cys Cys Cys Cys Gly Gly Cys
        755                 760                 765

Ala Thr Cys Cys Gly Gly Gly Gly Cys Ala Gly Cys Cys Cys Gly Cys
    770                 775                 780

Gly Gly Cys Thr Cys Gly Gly Gly Thr Ala Cys Cys Thr Gly Gly Thr
785                 790                 795                 800

Gly Gly Cys Gly Cys Ala Cys Ala Ala Cys Cys Thr Cys Cys Thr Cys
                805                 810                 815

Cys Thr Gly Gly Cys Thr Cys Ala Thr Gly Cys Cys Ala Ala Ala Gly
            820                 825                 830

Thr Cys Thr Gly Gly Cys Ala Thr Cys Thr Cys Thr Ala Cys Ala Ala
        835                 840                 845

Thr Ala Cys Thr Thr Cys Thr Thr Thr Cys Cys Gly Thr Cys Cys Cys
    850                 855                 860

Ala Cys Thr Cys Ala Gly Gly Gly Ala Gly Gly Thr Cys Ala Gly Gly
865                 870                 875                 880

Thr Gly Thr Cys Cys Ala Thr Thr Gly Cys Cys Cys Thr Ala Ala Gly
                885                 890                 895

Cys Thr Cys Thr Cys Ala Cys Thr Gly Gly Ala Thr Cys Ala Ala Thr
            900                 905                 910

Cys Cys Thr Cys Gly Ala Ala Gly Ala Ala Thr Gly Ala Cys Cys Gly
        915                 920                 925

Ala Cys Cys Ala Cys Ala Gly Cys Ala Thr Cys Ala Ala Ala Gly Ala
    930                 935                 940

Ala Thr Gly Thr Cys Ala Ala Ala Ala Ala Thr Cys Thr Cys Thr Gly
945                 950                 955                 960

Gly Ala Cys Thr Thr Thr Gly Thr Ala Cys Thr Ala Gly Gly Thr Thr
                965                 970                 975

Gly Gly Thr Thr Thr Gly Cys Cys Ala Ala Ala Cys Cys Cys Gly Thr
            980                 985                 990

Ala Thr Thr Thr Ala Thr Thr Gly  Ala Thr Gly Gly Thr  Gly Ala Cys
        995                 1000                1005
```

-continued

```
Thr Ala Thr Cys Cys Cys Gly Ala Gly Ala Cys Ala Thr Gly
    1010                1015                1020

Ala Ala Gly Ala Ala Thr Ala Ala Cys Cys Thr Thr Cys Ala
    1025                1030                1035

Thr Cys Thr Ala Thr Thr Cys Thr Gly Cys Cys Thr Gly Ala Thr
    1040                1045                1050

Thr Thr Thr Ala Cys Thr Gly Ala Ala Thr Cys Thr Gly Ala Gly
    1055                1060                1065

Ala Ala Ala Ala Ala Gly Thr Thr Cys Ala Thr Cys Ala Ala Ala
    1070                1075                1080

Gly Gly Ala Ala Cys Thr Gly Cys Thr Gly Ala Cys Thr Thr Thr
    1085                1090                1095

Thr Thr Thr Gly Cys Thr Cys Thr Thr Thr Gly Cys Thr Thr Thr
    1100                1105                1110

Gly Gly Ala Cys Cys Cys Ala Cys Cys Thr Thr Gly Ala Gly Thr
    1115                1120                1125

Thr Thr Thr Cys Ala Ala Cys Thr Thr Thr Thr Gly Gly Ala Cys
    1130                1135                1140

Cys Cys Thr Cys Ala Cys Ala Thr Gly Ala Ala Gly Thr Thr Cys
    1145                1150                1155

Cys Gly Cys Cys Ala Ala Thr Thr Gly Gly Ala Ala Thr Cys Thr
    1160                1165                1170

Cys Cys Cys Ala Ala Cys Cys Thr Gly Ala Gly Gly Cys Ala Ala
    1175                1180                1185

Cys Thr Gly Cys Thr Thr Thr Cys Cys Thr Gly Gly Ala Thr Thr
    1190                1195                1200

Gly Ala Cys Cys Thr Thr Gly Ala Ala Thr Thr Thr Ala Ala Cys
    1205                1210                1215

Cys Ala Thr Cys Cys Thr Cys Ala Ala Ala Thr Ala Thr Thr Thr
    1220                1225                1230

Ala Thr Thr Gly Thr Gly Gly Ala Ala Ala Ala Thr Gly Gly Cys
    1235                1240                1245

Thr Gly Gly Thr Thr Thr Gly Thr Cys Thr Cys Ala Gly Gly Gly
    1250                1255                1260

Ala Cys Cys Ala Cys Cys Ala Ala Gly Ala Gly Ala Gly Ala Thr
    1265                1270                1275

Gly Ala Thr Gly Cys Cys Ala Ala Ala Thr Ala Thr Ala Thr Gly
    1280                1285                1290

Thr Ala Thr Thr Ala Cys Cys Thr Cys Ala Ala Ala Ala Ala Gly
    1295                1300                1305

Thr Thr Cys Ala Thr Cys Ala Thr Gly Gly Ala Ala Ala Cys Cys
    1310                1315                1320

Thr Thr Ala Ala Ala Ala Gly Cys Cys Ala Thr Cys Ala Ala Gly
    1325                1330                1335

Cys Thr Gly Gly Ala Thr Gly Gly Gly Thr Gly Gly Ala Thr
    1340                1345                1350

Gly Thr Cys Ala Thr Cys Gly Gly Gly Thr Ala Thr Ala Cys Cys
    1355                1360                1365

Gly Cys Ala Thr Gly Gly Thr Cys Cys Cys Thr Cys Ala Thr Gly
    1370                1375                1380

Gly Ala Thr Gly Gly Thr Thr Thr Cys Gly Ala Gly Thr Gly Gly
    1385                1390                1395
```

```
Cys Ala  Cys Ala Gly Ala Gly  Gly Thr Thr Ala Cys  Ala Gly Cys
    1400             1405              1410

Ala Thr  Cys Ala Gly Gly Cys  Gly Thr Gly Gly Ala  Cys Thr Cys
    1415             1420              1425

Thr Thr  Cys Thr Ala Thr Gly  Thr Thr Gly Ala Cys  Thr Thr Thr
    1430             1435              1440

Cys Thr  Ala Ala Gly Cys Cys  Ala Gly Gly Ala Cys  Ala Ala Gly
    1445             1450              1455

Ala Thr  Gly Thr Thr Gly Thr  Thr Gly Cys Cys Ala  Ala Ala Gly
    1460             1465              1470

Thr Cys  Thr Thr Cys Ala Gly  Cys Cys Thr Thr Gly  Thr Thr Cys
    1475             1480              1485

Thr Ala  Cys Cys Ala Ala Ala  Ala Gly Cys Thr Gly  Ala Thr Ala
    1490             1495              1500

Gly Ala  Gly Ala Ala Ala Ala  Ala Thr Gly Gly Cys  Thr Thr Cys
    1505             1510              1515

Cys Cys  Thr Cys Cys Thr Thr  Thr Ala Cys Cys Thr  Gly Ala Ala
    1520             1525              1530

Ala Ala  Thr Cys Ala Gly Cys  Cys Cys Thr Ala Gly  Ala Ala
    1535             1540              1545

Gly Gly  Gly Ala Cys Ala Thr  Thr Thr Cys Cys Thr  Gly Thr
    1550             1555              1560

Gly Ala  Cys Thr Thr Thr Gly  Cys Thr Thr Gly Gly  Gly Gly Ala
    1565             1570              1575

Gly Thr  Thr Gly Thr Thr Gly  Ala Cys Ala Ala Cys  Thr Ala Cys
    1580             1585              1590

Ala Thr  Thr Cys Ala Ala Gly  Thr Ala Gly Ala Thr  Ala Cys Cys
    1595             1600              1605

Ala Cys  Thr Cys Thr Gly Thr  Cys Thr Cys Ala Gly  Thr Thr Thr
    1610             1615              1620

Ala Cys  Cys Gly Ala Cys Cys  Thr Gly Ala Ala Thr  Gly Thr Thr
    1625             1630              1635

Thr Ala  Cys Cys Thr Gly Thr  Gly Gly Gly Ala Thr  Gly Thr Cys
    1640             1645              1650

Cys Ala  Cys Cys Ala Cys Ala  Gly Thr Ala Ala Ala  Ala Gly Gly
    1655             1660              1665

Cys Thr  Thr Ala Thr Thr Ala  Ala Ala Gly Thr Gly  Gly Ala Thr
    1670             1675              1680

Gly Gly  Gly Gly Thr Thr Gly  Thr Gly Ala Cys Cys  Ala Ala Gly
    1685             1690              1695

Ala Ala  Gly Ala Gly Gly Ala  Ala Ala Thr Cys Cys  Thr Ala Cys
    1700             1705              1710

Thr Gly  Thr Gly Thr Thr Gly  Ala Cys Thr Thr Gly  Cys Thr
    1715             1720              1725

Gly Cys  Cys Ala Thr Cys Cys  Ala Gly Cys Cys Cys  Cys Ala Gly
    1730             1735              1740

Ala Thr  Cys Gly Cys Thr Thr  Thr Ala Cys Thr Cys  Cys Ala Gly
    1745             1750              1755

Gly Ala  Ala Ala Thr Gly Cys  Ala Cys Gly Thr Thr  Ala Cys Ala
    1760             1765              1770

Cys Ala  Thr Thr Thr Thr Cys  Gly Cys Thr Thr Cys  Thr Cys Cys
    1775             1780              1785

Cys Thr  Gly Gly Ala Cys Thr  Gly Gly Gly Cys Cys  Cys Thr Gly
```

```
    1790                1795                1800

Ala Thr  Thr Cys Thr Cys Cys  Cys Thr Cys Thr Gly  Gly Gly Thr
    1805                1810                1815

Ala Ala  Cys Cys Ala Gly Thr  Cys Cys Cys Ala Gly  Gly Thr Gly
    1820                1825                1830

Ala Ala  Cys Cys Ala Cys Ala  Cys Cys Ala Thr Cys  Cys Thr Gly
    1835                1840                1845

Cys Ala  Gly Thr Ala Cys Thr  Ala Thr Cys Gly Cys  Thr Gly Cys
    1850                1855                1860

Ala Thr  Gly Gly Cys Cys Ala  Gly Cys Gly Ala Gly  Cys Thr Thr
    1865                1870                1875

Gly Thr  Cys Cys Gly Thr Gly  Thr Cys Ala Ala Cys  Ala Thr Cys
    1880                1885                1890

Ala Cys  Cys Cys Cys Ala Gly  Thr Gly Gly Thr Gly  Gly Cys Cys
    1895                1900                1905

Cys Thr  Gly Thr Gly Gly Cys  Ala Gly Cys Cys Thr  Ala Thr Gly
    1910                1915                1920

Gly Cys  Cys Cys Cys Gly Ala  Ala Cys Cys Ala Ala  Gly Gly Ala
    1925                1930                1935

Cys Thr  Gly Cys Cys Gly Cys  Gly Cys Cys Thr Cys  Cys Thr Gly
    1940                1945                1950

Gly Cys  Cys Ala Gly Gly Cys  Ala Gly Gly Gly Cys  Gly Cys Cys
    1955                1960                1965

Thr Gly  Gly Gly Ala Gly Ala  Ala Cys Cys Cys Cys  Thr Ala Cys
    1970                1975                1980

Ala Cys  Thr Gly Cys Cys Cys  Thr Gly Gly Cys Cys  Thr Thr Thr
    1985                1990                1995

Gly Cys  Ala Gly Ala Gly Thr  Ala Thr Gly Cys Cys  Cys Gly Ala
    2000                2005                2010

Cys Thr  Gly Thr Gly Cys Thr  Thr Thr Cys Ala Ala  Gly Ala Gly
    2015                2020                2025

Cys Thr  Cys Gly Gly Cys Cys  Ala Thr Cys Ala Cys  Gly Thr Cys
    2030                2035                2040

Ala Ala  Gly Cys Thr Thr Thr  Gly Gly Ala Thr Ala  Ala Cys Gly
    2045                2050                2055

Ala Thr  Gly Ala Ala Thr Gly  Ala Gly Cys Cys Gly  Thr Ala Thr
    2060                2065                2070

Ala Cys  Ala Ala Gly Gly Ala  Ala Thr Ala Thr Gly  Ala Cys Ala
    2075                2080                2085

Thr Ala  Cys Ala Gly Thr Gly  Cys Thr Gly Gly Cys  Cys Ala Cys
    2090                2095                2100

Ala Ala  Cys Cys Thr Thr Cys  Thr Gly Ala Ala Gly  Gly Cys Cys
    2105                2110                2115

Cys Ala  Thr Gly Cys Cys Cys  Thr Gly Gly Cys Thr  Thr Gly Gly
    2120                2125                2130

Cys Ala  Thr Gly Thr Gly Thr  Ala Cys Ala Ala Thr  Gly Ala Ala
    2135                2140                2145

Ala Ala  Gly Thr Thr Thr Ala  Gly Gly Cys Ala Thr  Gly Cys Thr
    2150                2155                2160

Cys Ala  Gly Ala Ala Thr Gly  Gly Gly Ala Ala Ala  Ala Thr Ala
    2165                2170                2175

Thr Cys  Cys Ala Thr Ala Gly  Cys Cys Thr Thr Gly  Cys Ala Gly
    2180                2185                2190
```

```
Gly Cys Thr Gly Ala Thr Thr Gly Gly Ala Thr Ala Gly Ala Ala
    2195                2200                2205

Cys Cys Thr Gly Cys Cys Thr Gly Cys Cys Cys Thr Thr Thr Cys
    2210                2215                2220

Thr Cys Cys Cys Ala Ala Ala Ala Gly Gly Ala Cys Ala Ala Ala
    2225                2230                2235

Gly Ala Gly Gly Thr Gly Gly Cys Cys Gly Ala Gly Ala Gly Ala
    2240                2245                2250

Gly Thr Thr Thr Thr Gly Gly Ala Ala Thr Thr Gly Ala Cys
    2255                2260                2265

Ala Thr Thr Gly Gly Cys Thr Gly Gly Cys Thr Gly Gly Cys Thr
    2270                2275                2280

Gly Ala Gly Cys Cys Cys Ala Thr Thr Thr Thr Cys Gly Gly Cys
    2285                2290                2295

Thr Cys Thr Gly Gly Ala Gly Ala Thr Thr Ala Thr Cys Cys Ala
    2300                2305                2310

Thr Gly Gly Gly Thr Gly Ala Thr Gly Ala Gly Gly Gly Ala Cys
    2315                2320                2325

Thr Gly Gly Cys Thr Gly Ala Ala Cys Cys Ala Ala Ala Gly Ala
    2330                2335                2340

Ala Ala Cys Ala Ala Thr Thr Thr Thr Cys Thr Thr Cys Thr Thr
    2345                2350                2355

Cys Cys Thr Thr Ala Thr Thr Thr Cys Ala Cys Thr Gly Ala Ala
    2360                2365                2370

Gly Ala Thr Gly Ala Ala Ala Ala Ala Ala Gly Cys Thr Ala
    2375                2380                2385

Ala Thr Cys Cys Ala Gly Gly Gly Thr Ala Cys Cys Thr Thr Thr
    2390                2395                2400

Gly Ala Cys Thr Thr Thr Thr Gly Gly Cys Thr Thr Thr Ala
    2405                2410                2415

Ala Gly Cys Cys Ala Thr Thr Ala Thr Ala Cys Cys Ala Cys Cys
    2420                2425                2430

Ala Thr Cys Cys Thr Thr Gly Thr Ala Gly Ala Cys Thr Cys Ala
    2435                2440                2445

Gly Ala Ala Ala Ala Gly Ala Ala Gly Ala Thr Cys Cys Ala
    2450                2455                2460

Ala Thr Ala Ala Ala Thr Ala Cys Ala Ala Thr Gly Ala Thr
    2465                2470                2475

Thr Ala Cys Cys Thr Ala Gly Ala Ala Gly Thr Gly Cys Ala Ala
    2480                2485                2490

Gly Ala Ala Ala Thr Gly Ala Cys Cys Gly Ala Cys Ala Thr Cys
    2495                2500                2505

Ala Cys Gly Thr Gly Gly Cys Thr Cys Ala Ala Cys Thr Cys Cys
    2510                2515                2520

Cys Cys Cys Ala Gly Thr Cys Ala Gly Gly Thr Gly Gly Cys Gly
    2525                2530                2535

Gly Thr Ala Gly Thr Gly Cys Cys Thr Gly Gly Gly Gly Gly
    2540                2545                2550

Thr Thr Gly Cys Gly Cys Ala Ala Ala Gly Thr Gly Cys Thr Gly
    2555                2560                2565

Ala Ala Cys Thr Gly Gly Cys Thr Gly Ala Ala Gly Thr Thr Cys
    2570                2575                2580
```

```
Ala Ala Gly Thr Ala Cys Gly Gly Ala Gly Ala Cys Cys Thr Cys
        2585                2590                2595

Cys Cys Cys Ala Thr Gly Thr Ala Cys Ala Thr Ala Ala Thr Ala
        2600                2605                2610

Thr Cys Cys Ala Ala Cys Gly Gly Ala Ala Thr Cys Gly Ala Thr
        2615                2620                2625

Gly Ala Cys Gly Gly Gly Cys Thr Gly Cys Ala Thr Gly Cys Thr
        2630                2635                2640

Gly Ala Gly Gly Ala Cys Gly Ala Cys Cys Ala Gly Cys Thr Gly
        2645                2650                2655

Ala Gly Gly Gly Thr Gly Thr Ala Thr Thr Ala Thr Ala Thr Gly
        2660                2665                2670

Cys Ala Gly Ala Ala Thr Thr Ala Cys Ala Thr Ala Ala Ala Cys
        2675                2680                2685

Gly Ala Ala Gly Cys Thr Cys Thr Cys Ala Ala Ala Gly Cys Cys
        2690                2695                2700

Cys Ala Cys Ala Thr Ala Cys Thr Gly Gly Ala Thr Gly Gly Thr
        2705                2710                2715

Ala Thr Cys Ala Ala Thr Cys Thr Thr Thr Gly Cys Gly Gly Ala
        2720                2725                2730

Thr Ala Cys Thr Thr Thr Gly Cys Thr Ala Thr Thr Cys Gly
        2735                2740                2745

Thr Thr Thr Ala Ala Cys Gly Ala Cys Cys Gly Cys Ala Cys Ala
        2750                2755                2760

Gly Cys Thr Cys Cys Gly Ala Gly Gly Thr Thr Gly Gly Cys
        2765                2770                2775

Cys Thr Cys Thr Ala Thr Cys Gly Thr Thr Ala Thr Gly Cys Thr
        2780                2785                2790

Gly Cys Ala Gly Ala Thr Cys Ala Gly Thr Thr Thr Gly Ala Gly
        2795                2800                2805

Cys Cys Cys Ala Ala Gly Gly Cys Ala Thr Cys Ala Thr Gly
        2810                2815                2820

Ala Ala Ala Cys Ala Thr Thr Ala Cys Ala Gly Gly Ala Ala Ala
        2825                2830                2835

Ala Thr Thr Ala Thr Thr Gly Ala Cys Ala Gly Cys Ala Ala Thr
        2840                2845                2850

Gly Gly Thr Thr Thr Cys Cys Cys Gly Gly Gly Cys Cys Cys Ala
        2855                2860                2865

Gly Ala Ala Ala Cys Thr Cys Thr Gly Gly Ala Ala Ala Gly Ala
        2870                2875                2880

Thr Thr Thr Thr Gly Thr Cys Ala Gly Ala Ala Gly Ala Ala
        2885                2890                2895

Thr Thr Cys Ala Cys Cys Gly Thr Gly Thr Gly Thr Ala Cys Thr
        2900                2905                2910

Gly Ala Gly Thr Gly Cys Ala Gly Thr Thr Thr Thr Thr Thr Thr
        2915                2920                2925

Cys Ala Cys Ala Cys Cys Gly Ala Ala Ala Gly Thr Cys Thr
        2930                2935                2940

Thr Thr Ala Gly Gly Ala Thr Cys Cys Gly Gly Ala Gly Gly Thr
        2945                2950                2955

Gly Gly Ala Gly Gly Thr Thr Cys Ala Gly Gly Ala Gly Gly Thr
        2960                2965                2970

Gly Gly Ala Gly Gly Thr Thr Cys Ala Gly Gly Ala Gly Gly Thr
```

-continued

```
               2975                2980                2985
Gly Gly Ala Gly Gly Thr Thr Cys Ala Cys Thr Thr Ala Ala Gly
               2990                2995                3000
Thr Ala Thr Cys Cys Cys Ala Ala Thr Gly Cys Cys Thr Cys Cys
               3005                3010                3015
Cys Cys Ala Cys Thr Gly Cys Thr Cys Gly Gly Cys Thr Cys Cys
               3020                3025                3030
Ala Gly Cys Thr Gly Gly Gly Thr Gly Gly Cys Cys Thr Gly
               3035                3040                3045
Ala Thr Cys Cys Ala Cys Thr Gly Thr Ala Cys Ala Cys Ala
               3050                3055                3060
Gly Cys Cys Ala Cys Ala Gly Cys Cys Ala Gly Ala Ala Cys
               3065                3070                3075
Ala Gly Cys Thr Ala Cys Cys Ala Cys Thr Gly Cys Ala Gly
               3080                3085                3090
Ala Thr Cys Cys Ala Cys Ala Ala Gly Ala Ala Thr Gly Gly Cys
               3095                3100                3105
Cys Ala Thr Gly Thr Gly Gly Ala Thr Gly Gly Cys Gly Cys Ala
               3110                3115                3120
Cys Cys Cys Cys Ala Thr Cys Ala Gly Ala Cys Cys Ala Thr Cys
               3125                3130                3135
Thr Ala Cys Ala Gly Thr Gly Cys Cys Cys Thr Gly Ala Thr Gly
               3140                3145                3150
Ala Thr Cys Ala Gly Ala Thr Cys Ala Gly Ala Gly Gly Ala Thr
               3155                3160                3165
Gly Cys Thr Gly Gly Cys Thr Thr Thr Gly Thr Gly Gly Thr Gly
               3170                3175                3180
Ala Thr Thr Ala Cys Ala Gly Gly Thr Gly Thr Gly Ala Thr Gly
               3185                3190                3195
Ala Gly Cys Ala Gly Ala Ala Gly Ala Thr Ala Cys Cys Thr Cys
               3200                3205                3210
Thr Gly Cys Ala Thr Gly Gly Ala Thr Thr Cys Ala Gly Ala
               3215                3220                3225
Gly Gly Cys Ala Ala Cys Ala Thr Thr Thr Thr Gly Gly Ala
               3230                3235                3240
Thr Cys Ala Cys Ala Cys Thr Ala Thr Thr Thr Cys Gly Ala Cys
               3245                3250                3255
Cys Cys Gly Gly Ala Gly Ala Ala Cys Thr Gly Cys Ala Gly Gly
               3260                3265                3270
Thr Thr Cys Cys Ala Ala Cys Ala Cys Cys Ala Gly Ala Cys Gly
               3275                3280                3285
Cys Thr Gly Gly Ala Ala Ala Ala Cys Gly Gly Gly Thr Ala Cys
               3290                3295                3300
Gly Ala Cys Gly Thr Cys Thr Ala Cys Cys Ala Cys Thr Cys Thr
               3305                3310                3315
Cys Cys Thr Cys Ala Gly Thr Ala Thr Cys Ala Cys Thr Thr Cys
               3320                3325                3330
Cys Thr Gly Gly Thr Cys Ala Gly Thr Cys Thr Gly Gly Gly Cys
               3335                3340                3345
Cys Gly Gly Gly Cys Gly Ala Ala Gly Ala Gly Ala Gly Cys Cys
               3350                3355                3360
Thr Thr Cys Cys Thr Gly Cys Cys Ala Gly Gly Cys Ala Thr Gly
               3365                3370                3375
```

```
Ala Ala Cys Cys Cys Ala Cys Cys Cys Cys Gly Thr Ala Cys
    3380            3385            3390

Thr Cys Cys Cys Ala Gly Thr Thr Cys Cys Thr Gly Thr Cys Cys
    3395            3400            3405

Cys Gly Gly Ala Gly Gly Ala Ala Cys Gly Ala Gly Ala Thr Cys
    3410            3415            3420

Cys Cys Cys Cys Thr Ala Ala Thr Thr Cys Ala Cys Thr Thr Cys
    3425            3430            3435

Ala Ala Cys Ala Cys Cys Cys Cys Ala Thr Ala Cys Cys Ala
    3440            3445            3450

Cys Gly Gly Cys Gly Gly Cys Ala Cys Ala Cys Cys Ala Gly
    3455            3460            3465

Ala Gly Cys Gly Cys Cys Gly Ala Gly Gly Ala Cys Gly Ala Cys
    3470            3475            3480

Thr Cys Gly Gly Ala Gly Cys Gly Gly Ala Cys Cys Cys Cys
    3485            3490            3495

Cys Thr Gly Ala Ala Cys Gly Thr Gly Cys Thr Gly Ala Ala Gly
    3500            3505            3510

Cys Cys Cys Cys Gly Gly Gly Cys Cys Cys Gly Gly Ala Thr Gly
    3515            3520            3525

Ala Cys Cys Cys Cys Gly Gly Cys Cys Cys Cys Gly Gly Cys Cys
    3530            3535            3540

Thr Cys Cys Thr Gly Thr Thr Cys Ala Cys Ala Gly Gly Ala Gly
    3545            3550            3555

Cys Thr Cys Cys Cys Gly Ala Gly Cys Gly Cys Cys Gly Ala Gly
    3560            3565            3570

Gly Ala Cys Ala Ala Cys Ala Gly Cys Gly Cys Gly Ala Thr Gly
    3575            3580            3585

Gly Cys Cys Ala Gly Thr Gly Ala Cys Cys Cys Ala Thr Thr Ala
    3590            3595            3600

Gly Gly Gly Gly Thr Gly Gly Thr Cys Ala Gly Gly Gly Gly Cys
    3605            3610            3615

Gly Gly Thr Cys Gly Ala Gly Thr Gly Ala Ala Cys Ala Cys Gly
    3620            3625            3630

Cys Ala Cys Gly Cys Thr Gly Gly Gly Gly Ala Ala Cys Gly
    3635            3640            3645

Gly Gly Cys Cys Cys Gly Gly Ala Ala Gly Gly Cys Thr Gly Cys
    3650            3655            3660

Cys Gly Cys Cys Cys Cys Thr Thr Cys Gly Cys Cys Ala Ala Gly
    3665            3670            3675

Thr Thr Cys Ala Thr Cys Gly Gly Ala Gly Gly Thr Gly Gly Ala
    3680            3685            3690

Gly Gly Thr Thr Cys Ala Gly Cys Cys Cys Cys Ala Gly Ala Ala
    3695            3700            3705

Gly Cys Ala Gly Cys Ala Gly Gly Thr Gly Gly Thr Cys Cys Ala
    3710            3715            3720

Thr Cys Ala Gly Thr Thr Thr Thr Cys Thr Thr Thr Thr Cys
    3725            3730            3735

Cys Cys Thr Cys Cys Cys Ala Ala Ala Cys Cys Ala Ala Gly
    3740            3745            3750

Gly Ala Thr Ala Cys Gly Cys Thr Gly Ala Thr Gly Ala Thr Cys
    3755            3760            3765
```

-continued

```
Thr Cys Thr Cys Gly Cys Ala Cys Gly Cys Thr Gly Ala Gly
    3770            3775            3780

Gly Thr Gly Ala Cys Ala Thr Gly Cys Gly Thr Cys Gly Thr Ala
    3785            3790            3795

Gly Thr Ala Gly Ala Cys Gly Thr Gly Ala Gly Cys Cys Ala Cys
    3800            3805            3810

Gly Ala Ala Gly Ala Thr Cys Cys Cys Gly Ala Gly Gly Thr Gly
    3815            3820            3825

Ala Ala Gly Thr Thr Cys Ala Ala Thr Thr Gly Gly Thr Ala Thr
    3830            3835            3840

Gly Thr Gly Gly Ala Cys Gly Gly Ala Gly Thr Ala Gly Ala Ala
    3845            3850            3855

Gly Thr Gly Cys Ala Thr Ala Ala Cys Gly Cys Gly Ala Ala Ala
    3860            3865            3870

Ala Cys Thr Ala Ala Gly Cys Cys Gly Cys Gly Gly Gly Ala Gly
    3875            3880            3885

Gly Ala Ala Cys Ala Ala Thr Ala Thr Ala Ala Cys Ala Gly Thr
    3890            3895            3900

Ala Cys Thr Thr Ala Cys Ala Gly Gly Gly Thr Gly Gly Thr Ala
    3905            3910            3915

Thr Cys Cys Gly Thr Gly Cys Thr Cys Ala Cys Ala Gly Thr Cys
    3920            3925            3930

Cys Thr Gly Cys Ala Cys Cys Ala Gly Gly Ala Cys Thr Gly Gly
    3935            3940            3945

Cys Thr Gly Ala Ala Cys Gly Gly Thr Ala Ala Gly Gly Ala Ala
    3950            3955            3960

Thr Ala Cys Ala Ala Gly Thr Gly Cys Ala Ala Ala Gly Thr Ala
    3965            3970            3975

Ala Gly Cys Ala Ala Cys Ala Ala Gly Gly Cys Ala Cys Thr Thr
    3980            3985            3990

Cys Cys Cys Gly Cys Gly Cys Cys Thr Ala Thr Thr Gly Ala Gly
    3995            4000            4005

Ala Ala Ala Ala Cys Ala Ala Thr Cys Thr Cys Cys Ala Ala Gly
    4010            4015            4020

Gly Cys Gly Ala Ala Gly Gly Gly Ala Cys Ala Ala Cys Cys Ala
    4025            4030            4035

Ala Gly Ala Gly Ala Ala Cys Cys Thr Cys Ala Gly Gly Thr Thr
    4040            4045            4050

Thr Ala Cys Ala Cys Thr Cys Thr Cys Cys Cys Gly Cys Cys Thr
    4055            4060            4065

Thr Cys Cys Ala Gly Gly Gly Ala Ala Gly Ala Gly Ala Thr Gly
    4070            4075            4080

Ala Cys Cys Ala Ala Ala Ala Thr Cys Ala Ala Gly Thr Thr
    4085            4090            4095

Thr Cys Cys Cys Thr Gly Ala Cys Thr Thr Gly Cys Cys Thr Cys
    4100            4105            4110

Gly Thr Cys Ala Ala Ala Gly Gly Ala Thr Thr Cys Thr Ala Cys
    4115            4120            4125

Cys Cys Thr Thr Cys Cys Gly Ala Cys Ala Thr Thr Gly Cys Thr
    4130            4135            4140

Gly Thr Thr Gly Ala Ala Thr Gly Gly Gly Ala Ala Ala Gly Cys
    4145            4150            4155

Ala Ala Thr Gly Gly Ala Cys Ala Ala Cys Cys Ala Gly Ala Gly
```

```
                    4160                4165                4170
Ala Ala Cys Ala Ala Cys Thr Ala Cys Ala Ala Gly Ala Cys Ala
        4175                4180                4185
Ala Cys Ala Cys Cys Cys Cys Cys Gly Gly Thr Gly Cys Thr Gly
        4190                4195                4200
Gly Ala Thr Ala Gly Thr Gly Ala Cys Gly Gly Ala Thr Cys Thr
        4205                4210                4215
Thr Thr Cys Thr Thr Thr Cys Thr Cys Thr Ala Cys Thr Cys Ala
        4220                4225                4230
Ala Ala Gly Cys Thr Gly Ala Cys Cys Gly Thr Gly Gly Ala Thr
        4235                4240                4245
Ala Ala Gly Thr Cys Cys Ala Gly Gly Thr Gly Gly Cys Ala Gly
        4250                4255                4260
Cys Ala Gly Gly Gly Ala Ala Ala Cys Gly Thr Gly Thr Thr Thr
        4265                4270                4275
Thr Cys Cys Thr Gly Cys Thr Cys Gly Thr Cys Ala Thr Gly
        4280                4285                4290
Cys Ala Thr Gly Ala Ala Gly Cys Gly Cys Thr Gly Cys Ala Thr
        4295                4300                4305
Ala Ala Thr Cys Ala Cys Thr Ala Thr Ala Cys Cys Cys Ala Gly
        4310                4315                4320
Ala Ala Gly Thr Cys Thr Cys Thr Gly Ala Gly Cys Thr Thr Gly
        4325                4330                4335
Ala Gly Cys Cys Cys Ala Gly Gly Cys Ala Ala Gly Thr Ala Ala
        4340                4345                4350
```

<210> SEQ ID NO 49
<211> LENGTH: 1450
<212> TYPE: PRT
<213> ORGANISM: Artificial
<220> FEATURE:
<223> OTHER INFORMATION: fusion peptide derived from human

<400> SEQUENCE: 49

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
```

```
                165                 170                 175
Leu Glu Arg Leu Arg Glu Leu Gly Val Gln Pro Val Thr Leu Tyr
                180                 185                 190

His Trp Asp Leu Pro Gln Arg Leu Gln Asp Ala Tyr Gly Gly Trp Ala
                195                 200             205

Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
            530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590
```

```
Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
                675                 680                 685

Glu Pro Tyr Thr Arg Asn Met Thr Tyr Ser Ala Gly His Asn Leu Leu
                690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
                755                 760                 765

Asp Tyr Pro Trp Val Met Arg Asp Trp Leu Asn Gln Arg Asn Asn Phe
                770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
                850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
                915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
                980                 985                 990

Gly Ser Gly Gly Gly Gly Ser Leu  Lys Tyr Pro Asn Ala  Ser Pro Leu
        995                 1000                1005
```

-continued

Leu Gly Ser Ser Trp Gly Gly Leu Ile His Leu Tyr Thr Ala Thr
1010                1015                1020

Ala Arg Asn Ser Tyr His Leu Gln Ile His Lys Asn Gly His Val
1025                1030                1035

Asp Gly Ala Pro His Gln Thr Ile Tyr Ser Ala Leu Met Ile Arg
1040                1045                1050

Ser Glu Asp Ala Gly Phe Val Val Ile Thr Gly Val Met Ser Arg
1055                1060                1065

Arg Tyr Leu Cys Met Asp Phe Arg Gly Asn Ile Phe Gly Ser His
1070                1075                1080

Tyr Phe Asp Pro Glu Asn Cys Arg Phe Gln His Gln Thr Leu Glu
1085                1090                1095

Asn Gly Tyr Asp Val Tyr His Ser Pro Gln Tyr His Phe Leu Val
1100                1105                1110

Ser Leu Gly Arg Ala Lys Arg Ala Phe Leu Pro Gly Met Asn Pro
1115                1120                1125

Pro Pro Tyr Ser Gln Phe Leu Ser Arg Arg Asn Glu Ile Pro Leu
1130                1135                1140

Ile His Phe Asn Thr Pro Ile Pro Arg Arg His Thr Gln Ser Ala
1145                1150                1155

Glu Asp Asp Ser Glu Arg Asp Pro Leu Asn Val Leu Lys Pro Arg
1160                1165                1170

Ala Arg Met Thr Pro Ala Pro Ala Ser Cys Ser Gln Glu Leu Pro
1175                1180                1185

Ser Ala Glu Asp Asn Ser Pro Met Ala Ser Asp Pro Leu Gly Val
1190                1195                1200

Val Arg Gly Gly Arg Val Asn Thr His Ala Gly Gly Thr Gly Pro
1205                1210                1215

Glu Gly Cys Arg Pro Phe Ala Lys Phe Ile Gly Gly Gly Gly Ser
1220                1225                1230

Ala Pro Glu Ala Ala Gly Gly Pro Ser Val Phe Leu Phe Pro Pro
1235                1240                1245

Lys Pro Lys Asp Thr Leu Met Ile Ser Arg Thr Pro Glu Val Thr
1250                1255                1260

Cys Val Val Val Asp Val Ser His Glu Asp Pro Glu Val Lys Phe
1265                1270                1275

Asn Trp Tyr Val Asp Gly Val Glu Val His Asn Ala Lys Thr Lys
1280                1285                1290

Pro Arg Glu Glu Gln Tyr Asn Ser Thr Tyr Arg Val Val Ser Val
1295                1300                1305

Leu Thr Val Leu His Gln Asp Trp Leu Asn Gly Lys Glu Tyr Lys
1310                1315                1320

Cys Lys Val Ser Asn Lys Ala Leu Pro Ala Pro Ile Glu Lys Thr
1325                1330                1335

Ile Ser Lys Ala Lys Gly Gln Pro Arg Glu Pro Gln Val Tyr Thr
1340                1345                1350

Leu Pro Pro Ser Arg Glu Glu Met Thr Lys Asn Gln Val Ser Leu
1355                1360                1365

Thr Cys Leu Val Lys Gly Phe Tyr Pro Ser Asp Ile Ala Val Glu
1370                1375                1380

Trp Glu Ser Asn Gly Gln Pro Glu Asn Asn Tyr Lys Thr Thr Pro
1385                1390                1395

Pro Val Leu Asp Ser Asp Gly Ser Phe Phe Leu Tyr Ser Lys Leu

```
    1400                1405                1410

Thr Val  Asp Lys Ser Arg Trp  Gln Gln Gly Asn Val  Phe Ser Cys
    1415                1420                1425

Ser Val  Met His Glu Ala Leu  His Asn His Tyr Thr  Gln Lys Ser
    1430                1435                1440

Leu Ser  Leu Ser Pro Gly Lys
    1445                1450

<210> SEQ ID NO 50
<211> LENGTH: 1449
<212> TYPE: PRT
<213> ORGANISM: Artificial
<220> FEATURE:
<223> OTHER INFORMATION: fusion peptide derived from human

<400> SEQUENCE: 50

Ala Thr Gly Thr Thr Gly Gly Gly Gly Gly Cys Cys Cys Gly Cys Cys
1               5                   10                  15

Thr Cys Ala Gly Gly Cys Thr Cys Thr Gly Gly Gly Thr Cys Thr Gly
            20                  25                  30

Thr Gly Cys Cys Thr Thr Gly Thr Gly Cys Ala Gly Cys Gly Thr Cys
        35                  40                  45

Thr Gly Cys Ala Gly Cys Ala Thr Gly Ala Gly Cys Gly Thr Cys Cys
    50                  55                  60

Thr Cys Ala Gly Ala Gly Cys Cys Thr Ala Thr Cys Cys Cys Ala Ala
65                  70                  75                  80

Thr Gly Cys Cys Thr Cys Cys Cys Cys Ala Cys Thr Gly Cys Thr Cys
                85                  90                  95

Gly Gly Cys Thr Cys Cys Ala Gly Cys Thr Gly Gly Gly Gly Thr Gly
            100                 105                 110

Gly Cys Cys Thr Gly Ala Thr Cys Cys Ala Cys Cys Thr Gly Thr Ala
        115                 120                 125

Cys Ala Cys Ala Gly Cys Cys Ala Cys Ala Gly Cys Cys Ala Gly Gly
    130                 135                 140

Ala Ala Cys Ala Gly Cys Thr Ala Cys Cys Ala Cys Cys Thr Gly Cys
145                 150                 155                 160

Ala Gly Ala Thr Cys Cys Ala Cys Ala Ala Gly Ala Ala Thr Gly Gly
                165                 170                 175

Cys Cys Ala Thr Gly Thr Gly Gly Ala Thr Gly Gly Cys Gly Cys Ala
            180                 185                 190

Cys Cys Cys Cys Ala Thr Cys Ala Gly Ala Cys Cys Ala Thr Cys Thr
        195                 200                 205

Ala Cys Ala Gly Thr Gly Cys Cys Cys Thr Gly Ala Thr Gly Ala Thr
    210                 215                 220

Cys Ala Gly Ala Thr Cys Ala Gly Ala Gly Gly Ala Thr Gly Cys Thr
225                 230                 235                 240

Gly Gly Cys Thr Thr Thr Gly Thr Gly Gly Thr Gly Ala Thr Thr Ala
                245                 250                 255

Cys Ala Gly Gly Thr Gly Thr Gly Ala Thr Gly Ala Gly Cys Ala Gly
            260                 265                 270

Ala Ala Gly Ala Thr Ala Cys Cys Thr Cys Thr Gly Cys Ala Thr Gly
        275                 280                 285

Gly Ala Thr Thr Thr Cys Ala Gly Ala Gly Gly Cys Ala Ala Cys Ala
    290                 295                 300

Thr Thr Thr Thr Thr Gly Gly Ala Thr Cys Ala Cys Ala Cys Thr Ala
```

-continued

```
            305                 310                 315                 320
        Thr Thr Thr Cys Gly Ala Cys Cys Gly Ala Gly Ala Ala Cys
                        325                 330                 335
        Thr Gly Cys Ala Gly Gly Thr Cys Cys Ala Ala Cys Ala Cys Cys
                        340                 345                 350
        Ala Gly Ala Cys Gly Cys Thr Gly Ala Ala Ala Cys Gly Gly
                        355                 360                 365
        Gly Thr Ala Cys Gly Ala Cys Gly Thr Cys Thr Ala Cys Cys Ala Cys
        370                     375                 380
        Thr Cys Thr Cys Cys Thr Cys Ala Gly Thr Ala Thr Cys Ala Cys Thr
        385                     390                 395                 400
        Thr Cys Cys Thr Gly Gly Thr Cys Ala Gly Thr Cys Thr Gly Gly Gly
                        405                 410                 415
        Cys Cys Gly Gly Gly Cys Gly Ala Ala Gly Ala Gly Cys Cys
                        420                 425                 430
        Thr Thr Cys Cys Thr Gly Cys Cys Ala Gly Gly Cys Ala Thr Gly Ala
                        435                 440                 445
        Ala Cys Cys Cys Ala Cys Cys Cys Cys Gly Thr Ala Cys Thr Cys
                        450                 455                 460
        Cys Cys Ala Gly Thr Thr Cys Cys Thr Gly Thr Cys Cys Cys Gly Gly
        465                     470                 475                 480
        Ala Gly Gly Ala Ala Cys Gly Ala Gly Ala Thr Cys Cys Cys Cys
                        485                 490                 495
        Thr Ala Ala Thr Thr Cys Ala Cys Thr Thr Cys Ala Ala Cys Ala Cys
                            500                 505                 510
        Cys Cys Cys Cys Ala Thr Ala Cys Cys Ala Cys Gly Gly Cys Gly Gly
                        515                 520                 525
        Cys Ala Cys Ala Cys Cys Ala Gly Ala Gly Cys Gly Cys Cys Gly
                        530                 535                 540
        Ala Gly Gly Ala Cys Gly Ala Cys Thr Cys Gly Gly Ala Gly Cys Gly
        545                     550                 555                 560
        Gly Gly Ala Cys Cys Cys Cys Thr Gly Ala Ala Cys Gly Thr Gly
                        565                 570                 575
        Cys Thr Gly Ala Ala Gly Cys Cys Cys Gly Gly Gly Cys Cys Cys
                        580                 585                 590
        Gly Gly Ala Thr Gly Ala Cys Cys Cys Gly Gly Cys Cys Cys Cys
                        595                 600                 605
        Gly Gly Cys Cys Thr Cys Cys Thr Gly Thr Thr Cys Ala Cys Ala Gly
                        610                 615                 620
        Gly Ala Gly Cys Thr Cys Cys Gly Ala Gly Cys Gly Cys Cys Gly
        625                     630                 635                 640
        Ala Gly Gly Ala Cys Ala Ala Cys Ala Gly Cys Cys Cys Gly Ala Thr
                        645                 650                 655
        Gly Gly Cys Cys Ala Gly Thr Gly Ala Cys Cys Cys Ala Thr Thr Ala
                        660                 665                 670
        Gly Gly Gly Gly Thr Gly Gly Thr Cys Ala Gly Gly Gly Cys Gly
                        675                 680                 685
        Gly Thr Cys Gly Ala Gly Thr Gly Ala Ala Cys Ala Cys Gly Cys Ala
                        690                 695                 700
        Cys Gly Cys Thr Gly Gly Gly Gly Ala Ala Cys Gly Gly Gly Cys
        705                     710                 715                 720
        Cys Cys Gly Gly Ala Ala Gly Gly Cys Thr Gly Cys Cys Gly Cys Cys
                        725                 730                 735
```

Cys Cys Thr Thr Cys Gly Cys Cys Ala Ala Gly Thr Thr Cys Ala Thr
740 745 750

Cys Gly Gly Ala Gly Gly Thr Gly Gly Ala Gly Gly Thr Thr Cys Ala
755 760 765

Ala Ala Ala Ala Cys Cys Cys Ala Cys Ala Cys Gly Thr Gly Thr Cys
770 775 780

Cys Thr Cys Cys Thr Thr Gly Thr Cys Cys Thr Gly Cys Cys Cys Cys
785 790 795 800

Ala Gly Ala Ala Gly Cys Ala Gly Cys Ala Gly Gly Thr Gly Gly Thr
805 810 815

Cys Cys Ala Thr Cys Ala Gly Thr Thr Thr Thr Thr Cys Thr Thr Thr
820 825 830

Thr Cys Cys Cys Thr Cys Cys Cys Ala Ala Ala Cys Cys Cys Ala Ala
835 840 845

Gly Gly Ala Thr Ala Cys Gly Cys Thr Gly Ala Thr Gly Ala Thr Cys
850 855 860

Thr Cys Thr Cys Gly Cys Ala Cys Gly Cys Cys Thr Gly Ala Gly Gly
865 870 875 880

Thr Gly Ala Cys Ala Thr Gly Cys Gly Thr Cys Gly Thr Ala Gly Thr
885 890 895

Ala Gly Ala Cys Gly Thr Gly Ala Gly Cys Cys Ala Cys Gly Ala Ala
900 905 910

Gly Ala Thr Cys Cys Cys Gly Ala Gly Gly Thr Gly Ala Ala Gly Thr
915 920 925

Thr Cys Ala Ala Thr Thr Gly Gly Thr Ala Thr Gly Thr Gly Gly Ala
930 935 940

Cys Gly Gly Ala Gly Thr Ala Gly Ala Ala Gly Thr Gly Cys Ala Thr
945 950 955 960

Ala Ala Cys Gly Cys Gly Ala Ala Ala Ala Cys Thr Ala Ala Gly Cys
965 970 975

Cys Gly Cys Gly Cys Gly Ala Gly Gly Ala Ala Cys Ala Ala Thr Ala
980 985 990

Thr Ala Ala Cys Ala Gly Thr Ala Cys Thr Thr Ala Cys Ala Gly Gly
995 1000 1005

Gly Thr Gly Gly Thr Ala Thr Cys Cys Gly Thr Gly Cys Thr Cys
1010 1015 1020

Ala Cys Ala Gly Thr Cys Cys Thr Gly Cys Ala Cys Cys Ala Gly
1025 1030 1035

Gly Ala Cys Thr Gly Gly Cys Thr Gly Ala Ala Cys Gly Gly Thr
1040 1045 1050

Ala Ala Gly Gly Ala Ala Thr Ala Cys Ala Ala Gly Thr Gly Cys
1055 1060 1065

Ala Ala Ala Gly Thr Ala Ala Gly Cys Ala Ala Cys Ala Ala Gly
1070 1075 1080

Gly Cys Ala Cys Thr Thr Cys Cys Cys Gly Cys Gly Cys Cys Thr
1085 1090 1095

Ala Thr Thr Gly Ala Gly Ala Ala Ala Ala Cys Ala Ala Thr Cys
1100 1105 1110

Thr Cys Cys Ala Ala Gly Gly Cys Gly Ala Ala Gly Gly Gly Ala
1115 1120 1125

Cys Ala Ala Cys Cys Ala Ala Gly Ala Gly Ala Ala Cys Cys Thr
1130 1135 1140

```
Cys Ala Gly Gly Thr Thr Thr Ala Cys Ala Cys Thr Cys Thr Cys
    1145                1150                1155

Cys Cys Gly Cys Cys Thr Thr Cys Cys Ala Gly Gly Gly Ala Ala
    1160                1165                1170

Gly Ala Gly Ala Thr Gly Ala Cys Cys Ala Ala Ala Ala Ala Thr
    1175                1180                1185

Cys Ala Ala Gly Thr Thr Thr Cys Cys Cys Thr Gly Ala Cys Thr
    1190                1195                1200

Thr Gly Cys Cys Thr Cys Gly Thr Cys Ala Ala Ala Gly Gly Ala
    1205                1210                1215

Thr Thr Cys Thr Ala Cys Cys Cys Thr Thr Cys Cys Gly Ala Cys
    1220                1225                1230

Ala Thr Thr Gly Cys Thr Gly Thr Thr Gly Ala Ala Thr Gly Gly
    1235                1240                1245

Gly Ala Ala Ala Gly Cys Ala Ala Thr Gly Gly Ala Cys Ala Ala
    1250                1255                1260

Cys Cys Ala Gly Ala Gly Ala Ala Cys Ala Ala Cys Thr Ala Cys
    1265                1270                1275

Ala Ala Gly Ala Cys Ala Ala Cys Ala Cys Cys Cys Cys Cys Gly
    1280                1285                1290

Gly Thr Gly Cys Thr Gly Gly Ala Thr Ala Gly Thr Gly Ala Cys
    1295                1300                1305

Gly Gly Ala Thr Cys Thr Thr Thr Cys Thr Thr Thr Cys Thr Cys
    1310                1315                1320

Thr Ala Cys Thr Cys Ala Ala Ala Gly Cys Thr Gly Ala Cys Cys
    1325                1330                1335

Gly Thr Gly Gly Ala Thr Ala Ala Gly Thr Cys Cys Ala Gly Gly
    1340                1345                1350

Thr Gly Gly Cys Ala Gly Cys Ala Gly Gly Gly Ala Ala Ala Cys
    1355                1360                1365

Gly Thr Gly Thr Thr Thr Thr Cys Cys Thr Gly Cys Thr Cys Thr
    1370                1375                1380

Gly Thr Cys Ala Thr Gly Cys Ala Thr Gly Ala Ala Gly Cys Gly
    1385                1390                1395

Cys Thr Gly Cys Ala Thr Ala Ala Thr Cys Ala Cys Thr Ala Thr
    1400                1405                1410

Ala Cys Cys Cys Ala Gly Ala Ala Gly Thr Cys Thr Cys Thr Gly
    1415                1420                1425

Ala Gly Cys Thr Thr Gly Ala Gly Cys Cys Cys Ala Gly Gly Cys
    1430                1435                1440

Ala Ala Gly Thr Ala Ala
    1445

<210> SEQ ID NO 51
<211> LENGTH: 482
<212> TYPE: PRT
<213> ORGANISM: Artificial
<220> FEATURE:
<223> OTHER INFORMATION: fusion peptide derived from human

<400> SEQUENCE: 51

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30
```

-continued

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
 50                  55                  60

Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                 85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His

```
                450            455            460
Glu Ala Leu His Asn His Tyr Thr Gln Lys Ser Leu Ser Leu Ser Pro
465                 470                475                480

Gly Lys

<210> SEQ ID NO 52
<211> LENGTH: 1422
<212> TYPE: PRT
<213> ORGANISM: Artificial
<220> FEATURE:
<223> OTHER INFORMATION: fusion peptide derived from human

<400> SEQUENCE: 52

Ala Thr Gly Thr Thr Gly Gly Gly Gly Cys Cys Cys Gly Cys Cys
1               5                   10                  15

Thr Cys Ala Gly Gly Cys Thr Cys Thr Gly Gly Gly Thr Cys Thr Gly
                20                  25                  30

Thr Gly Cys Cys Thr Thr Gly Thr Gly Cys Ala Gly Cys Gly Thr Cys
            35                  40                  45

Thr Gly Cys Ala Gly Cys Ala Thr Gly Ala Gly Cys Gly Thr Cys Cys
            50                  55                  60

Thr Cys Ala Gly Ala Gly Cys Cys Thr Ala Thr Cys Cys Cys Ala Ala
65                  70                  75                  80

Thr Gly Cys Cys Thr Cys Cys Cys Ala Cys Thr Gly Cys Thr Cys
                85                  90                  95

Gly Gly Cys Thr Cys Cys Ala Gly Cys Thr Gly Gly Gly Thr Gly
                100                 105                 110

Gly Cys Cys Thr Gly Ala Thr Cys Cys Ala Cys Cys Thr Gly Thr Ala
                115                 120                 125

Cys Ala Cys Ala Gly Cys Ala Cys Ala Gly Cys Cys Ala Gly Gly
                130                 135                 140

Ala Ala Cys Ala Gly Cys Thr Ala Cys Ala Cys Cys Thr Gly Cys
145                 150                 155                 160

Ala Gly Ala Thr Cys Cys Ala Cys Ala Ala Gly Ala Ala Thr Gly Gly
                165                 170                 175

Cys Cys Ala Thr Gly Thr Gly Gly Ala Thr Gly Gly Cys Gly Cys Ala
                180                 185                 190

Cys Cys Cys Cys Ala Thr Cys Ala Gly Ala Cys Ala Thr Cys Thr
                195                 200                 205

Ala Cys Ala Gly Thr Gly Cys Cys Thr Gly Ala Thr Gly Ala Thr
            210                 215                 220

Cys Ala Gly Ala Thr Cys Ala Gly Ala Gly Gly Ala Thr Gly Cys Thr
225                 230                 235                 240

Gly Gly Cys Thr Thr Thr Gly Thr Gly Thr Gly Ala Thr Thr Ala
                245                 250                 255

Cys Ala Gly Gly Thr Gly Thr Gly Ala Thr Ala Gly Cys Ala Gly
                260                 265                 270

Ala Ala Gly Ala Thr Ala Cys Cys Thr Cys Thr Gly Cys Ala Thr Gly
            275                 280                 285

Gly Ala Thr Thr Cys Ala Gly Ala Gly Gly Cys Ala Ala Cys Ala
            290                 295                 300

Thr Thr Thr Thr Thr Gly Gly Ala Thr Cys Ala Cys Ala Thr Ala
305                 310                 315                 320

Thr Thr Thr Cys Gly Ala Cys Cys Cys Gly Gly Ala Gly Ala Ala Cys
                325                 330                 335
```

-continued

```
Thr Gly Cys Ala Gly Gly Thr Cys Cys Ala Ala Cys Ala Cys Cys
        340                 345                 350
Ala Gly Ala Cys Gly Cys Thr Gly Ala Ala Ala Cys Gly Gly
            355                 360                 365
Gly Thr Ala Cys Gly Ala Cys Gly Thr Cys Thr Ala Cys Cys Ala Cys
    370                 375                 380
Thr Cys Thr Cys Cys Thr Cys Ala Gly Thr Ala Thr Cys Ala Cys Thr
385                 390                 395                 400
Thr Cys Cys Thr Gly Gly Thr Cys Ala Gly Thr Cys Thr Gly Gly Gly
                405                 410                 415
Cys Cys Gly Gly Gly Cys Gly Ala Ala Gly Ala Gly Ala Gly Cys Cys
            420                 425                 430
Thr Thr Cys Cys Thr Gly Cys Cys Ala Gly Gly Cys Ala Thr Gly Ala
        435                 440                 445
Ala Cys Cys Cys Ala Cys Cys Cys Cys Gly Thr Ala Cys Thr Cys
    450                 455                 460
Cys Cys Ala Gly Thr Thr Cys Cys Thr Gly Thr Cys Cys Cys Gly Gly
465                 470                 475                 480
Ala Gly Gly Ala Ala Cys Gly Ala Gly Ala Thr Cys Cys Cys Cys
                485                 490                 495
Thr Ala Ala Thr Thr Cys Ala Cys Thr Thr Cys Ala Ala Cys Ala Cys
            500                 505                 510
Cys Cys Cys Cys Ala Thr Ala Cys Cys Ala Cys Gly Gly Cys Gly Gly
        515                 520                 525
Cys Ala Cys Ala Cys Cys Ala Gly Ala Gly Cys Gly Cys Cys Gly
    530                 535                 540
Ala Gly Gly Ala Cys Gly Ala Cys Thr Cys Gly Gly Ala Gly Cys Gly
545                 550                 555                 560
Gly Gly Ala Cys Cys Cys Cys Thr Gly Ala Ala Cys Gly Thr Gly
                565                 570                 575
Cys Thr Gly Ala Ala Gly Cys Cys Cys Gly Gly Gly Cys Cys Cys
            580                 585                 590
Gly Gly Ala Thr Gly Ala Cys Cys Cys Cys Gly Gly Cys Cys Cys Cys
        595                 600                 605
Gly Gly Cys Cys Thr Cys Cys Thr Gly Thr Thr Cys Ala Cys Ala Gly
    610                 615                 620
Gly Ala Gly Cys Thr Cys Cys Cys Gly Ala Gly Cys Gly Cys Cys Gly
625                 630                 635                 640
Ala Gly Gly Ala Cys Ala Ala Cys Ala Gly Cys Cys Gly Ala Thr
                645                 650                 655
Gly Gly Cys Cys Ala Gly Thr Gly Ala Cys Cys Ala Thr Thr Ala
            660                 665                 670
Gly Gly Gly Gly Thr Gly Gly Thr Cys Ala Gly Gly Gly Cys Gly
        675                 680                 685
Gly Thr Cys Gly Ala Gly Thr Gly Ala Ala Cys Ala Cys Gly Cys Ala
    690                 695                 700
Cys Gly Cys Thr Gly Gly Gly Gly Ala Ala Cys Gly Gly Gly Cys
705                 710                 715                 720
Cys Cys Gly Gly Ala Ala Gly Gly Cys Thr Gly Cys Cys Gly Cys Cys
                725                 730                 735
Cys Cys Thr Thr Cys Gly Cys Cys Ala Ala Gly Thr Thr Cys Ala Thr
            740                 745                 750
```

-continued

```
Cys Gly Gly Ala Gly Gly Thr Gly Ala Gly Gly Thr Thr Cys Ala
            755                 760                 765
Gly Cys Cys Cys Cys Ala Gly Ala Ala Gly Cys Ala Gly Cys Ala Gly
            770                 775                 780
Gly Thr Gly Gly Thr Cys Cys Ala Thr Cys Ala Gly Thr Thr Thr
785                 790                 795                 800
Thr Cys Thr Thr Thr Thr Cys Cys Thr Cys Cys Ala Ala Ala
                805                 810                 815
Cys Cys Cys Ala Ala Gly Gly Ala Thr Ala Cys Gly Cys Thr Gly Ala
                820                 825                 830
Thr Gly Ala Thr Cys Thr Cys Thr Cys Gly Cys Ala Cys Gly Cys Cys
                835                 840                 845
Thr Gly Ala Gly Gly Thr Gly Ala Cys Ala Thr Gly Cys Gly Thr Cys
                850                 855                 860
Gly Thr Ala Gly Thr Ala Gly Ala Cys Gly Thr Gly Ala Gly Cys Cys
865                 870                 875                 880
Ala Cys Gly Ala Ala Gly Ala Thr Cys Cys Gly Ala Gly Gly Thr
                885                 890                 895
Gly Ala Ala Gly Thr Thr Cys Ala Ala Thr Thr Gly Gly Thr Ala Thr
                900                 905                 910
Gly Thr Gly Gly Ala Cys Gly Gly Ala Gly Thr Ala Gly Ala Ala Gly
                915                 920                 925
Thr Gly Cys Ala Thr Ala Ala Cys Cys Gly Cys Gly Ala Ala Ala Cys
                930                 935                 940
Thr Ala Ala Gly Cys Cys Gly Cys Gly Gly Ala Gly Gly Ala Ala
945                 950                 955                 960
Cys Ala Ala Thr Ala Thr Ala Ala Cys Ala Gly Thr Ala Cys Thr Thr
                965                 970                 975
Ala Cys Ala Gly Gly Gly Thr Gly Gly Thr Ala Thr Cys Cys Gly Thr
                980                 985                 990
Gly Cys Thr Cys Ala Cys Ala Gly  Thr Cys Cys Thr Gly  Cys Ala Cys
                995                  1000                 1005
Cys Ala  Gly Gly Ala Cys Thr  Gly Gly Cys Thr Gly  Ala Ala Cys
                1010                 1015                 1020
Gly Gly  Thr Ala Ala Gly Gly  Ala Ala Thr Ala Cys  Ala Ala Gly
                1025                 1030                 1035
Thr Gly  Cys Ala Ala Ala Gly  Thr Ala Ala Gly Cys  Ala Ala Cys
                1040                 1045                 1050
Ala Ala  Gly Gly Cys Ala Cys  Thr Thr Cys Cys Cys  Gly Cys Gly
                1055                 1060                 1065
Cys Cys  Thr Ala Thr Thr Gly  Ala Gly Ala Ala Ala  Ala Cys Ala
                1070                 1075                 1080
Ala Thr  Cys Thr Cys Cys Ala  Ala Gly Gly Cys Gly  Ala Ala Gly
                1085                 1090                 1095
Gly Gly  Ala Cys Ala Ala Cys  Cys Ala Ala Gly Ala  Gly Ala Ala
                1100                 1105                 1110
Cys Cys  Thr Cys Ala Gly Gly  Thr Thr Thr Ala Cys  Ala Cys Thr
                1115                 1120                 1125
Cys Thr  Cys Cys Cys Gly Cys  Cys Thr Cys Cys Ala  Ala Gly Gly
                1130                 1135                 1140
Gly Ala  Ala Gly Ala Gly Ala  Thr Gly Ala Cys Cys  Ala Ala Ala
                1145                 1150                 1155
Ala Ala  Thr Cys Ala Ala Gly  Thr Thr Thr Cys Cys  Cys Thr Gly
```

-continued

```
            1160                1165                1170
Ala Cys Thr Thr Gly Cys Cys Thr Cys Gly Thr Cys Ala Ala Ala
    1175                1180                1185

Gly Gly Ala Thr Thr Cys Thr Ala Cys Cys Thr Thr Cys Cys
    1190                1195                1200

Gly Ala Cys Ala Thr Thr Gly Cys Thr Gly Thr Thr Gly Ala Ala
    1205                1210                1215

Thr Gly Gly Gly Ala Ala Gly Cys Ala Ala Thr Gly Gly Ala
    1220                1225                1230

Cys Ala Ala Cys Cys Ala Gly Ala Gly Ala Ala Cys Ala Ala Cys
    1235                1240                1245

Thr Ala Cys Ala Ala Gly Ala Cys Ala Ala Cys Ala Cys Cys Cys
    1250                1255                1260

Cys Cys Gly Gly Thr Gly Cys Thr Gly Gly Ala Thr Ala Gly Thr
    1265                1270                1275

Gly Ala Cys Gly Gly Ala Thr Cys Thr Thr Thr Cys Thr Thr Thr
    1280                1285                1290

Cys Thr Cys Thr Ala Cys Thr Cys Ala Ala Ala Gly Cys Thr Gly
    1295                1300                1305

Ala Cys Cys Gly Thr Gly Gly Ala Thr Ala Ala Gly Thr Cys Cys
    1310                1315                1320

Ala Gly Gly Thr Gly Gly Cys Ala Gly Cys Ala Gly Gly Gly Ala
    1325                1330                1335

Ala Ala Cys Gly Thr Gly Thr Thr Thr Cys Cys Thr Gly Cys
    1340                1345                1350

Thr Cys Thr Gly Thr Cys Ala Thr Gly Cys Ala Thr Gly Ala Ala
    1355                1360                1365

Gly Cys Gly Cys Thr Gly Cys Ala Thr Ala Ala Thr Cys Ala Cys
    1370                1375                1380

Thr Ala Thr Ala Cys Cys Cys Ala Gly Ala Ala Gly Thr Cys Thr
    1385                1390                1395

Cys Thr Gly Ala Gly Cys Thr Gly Ala Gly Cys Cys Cys Ala
    1400                1405                1410

Gly Gly Cys Ala Ala Gly Thr Ala Ala
    1415                1420
```

<210> SEQ ID NO 53
<211> LENGTH: 473
<212> TYPE: PRT
<213> ORGANISM: Artificial
<220> FEATURE:
<223> OTHER INFORMATION: fusion peptide derived from human

<400> SEQUENCE: 53

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95
```

```
Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470
```

METHODS AND COMPOSITIONS USING A KLOTHO-FGF23 FUSION POLYPEPTIDE

This application is a divisional of U.S. application Ser. No. 13/796,711 filed Mar. 12, 2013 which is a divisional of U.S. application Ser. No. 12/360,970 filed Jan. 28, 2009, which claims priority to U.S. Provisional Application No. 61/063,015 filed Jan. 28, 2008, the contents of which are incorporated herein by reference in their entirety.

1. BACKGROUND

The alpha-Klotho gene encodes a 130 kDa single pass type I transmembrane protein with an extracellular domain and a short cytoplasmic domain. The extracellular domain of alpha-Klotho protein comprises two subdomains termed, KL-D1 and KL-D2. These two subdomains share sequence homology to β-glucosidase of bacteria and plants. The extracellular domain of the alpha-Klotho protein may be bound to the cell surface by the transmembrane domain or may be cleaved and released into the extracellular milieu. Cleavage of the extracellular domain appears to be facilitated by local low extracellular $Ca^{2+}$ concentrations.

In addition to alpha-Klotho, a homolog of alpha-Klotho, beta-Klotho, has been identified (Ito et al., Mech. Dev. 98:115-9 (2000)). Beta-Klotho is also a single pass type I transmembrane protein with extracellular KL-D1 and KL-D2 subdomains.

Modulation of alpha-Klotho expression has been demonstrated to produce aging related characteristics in mammals. Mice homozygous for a loss of function mutation in the alpha-Klotho gene develop characteristics resembling human aging, including shortened lifespan, skin atrophy, muscle wasting, arteriosclerosis, pulmonary emphysema and osteoporosis (Kuro-o et al., Nature, 390:45-51 (1997)). In contrast, overexpression of the alpha-Klotho gene in mice extends lifespan and increases resistance to oxidative stress relative to wild-type mice (Kurosu et al., Science 309:1829-1833 (2005); Yamamoto et al., J. Biol. Chem. 280:38029-38034 (2005)).

Fibroblast growth factors (FGFs) constitute a family of homologous polypeptide growth factors expressed in many organisms (Ornitz and Itoh, Genome Biol. 2: reviews, 3005.1-3005.12 (2001)). Among vertebrate species, FGFs are highly conserved in both gene structure and amino-acid sequence, having between 13-71% amino acid identity with one another. In humans, there are 22 known members of the FGF family (FGF15 is the mouse ortholog of human FGF19, hence there is no human FGF15). During early development, FGFs regulate cell proliferation, migration, and differentiation, but in the adult organism, FGFs maintain homeostasis, function in tissue repair, and respond to injury.

FGFs function as growth factors by binding and thereby activating cell-surface FGF receptors. FGF receptors (FGFRs) are tyrosine kinase receptors that activate signal transduction through autophosphorylation of FGFR, phosphorylation of FRS2 (FGF receptor substrate 2) and ERK1/2 (extracellular signal-regulated protein kinase 1/2), and activating Egr-1 (early growth response-1). FGFs also have a high affinity for heparin sulfate proteoglycans. When bound to FGFs, heparin sulfate enhances the activation of FGFRs.

Recent studies have demonstrated strikingly similar biological characteristics between FGF23-deficient mice and alpha-Klotho-deficient mice (Shimada et al., J. Clin. Invest. 113:561-568 (2004); Yoshida et al. Endocrinology 143:683-689 (2002)), indicating functional crosstalk between FGF23 and alpha-Klotho. These studies led to the identification of alpha-Klotho as an obligatory partner of FGF23, in terms of both binding and signaling through its cognate FGF receptors (Urakawa et al., Nature 22:1524-6 (2007)). The alpha-Klotho gene is mainly expressed in kidney, parathyroid gland and choroid plexus. It is hypothesized that the tissue-specific expression of alpha-Klotho restricts activation of FGF23 signaling to those tissues.

Similar to FGF23/alpha-Klotho, beta-Klotho is an obligatory partner of FGF19 and FGF21, both in binding and in signaling through their respective cognate FGF receptors (Ogawa et al., Proc. Natl. Acad. Sci. USA 104:7432-7 (2007); Lin et al., J. Biol Chem. 282:27227-84 (2007); and Wu et al., J. Biol. Chem. 282:29069-72 (2007)). Such studies have also demonstrated the involvement of beta-Klotho in regulating tissue-specific metabolic activity. Beta-Klotho was initially shown to act with FGF21 as a cofactor for regulating carbohydrate and lipid metabolism in adipose tissue. Beta-Klotho in conjunction with FGF19 regulates bile acid metabolism in liver, thus explaining elevated bile synthesis in beta-Klotho deficient mice (Ito et al., J Clin Invest. 2005 August; 115(8):2202-8).

U.S. Pat. No. 6,579,850 describes polypeptides and compositions comprising an alpha-Klotho polypeptide. Human and mouse alpha-Klotho polypeptides are disclosed. The patent also disclosed that compositions comprising the polypeptides are useful in treating a syndrome resembling premature aging, treating adult diseases, and suppressing aging.

U.S. Pat. No. 7,223,563 describes isolated nucleic acids encoding the FGF23 polypeptide sequence or recombinant cells comprising such an isolated nucleic acid. The patent further relates to methods of diagnosing and treating hypophosphatemic and hyperphosphatemic disorders, osteoporosis, dermatomyositis, and coronary artery disease.

U.S. Pat. No. 7,259,248 describes isolated nucleic acids encoding the FGF21 polypeptide sequence. The patent further relates to methods of diagnosing and treating liver disease, conditions related to thymic function, and methods of treating conditions of the testis.

2. SUMMARY OF THE INVENTION

The present invention is directed to methods, kits and compositions for preventing or treating age-related conditions or metabolic disorders with Klotho fusion polypeptides or soluble Klotho polypeptides. The Klotho fusion polypeptides of the present invention are formed of a Klotho protein or an active fragment thereof (e.g., sKlotho). In some embodiments, the present invention provides a Klotho fusion polypeptide comprising a Klotho protein or an active fragment thereof and a fibroblast growth factor or an active fragment thereof. In some embodiments, the fusion polypeptide comprises a Klotho polypeptide, a FGF (such as FGF23) and a modified Fc fragment. The Fc fragment can, for example, have decreased binding to Fc-gamma-receptor and increased serum half-life. Fusion proteins comprising sKlotho, FGF23 and FcLALA (a modified Fc fragment having decreased affinity for Fc-gamma-receptor and/or increased serum half-life) are described in SEQ ID NOs. 46, 47, 48, and 49. In some embodiments, the fusion polypeptide or protein comprises a FGF (e.g., FGF23) and a modified Fc fragment. Fusion proteins comprising FGF23 and FcLALA are described in SEQ ID NOs. 50, 51, 52 and 53.

In a first aspect, the invention provides a fusion polypeptide having at least one extracellular subdomain of a Klotho protein and a fibroblast growth factor or an active fragment thereof. In some embodiments, the fusion further comprises a modified Fc fragment having decreased affinity (e.g., decreased Ka or increased Kd) for Fc-gamma-receptor and/or increased serum half-life. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs can be used in practicing the invention. The reader of the instant application may assume that each of every combination of alpha or beta extracellular domain with each human FGF protein or an active fragment thereof are individually and specifically contemplated.

According to the present invention, the extracellular domain of the Klotho protein can include one or both of the KL-D1 and KL-D2 domains of a Klotho protein. In some embodiments, the Klotho fusion polypeptide of the invention has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain. In one embodiment, the fusion polypeptide of the invention comprises amino acids 28-292 of the full length alpha Klotho protein. In another embodiment, the fusion polypeptide of the invention comprises amino acids 52-997 of the full length beta Klotho protein.

According to the present invention, the components of a fusion polypeptide comprising (1) at least one extracellular subdomain of a Klotho protein, (2) a FGF or an active fragment thereof, and (3) a modified Fc fragment having decreased affinity for Fc-gamma-receptor and/or increased serum half-life may be linked together covalently, for example, chemically linked or fused in frame by a peptide bond. They may also linked via a linker. Non-limiting examples of polypeptide linker are SEQ ID NOs:11, 12, 13, 14, 15, 16, 17, and 18. Such linkers may comprise at least one and up to about 30 repeats of SEQ ID NOs:11, 12, 13, 14, 15, 16, 17 and 18. In another non-limiting embodiment, the fusion comprises (2) a FGF or an active fragment thereof and (3) a modified Fc fragment. The various components of the fusion can be operatively linked in any order; the polypeptide (1) can be operatively linked to the N-terminus of the polypeptide for (2) or (3); the polypeptide for (2) can be operatively linked to the N-terminus of the polypeptide for (1) or (3); the polypeptide for (3) can be operatively linked to the N-terminus of the polypeptide for (1) or (2).

According to the present invention, the extracellular subdomain of a Klotho protein, the fibroblast growth factor and the (optional) modified Fc fragment having decreased affinity for Fc-gamma-receptor and/or increased serum half-life can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of an extracellular subdomain of the Klotho protein.

In one embodiment, the present invention provides a fusion polypeptide comprising a sKlotho of a Klotho protein and a linker. In another embodiment, the present invention provides a fusion polypeptide comprising a sKlotho of the alpha Klotho protein and a linker. In another embodiment, the present invention provides a fusion polypeptide comprising a sKlotho of the beta Klotho protein and a linker. In yet another embodiment, the present invention provides a human FGF protein or an active fragment thereof (e.g., without signal peptide) and a linker. Pharmaceutical compositions comprising the fusion proteins of the invention and their uses for treating or preventing age-related conditions or metabolic disorders are also encompassed by the present invention. In some embodiments, the fusion protein further comprises a modified Fc fragment having decreased affinity for Fc-gamma-receptor and/or increased serum half-life.

In one embodiment, the present invention provides a fusion polypeptide comprising a sKlotho of alpha Klotho protein with signal peptide fused (directly or indirectly via a linker) to FGF-23. In another embodiment, the present invention provides a fusion polypeptide comprising a sKlotho of alpha Klotho protein without signal peptide fused (directly or indirectly via a linker) to FGF-23. In another embodiment, the present invention provides sKlotho of alpha Klotho protein with signal peptide fused (directly or indirectly via a linker) to FGF-23 without signal peptide. In another embodiment, the present invention provides a fusion polypeptide comprising sKlotho of alpha Klotho protein without signal peptide fused (directly or indirectly via a linker) to FGF-23 without signal peptide. In some embodiments, the fusion protein further comprises a modified Fc fragment having decreased affinity for Fc-gamma-receptor and/or increased serum half-life.

In one embodiment, the present invention provides a fusion polypeptide comprising a sKlotho of alpha Klotho protein with signal peptide fused (directly or indirectly via a linker) to FGF-23 (R179Q) variant. In another embodiment, the present invention provides a fusion polypeptide comprising a sKlotho of alpha Klotho protein without signal peptide fused (directly or indirectly via a linker) to FGF-23 (R179Q) variant. In another embodiment, the present invention provides sKlotho of alpha Klotho protein with signal peptide fused (directly or indirectly via a linker) to FGF-23 (R179Q) variant without signal peptide. In another embodiment, the present invention provides a fusion polypeptide comprising sKlotho of alpha Klotho protein without signal peptide fused (directly or indirectly via a linker) to FGF-23 (R179Q) variant without signal peptide. In some embodiments, the fusion protein further comprises a modified Fc fragment having decreased affinity for Fc-gamma-receptor and/or increased serum half-life.

In one embodiment, the present invention provides a fusion polypeptide comprising (1) sKlotho of alpha Klotho protein with signal peptide; (2) a linker; and (3) FGF-23 (R179Q) variant without signal peptide. In another embodiment, the present invention provides a fusion polypeptide comprising (1) sKlotho of alpha Klotho protein without signal peptide; (2) a linker; and (3) FGF-23 (R179Q) variant without signal peptide. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a fusion polypeptide comprising (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43). In another embodiment, the present invention provides a fusion polypeptide comprising (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43). In one embodiment, the present invention provides a fusion polypeptide comprising the amino acid sequence of SEQ ID NO:19, 20, 40, or 41. In some embodiments, the fusion polypeptides of the invention are glycosylated.

In one embodiment, the present invention provides a fusion polypeptide comprising sKlotho of alpha Klotho protein with signal peptide (SEQ ID NO:44 or SEQ ID NO:45); and a linker comprising SEQ ID NO:11. In another embodiment, the present invention provides a fusion polypeptide comprising sKlotho of alpha Klotho protein without signal peptide (SEQ ID NO:7); and a linker comprising SEQ ID NO:11. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a fusion polypeptide comprising a human FGF protein or an active fragment thereof (e.g., without the signal peptide); and a linker comprising SEQ ID NO:11. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43); and (4) optionally, a modified Fc fragment having decreased affinity for Fc-gamma-receptor and/or increased serum half-life; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43); and (4) optionally, a modified Fc fragment having decreased affinity for Fc-gamma-receptor and/or increased serum half-life; and uses of the pharmaceutical composition for treating and/or preventing age-related conditions, such as muscular atrophy. In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising the amino acid sequence of SEQ ID NO:19, 20, 40, or 41; and uses of the pharmaceutical composition for treating and/or preventing age-related conditions, such as muscular atrophy.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises sKlotho of alpha Klotho protein with signal peptide (SEQ ID NO:44 or SEQ ID NO:45); and a linker comprising SEQ ID NO:11; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising sKlotho of alpha Klotho protein without signal peptide (SEQ ID NO:7); and a linker comprising SEQ ID NO:11; and uses of the pharmaceutical composition for treating and/or preventing age-related conditions, such as muscular atrophy. In some embodiments, the fusion protein further comprises a modified Fc fragment.

In one embodiment, the present invention provides a pharmaceuticals composition comprising (e.g., as a sole pharmaceutically active ingredient) a fusion polypeptide (e.g., glycosylated or non-glycosylated) that comprises a human FGF protein or an active fragment thereof (e.g., without the signal peptide); and a linker comprising SEQ ID NO:11.

Pharmaceutical compositions comprising the fusion proteins of the invention and their uses for treating or preventing age-related conditions (e.g., muscle atrophy) or metabolic disorders (e.g., diabetes) are also encompassed by the present invention.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 19. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 20.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 40. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 41.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 46. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 47.

In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 48. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 49.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 50. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 51.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 52. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 53.

In one embodiment, the present invention provides a fusion polypeptide comprising a sKlotho of beta Klotho protein with signal peptide fused (directly or indirectly via a linker) to FGF-19 or an active fragment thereof. In some embodiments, the fusion further comprises a modified Fc fragment having decreased affinity for Fc-gamma-receptor and/or increased serum half-life. In another embodiment, the present invention provides a fusion polypeptide comprising a sKlotho of beta Klotho protein without signal peptide fused (directly or indirectly via a linker) to FGF-19 or an active fragment thereof. In another embodiment, the present invention provides a fusion polypeptide comprising a sKlotho of beta Klotho protein with signal peptide fused (directly or indirectly via a linker) to FGF-21 or an active fragment thereof. In another embodiment, the present invention provides a fusion polypeptide comprising a sKlotho of beta Klotho protein without signal peptide fused (directly or indirectly via a linker) to FGF-21 or an active fragment thereof.

The invention provides nucleic acid sequences encoding any of the Klotho fusion polypeptides described herein and host cells containing the nucleic acids. In some embodiments, the fusion further comprises a modified Fc fragment having decreased affinity for Fc-gamma-receptor and/or increased serum half-life.

The invention also provides composition having any of the Klotho fusion polypeptides contemplated herein. The compositions of the invention can further include heparin. In some embodiments, the fusion further comprises a modified Fc fragment having decreased affinity for Fc-gamma-receptor and/or increased serum half-life.

The invention also provides a method for treating or preventing an age-related condition in an individual. An individual (e.g., human) is administered a therapeutically effective dose of a pharmaceutical composition containing a Klotho fusion polypeptide, having at least one extracellular subdomain of a Klotho protein (e.g., alpha Klotho protein) and a fibroblast growth factor or an active fragment thereof so as to treat or prevent the age-related condition. In some embodiments, the fusion further comprises a modified Fc fragment having decreased affinity for Fc-gamma-receptor and/or increased serum half-life. In particular, the invention provides a method of treating or preventing muscle wasting comprising administering to an individual (e.g., human) an therapeutically effective amount of a fusion polypeptide having at least one extracellular subdomain of an alpha Klotho protein and a fibroblast growth factor (or an active fragment thereof).

Additionally, the invention provides a method for treating or preventing a metabolic disorder in an individual. An individual is administered a therapeutically effective dose of a pharmaceutical composition containing a fusion polypeptide of the invention, having at least one extracellular subdomain of a Klotho protein and a fibroblast growth factor (or an active fragment thereof) so as to treat the metabolic disorder. In some embodiments, the fusion further comprises a modified Fc fragment having decreased affinity for Fc-gamma-receptor and/or increased serum half-life. In particular, a fusion polypeptide of the invention having at least one extracellular subdomain of a beta-Klotho protein and a fibroblast growth factor 21 is useful for treating a metabolic disorder.

Klotho-FGF23 fusion polypeptides of the invention can be used for treating or preventing hyperphosphatemia or calcinosis in an individual. In some embodiments, the fusion further comprises a modified Fc fragment having decreased affinity for Fc-gamma-receptor and/or increased serum half-life. A pharmacologically effective dose of a pharmaceutical composition containing the Klotho fusion polypeptide of the invention, having at least one extracellular subdomain of a Klotho protein and a fibroblast growth factor, is administered to treat or prevent hyperphosphatemia or calcinosis. In particular, a Klotho fusion polypeptide of the invention having at least one extracellular subdomain of an alpha Klotho protein and a fibroblast growth factor 23 is useful for treating hyperphosphatemia or calcinosis.

Klotho-FGF23 fusion polypeptides of the invention can be used for treating or preventing chronic renal disease or chronic renal failure in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent chronic renal disease or chronic renal failure.

Klotho-FGF23 fusion polypeptides of the invention can be used for treating or preventing cancer (e.g., breast cancer) in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent cancer or breast cancer.

The present invention provides fusion polypeptides comprising at least one extracellular subdomain of Klotho protein and a FGF or an active fragment thereof for use in medicine. In some embodiments, the fusion further comprises a modified Fc fragment having decreased affinity for Fc-gamma-receptor and/or increased serum half-life. In one embodiment, the present invention provides fusion polypeptides comprising at least one extracellular subdomain of Klotho protein and a FGF or an active fragment thereof for use in treating or preventing muscle atrophy. The present invention also provides a method of treating or preventing an age related condition (e.g., muscle atrophy) comprising administering to an individual in need thereof a therapeutically effective dose of a pharmaceutical composition comprising a soluble Klotho protein.

The invention also includes kits for treating or preventing an age-related disorder or metabolic disorder in an individual. The kit includes instructions for use and a purified Klotho fusion polypeptide having at least one extracellular subdomain of a Klotho protein and a fibroblast growth factor. In some embodiments, the fusion further comprises a modified Fc fragment having decreased affinity for Fc-gamma-receptor and/or increased serum half-life.

The invention also provides a kit for producing a Klotho fusion polypeptide of the invention. The kit of the invention includes instructions for use and a nucleic acid encoding a Klotho fusion polypeptide, having at least one extracellular subdomain of Klotho protein and a fibroblast growth factor. In some embodiments, the fusion further comprises a modified Fc fragment having decreased affinity for Fc-gamma-receptor and/or increased serum half-life.

In one embodiment of the invention, the fusion polypeptide comprises: (a) a polypeptide comprising a fibroblast growth factor; and (b) a modified Fc fragment having decreased affinity for Fc-gamma-receptor and/or increased serum half-life In one embodiment of the invention, the polypeptide of (a) and the polypeptide of (b) are connected by a polypeptide linker. The linker can be repeated 1 to 30 times, or more.

In one embodiment of the invention, the polypeptide linker comprises an amino acid sequence selected from the group consisting of: SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

In one embodiment of the invention, the polypeptide of (a) is connected by a peptide bond to the N-terminus of said polypeptide linker, and the polypeptide of (b) is connected by a peptide bond to the C-terminus of said polypeptide linker.

In one embodiment of the invention, the fusion polypeptide further comprises a signal peptide.

In one embodiment of the invention, the signal peptide is the IgG signal peptide.

In one embodiment of the invention, the fibroblast growth factor is fibroblast growth factor-23 or a fibroblast growth factor-23 variant (R179Q).

In one embodiment of the invention, the fibroblast growth factor is fibroblast growth factor-19 or fibroblast growth factor-21.

In one embodiment of the invention, fusion polypeptide comprises an amino acid sequence which is 95% or more identical to the amino acid sequence of SEQ ID NO: 51, or SEQ ID NO: 53.

In one embodiment of the invention, fusion polypeptide comprises the amino acid sequence of SEQ ID NO:51, or SEQ ID NO:53.

In one embodiment of the invention, fusion polypeptide comprises FcLALA.

3. BRIEF DESCRIPTION OF THE DRAWINGS

Figure 1B:
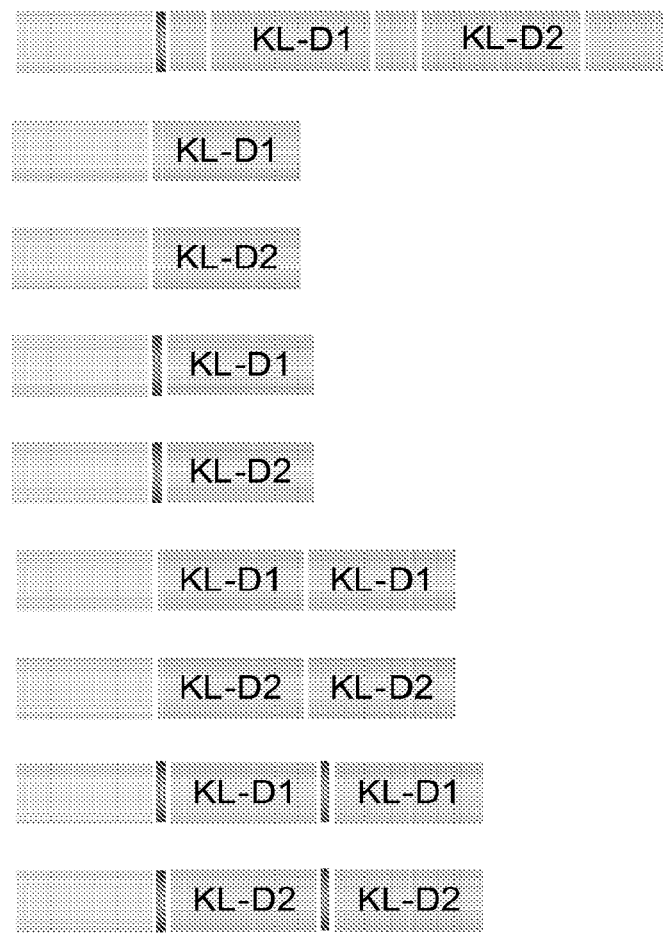

FIG. 1 illustrates several different embodiments of the Klotho fusion polypeptides of the invention. The represented fusion polypeptides include one or more Klotho extracellular subdomains operatively linked to a fibroblast growth factor. Polypeptides containing one or more Klotho extracellular subdomains include, for example, an extracellular domain of Klotho (e.g., aa 1 to 982 of human Klotho), or an active fragment of Klotho.

FIG. 2 illustrates the amino acid and nucleic acid sequences of several Klotho fusion polypeptides of the invention and components thereof (e.g., Klotho extracellular domain, FGF). Fusion proteins comprising sKlotho, FGF23 and FcLALA (a modified Fc fragment having decreased affinity for Fc-gamma-receptor and/or increased serum half-life) are described in SEQ ID NOs. 46, 47, 48, and 49. Fusion proteins comprising FGF23 and FcLALA are described in SEQ ID NOs. 50, 51, 52 and 53.

Figure 3A:
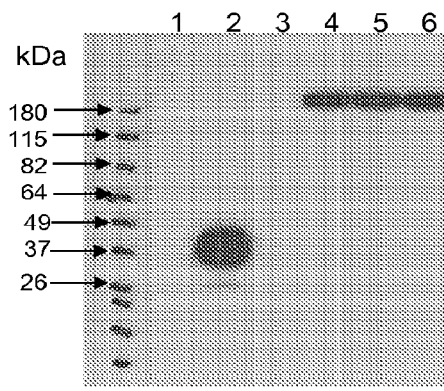
Figure 3B:
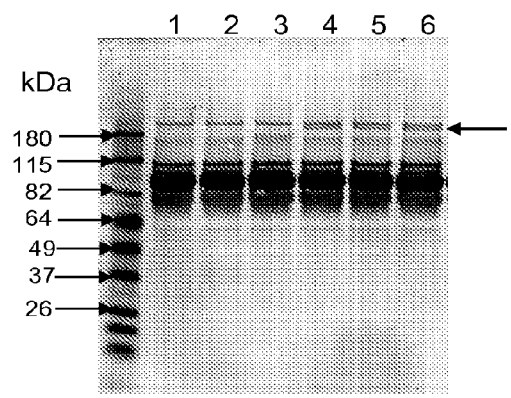
Figure 3C:
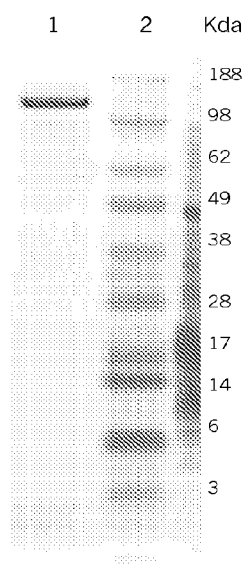

FIGS. 3A-3C depict protein expression of an sKlotho-FGF23 fusion protein. FIG. 3A shows that sKlotho-FGF23 fusion protein was detected in conditioned media by Western blotting with anti-FGF23 antibodies. FIG. 3B shows that sKlotho-FGF23 fusion protein was detected in conditioned media by SDS-PAGE and Coomassie blue staining FIG. 3C shows a highly purified sKlotho-FGF23-6× His fusion protein, analyzed by SDS-PAGE and Coomassie blue staining.

Figure 4:
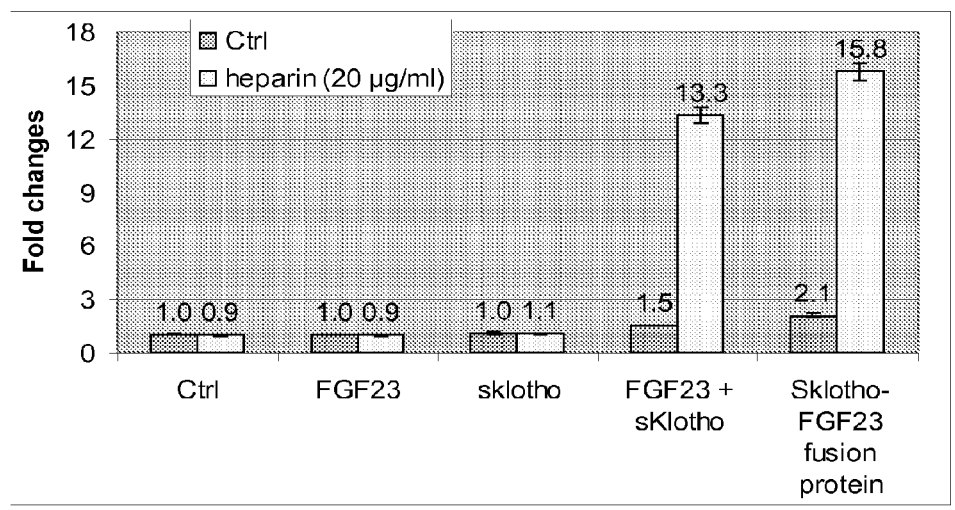

FIG. 4 illustrates the results of an Egr-1 luciferase assay comparing the activation level of Egr-1 in cells treated with conditioned media containing either a Klotho fusion polypeptide, a FGF 23 polypeptide only, a soluble Klotho (sKlotho) polypeptide only, and a soluble Klotho polypeptide in combination with a FGF 23 polypeptide in the absence or presence of heparin (20 μg/ml).

Figure 5A:
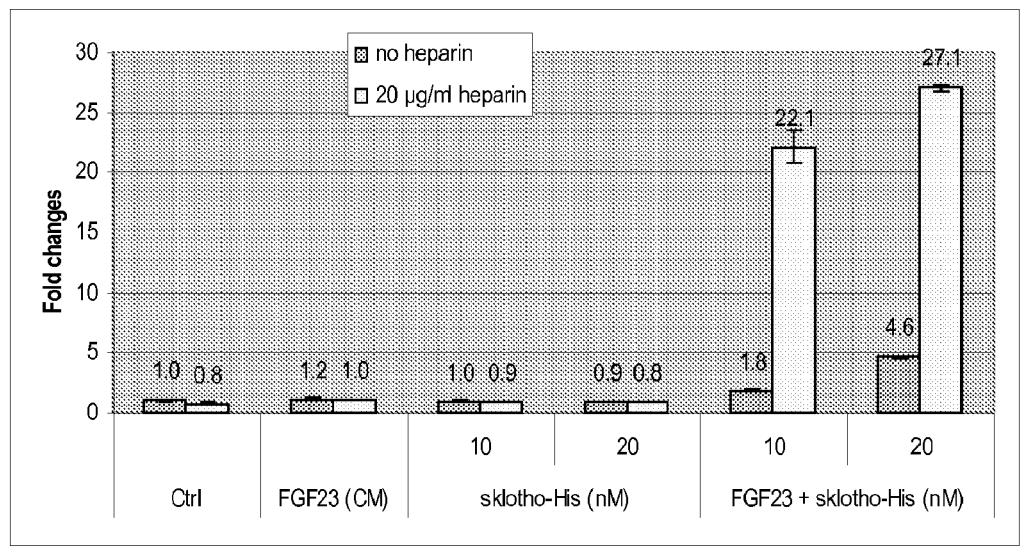
Figure 5B:
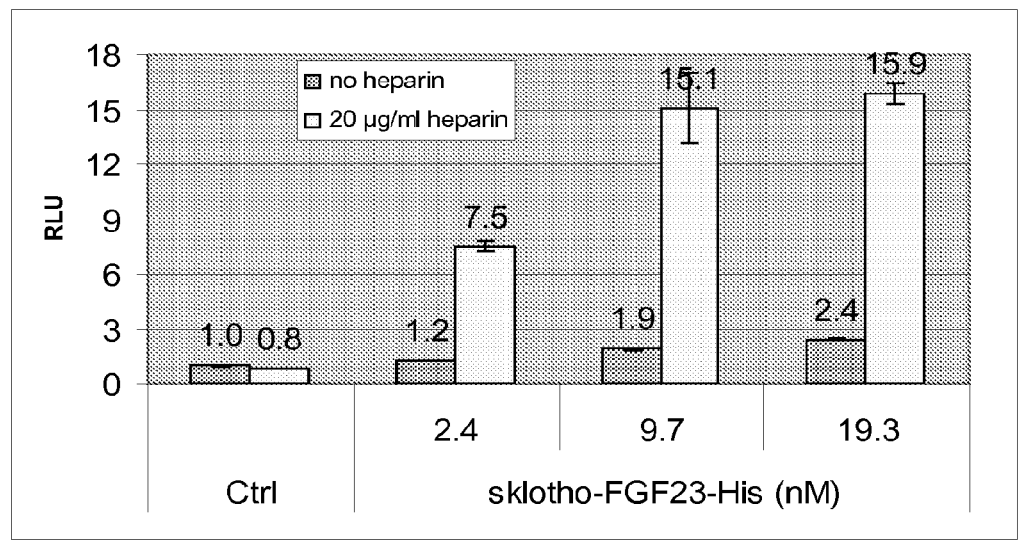

FIGS. 5A-5B depict the results of an Egr-1 luciferase assay comparing the activation level of Egr-1 in cells treated with purified Klotho fusion polypeptide, FGF 23 polypeptide, or soluble Klotho polypeptide in the absence or presence of heparin. FIG. 5A shows an the results of an experiment comparing the activation level of Egr-1 in cells treated with FGF 23 alone, sKlotho-His (10 nM or 20 nM) and a combination of FGF 23 and sKlotho-His (10 nM or 20 nM) in the absence or presence of heparin (20 μg/ml). FIG. 5B shows Egr-1 luciferase reporter activity in cells treated with sKlotho-FGF23-His fusion (0 nM, 0.6 nM, 1.21 nM, 2.41 nM, 4.83 nM, 9.65 nM, and 19.3 nM).

Figure 6A:
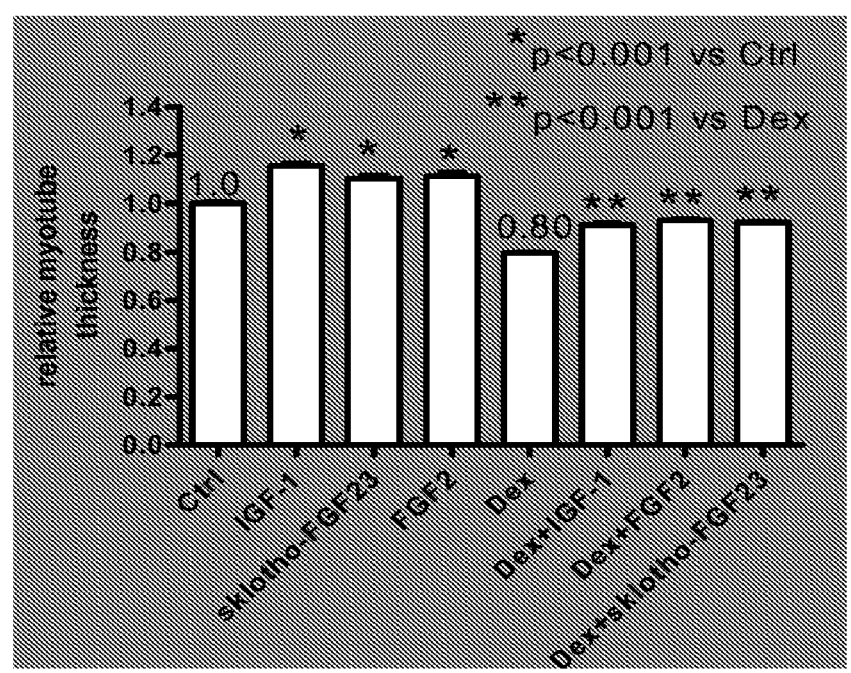
Figure 6B:
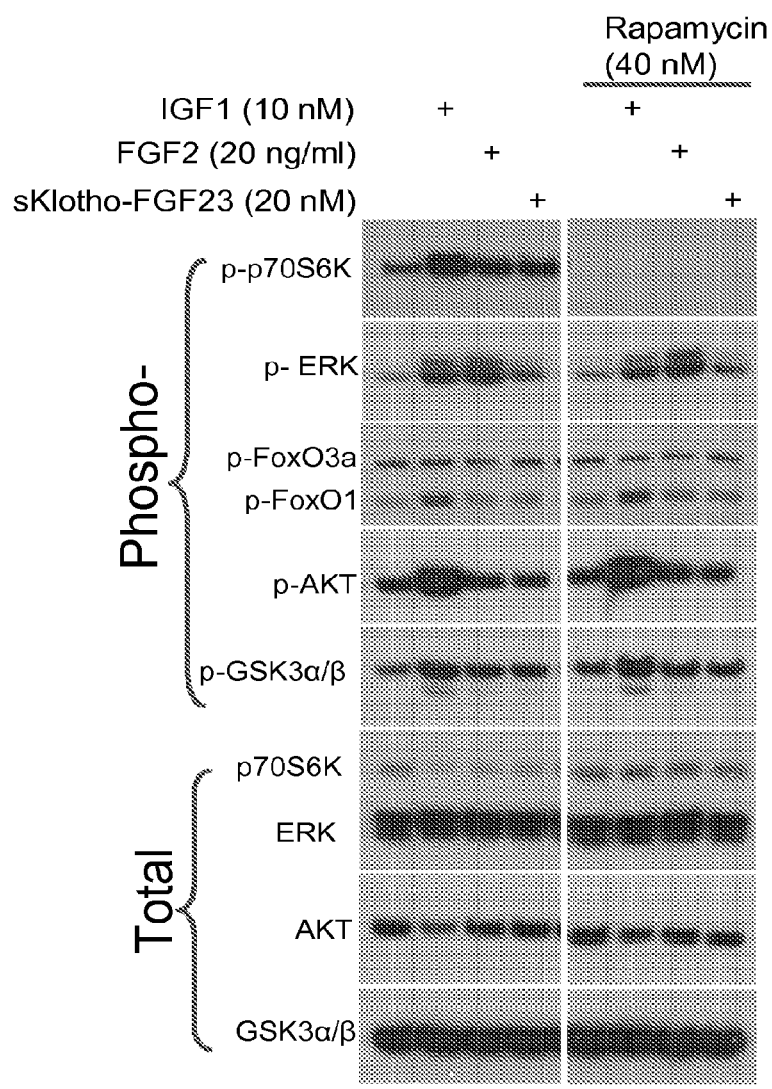

FIGS. 6A-6B illustrate the effect of treatment with a purified sKlotho fusion polypeptide on C2C12 muscle cells. FIG. 6A shows measurements of myotube diameter in C2C12 muscle cells treated with either IGF-1 (10 nM), FGF2 (20 ng/ml), or a purified Klotho fusion polypeptide (20 nM), in the absence or presence of dexamethasone (100 μM). FIG. 6B shows the phosphorylation of signaling pathway proteins in C2C12 muscle cells by IGF-1 (10 nM), FGF2 (20 ng/ml), or a purified Klotho fusion polypeptide (20 nM), in the absence or presence of rapamycin (40 nM).

4. DETAILED DESCRIPTION

The present invention is directed to methods, kits and compositions for preventing or treating age-related conditions and metabolic disorders. The fusion polypeptides of the invention include a Klotho protein or active fragment thereof. In some embodiments, the fusion polypeptides of the invention include a Klotho protein or an active fragment thereof operatively linked to a fibroblast growth factor polypeptide or active fragment thereof. In some embodiments, the fusion further comprises a modified Fc fragment with decreased ability to bind FcRn and/or increased stability in serum. In another embodiment, the fusion polypeptide comprises a FGF (e.g., FGF23) and a modified Fc fragment with decreased ability to bind FcRn and/or increased stability in serum.

The fusion proteins or sKlotho of the present invention are useful in the treatment and prevention of a variety of age-related conditions including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders including Type II Diabetes, Metabolic Syndrome, hyperglycemia, and obesity.

The present invention is based at least in part on the finding that despite the physical constraints (e.g., large size of both the Klotho and FGF polypeptides) the Klotho-FGF fusion polypeptides are highly effective in activating an FGF receptor. This finding is unexpected given that fusion of these two proteins would likely interfere with the heterodimerization and thus the activities of the proteins; e.g., the binding domains of the proteins may be perturbed by the fusion or the proteins may be mis-oriented spatially if put together in a "cis" formation.

The fusion polypeptides described herein are advantageous because they allow the administration of a single therapeutic protein that has enhanced activity compared to Klotho or FGF administered alone or together as separate polypeptides. The use of Klotho and FGF as a single fusion polypeptide rather than as two separate polypeptides (i.e., a Klotho polypeptide and a separate FGF polypeptide) is more effective at activating the FGF receptor.

Definitions

"Klotho polypeptide", "Klotho protein", or "Klotho" as used herein, includes active fragments, derivatives, mimetics, variants and chemically modified compounds or hybrids thereof of wild-type "Klotho". A Klotho active fragment has the ability to bind to an FGF polypeptide. Generally, a Klotho active polypeptide contains at least a Klotho subdomain (e.g., KL-D1 and KL-D2). Wild-type Klotho has the amino acid sequence as is found in nature. Exemplary Klotho polypeptides suitable for use with the present invention include alpha-Klotho (SEQ ID NO: 2) and beta-Klotho (SEQ ID NO: 4). Nucleotide and amino acid sequences of the alpha-Klotho and beta-Klotho are found in the GenBank database at Accession No. NM_004795; NP_004786 and NM_175737; NP_783864, respectively. Klotho polypeptides include those described in U.S. Pat. No. 6,579,850, the content of which is herein incorporated by reference in its entirety. The Klotho polypeptides include those from other species besides humans, including alpha-Klotho from mouse (NP_038851), rat (NP_112626), rabbit (NP_001075692) and beta-Klotho from mouse (NP_112457). Species predicted to have alpha-Klotho include chimpanzee (XP_522655), macaque (XP_001101127), horse (XP_001495662), cow (XP_001252500), platypus (XP_001510981), and chicken (XP_417105). Species predicted to have beta-Klotho include chimpanzee (XP_526550), macaque (XP_001091413), horse (XP_001495248), dog (XP_536257), rat (XP_001078178), platypus (XP_001512722), and chicken (XP_423224). The Klotho polypeptides have an amino acid sequence that is substantially identical to the amino acid sequence of SEQ ID NO: 2 or SEQ ID NO:4; i.e., at least 70%, 75%, 80%, 85%, 90%, 95%, 96%, 97%, 98%, 99% or more identical at the amino acid sequences of SEQ ID NO:2 or SEQ ID NO:4, or active fragment thereof.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond. As used herein a "Klotho fusion polypeptide" is a fusion polypeptide which includes an amino acid sequence from a Klotho polypeptide or active fragment thereof. A fusion polypeptide can comprise, as non-limiting examples, Klotho (e.g., sKlotho), FGF (e.g., FG23), and (optionally) a modified Fc fragment (e.g., a modified Fc fragment with decreased binding affinity to FC-gamma-receptor and/or increased serum half-life). Examples of this type of fusion polypeptide are presented in SEQ ID NOs. 46 to 49. In another embodiment, the fusion proteins comprise FGF (e.g., FGF23) and a modified Fc (e.g., FcLALA). Fusion proteins comprising FGF23 and FcLALA are described in SEQ ID NOs. 50, 51, 52 and 53. FcLALA is a Fc fragment with a LALA mutation (L234A, L235A), which triggers ADCC with lowered efficiency, and binds and activates human complement weakly. Hessell et al. 2007 Nature 449:101-104.

"Fibroblast growth factor" and "FGF" are used interchangeably herein and shall refer to polypeptides that regulate cell proliferation, migration, differentiation, homeostasis, tissue repair and response to injury in an animal, including a human subject. FGFs have the ability to bind to a fibroblast growth factor receptor and regulate its activity, including autophosphorylation of FGFR, phosphorylation of FRS2 (FGF receptor substrate 2) and ERK1/2 (extracellular signal-regulated protein kinase 1/2), and activating Egr-1 (early growth response-1). The term "FGF" includes active fragments, derivatives, mimetics, variants and chemically modified compounds or hybrids thereof of wild-type "FGF", e.g., as known in the art and as described in U.S. Pat. No. 7,223,563 and U.S. Pat. No. 7,259,248, the contents of which are incorporated by reference in their entirety. Wild-type FGF has an amino acid sequence as is found in nature. Exemplary fibroblast growth factors suitable for use with the present invention include fibroblast growth factor-19 (FGF19; SEQ ID NO: 31), fibroblast growth factor-21 (FGF21; SEQ ID NO: 33), and fibroblast growth factor-23 (FGF23; SEQ ID NO: 35). The FGF polypeptides include those from other species besides humans, including murine FGFs. Generally, FGF polypeptides have an amino acid sequence that is substantially identical to the amino acid sequence of SEQ ID NO: 31, SEQ ID NO:33 or SEQ ID NO:35; i.e., having an amino acid sequence is which is at least 70%, 75%, 80%, 85%, 90%, 95%, 96%, 97%, 98%, 99% or more or 100% identical to the amino acid sequences of SEQ ID NO: 31 SEQ ID NO:33 or SEQ ID NO:35, or active fragments thereof. Additional non-limiting examples of FGF, particularly FGF23, are provided at aa 1002-1228 of SEQ ID NO:47; aa 1002-1228 of SEQ ID NO: 49; aa 1-251 of SEQ ID NO: 51, and aa 1-251 of SEQ ID NO:53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

The term "FGF", includes active fragments of the full-length polypeptide. Active FGF fragments that are able to bind to their corresponding FGF receptors are known in the art and also contemplated for use in the present invention. One skilled in the art would appreciate, based on the sequences disclosed herein, that overlapping fragments of the FGFs can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF fragments could be tested by methods well known in the art and described herein, including binding to the FGF receptor. Similarly, cell culture models which possess the necessary FGF signal transduction machinery (i.e. FGF receptor) may be transfected with FGF fragments and subsequently tested for alterations in FGF signaling, relative to wild type FGF.

FGFs are grouped into seven subfamilies based on the homology of the FGF core homology domain (approximately 120 amino acids long), which is flanked by N- and C-terminal sequences that are highly variable in both length and primary sequence, particularly among different FGF subfamilies (Goetz et al., Molecular and Cellular Biology, 2007, Vol. 27, 3417-3428). An FGF active polypeptide generally contains at least an FGF core homology domain. In some embodiments, an FGF active polypeptide may contain, in addition to an FGF core homology domain, flanking sequences which may confer additional specificity in binding FGF receptors. FGF19, FGF21, and FGF23 are grouped in the FGF19 subfamily because the core region of these ligands share high sequence identity relative to other FGFs (FGF19 v. FGF21: 38% identity; FGF19 v. FGF23: 36% identity). FGF19 subfamily members act analogously to signaling molecules of the endocrine system and regulate diverse physiological processes uncommon to classical FGFs (e.g., FGF19: energy and bile acid homeostasis; FGF21: glucose and lipid metabolism; and FGF 23: phosphate and vitamin D homeostasis).

"Fibroblast growth factor receptor" and "FGFR" as used herein refer to any one of FGFRs 1-4 known in the art, or splice variants thereof (e.g., FGFR1c). Exemplary fibroblast growth factor receptors suitable for use with the present invention include fibroblast growth factor receptor-19 (e.g., FGFR4-beta Klotho), fibroblast growth factor receptor-21 (e.g., FGFR1c-alpha Klotho), and fibroblast growth factor receptor-23 (e.g., FGFR1c-alpha Klotho, FGFR3-alpha Klotho, FGFR4-alpha Klotho).

"Extracellular domain", as used herein, refers to the fragment of a transmembrane protein existing outside of a cell (e.g., not including the intracellular or transmembrane region). The "extracellular domain of the Klotho protein", "soluble Klotho", or "sKlotho" (e.g., SEQ ID NO: 7; SEQ ID NO: 39), refers to an extracellular domain of the Klotho polypeptide that is capable of binding a fibroblast growth factor, and/or capable of enabling the binding of a fibroblast growth factor to a fibroblast growth factor receptor by binding to the fibroblast growth factor. The Klotho extracellular domain corresponds to amino acid residues 28-982 of the full length alpha Klotho sequence (SEQ ID NO: 2) and to amino acid residues 52-997 of the full length beta Klotho sequence (SEQ ID NO:4).

"Extracellular subdomain of Klotho protein" and "extracellular subdomain of Klotho protein" are used interchangeably herein and shall refer to a region in the extracellular domain of the Klotho polypeptide that is capable of binding a fibroblast growth factor, and/or is capable of enabling the binding of a fibroblast growth factor to a fibroblast growth factor receptor by binding to the fibroblast growth factor. In various embodiments, the fusion comprises a polypeptide comprising at least one extracellular subdomain of a Klotho protein; a polypeptide comprising a fibroblast growth factor; and, optionally, a modified Fc fragment having decreased affinity for Fc-gamma-receptor and/or increased serum half-life. The Klotho extracellular domain has two homologous subdomains that are repeated, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and respectively to amino acid residues 77-508 and 571-967 of the full length beta Klotho polypeptide (SEQ ID NO:4) and are suitable for use with the present invention. Generally, a polypeptide that contains at least one Klotho subdomain is a Klotho active polypeptide. The Klotho extracellular subdomain for use with the polypeptide of the invention may be an alpha Klotho or beta Klotho KL-D1 domain with an amino acid sequence that is substantially identical to the amino acid sequence of SEQ ID NO: 5 or SEQ ID NO: 37, respectively. Further, the Klotho KL-D1 domain may have an amino acid sequence that is at least 70%, 75%, 80%, 85%, 90%, 95%, 96%, 97%, 98%, 99% or more identical to the amino acid sequence of SEQ ID NO: 5 or SEQ ID NO: 37. The Klotho extracellular subdomain may also be an alpha or beta Klotho polypeptide KL-D2 domain that is substantially identical to the amino acid sequence of SEQ ID NO: 6 or SEQ ID NO: 38, respectively. In a further embodiment, the KL-D2 domain has an amino acid sequence that is at least at least 70%, 75%, 80%, 85%, 90%, 95%, 96%, 97%, 98%, 99% or more identical to the amino acid sequence of SEQ ID NO: 6 or SEQ ID NO: 38. In some embodiments, the fusion comprises at least two extracellular subdomains of the Klotho protein (e.g., KL-D1 and KL-D2; KL-D1 and KL-D1 in tandem repeats; KL-D2 and KL-D2 in tandem repeats, etc.).

"Modified Fc fragment", as used herein, shall mean an Fc fragment of an antibody comprising a modified sequence. The Fc fragment is a portion of an antibody comprising the CH2, CH3 and part of the hinge region. The modified Fc fragment can be derived from, for example, IgG1, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798. For example, in various modified Fc fragments: (a) amino acid residue 250 is glutamic acid and amino acid residue 428 is phenylalanine; or (b) amino acid residue 250 is glutamine and amino acid residue 428 is phenylalanine; or (c) amino acid residue 250 is glutamine and amino acid residue 428 is leucine. In some embodiments, amino acid residues 250 and 428 differ from the residues present in an unmodified Fc-fusion protein by amino acid residue 250 being glutamic acid or glutamine and amino acid residue 428 being leucine or phenylalanine, and wherein amino acid residues are numbered by the EU numbering system, as described in U.S. Pat. No. 7,217,798. In some embodiments, the modified Fc-fusion protein has a higher affinity for FcRn at pH 6.0 than at pH 8.0. Preferably, the modified Fc fragment has decreased affinity to FcRn and/or increased serum half-life. Non-limiting examples of modified Fc fragments include that at aa (amino acids) 1234-1459 of SEQ ID NO: 47; aa 1234 to 1450 of SEQ ID NO: 49; aa 257 to 482 of SEQ ID NO: 51; and aa 257 to 473 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

"Signal peptide", as used herein, shall mean a peptide chain (3-60 amino acids long) that directs the post-translational transport of a protein to the endoplasmic reticulum and may be cleaved off. Exemplary signal peptides suitable for use with the present invention include the Klotho signal peptide (SEQ ID NO:19) and the IgG signal peptide (SEQ ID NO:20).

"Linker", as used herein, shall mean a functional group (e.g., chemical or polypeptide) that covalently attaches two or more polypeptides or nucleic acids so that they are connected with one another. As used herein, a "peptide linker" refers to one or more amino acids used to couple two proteins together (e.g., to couple the extracellular domain of Klotho and fibroblast growth factor-23). Peptide linkers suitable for use with the present invention include, but are not limited to, polypeptides with amino acid sequences represented by SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18. A polypeptide linker can comprise at least 1 and up to about 30 repeats of any of these amino acid sequences.

"Operatively linked", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

"Specifically binds", as used herein, shall refer to the ability of a first molecule to bind to a target molecule out of many, different types of molecules to which it may be exposed because of the ability of the first molecule to adopt a particular structure conducive to forming non-covalent interactions between itself and the other target molecule. The first molecule binds to the target forming a stable complex while there is substantially less recognition, contact, or complex formation of the first molecule with any other non-specific molecules.

"Polypeptide variant" or "protein variant", as used herein, refers to polypeptides in which one or more amino acids have been substituted by different amino acids from a reference sequence. It is well understood in the art that some amino acids may be substituted by others with broadly similar properties without changing the nature of the activity of the polypeptide (conservative substitutions) as described hereinafter. These terms also encompass polypeptides in which one or more amino acids have been added or deleted, or replaced with different amino acids, e.g., protein isoforms. An exemplary variant of fibroblast growth factor-23 suitable for use with the present invention is the fibroblast growth factor-23 variant (R179Q).

"Pharmaceutical composition", as used herein, shall mean a composition containing a compound (e.g., a fusion polypeptide of the invention) that may be administered to treat or prevent a disease or disorder in an individual.

"Individual" or "subject", as used herein, shall refer to a mammal, including, but not limited to, a human or non-human mammal, such as a bovine, equine, canine, ovine, or feline.

"Treat", as used herein, shall mean decrease, suppress, attenuate, diminish, arrest, or stabilize the development or progression of a disease. In the context of the invention, the administration of the polypeptides of the invention may be used to treat age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity.

"Prevent", as used herein, shall refer to a decrease in the occurrence of a disorder or decrease in the risk of acquiring a disorder or its associated symptoms in a subject. In the context of the invention, the administration of the polypeptides of the invention may be used to prevent age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity. The prevention may be complete, e.g., the total absence of an age-related condition or metabolic disorder. The prevention may also be partial, such that the likelihood of the occurrence of the age-related condition or metabolic disorder in a subject is less likely to occur than had the subject not received the present invention.

"Disease", as used herein, shall mean any condition or disorder that damages or interferes with the normal function of a cell, tissue, or organ.

"Age-related condition", as used herein, shall mean any disease or disorder whose incidence in a population or severity in an individual correlates with the progression of age. In one embodiment, the age-related condition is a disease or disorder whose incidence is at least 1.5 fold higher among human individuals greater than 60 years of age relative to human individuals between the ages of 30-40 and in a selected population of greater than 100,000 individuals. Age-related conditions relevant to the present invention include, but are not limited to, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

"Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present invention include, but are not limited to, Type II Diabetes, Metabolic Syndrome, hyperglycemia, and obesity.

An "effective dose" or "effective amount" is an amount sufficient to effect a beneficial or desired clinical result. In the context of the invention, it is an amount of a Klotho fusion polypeptide or sKlotho effective to produce the intended pharmacological, therapeutic or preventive result. A therapeutically effective dose results in the prevention or amelioration of the disorder or one or more symptoms of the disorder, (e.g., an age-related condition or metabolic disorder). Therapeutically effective doses will vary depending upon the subject and disease condition being treated, the weight and age of the subject, the severity of the disease condition, the manner of administration and the like which can be readily be determined by one of ordinary skill in the art.

"Klotho nucleic acid molecule", as used herein is a gene encoding a Klotho protein. An exemplary human Klotho gene is provided at GenBank Accession No. NM_004795 (SEQ ID NO:1). Additional non-limiting examples of Klotho are provided at aa 1-982 of SEQ ID NO:47 and aa 1-982 of SEQ ID NO: 49; and sequences which are at least 70%, 75%, 80%, 85%, 90%, 95%, 96%, 97%, 98%, 99% or more or 100% identical to these sequences.

"Fragment", as used herein, refers to a portion of a polypeptide or nucleic acid molecule. This portion contains, preferably, at least 10%, 20%, 30%, 40%, 50%, 60%, 70%, 80%, 90% or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or up to 3000 nucleotides or amino acids.

The term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, 70%, 75%, 80% or 85%, 90%, 91%, 92%, 93%, 94%, 95%, 96%, 97%, 98%, 99% or more identical at the amino acid level or nucleic acid to the sequence used for comparison.

The present invention is directed to methods, kits and compositions for preventing or treating age-related conditions and metabolic disorders. In some embodiments, the invention provides a fusion polypeptide having at least one extracellular subdomain of a Klotho protein. In some embodiments, the fusion polypeptides further comprise a fibroblast growth factor or an active fragment thereof. In some embodiments, the fusion further comprises a modified Fc fragment having decreased affinity for Fc-gamma-receptor and/or increased serum half-life. In other embodiments, the fusion comprises an FGF (e.g., FGF19, FGF21, FGF23 or FGF23 variant R179Q) fused to a modified Fc (e.g., FcLALA). FcLALA is a Fc fragment with a LALA mutation (L234A, L235A), which triggers ADCC with lowered efficiency, and binds and activates human complement weakly. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs or an active fragment thereof can be used in practicing the invention.

The extracellular domain of the Klotho protein can include one or both of the KL-D1 and KL-D2 domains of a Klotho protein. In some embodiments, the Klotho fusion polypeptide has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain.

The extracellular subdomain of a Klotho protein and the fibroblast growth factor (or an active fragment thereof) can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of the at least one extracellular subdomain of the Klotho protein.

The fusion polypeptide of the invention may include one or both of the Klotho extracellular domains, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and to amino acid residues 77-508 and 571-967 of the full length beta Klotho polypeptide (SEQ ID NO:4) and are suitable for use with the present invention. The Klotho fusion polypeptide may have a KL-D1 domain of an alpha Klotho polypeptide having an amino acid sequence that is substantially identical to the amino acid sequence of SEQ ID NO: 5 or of a beta Klotho polypeptide having an amino acid sequence that is substantially identical to the amino acid sequence of SEQ ID NO: 37. Specifically, the Klotho fusion polypeptide may have an amino acid sequence that is at least at least 70%, 75%, 80%, 85%, 90%, 95%, 96%, 97%, 98%, 99% or more identical to SEQ ID NO: 5 or SEQ ID NO: 37. The Klotho fusion polypeptide may have a KL-D2 domain of an alpha Klotho polypeptide with an amino acid sequence that is substantially identical to the amino acid sequence of SEQ ID NO: 6 or of a beta Klotho polypeptide having an amino acid sequence that is substantially identical to the amino acid sequence of SEQ ID NO: 38. Specifically, the Klotho fusion polypeptide may have an amino acid sequence that is at least at least 70%, 75%, 80%, 85%, 90%, 95%, 96%, 97%, 98%, 99% or more identical to SEQ ID NO: 6 or SEQ ID NO: 38, respectively.

In some embodiments, the Klotho fusion polypeptide of the invention is soluble and is capable of binding to an FGF receptor.

The Klotho fusion polypeptides of the invention can contain a polypeptide linker which connects the polypeptide having at least one extracellular subdomain of a Klotho protein and the fibroblast growth factor and the (optional) modified Fc fragment. Suitable linkers are well known in the art and generally contain several Gly and several Ser residues, e.g., $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). In some embodiments, the linker will have at least 2 and up to about 30 repeats of an amino acid sequence represented by any one of SEQ ID NO:12, SEQ ID NO:13, SEQ ID NO:14, SEQ ID NO:15, SEQ ID NO:16, SEQ ID NO:17, or SEQ ID NO:18.

When a polypeptide linker is present in the Klotho fusion polypeptide of the invention, the polypeptide having at least one extracellular subdomain of a Klotho protein may be connected by a peptide bond to the N-terminus of the linker polypeptide with the FGF connected by a peptide bond to the C-terminus of the polypeptide linker. Alternatively, the FGF may be connected by a peptide bond to the N-terminus of the linker polypeptide with the polypeptide having at least one extracellular subdomain of Klotho connected by a peptide bond to the C-terminus of the polypeptide linker A chemical linker can also be used to link the two polypeptides.

The Klotho fusion polypeptide of the invention may include a signal peptide. Exemplary signal peptides for use with the Klotho fusion polypeptide include, but are not limited to the Klotho signal peptide (SEQ ID NO: 8) and the IgG signal peptide (SEQ ID NO: 9).

In some embodiments, the invention provides a fusion between a FGF (e.g., FGF19, FGF21, FGF23, or FGF23 variant R179Q) and a modified Fc (e.g., FcLALA). The fusion can also optionally comprise linkers between the FGF and Fc portions. The fusion can also optionally comprise a signal peptide. In various embodiments, the invention encompasses nucleic acids encoding these fusion polypeptides, vectors comprising these nucleic acids, and host cells containing these nucleic acids.

4.1. Klotho and Fibroblast Growth Factor Polypeptides

The Klotho fusion polypeptides of the invention are expected to exhibit biological activities comparable to FGF in nature, such as binding to an FGF receptor and inducing the phosphorylation of an FGF receptor, FRS2 (FGF receptor substrate 2) and ERK1/2 (extracellular signal-regulated protein kinase 1/2) and activating Egr-1 (early growth response-1) gene. FGF is a secreted peptide growth factor that binds the FGF receptor. The amino acid and nucleic acid sequences of FGF are readily available to those of skill in the art. For example, exemplary nucleotide sequences for FGF19, FGF21, and FGF23 can be found in the GenBank database at Accession numbers: NM_005117, NM_019113, and NM_020638, respectively, and herein as SEQ ID NOs: 30, 32, and 34, respectively. Exemplary amino sequences for FGF19, FGF21, and FGF23 can be found in the GenBank database at Accession numbers: NP_005108, NP_061986, and NP_065689, respectively, and herein as SEQ ID NOs: 31, 35, and 35, respectively. Additionally, FGF may include one or more alterations which aid in the expression of the protein, e.g., the FGF23 (R179Q) variant (SEQ ID NO: 36).

The Klotho protein is a 130 kDa single pass type I transmembrane protein with an extracellular domain and a short cytoplasmic domain. The amino acid and nucleic acid sequences of Klotho are readily available to those of skill in the art. For example, exemplary nucleotide sequences for alpha-Klotho and beta-Klotho can be found in the GenBank database at Accession numbers: NM_004795 and NM_175737, respectively, and herein as SEQ ID NOs: 7 and 8, respectively. Exemplary amino acid sequences for alpha-Klotho and beta-Klotho can be found in the GenBank database at Accession numbers: NP_004786 and NP_783864, respectively, and herein as SEQ ID NOs: 2 and 4, respectively.

The Klotho fusion polypeptide of the invention can bind to a fibroblast growth factor receptor and has an alpha-Klotho or beta-Klotho extracellular domain operatively linked to either fibroblast growth factor-19 (SEQ ID NO: 31), fibroblast growth factor-21 (SEQ ID NO: 33), fibroblast growth factor-23 (SEQ ID NO: 35), or variants thereof (which include fibroblast growth factor-23 variant (R179Q) (SEQ ID NO: 36)).

Specifically, the Klotho fusion polypeptide of the invention may include an alpha-Klotho (SEQ ID NO: 2) which is operatively coupled to fibroblast growth factor-23 (SEQ ID NO: 35) or fibroblast growth factor-23 variant (R179Q) (SEQ ID NO: 36). Additionally, the Klotho fusion polypeptide of the invention may have beta-Klotho (SEQ ID NO: 4), which is operatively coupled to fibroblast growth factor-19 (SEQ ID NO: 31). The Klotho fusion polypeptide of the invention may include a beta-Klotho (SEQ ID NO: 4), which is operatively coupled to fibroblast growth factor-21 (SEQ ID NO: 33).

The invention includes homologs of the various Klotho and FGF genes and proteins encoded by those genes. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of Homologs of the genes described herein can be identified by percent identity between amino acid or nucleotide sequences for putative homologs and the sequences for the genes or proteins encoded by them (e.g., nucleotide sequences for genes encoding Klotho and FGF or their complementary strands). Percent identity may be determined, for example, by visual inspection or by using various computer programs known in the art or as described herein. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "homology" and "homologous" are not limited to designate proteins having a theoretical common genetic ancestor, but includes proteins which may be genetically unrelated that have, nonetheless, evolved to perform similar functions and/or have similar structures. Functional homology to the various proteins described herein also encompasses proteins that have an activity of the corresponding protein of which it is a homolog. For proteins to have functional homology, it is not required that they have significant identity in their amino acid sequences, but, rather, proteins having functional homology are so defined by having similar or identical activities. For example, with respect to a Klotho molecule, the polypeptide should have the functional characteristics of binding to an FGF polypeptide and enable the binding of the FGF to an FGFR. With respect to an FGF molecule, the polypeptide should have the functional characteristics of binding to an FGFR and causing the activation of FGFR (e.g., phosphorylation). Assays for assessing FGF binding to the FGF receptor and/or activation of the FGF signaling pathway are known in the art and described herein (See Example 2). Assays for assessing Klotho activity are also known in the art and described herein (e.g., binding to a FGF polypeptide). Proteins with structural homology are defined as having analogous tertiary (or quaternary) structure and do not necessarily require amino acid identity or nucleic acid identity for the genes encoding them. In certain circumstances, structural homologs may include proteins which maintain structural homology only at the active site or binding site of the protein.

In addition to structural and functional homology, the present invention further encompasses proteins having amino acid identity to the various Klotho and FGF amino acid sequences described herein. To determine the percent identity/homology of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

The amino acid sequences of molecules of the invention described herein have an amino acid sequence which is at least about 60%, 70%, 80%, 90%, 95%, 96%, 97%, 98%, 99% or more identical or homologous to an amino acid sequence described herein.

The nucleic acid sequences of molecules of the invention described herein have a nucleotide sequence which hybridizes to or is at least about 60%, 70%, 80%, 90%, 95%, 96%, 97%, 98%, 99% or more identical or homologous to a nucleotide sequence described herein.

Nucleic acid molecules appropriate for use in the fusion polypeptides of the invention may have a Klotho or FGF nucleotide sequence which hybridizes under stringent conditions to the complement of a nucleic acid molecule encoding Klotho or FGF, respectively. As used herein, the term "hybridizes under stringent conditions" is intended to describe conditions for hybridization and washing under which nucleotide sequences at least about 70%, 80%, 85%, 90% or more homologous to each other typically remain hybridized to each other. Such stringent conditions are known to those skilled in the art and can be found in Ausubel et al. *Current Protocols in Molecular Biology*, Wiley Interscience, New York (2001), 6.3.1-6.3.6. A specific, non-limiting example of stringent hybridization conditions are hybridization in 6× sodium chloride/sodium citrate (SSC) at about 45° C., followed by one or more washes in 0.2×SSC, 0.1% SDS at 50-65° C.

4.2. Klotho-FGF Fusion Polypeptides of the Invention

In some embodiments of the invention, a Klotho fusion polypeptide has a polypeptide chain having a first polypeptide sequence of a Klotho polypeptide or an active fragment thereof and a second polypeptide sequence encoding FGF or an active fragment thereof. In some embodiments, the fusion further comprises a modified Fc fragment having decreased affinity for Fc-gamma-receptor and/or increased serum half-life.

The invention includes fusion polypeptides which are at least about 95% or more homologous to an amino acid sequence presented in SEQ ID NO:19-28. The amino acid sequence of SEQ ID NO: 19 encodes a Klotho fusion polypeptide having a Klotho extracellular domain N-terminally linked to the FGF23 (R179Q) variant (SEQ ID NO: 36). The amino acid sequence of SEQ ID NO: 20 encodes a Klotho fusion polypeptide having an IgG signal peptide N-terminally linked to a Klotho extracellular domain lacking a signal peptide N-terminally linked to the FGF23 (R179Q) variant. The amino acid sequence of SEQ ID NO: 21 encodes a Klotho fusion polypeptide having a KL-D1 extracellular subdomain N-terminally linked to the FGF23 (R179Q) variant. The amino acid sequence of SEQ ID NO: 22 encodes a Klotho fusion polypeptide having a KL-D2 extracellular subdomain N-terminally linked to the FGF23 (R179Q) variant. The amino acid sequence of SEQ ID NO: 23 encodes a Klotho fusion polypeptide having two KL-D1 extracellular subdomains N-terminally linked to the FGF23 (R179Q) variant. The amino acid sequence of SEQ ID NO: 24 encodes a Klotho fusion polypeptide having two KL-D2 extracellular subdomains N-terminally linked to the FGF23 (R179Q) variant. The amino acid sequence of SEQ ID NO: 25 encodes a Klotho fusion polypeptide having the FGF23 (R179Q) variant N-terminally linked to a Klotho extracellular domain. The amino acid sequence of SEQ ID NO: 26 encodes a Klotho fusion polypeptide having the FGF23 (R179Q) variant N-terminally linked to a KL-D1 extracellular subdomain. The amino acid sequence of SEQ ID NO: 27 encodes a Klotho fusion polypeptide having the FGF23 (R179Q) variant N-terminally linked to a KL-D2 extracellular subdomain. The amino acid sequence of SEQ ID NO: 28 encodes a Klotho fusion polypeptide having the FGF23 (R179Q) variant N-terminally linked to two KL-D1 extracellular subdomains. The amino acid sequence of SEQ ID NO: 29 encodes a Klotho fusion polypeptide having the FGF23 (R179Q) variant N-terminally linked to two KL-D2 extracellular subdomains. In some embodiments, the fusion further comprises a modified Fc fragment having decreased affinity for Fc-gamma-receptor and/or increased serum half-life.

The Klotho fusion polypeptide of the invention may include an amino acid sequence which is at least about 95% identical to the amino acid sequence set forth in SEQ ID NO:7. The amino acid sequence of SEQ ID NO: 7 encodes a Klotho extracellular domain lacking a signal peptide. In some embodiments, the fusion further comprises a modified Fc fragment having decreased affinity for Fc-gamma-receptor and/or increased serum half-life.

The subject fusion proteins are described herein and can be made using methods known in the art. For example, the fusion polypeptides of the invention may be constructed as described in U.S. Pat. No. 6,194,177. The use of Klotho polypeptides is described in U.S. Pat. No. 6,579,850. The use of FGF nucleic acid molecules is described in U.S. Pat. No. 7,223,563.

In some embodiments, a nucleic acid molecule encoding the Klotho is cloned by PCR and ligated, in frame, with a nucleic acid molecule encoding FGF. In some embodiments, the fusion further comprises a modified Fc fragment having decreased affinity for Fc-gamma-receptor and/or increased serum half-life. The nucleic acid encoding the fusion polypeptide is operatively linked to a promoter to allow for expression. The nucleic acid molecule encoding the fusion polypeptide is subsequently transfected into a host cell for expression. The sequence of the final construct can be confirmed by sequencing.

When preparing the fusion proteins of the present invention, a nucleic acid molecule encoding an extracellular subdomain of Klotho will be fused in frame to the nucleic acid molecule encoding FGF and the (optional) nucleic acid encoding the modified Fc fragment. Expression of the resulting nucleic acid molecule results in the extracellular subdomain of Klotho being fused N-terminal in relation to the FGF polypeptide. Fusions are also possible in which the extracellular subdomain of Klotho is fused C-terminal in relation to the FGF polypeptide. Methods for making fusion proteins are well known in the art.

The fusion polypeptides of the invention have at least two polypeptides that are covalently linked, in which one polypeptide comes from one protein sequence or domain, e.g., Klotho, and the other polypeptide comes from another protein sequence or domain, e.g., FGF. In some embodiments, the fusion further comprises a modified Fc fragment having decreased affinity for Fc-gamma-receptor and/or increased serum half-life. In another embodiment, the invention comprises a FGF fused to a modified Fc fragment. Klotho and/or FGF and/or the (optional) modified Fc fragment, of the fusion polypeptides of the invention, can be joined by methods well known to those of skill in the art. These methods include both chemical and recombinant means.

Nucleic acids encoding the domains to be incorporated into the fusion polypeptides of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). In nucleic acids encoding a Klotho fusion polypeptide of the invention, the nucleic acid sequence encoding alpha-Klotho or beta-Klotho, represented by SEQ ID NO: 1 and SEQ ID NO: 3, respectively, may be used. In nucleic acids encoding a Klotho fusion polypeptide, the nucleic acid sequence encoding FGF19, FGF21, or FGF23, represented by SEQ ID NO: 30, SEQ ID NO: 32 and SEQ ID NO: 34, respectively, may be used. Nucleic acid sequences of molecules of the invention described herein comprise a nucleotide sequence which hybridizes to or is at least about 60%, 70%, 80%, 90%, 95%, 96%, 97%, 98%, 99% or more identical or homologous to SEQ ID NO: 1, SEQ ID NO:3, SEQ ID NO: 30, SEQ ID NO: 32, or SEQ ID NO: 34.

Nucleic acid sequences that encode the various components of the fusion [Klotho, and/or FGF peptide and/or the (optional) modified Fc fragment] can be obtained using any of a variety of methods. For example, the nucleic acid sequences encoding the polypeptides may be cloned from cDNA and genomic DNA libraries by hybridization with probes, or isolated using amplification techniques with oligonucleotide primers. More commonly, amplification techniques are used to amplify and isolate the Klotho and FGF sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding Klotho or FGF can also be isolated from expression libraries using antibodies as probes.

According to the present invention, the various components of the fusion [Klotho, and/or, FGF and/or the (optional) modified Fc fragment] can be linked either directly or via a covalent linker, including amino acid linkers, such as a polyglycine linker, or another type of chemical linker, including, carbohydrate linkers, lipid linkers, fatty acid linkers, polyether linkers, such as PEG, etc. (See for example, Hermanson, Bioconjugate techniques (1996)). The polypeptides forming the fusion/fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a fusion polypeptide of the invention. The polypeptides of the fusion protein can be in any order. The fusion polypeptides may be produced by covalently linking a chain of amino acids from one protein sequence, e.g., an extracellular subdomain of Klotho, to a chain of amino acids from another protein sequence, e.g., FGF, by preparing a recombinant polynucleotide contiguously encoding the fusion protein. The different chains of amino acids in a fusion protein may be directly spliced together or may be indirectly spliced together via a chemical linking group or an amino acid linking group. The amino acid linking group can be about 200 amino acids or more in length, or generally 1 to 100 amino acids. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

According to the present invention, the amino acid sequences of the fusion [an extracellular subdomain of Klotho and/or the FGF and/or the (optional) modified Fc fragment] may be linked via a peptide linker. Exemplary peptide linkers are well known in the art and described herein. For example, peptide linkers generally include several Gly and several Ser residues, such as: (Gly$_4$ Ser)$_3$ (SEQ ID NO: 11), Gly$_4$ Ser polypeptide (SEQ ID NO: 12), Gly (SEQ ID NO: 13), Gly Gly (SEQ ID NO: 14), Gly Ser (SEQ ID NO: 15), Gly$_2$ Ser (SEQ ID NO: 16), Ala (SEQ ID NO: 17), and Ala Ala (SEQ ID NO: 18). Specifically, a peptide linker for use in a fusion protein of the invention may act as a flexible hinge.

The signal sequence of Klotho or FGF may be excluded prior to incorporation of Klotho into a fusion protein of the invention. The signal sequence for Klotho or FGF of the fusion protein may be included, e.g., the polypeptide represented by SEQ ID NO: 19. However, such sequences may also be omitted and replaced with the signal sequence of a different protein, e.g., the IgG signal sequence (SEQ ID NO: 9). Generally, the pharmaceutical compositions of the invention will contain the mature form of Klotho and FGF.

Generally, introns are excluded from either one or both the Klotho or the FGF moieties prior to incorporation into a fusion polypeptide.

The fusion polypeptides of the invention may include one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, PEGylation of the fusion polypeptides of the invention is expected to provide such improved properties as increased half-life, solubility, and protease resistance. The fusion polypeptides of the invention may alternatively be modified by the covalent addition of polymers to free amino groups such as the lysine epsilon or the N-terminal amino group. Preferred cysteines and lysines for covalent modification will be those not involved in receptor binding, heparin binding, or in proper protein folding. It will be apparent to one skilled in the art that the methods for assaying the biochemical and/or biological activity of the fusion polypeptides may be employed in order to determine if modification of a particular amino acid residue affects the activity of the protein as desired. Other similar suitable modifications are contemplated and known in the art.

The invention is also directed to the expression of a fusion polypeptide that is at least about 95% or more homologous to an amino acid sequence presented in SEQ ID NO:19-28.

4.3. Expression of Fusion Polypeptides of the Invention

In order to express the fusion protein of the invention, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids and bacteriophages) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a Klotho-FGF23 fusion operatively linked to regulatory sequences, e.g., promoter sequences, terminator sequences and/or artificial ribosome binding sites (RBSs), as defined herein. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast ga14 gene promoter, etc. Transcriptional initiation regulatory signals may be selected which allow for repression or activation, so that expression of the genes can be modulated.

In some of the molecules of the invention described herein, one or more DNA molecules having a nucleotide sequence encoding one or more polypeptide chains of a fusion polypeptide are operatively linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express fusion polypeptides of the invention. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particularly preferred method of high-yield production of the fusion polypeptides of the invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

4.4. Assays for Assessing Fusion Polypeptide Activity

Assays described herein (See Example 2) and those known in the art can be used for detecting Klotho or FGF activity of the fusion polypeptides of the invention. Suitable activity assays include receptor binding assays, cellular proliferation assays and cell signaling assays. For example, a binding assay which may be used for determining whether a fusion polypeptide has Klotho or FGF activity includes, assaying the binding of a fusion polypeptide to an FGF receptor. FGF receptor binding assays include, but are not limited to, both competitive and non-competitive assay. For example, FGF receptor binding can be detected by contacting cells expressing an FGF receptor with a labeled FGF (for example, radio-active label) and increasing concentrations of an unlabeled Klotho-FGF fusion polypeptide. The two ligands that compete for binding to the same receptor are added to a reaction mixture containing the cell. The cells are subsequently washed and labeled FGF is measured. A decrease in the amount of the labeled FGF to its receptor in the presence of the unlabeled fusion polypeptide is indicative of binding of the Klotho-FGF fusion polypeptide to the receptor. Alternatively, the Klotho-FGF fusion polypeptide may be labeled and direct binding of the fusion polypeptide to the cell is detected.

Klotho or FGF activity can also be measured by determining whether the fusion polypeptide induces a cellular response. For example, in some embodiments, an assay for detecting the biological activity of a Klotho-FGF fusion polypeptide involves contacting cells which express an FGF receptor with a fusion polypeptide, assaying a cellular response such as, for example, cell proliferation or Egr-1 activation, myotube diameter in C2C12 cells, and comparing the cellular response in the presence and absence of the fusion polypeptide. An increase in the cellular response in the presence of the fusion polypeptide complex relative to the absence indicates that the fusion polypeptide has biological activity. Also, an increase in a downstream signaling event from the receptor can also be measured as indicia of biological activity (e.g., phosphorylation of FGFR, FRS2, ERK1/2, p70S6K etc.).

4.5 Pharmaceutical Compositions and Methods of Treatment

The invention also pertains to pharmaceutical compositions containing one or more fusion polypeptides of the invention and a pharmaceutically acceptable diluent or carrier. The pharmaceutical compositions can further include a pharmaceutically effective dose of heparin. Such pharmaceutical compositions may be included in a kit or container. Such kit or container may be packaged with instructions pertaining to the extended in vivo half-life or the in vitro shelf life of the fusion polypeptides. Optionally associated with such kit or container(s) can be a notice in the form prescribed by a governmental agency regulating the manufacture, use or sale of pharmaceuticals or biological products, which notice reflects approval by the agency of manufacture, use or sale for human administration. Such compositions may be used in methods of treating, preventing, or ameliorating a disease or a disease symptom (e.g., age-related condition or metabolic disorder) in a patient, preferably a mammal and most preferably a human, by administering the pharmaceutical composition to the patient.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight. Commonly, a therapeutically effective amount of a fusion polypeptide is from about 0.001 mg to about 0.01 mg, about 0.01 mg to about 100 mg, or from about 100 mg to about 1000 mg, for example. Preferably, a therapeutically effective amount of a fusion polypeptide is from about 0.001 mg/kg to 2 mg/kg.

The optimal pharmaceutical formulations for a fusion polypeptide can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The fusion polypeptides of the invention may be administered as a pharmaceutical composition that may be in the form of a solid, liquid or gas (aerosol). Typical routes of administration may include, without limitation, oral, topical, parenteral, sublingual, rectal, vaginal, intradermal and intranasal. Parenteral administration includes subcutaneous injections, intravenous, intramuscular, intraperitoneal, intrapleural, intrasternal injection or infusion techniques. Preferably, the compositions are administered parenterally. More preferably, the compositions are administered intravenously. Pharmaceutical compositions of the invention can be formulated so as to allow a polypeptide of the invention to be bioavailable upon administration of the composition to a subject. Compositions can take the form of one or more dosage units, where, for example, a tablet can be a single dosage unit, and a container of a polypeptide of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of age-related condition or metabolic disorder the subject in need of treatment of, the use of the composition as part of a multi-drug regimen, the particular form of the polypeptide of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a polypeptide of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the polypeptides of the invention and pharmaceutically acceptable carriers are sterile. Water is a preferred carrier when the polypeptide of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can contain one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions contain an effective amount of a compound of the invention (e.g., fusion polypeptide) such that a suitable dosage will be obtained. The pharmaceutical compositions may contain the known effective amount of the compounds as currently prescribed for their respective disorders.

The route of administration of the polypeptide of the invention used in the prophylactic and/or therapeutic regimens which will be effective in the prevention, treatment, and/or management of a age-related condition or metabolic disorder can be based on the currently prescribed routes of administration for other therapeutics known in the art. The polypeptides of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a polypeptide of the invention. More than one polypeptides of the invention may be administered to a subject. Methods of administration may include, but are not limited to, oral administration and parenteral administration; parenteral administration including, but not limited to, intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin.

The polypeptides of the invention may be administered parenterally. Specifically, the polypeptides of the invention may be administered intravenously.

Pulmonary administration can also be employed, e.g., by use of an inhaler or nebulizer, and formulation with an aerosolizing agent, or via perfusion in a fluorocarbon or synthetic pulmonary surfactant. The polypeptides of the invention can also be formulated as a suppository, with traditional binders and carriers such as triglycerides.

The polypeptides of the invention can be delivered in a controlled release system. For example, a pump can be used (see Sefton, *CRC Crit. Ref Biomed. Eng.* 1987, 14, 201; Buchwald et al., Surgery 1980, 88: 507; Saudek et al., *N. Engl. J. Med.* 1989, 321: 574). Polymeric materials can also be used for controlled release of the polypeptides of the invention (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.,* 1989, 25, 351; Howard et al., *J. Neurosurg.,* 1989, 71, 105). Specifically, a controlled-release system can be placed in proximity of the target of the polypeptides of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (Science 1990, 249, 1527-1533) can be used.

Polymeric materials used to achieve controlled or sustained release of the polypeptides of the invention are disclosed, e.g., in U.S. Pat. Nos. 5,679,377; 5,916,597; 5,912,015; 5,989,463; and 5,128,326; PCT Publication No. WO 99/15154; and PCT Publication No. WO 99/20253.

Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Preferably, the polymer used in a sustained release formulation is inert, free of leachable impurities, stable on storage, sterile, and biodegradable.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight.

In other embodiments, the prophylactic and/or therapeutic regimen involves administering to a patient one or more doses of an effective amount of a polypeptide of the invention, wherein the dose of an effective amount achieves a plasma level of at least 0.01 µg/mL to at least 400 µg/mL of the polypeptide of the invention.

A prophylactic and/or therapeutic regimen may involve administering to a patient a plurality of doses of an effective amount of a polypeptide of the invention, wherein the plurality of doses maintains a plasma level of at least 0.01 µg/mL, to 400 µg/mL of the polypeptide of the invention. The prophylactic and/or therapeutic regimen may be administered for at least 1 day, 1 month, 2 months, 3 months, 4 months, 5 months, 6 months, 7 months, 8 months or 9 months.

The prophylactic and/or therapeutic regimen may involve administration of a polypeptide of the invention in combination with one or more additional therapeutics. The recommended dosages of the one or more therapeutics currently used for the prevention, treatment, and/or management of an age-related condition or metabolic disorder can be obtained from any reference in the art including, but not limited to, Hardman et al., eds., *Goodman & Gilman's The Pharmacological Basis Of Basis Of Therapeutics*, 10*th ed.*, McGraw-Hill, New York, 2001*; Physician's Desk Reference* (60$^{th}$ ed., 2006), which is incorporated herein by reference in its entirety.

The invention includes methods of treating disorders wherein agonistic activity of Klotho protein and FGF are desirable. Examples of such methods of the invention include, but are not limited to age-related condition or metabolic disorders.

The invention includes methods for treating or preventing an age-related condition in an individual. An individual in need of treatment is administered a pharmacologically effective dose of a pharmaceutical composition containing a Klotho fusion polypeptide, having at least one extracellular subdomain of a Klotho protein and a fibroblast growth factor and an (optional) modified Fc fragment, so as to treat or prevent the age-related condition. In some embodiments, the Klotho fusion polypeptide is co-administered with a pharmacologically effective dose of heparin. Age-related conditions include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. In some embodiments, the Klotho fusion polypeptide contains at least one extracellular domain of an alpha Klotho protein. In a particular embodiment, a Klotho fusion protein containing at least one extracellular domain of alpha Klotho protein and fibroblast growth factor 23 is administered to an individual in need of treatment for muscle wasting.

The invention is also directed to a method for treating or preventing a metabolic disorder in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat the metabolic disorder, and an (optional) modified Fc fragment having decreased binding to FcRn and/or increased serum half-life and/or stability. In some embodiments, the Klotho fusion polypeptide is co-administered with a pharmacologically effective dose of heparin. The method may be used in the treatment or prevention of Type II Diabetes, Metabolic Syndrome, hyperglycemia, and obesity. In a particular embodiment, a Klotho fusion protein containing at least one extracellular domain of a beta-Klotho protein and fibroblast growth factor 21 is administered to an individual in need of treatment for a metabolic disorder.

The invention also provides methods for treating or preventing hyperphosphatemia or calcinosis in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat hyperphosphatemia or calcinosis. In some embodiments, the Klotho fusion polypeptide is co-administered with a pharmacologically effective dose of heparin. In a particular embodiment, a Klotho fusion protein containing at least one extracellular domain of an alpha Klotho protein and fibroblast growth factor 23 and an (optional) modified Fc fragment is administered to an individual in need of treatment for a hyperphosphatemia or calcinosis.

The invention is also directed to a method for treating or preventing chronic renal disease or chronic renal failure in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat chronic renal disease or chronic renal failure. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for chronic renal disease or chronic renal failure.

The invention also includes methods for treating or preventing cancer in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat cancer. The method may be used in the treatment or prevention of breast cancer. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for cancer.

In methods of treating disorders by administering a pharmaceutical composition containing a Klotho fusion polypeptide, the Klotho fusion polypeptide and an (optional) modified Fc fragment has at least one extracellular subdomain of a Klotho protein and a fibroblast growth factor. In a particular embodiment, the Klotho fusion protein contains at least one extracellular domain of a beta Klotho protein and fibroblast growth factor 21.

In another embodiment, the fusion comprises a FGF (e.g., FGF19, FGF21, FGF23 or FGF23 variant) and a modified Fc fragment with decreased binding to FcRn and/or increased serum stability. This type of fusion can be used in various diseases, as described above, or used to treat or prevent any FGF-related disease known in the art. The fusion can be administered to an individual in need thereof.

The fusion polypeptide compositions can be administered according to any method of administration known to those of skill in the art and described herein. Preferred methods of administration include subcutaneous or intravenous. Other effective modes of administration are described herein.

4.6. Methods of Treatment and Assays for Assessing Efficacy

Methods of the invention which provide administering the fusion polypeptides described herein to an individual can be used to treat a variety of disorders including an age-related disorder or a metabolic disorder. Without being limited by any particular theory, fusion polypeptides may be used to treat disorders in which there is dysregulation of Klotho or FGF. Exemplary disorders include metabolic disorders and age-related disorders. For example, both FGF23 or Klotho knock-out mice display a variety of similar phenotypes including, low physical activity, growth retardation, muscle wasting, skin atrophy, atherosclerosis, short life spans, etc. (See Razzaque and Lanske, *J. of Endrocrinology,* 194:1-10 (2007), which is herein incorporated by reference).

In particular, fusion polypeptides of the invention are particularly useful in the treatment of aging-related disorders, including muscle wasting. Without being bound to theory, the ability of Klotho and FGF23 to control mineral (e.g., phosphate and calcium) and vitamin D homeostasis may be the means by which these proteins modulate aging and muscle atrophy.

On the other hand, fusion polypeptides of the invention may be used for treating a metabolic disorder. For example, beta-Klotho and FGF19 have been shown to control bile acid homeostasis by regulating cholesterol 7-α-hydroxylase (CYP7A1). A non-limiting example of bile homeostasis disorder is cholestasis. The beta-Klotho and FGF21 have been shown to induce lipolysis in adipocytes and, therefore, reduced fat storage and increased glucose uptake. Non-limiting examples of lipolysis/fat storage disorders are obesity and associated metabolic and cardiovascular diseases.

Based at least in part on the finding that FGF23 is able to stimulate excretion of phosphate in the urine and thereby reduce phosphate levels in the serum, Klotho-FGF23 fusion polypeptides of the invention can be used for treating or preventing hyperphosphatemia or calcinosis in an individual. For example, it has been shown that a homozygous missense mutation in Klotho resulting in a deficiency in Klotho in a patient can cause severe tumoral calcinosis and artery calcification (Ichikawa et al., *J. Clin. Invest.* 117: 2684-2691 (2007), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent hyperphosphatemia or calcinosis. In particular, a Klotho fusion polypeptide containing at least one extracellular domain of an alpha Klotho protein, a fibroblast growth factor and an (optional) modified Fc fragment is useful for treating hyperphosphatemia or calcinosis.

Klotho fusion polypeptides of the invention can also be used for treating or preventing chronic renal disease or chronic renal failure in an individual. For example, it has been shown that Klotho expression is reduced in kidney of patients with chronic renal failure, compared to that in unaffected kidneys (Koh et al., *Biochem. Biophys. Res. Comm.* 280:1015-1020 (2001), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent chronic renal disease or chronic renal failure. In particular, a Klotho fusion polypeptide containing at least one extracellular domain of an alpha Klotho protein is useful for treating chronic renal disease or chronic renal failure.

Klotho fusion polypeptides of the invention can also be used for treating or preventing cancer in an individual. For example, it has been shown that Klotho expression is reduced in breast cancer tissue, compared to normal breast cancer tissue (Wolf et al., *Oncogene* (2008) advance online publication, which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent cancer or breast cancer. In particular, a Klotho fusion protein containing at least one extracellular domain of an alpha Klotho protein is useful for treating cancer or breast cancer.

Methods for evaluating the efficacy and/or determining the effective dose of a Klotho fusion polypeptide of the invention on an age-related disorder or metabolic disorder include organismal based assays, e.g., using a mammal (e.g., a mouse, rat, primate, or some other non-human), or other animal (e.g., *Xenopus*, zebrafish, or an invertebrate such as a fly or nematode). The Klotho fusion polypeptide can be administered to the organism once or as a regimen (regular or irregular). A parameter of the organism is then evaluated, e.g., an age-associated parameter. Klotho fusion polypeptides that are of interest result in a change in the parameter relative to a reference, e.g., a parameter of a control organism. Other parameters (e.g., related to toxicity, clearance, and pharmacokinetics) can also be evaluated.

The Klotho fusion polypeptide of the invention may be evaluated using an animal that has a particular disorder, e.g., a disorder described herein, e.g., an age-related disorder, a metabolic disorder. These disorders can also provide a sensitized system in which the test polypeptide's effects on physiology can be observed. Exemplary disorders include: denervation, disuse atrophy; metabolic disorders (e.g., disorder of obese and/or diabetic animals such as db/db mouse and ob/ob mouse); cerebral, liver ischemia; cisplatin/taxol/vincristine models; various tissue (xenograph) transplants; transgenic bone models; pain syndromes (include inflammatory and neuropathic disorders); Paraquat, genotoxic, and oxidative stress models; and tumor I models.

For measuring an age-related disorder, the animal model can be an animal that has an altered phenotype when calorically restricted. For example, F344 rats provide a useful assay system for evaluating a Klotho fusion polypeptide. When calorically restricted, F344 rats have a 0 to 10% incidence of nephropathy. However, when fed ad libitum, they have a 60 to 100% incidence of nephropathy.

To evaluate a Klotho fusion polypeptide of the invention, it is administered to the animal (e.g., an F344 rat or other suitable animal) and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test polypeptide can be indicated as favorably altering lifespan regulation in the animal if the test polypeptide affects the parameter in the direction of the phenotype of a similar animal subject to caloric restriction. Such test polypeptides may cause at least some of the lifespan regulatory effects of caloric restriction, e.g., a subset of such effects, without having to deprive the organism of caloric intake.

The parameter to be tested may be an age-associated or disease associated parameter, e.g., a symptom of the disorder associated with the animal model. For example, the test polypeptide can be administered to a SH Rat, and blood pressure is monitored. A test polypeptide that is favorably indicated can cause an amelioration of the symptom relative to a similar reference animal not treated with the polypeptide. Other parameters relevant to a disorder or to aging can include: antioxidant levels (e.g. antioxidant enzyme levels or activity), stress resistance (e.g., paraquat resistance), core body temperature, glucose levels, insulin levels, thyroid-stimulating hormone levels, prolactin levels, and leutinizing hormone levels.

To measure the effectiveness of the polypeptides of the invention for treating an age-related disorder, an animal having decreased Klotho expression may be used, e.g., mouse with a mutant Klotho; See Kuroo, et al. Nature, 390; 45 (1997) and U.S. Pub. No. 2003/0119910, both of which are herein incorporated by reference in their entirety. For example, the test polypeptide is administered to the mutant mouse and age-related parameters are monitored. A test polypeptide that is favorably indicated can cause an amelioration of the symptom relative to a similar reference animal not treated with the polypeptide. A parameter relevant to a metabolic disorder or to aging can be assessed by measurement of body weight, examination on the acquisition of reproductive ability, measurement of blood sugar level, observation of life span, observation of skin, observation of motor functions such as walking, and the like. The assessment can also be made by measurement of thymus weight, observation of the size of calcified nodules formed on the inner surface of thoracic cavity, and the like. Further, quantitative determination of mRNA for the Klotho gene or Klotho protein is also useful for the assessment.

Still other in vivo models and organismal assays include evaluating an animal for a metabolic parameter, e.g., a parameter relevant to an insulin disorder, type II diabetes. Exemplary metabolic parameters include: glucose concentration, insulin concentration, and insulin sensitivity.

Another exemplary system features tumors, e.g., in an animal model. The tumors can be spontaneous or induced. For example, the tumors can be developed from cells that have a variety of genetic constitutions, e.g., they can be p53+ or p53−. It is also possible to use organisms that an autoimmune disorder, e.g., an NZB mouse, which is predisposed to SLE. To evaluate features of bone disease, it is possible, for example, to use an animal that has an ovariectomy as a model, e.g., for osteoporosis. Similarly, for joint disease, the model can be based on adjuvant arthritis (e.g., mice can be immunized with cartilage proteoglycans, high mobility group proteins, streptococcal cell wall material, or collagens); for kidney disease, kd/kd mice can be used. Animal models of cognition, particularly learning and memory are also available. Animal models of diabetes and its complications are also available, e.g., the streptozotocin model. Canine models can be used, for example, for evaluating stroke and ischemia.

In assessing whether a test polypeptide is capable of altering life span regulation, a number of age-associated parameters or biomarkers can be monitored or evaluated. Exemplary age associated parameters include: (i) lifespan of the cell or the organism; (ii) presence or abundance of a gene transcript or gene product in the cell or organism that has a biological age dependent expression pattern; (iii) resistance of the cell or organism to stress; (iv) one so or more metabolic parameters of the cell or organism (exemplary parameters include circulating insulin levels, blood glucose levels; fat content; core body temperature and so forth); (v) proliferative capacity of the cell or a set of cells present in the organism; and (vi) physical appearance or behavior of the cell or organism.

The term "average lifespan" refers to the average of the age of death of a cohort of organisms. In some cases, the "average lifespan" is assessed using a cohort of genetically identical organisms under controlled environmental conditions. Deaths due to mishap are discarded. Where average lifespan cannot be determined (e.g., for humans) under controlled environmental conditions, reliable statistical information (e.g., from actuarial tables) for a sufficiently large population can be used as the average lifespan.

Characterization of molecular differences between two such organisms, e.g., one reference organism and one organism treated with a Klotho fusion polypeptide can reveal a difference in the physiological state of the organisms. The reference organism and the treated organism are typically the same chronological age. The term "chronological age" as used herein refers to time elapsed since a preselected event, such as conception, a defined embryological or fetal stage, or, more preferably, birth. A variety of criteria can be used to determine whether organisms are of the "same" chronological age for the comparative analysis. Typically, the degree of accuracy required is a function of the average lifespan of a wildtype organism. For example, for the nematode *C. elegans*, for which the laboratory wildtype strain N2 lives an to average of about 16 days under some controlled conditions, organisms of the same age may have lived for the same number of days. For mice, organism of the same age may have lived for the same number of weeks or months; for primates or humans, the same number of years (or within 2, 3, or 5 years); and so forth. Generally, organisms of the same chronological age may have lived for an amount of time within 15, 10, 5, 3, 2 or 1% of the average lifespan of a wildtype organism of that species. Preferably, the organisms are adult organisms, e.g., the organisms have lived for at least an amount of time in which the average wildtype organism has matured to an age at which it is competent to reproduce.

The organismal screening assay can be performed before the organisms exhibit overt physical features of aging. For example, the organisms may be adults that have lived only 10, 30, 40, 50, 60, or 70% of the average lifespan of a wildtype organism of the same species. Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein.

A marker associated with caloric restriction can also be evaluated in a subject organism of a screening assay (or a treated subject). Although these markers may not be age-associated, they may be indicative of a physiological state that is altered when the Klotho pathway is modulated. The marker can be an mRNA or protein whose abundance changes in calorically restricted animals. WO01/12851 and U.S. Pat. No. 6,406,853 describe exemplary markers. Cellular models derived from cells of an animal described herein or analogous to an animal model described herein can be used for a cell-based assay.

Models for evaluating the effect of a test polypeptide on muscle atrophy include: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, *Shock* 7, 1-16 (1997)); and 5) skeletal muscle atrophy resulting from treatment with the glucocorticoid, dexamethasone (A. L. Goldberg, *J. Biol. Chem.* 244, 3223-9 (1969).)

Exemplary animal models for AMD include: laser-induced mouse model simulating exudative (wet) macular degeneration Bora et al., *Proc. Natl. Acad. Sci. USA.*, 100:2679-84 (2003); a transgenic mouse expressing a mutated form of cathepsin D resulting in features associated with the "geographic atrophy" form of AMD (Rakoczy et al., *Am. J. Pathol.*, 161:1515-24 (2002)); and a transgenic mouse over expressing VEGF in the retinal pigment epithelium resulting in CNV. Schwesinger et al., *Am. J. Pathol.* 158:1161-72 (2001).

Exemplary animal models of Parkinson's disease include primates rendered Parkinsonian by treatment with the dopaminergic neurotoxin 1-methyl-4 phenyl 1,2,3,6-tetrahydropyridine (MPTP) (see, e.g., U.S. Patent Publication No. 20030055231 and Wichmann et al., *Ann. N.Y. Acad. Sci.*, 991:199-213 (2003); 6-hydroxydopamine-lesioned rats (e.g., Lab. Anim. Sci., 49:363-71 (1999)); and transgenic invertebrate models (e.g., Lakso et al., *J. Neurochem.* 86:165-72 (2003) and Link, *Mech. Ageing Dev.*, 122:1639-49 (2001)).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., *Diabetes*, 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (U.S. Pat. No. 5,420,112) or rabbits (Ogawa et al., *Neurotoxicology*, 21:501-11 (2000)); a streptozotocin (STZ)-diabetic rat for study of autonomic neuropathy (Schmidt et al., *Am. J. Pathol.*, 163:21-8 (2003)); and a progressive motor neuropathy (pmn) mouse (Martin et al., *Genomics*, 75:9-16 (2001)).

Exemplary animal models of hyperphosphatemia or tumoral calcinosis include Klotho knockout mice and FGF23 knockout mice (Yoshida et al., *Endocrinology* 143: 683-689 (2002)).

Exemplary animal models of chronic renal disease or chronic renal failure include COL4A3+/−mice (Beirowski et al., *J. Am. Soc. Nephrol.* 17:1986-1994 (2006)).

Exemplary animal models of cancer include the transplantation or implantation of cancer cells or tissue into nude mice, as is known in the art (Giovanella et al., *Adv. Cancer Res.* 44:69-120 (1985)). For example, animal models of breast cancer include nude mice transplanted or implanted with breast cancer cells or tissue (e.g., Yue et al., *Cancer Res.* 54:5092-5095 (1994); Glinsky et al., *Cancer Res.* 56:5319-5324 (1996); Visonneau *Am. J. Path.* 152:1299-1311 (1998)).

The compositions can be administered to a subject, e.g., an adult subject, particularly a healthy adult subject or a subject having an age-related disease. In the latter case, the method can include evaluating a subject, e.g., to characterize a symptom of an age-related disease or other disease marker, and thereby identifying a subject as having a neurodegenerative disease, e.g., Alzheimer's or an age-related disease or being pre-disposed to such a disease.

Skeletal Muscle Atrophy

Methods of the invention which provide administering the Klotho fusion polypeptide to an individual can be used to treat skeletal muscle atrophy. Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al., *J. Biol. Chem.,* 265:8550-8557, 1990). The breakdown of these proteins can be followed, e.g., by measuring 3-methyl-histidine production, which is a specific constituent of actin, and in certain muscles of myosin (Goodman, Biochem. J. 241:121-12, 1987 and Lowell, et al., Metabolism, 35:1121-112, 1986; Stein and Schluter, *Am. J. Physiol. Endocrinol. Metab.* 272: E688-E696, 1997). Release of creatine kinase (a cell damage marker) (Jackson, et al., Neurology, 41: 101 104, 1991) can also be indicative.

Non-insulin-dependent Diabetes

Methods of the invention which provide administering the Klotho fusion polypeptide to an individual can be used to treat Non-insulin-dependent Diabetes. Non-insulin-dependent Diabetes is also called "adult onset" diabetes and Type 2 diabetes. Type 2 diabetes also includes "non-obese type 2" and "obese type 2." Type II diabetes can be characterized by (1) reduced pancreatic-beta-islet-cell secretion of insulin such that less than necessary amounts of insulin are produced to keep blood glucose levels in balance and/or (2) "insulin resistance," wherein the body fails to respond normally to insulin. (U.S. Pat. No. 5,266,561 and U.S. Pat. No. 6,518,069). For example, glucose-stimulated insulin levels typically fail to rise above 4.0 nmol/L. (U.S. Pat. No. 5,266,561). Exemplary symptoms of Type II diabetes include: hyperglycemia while fasting (U.S. Pat. No. 5,266, 561); fatigue; excessive thirst; frequent urination; blurred vision; and an increased rate of infections. Molecular indications of Type II diabetes include islet amyloid deposition in the pancreases.

Neuropathy

Neuropathy can include a central and/or peripheral nerve dysfunction caused by systemic disease, hereditary condition or toxic agent affecting motor, sensory, sensorimotor or autonomic nerves. (see, e.g., US Patent Application No. 20030013771). Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (U.S. Patent Application No. 20030013771) symptoms of autonomic neuropathy include constipation, cardiac irregularities and attenuation of the postural hypotensive reflex. (U.S. Patent Application No. 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Alzheimer's Disease

Methods of the invention which provide administering the Klotho fusion polypeptide to an individual can be used to treat Alzheimer's Disease (AD) Alzheimer's Disease is a complex neurodegenerative disease that results in the irreversible loss of neurons. It provides merely one example of a neurodegenerative disease that is also an age-related condition. Clinical hallmarks of Alzheimer's Disease include progressive impairment in memory, judgment, orientation to physical surroundings, and language. Neuropathological hallmarks of AD include region-specific neuronal loss, amyloid plaques, and neurofibrillary tangles. Amyloid plaques are extracellular plaques containing the amyloid peptide (also known as Ap, or Ap42), which is a cleavage product of the, 8-amyloid precursor protein (also known as APP). Neurofibrillary tangles are insoluble intracellular aggregates composed of filaments of the abnormally hyperphosphorylated microtubule-associated protein, taut Amyloid plaques and neurofibrillary tangles may contribute to secondary events that lead to neuronal loss by apoptosis (Clark and Karlawish, *Ann. Intern. Med.* 138(5):400-410 (2003). For example, p-amyloid induces caspase-2-dependent apoptosis in cultured neurons (Troy et al. *J Neurosci.* 20(4):1386-1392). The deposition of plaques in viva may trigger apoptosis of proximal neurons in a similar manner.

A variety of criteria, including genetic, biochemical, physiological, and cognitive criteria, can be used to evaluate AD in a subject. Symptoms and diagnosis of AD are known to medical practitioners. Some exemplary symptoms and markers of AD are presented below. Information about these indications and other indications known to be associated with AD can be used as an "AD-related parameter." An AD related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, *New Eng J. Med.* 348(14):1356 35 1364 (2003)). Exclusion of other forms of dementia can assist in making a diagnosis of AD. Neuronal death leads to progressive cerebral atrophy in AD patients. Imaging techniques (e.g., magnetic resonance imaging, or computer assisted tomography) can be used to detect AD-associated lesions in the brain and/or brain atrophy.

AD patients may exhibit biochemical abnormalities that result from the pathology of the disease. For example, levels of tan protein in the cerebrospinal fluid is elevated in AD patients (Andreasen, N. et al. *Arch Neurol.* 58:349-350 (2001)).

Levels of amyloid beta 42 (A,B42) peptide can be reduced in CSF of AD patients. Levels of Ap42 can be increased in the plasma of AD patients (Ertekein-Taner, N., et al. *Science* 290:2303 2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3r Edition, Cold Spring Harbor Laboratory, N.Y. (2001), Ausubel et al., Current Protocols in Molecular Biology (Greene Publishing Associates and Wiley Interscience, N.Y. (1989), (Harrow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). *Nature Biotech.* 18, 989-994; Lucking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760 to 1 763; and WO 99/5 1 773A1.

In one assay, a non-human animal model of AD (e.g., a mouse model) is used, e.g., to evaluate a polypeptide or a therapeutic regimen. For example, U.S. Pat. No. 6,509,515 describes one such model animal which is naturally able to be used with learning and memory tests. The animal expresses an amyloid precursor protein (APP) sequence at a level in brain tissues such that the animal develops a progressive necrologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant as foster female. The amyloid precursor protein genes are introduced into an animal embryo so as to be chromosomally incorporated in a state which results in super endogenous expression of the amyloid precursor protein and the development of a progressive necrologic disease in the cortico-limbic areas of the brain, areas of the brain which are prominently affected in progressive necrologic disease states such as AD. The gliosis and clinical manifestations in affected transgenic animals model necrologic disease. The progressive aspects of the neurologic disease are characterized by diminished exploratory and/or locomotor behavior and diminished deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6,187,992.

Parkinson's Disease

Methods of the invention which provide administering the Klotho fusion polypeptide to an individual can be used to treat Parkinson's Disease. Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., *Nat. Rev. Neurosci.*, 3:932-42 (2002)). Exemplary motor symptoms include: akinesia, stooped posture, gait difficulty, postural instability, catalepsy, muscle rigidity, and tremor. Exemplary non-motor symptoms include: depression, lack of motivation, passivity, dementia and gastrointestinal dysfunction (see, e. g., Fahn, *Ann. N.Y. Acad. Sci.*, 991:1-14 (2003) and Pfeiffer, *Lancet Neurol.*, 2:107-16 (2003)) Parkinson's has been observed in 0.5 to 1 percent of persons 65 to 69 years of age and 1 to 3 percent among persons 80 years of age and older. (see, e.g., Nussbaum et al., *N. Engl. J. Med.*, 348:1356-64 (2003)). Molecular markers of Parkinson's disease include reduction in aromatic L amino acid decarboxylase (AADC) (see, e.g., US App. No. 20020172664); and loss of dopamine content in the nigrostriatal neurons (see, e.g., Fahn, Ann. *N.Y. Acad. Sci.*, 991: 1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:13 10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

Huntington's Disease

Methods of the invention which provide administering the Klotho fusion polypeptide to an individual can be used to treat Huntington's Disease. Methods for evaluating the efficacy and/or determining the effective dose of a Klotho fusion polypeptide on Huntington's Disease include organismal based assays, e.g., using a mammal (e.g., a mouse, rat, primate, or some other non-human), or other animal (e.g., *Xenopus*, zebrafish, or an invertebrate such as a fly or nematode). A number of animal model system for Huntington's disease are available. See, e.g., Brouillet, Functional *Neurology* 15(4): 239-251 (2000); Ona et al. *Nature* 399: 263-267 (1999), Bates et al. *Hum Mol Genet.* 6(10):1633-7 (1997); Hansson et al. *J. of Neurochemistry* 78: 694-703; and Rubinsztein, D. C., *Trends in Genetics*, Vol. 1S, No. 4, pp. 202-209 (a review on various animal and non-human models of HD).

An example of such an animal model is the transgenic mouse strain is the R6/2 line (Mangiarini et al. Cell 87: 493-506 (1996)). The R6/2 mice are transgenic Huntington's disease mice, which over-express exon 1 of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N terminal part of Huntingtin (encoded by HD exon 1), are observed in R6/2 mice, both 45 in the cytoplasm and nuclei of cells (Davies et al. *Cell* 90: 537-548 (1997)). For example, the human Huntingtin protein in the transgenic animal is encoded by a gene that includes at least 55 CAG repeats and more preferably about 150 CAG repeats. These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. *Cell* 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. *Cell* 87: 493-506 (1996), Davies et al. *Cell* 90: 537-548 (1997), Brouillet, Functional Neurology 15(4): 239-251 (2000) and Cha et al. *Proc. Natl. Acad. Sci. USA* 95: 6480-6485 (1998).

To test the effect of the test polypeptide or known polypeptide described in the application in an animal model, different concentrations of test polypeptide are administered to the transgenic animal, for example by injecting the test polypeptide into circulation of the animal. A Huntington's disease-like symptom may be evaluated in the animal. The progression of the Huntington's disease-like symptoms, e.g., as described above for the mouse model, is then monitored to determine whether treatment with the test polypeptide results in reduction or delay of symptoms. In another assay, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntington's antibody (e.g., the anti-Huntingtin antibody is mouse anti-human antibody and the secondary antibody is specific for human antibody) and visualizing the protein aggregates by fluorescent microscopy.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

Exemplary motor evaluations include: ocular pursuit, saccade initiation, saccade velocity, dysarthria, tongue protrusion, finger tap ability, pronate/supinate, a lo fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

Cancer

Methods of the invention which provide administering the Klotho fusion polypeptide to an individual can be used to treat cancer. Cancer includes any disease that is caused by or results in inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

All patents, patent applications, and published references cited herein are hereby incorporated by reference in their entirety. While this invention has been particularly shown and described with references to embodiments thereof, it will be understood by those skilled in the art that various changes in form and details may be made therein without departing from the scope of the invention encompassed by the appended claims.

5. EXAMPLES

Example 1

Expression and Purification of Klotho Fusion Polypeptides

Expression of the Klotho Fusion Polypeptide

The polypeptides of the invention were made by transiently transfecting HEK293T cells with an expression vector encoding a Klotho fusion polypeptide having the extracellular domain of alpha Klotho and the FGF23 (R179Q) variant. Conditioned media containing expressed polypeptides were generated by transient transfection of the respective expression plasmids for Klotho, FGF23, and the Klotho-FGF23(R179Q) fusion protein. The transfections were performed in 6-well plates using Lipofectamine 2000 (Invitrogen, Cat #11668-019). Five hours after transfection, the transfection mix was replaced with 3 ml DMEM plus 1% FBS. Conditioned media were collected 72 hours after the addition of 3 ml DMEM plus 1% FBS. Samples of conditioned medium from various transiently transfected HEK293T cells were separated by SDS-polyacrylamide gel electrophoresis (SDS-PAGE) and analyzed by Western blot (FIG. 3A) or stained with Coomassie blue (FIG. 3B).

SDS-polyacrylamide gel electrophoresis was performed on various samples (lane 1, Control; lane 2, FGF23; lane 3, sKlotho; lanes 4-6, sKlotho-FGF23). Coomassie blue staining revealed the expression of a high, >180 kDa band (FIG. 3B, indicated by arrow on the right) that was not present in lanes 1-3, which contained samples that had not been transfected with the vector encoding the Klotho fusion polypeptide. The quality of the Klotho fusion polypeptide secreted into the media was evaluated by Western blot (FIG. 3A). An anti-FGF23 rat monoclonal IgG2A (R&D Systems, Cat# MAB26291) was used as the primary antibody to detect the Klotho fusion polypeptides by Western blot. The Western blot confirmed that the additional bands observed in the Coomassie stained gels were Klotho fusion polypeptides. The Western blot confirmed that the Klotho fusion polypeptides had the expected molecular weight for the Klotho fusion polypeptide. This analysis shows the expression of the Klotho-FGF23(R179Q) fusion protein.

Purification of the Klotho Fusion Polypeptide

The polypeptides of the invention were purified from conditioned media from a culture of HEK293T cells transiently transfected with an expression vector encoding a Klotho fusion polypeptide having the extracellular domain of alpha Klotho and the FGF23 R179Q variant. To generate conditioned medium, an expression vector encoding sKlotho-FGF23-6× His was transfected (500 μg DNA in 18 ml of OptiMEM 1 (GIBCO, Cat #11058) mixed with 18 ml of 2 μg/ml polyethlinimine (PEI) into HEK293 cells grown in suspension in expression medium (464 ml of HEK293T cells at $10^6$ cells/ml in Freestype 293 expression medium (GIBCO, Cat #12338)). After transfection, the culture was allowed to grow (120 hours; 37° C. in a 5% $CO_2$ incubator; shaking at 125 rpm). At the end of incubation, conditioned medium was harvested by centrifugation (1000 rpm for five minutes). The conditioned medium was then applied to a nickel-agarose column. The sKlotho-FGF23-6× His bound tightly to the column and was eluted with 50 mM imidazole. The resulting purified material was then dialyzed in PBS to remove imidazole. A sample of the purified sKlotho-FGF23-6× His was separated by SDS-PAGE (lane 1, purified sKlotho-FGF23-6× His; lane 2, molecular weight marker) and analyzed by staining with Coomassie blue (FIG. 3C). The stained SDS-PAGE gel confirmed that the purified sKlotho-FGF23-6× His had the expected molecular weight. The inability to detect bands corresponding to proteins other than full-length sKlotho-FGF23-6× His in the lane loaded with the purified material also showed that the sKlotho-FGF23-6× His was purified.

Example 2

In Vitro Assay Assessing the Activity of the Klotho Fusion Polypeptide

Egr-1-luciferase

The biological activity of the expressed alpha Klotho fusion polypeptide was tested in Egr-1-luciferase reporter assays. Binding of the Klotho fusion polypeptide to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol 444, 770-774). HEK293T cells seeded in 48-well poly-D-lysine plate were transfected with the Egr-1-luciferase reporter gene together with a transfection normalization reporter gene (Renilla luciferase). Five hours after transfection of the Egr-1 luciferase reporter gene, the transfection mix was replaced with 3 ml DMEM plus 1% FBS. Conditioned media were collected 72 hours after the addition of 3 ml DMEM plus 1% FBS. Five hours later, the transfection mix was replaced with a sample to be tested for activity. In initial experiments, 50% conditioned medium (alone or containing Klotho, FGF23, Klotho and FGF23, and the Klotho-FGF23(R179Q) fusion protein) and 50% DMEM with 1% FBS in the presence or absence of 20 μg/ml heparin (Sigma, Cat#H8537; dissolved in DMEM as 2 mg/ml stock) were tested in the Egr-1-luciferase reporter assays (FIG. 4). Further experiments used defined quantities of the purified polypeptides (FIGS. 5A and 5B). Cells were lysed 20 hours later in passive lysis buffer (Promega, Cat #E194A) and luciferase activities were determined using Dual-Glo Luciferase Assay System (Promega, Cat #E2940).

In initial experiments, Klotho fusion polypeptide activity was demonstrated in unfractionated conditioned medium. Using the Egr-1-luciferase reporter gene (FIG. 4) these experiments quantified the fold changes in the expression of the luciferase reporter. Conditioned medium containing a combination of FGF23 and the extracellular domain of Klotho protein activated Egr-1-luciferase, but conditioned medium containing only FGF23 or conditioned medium containing only the extracellular domain of Klotho, did not activate Egr-1-luciferase. Conditioned medium containing the fusion protein sKlotho-FGF23(R179Q) activated the Egr-1-luciferase reporter gene in contrast to conditioned media containing either FGF23 or Klotho alone. In these experiments, conditioned medium containing the fusion protein sKlotho-FGF23(R179Q) activated the Egr-1-luciferase reporter gene significantly better than conditioned medium containing a combination of FGF23 and Klotho. In the presence of heparin, the inductions by conditioned medium containing the fusion protein sKlotho-FGF23 (R179Q) and the conditioned medium containing a combination of FGF23 and Klotho were significantly enhanced. Table 1 lists the relative expression of various FGF-Klotho fusion polypeptides in conditioned medium and the relative activity of the unfractionated conditioned medium corresponding to the various FGF-Klotho fusion polypeptides in Egr-1-luciferase reporter assays.

TABLE 1

Expression and Activities of sKlotho-FGF23 fusion variants

| | sKlotho-FGF23 fusion constructs | Expression | Activity in Egr-1-luc reporter gene |
|---|---|---|---|
| 1 | sKlotho-FGF23 | good | yes |
| 2 | IgG sp-sKlotho-FGF23 | good | yes |
| 3 | sKL-D1-FGF23 | good | no |
| 4 | sKL-D2-FGF23 | no | n.a. |
| 5 | s(KL-D1)2-FGF23 | good | no |
| 6 | sKL-D1/D2-FGF23 | no | n.a. |
| 7 | ssKlotho(ΔN-26)-FGF23 | poor | no* |
| 8 | sKLD1-D2(Δ692-965)-FGF23 | poor | no* |
| 9 | sKL-D1-D2(Δ507-798)-FGF23 | poor | no* |
| 10 | FGF23-sKlotho | poor | no* |

*lack of activity may be the result of low expression

Egr-1-luciferase reporter assays were also performed using defined quantities of proteins purified from the conditioned medium, using the purification procedure as described in Example 1. Consistent with previous results using unfractionated conditioned medium containing the expressed polypeptides, treatment with a combination of purified FGF23 and sKlotho resulted in luciferase reporter activity, but treatment with purified FGF23 alone did not (FIG. 5A). The luciferase reporter activity from the combination of purified FGF23 and sKlotho was further dependent on the dose of purified sKlotho, and the effect could be enhanced by the presence of heparin (20 μg/ml). An effect of the sKlotho-FGF23-6× His fusion polypeptide on luciferase activity could be detected at concentrations as low as about 1.21 nM (1.2 fold change) and at least up to about 19.3 nM (2.4 fold change) in Egr-1-luciferase reporter assays (FIG. 5B). The activity of the sKlotho-FGF23-6× His fusion polypeptide on luciferase activity was significantly enhanced in the presence of heparin (20 μg/ml). In the presence of heparin, the effect of the sKlotho-FGF23-6× His fusion polypeptide on luciferase activity could be detected at a concentration as low as about 0.6 nM (2.0 fold change). The result showed that purified sKlotho-FGF23-6× His dose-dependently induced the EGR-1-luc reporter gene, and that treatment with sKlotho-FGF23-6× His.

Example 3

In Vitro Assay Assessing the Effect of the Klotho Fusion Polypeptide on Muscle Cells The biological effect of the expressed Klotho fusion polypeptide was tested on C2C12 myoblasts. Treatment of C2C12 myoblasts with IGF-1, FGF2, or sKlotho-FGF23 resulted in myotube growth and phosphorylation of signaling proteins. C2C12 myoblasts were seeded at a density of 40,000 cells/well in 6-well poly-D-lysine and fibronectin coated plates in growth medium (3 parts DMEM and 1 part F12), 10% FBS, 1% Glut; 1% P/S; 1% Linolic acid; 0.1% ITS: [insulin (10 mg/ml), transferrin (5.5 mg/ml), and selenium (5 ng/ml)]. After myoblasts reached confluence (3 days), medium was changed into differentiation medium (DMED with 2% horse serum; 1% Glut; 1% P/S).

For the myotube diameter experiments, three days after confluent media was changed into differentiation medium, cells were treated with IGF-1 (10 nM), FGF2 (20 ng/ml) or sKlotho-FGF23 (20 nM) in the absence or presence of dexamethasone (100 μM) for 24 hours in differentiation medium. At the end of treatment, cells were fixed with glutaraldehyde (5% in PBS) and multiple fluorescent images were collected. Myotube diameter was measured using the Pipeline Pilot program to determine hypertrophy or atrophy.

For the signaling protein phosphorylation, experiments, three days after confluent media was changed into differentiation medium, cells were starved for four hours with DMEM without FBS and then treated with IGF-1 (10 nM), FGF2 (20 ng/ml) or sKlotho-FGF23 (20 nM) in the absence or presence of Rapamycin (40 nM) for 30 min. Cells were lysed in RIPA buffer in the presence of protease and phosphatase inhibitors. Western blot analysis was carried out and membranes were probed with different antibodies as indicated in the figure and developed on X-ray films, which were scanned.

The results of this study showed that sKlotho-FGF23 resulted in an increase in myotube diameter compared to the control and induced C2C12 myotube hypertrophy similar to results for IGF-1 and FGF2 (FIG. 5A). In addition, treatment with sKlotho-FGF23, IGF-1, and FGF2 could partially reverse myotube atrophy induced by dexamethasone, based on measurements of myotube diameter. No difference was observed between sKlotho-FGF23 and FGF2 on myotube morphology (measured by thickness of the myotubes) in the absence or presence of dexamethasone. The trophic effects of sKlotho-FGF23, IGF-1, and FGF2 were statistically significant.

Consistent with the effects on C2C12 myotubes, sKlotho-FGF23 fusion protein signaling led to the phosphorylation of p70S6K and ERK, but not AKT or FoxO, in C2C12 myotubes (FIG. 5B). The effect of sKlotho-FGF23 on signaling was similar to that of FGF2, but was distinct from that of IGF-1. The extent of ERK phosphorylation by sKlotho-FGF23 was observed to be less than that of IGF-1 or FGF2. The phosphorylation of p70S6K by sKlotho-FGF23 was rapamycin sensitive. In the experiments involving C2C12 cells, heparin was not required to activate signaling. These results show that a sKlotho-FGF23 fusion polypeptide activated signaling in C2C12 myotubes.

Example 4

Fusion Polypeptides Comprising sKlotho, FGF23 and FcLALA

Various fusion polypeptides are constructed using sKlotho, FGF23, and a modified Fc fragment of an antibody. These modified Fc molecules have altered (decreased) binding to FcRn and thus increased serum half-life. They also have modified bioavailability and altered transport to mucosal surfaces and other targets in the body. In this example, the FGF23 and sKlotho are fused to FcLALA, which is described in U.S. Pat. No. 7,217,798 and Hessell et al. 2007 Nature 449:101-104, Intervening between the various components of these fusion polypeptides are linkers, as described in Lode et al. 1998 Proc. Natl. Acad. Sci. USA 95: 2475-2480. These fusions are inserted into constructs, e.g., pcDNA3.1 (Invitrogen, Carlsbad, Calif.), and expressed in HEK293 cells.

A. sKlotho-FGF23-FcLALA v1

A fusion is constructed which comprises: sKlotho, a linker, FGF23, another linker, and FcLALA. This embodiment, designated sKlotho-FGF23-FcLALA v1, is presented in SEQ ID NOs: 46 and 47, below.

The nucleotide sequence of sKlotho-FGF23-FcLALA v1 (wherein initiation ATG as 1) is presented as SEQ ID NO: 46.

The amino acid sequence of sKlotho-FGF23-FcLALA v1 is presented below as SEQ ID NO: 47.

In this sequence, the various components of the fusion are as follows:

sKlotho: 1-982; Linked: 983-1001; FGF23: 1002-1228; Linker 2; 1229-1233; FcLALA: 1234-1459.

B. sKlotho-FGF23-FcLALA v2

A fusion is constructed which comprises: sKlotho, a linker, FGF23, another linker, and FcLALA. This embodiment is designated sKlotho-FGF23-FcLALA v2 and presented as SEQ ID NOs: 48 and 49, below.

The nucleotide sequence of sKlotho-FGF23-FcLALA v2 (wherein initiation ATG as 1) is presented as SEQ ID NO: 48.

The amino acid sequence of sKlotho-FGF23-FcLALA v2 is presented below as SEQ ID NO: 49.

In this sequence, the various components of the fusion are as follows:

sKlotho: (aa or amino acids) 1-982; Linker 1: 983-1001; FGF23: 1002-1228; Linker 2; 1229-1233; FcLALA: 1234-1450.

Other fusion polypeptides can be constructed by combining in various combinations the FGF, Klotho, modified Fc fragments, and (optionally) linker sequences, and variants and derivatives thereof, as described herein or known in the art.

Example 5

Fusion Polypeptides Comprising FGF23 and FcLALA

Various fusion polypeptides are constructed using FGF23, and a modified Fc fragment of an antibody, as described in U.S. Pat. No. 7,217,798. These modified Fc molecules have altered (decreased) binding to FcRn and thus increased serum half-life. They also have modified bioavailability and altered transport to mucosal surfaces and other targets in the body. In this example, FGF23 is fused to FcLALA, Intervening between the various components of these fusion polypeptides are linkers, as described in Lode et al. 1998 Proc. Natl. Acad. Sci. USA 95: 2475-2480. These fusions are inserted constructs, e.g., pcDNA3.1 (Invitrogen, Carlsbad, Calif.), and expressed in HEK293 cells.

C. FGF23-FcLALA v1

A fusion is constructed which comprises: FGF23, a linker, and FcLALA. This construct is designated FGF23-FcLALA v1 and presented below as SEQ ID NOs: 50 and 51.

The nucleotide sequence of FGF23-FcLALA v1 (wherein initiation ATG as 1) is presented below as SEQ ID NO: 50.

The amino acid sequence of FGF23(R179Q)-FcLALAv1 is presented below as SEQ ID NO: 51.

In this sequence, the various components of the fusion are as follows:

FGF23: (aa) 1-251; Linker: 252-256; FcLALA: 257-482.

D. FGF23-FcLALA v2

A fusion is constructed which comprises: FGF23-FcLALA v2, which comprises FGF23 and FcLALA.

The nucleotide sequence of FGF23-FcLALA v2 (wherein initiation ATG as 1) is presented below as SEQ ID NO: 52.

The amino acid sequence of FGF23(R179Q)-FcLALAv2 is presented below as SEQ ID NO: 53.

In this sequence, the various components of the fusion are as follows:

FGF23: 1-251; Linker: 252-256; FcLALA: 257-473.

Other fusion polypeptides can be constructed by combining in various combinations the FGF sequences, modified Fc fragments, and (optionally) linkers, and variants and derivatives thereof, as described herein or known in the art.

Sequence Listing (FIG. 2)

```
Human Klotho nucleic acid sequence (NM_004795)
Protein coding region: 9-3047
                                                              (SEQ ID NO: 1)
   1 cgcgcagcat gcccgccagc gccccgccgc gccgcccgcg gccgccgccg ccgtcgctgt 61 cgctgctgct ggtgctgctg ggcctgggcg gccgccgcct gcgtgcggag ccgggcgacg 121 gcgcgcagac ctgggcccgt ttctcgcggc ctcctgcccc cgaggccgcg ggcctcttcc 181 agggcacctt ccccgacggc ttcctctggg ccgtgggcag cgccgcctac cagaccgagg 241 gcggctggca gcagcacggc aagggtgcgt ccatctggga tacgttcacc caccaccccc 301 tggcaccccc gggagactcc cggaacgcca gtctgccgtt gggcgccccg tcgccgctgc 361 agcccgccac cggggacgta gccagcgaca gctacaacaa cgtcttccgc gacacggagg 421 cgctgcgcga gctcggggtc actcactacc gcttctccat ctcgtgggcg cgagtgctcc 481 ccaatggcag cgcgggcgtc cccaaccgcg aggggctgcg ctactaccgg cgcctgctgg 541 agcggctgcg ggagctgggc gtgcagcccg tggtcaccct gtaccactgg gacctgcccc 601 agcgcctgca ggacgcctac ggcggctggg ccaaccgcgc cctggccgac cacttcaggg 661 attacgcgga gctctgcttc cgccacttcg gcggtcaggt caagtactgg atcaccatcg 721 acaaccccta cgtggtggcc tggcacggct acgccaccgg gcgcctggcc cccggcatcc 781 ggggcagccc gcggctcggg tacctggtgg cgcacaacct cctcctggct catgccaaag 841 tctggcatct ctacaatact tctttccgtc ccactcaggg aggtcaggtg tccattgccc 901 taagctctca ctggatcaat cctcgaagaa tgaccgacca cagcatcaaa gaatgtcaaa 961 aatctctgga ctttgtacta ggttggtttg ccaaaccgt atttattgat ggtgactatc 1021 ccgagagcat gaagaataac ctttcatcta ttctgcctga ttttactgaa tctgagaaaa 1081 agttcatcaa aggaactgct gacttttttg ctctttgctt tggacccacc ttgagttttc 1141 aacttttgga ccctcacatg aagttccgcc aattggaatc tcccaacctg aggcaactgc 1201 tttcctggat tgaccttgaa tttaaccatc ctcaaatatt tattgtggaa aatggctggt 1261 ttgtctcagg gaccaccaag agagatgatg ccaaatatat gtattacctc aaaaagttca 1321 tcatggaaac cttaaaagcc atcaagctgg atgggGtgga tgtcatcggg tataccgcat
```

-continued

```
1381 ggtccctcat ggatggtttc gagtggcaca gaggttacag catcaggcgt ggactcttct
1441 atgttgactt tctaagccag acaagatgt tgttgccaaa gtcttcagcc ttgttctacc
1501 aaaagctgat agagaaaaat ggcttccctc ctttacctga aaatcagccc ctagaaggga
1561 catttccctg tgactttgct tggggagttg ttgacaacta cattcaagta gataccactc
1621 tgtctcagtt taccgacctg aatgtttacc tgtgggatgt ccaccacagt aaaaggctta
1681 ttaaagtgga tggggttgtg accaagaaga ggaaatccta ctgtgttgac tttgctgcca
1741 tccagcccca gatcgcttta ctccaggaaa tgcacgttac acattttcgc ttctccctgg
1801 actgggccct gattctccct ctgggtaacc agtcccaggt gaaccacacc atcctgcagt
1861 actatcgctg catggccagc gagcttgtcc gtgtcaacat caccccagtg gtggccctgt
1921 ggcagcctat ggccccgaac caaggactgc cgcgcctcct ggccaggcag ggcgcctggg
1981 agaaccccta cactgccctg cctttgcag agtatgcccg actgtgcttt caagagctcg
2041 gccatcacgt caagctttgg ataacgatga atgagccgta tacaaggaat atgacataca
2101 gtgctggcca caaccttctg aaggcccatg ccctggcttg gcatgtgtac aatgaaaagt
2161 ttaggcatgc tcagaatggg aaaatatcca tagccttgca ggctgattgg atagaacctg
2221 cctgcccttt ctcccaaaag acaaagagg tggccgagag agttttggaa tttgacattg
2281 gctggctggc tgagcccatt ttcggctctg gagattatcc atgggtgatg agggactggc
2341 tgaaccaaag aaacaatttt cttcttcctt atttcactga agatgaaaaa aagctaatcc
2401 agggtacctt tgactttttg gctttaagcc attataccac catccttgta gactcagaaa
2461 aagaagatcc aataaaatac aatgattacc tagaagtgca agaaatgacc gacatcacgt
2521 ggctcaactc ccccagtcag gtggcggtag tgccctgggg gttgcgcaaa gtgctgaact
2581 ggctgaagtt caagtacgga gacctcccca tgtacataat atccaacgga atcgatgacg
2641 ggctgcatgc tgaggacgac cagctgaggg tgtattatat gcagaattac ataaacgaag
2701 ctctcaaagc ccacatactg gatggtatca atctttgcgg atactttgct tattcgttta
2761 acgaccgcac agctccgagg tttggcctct atcgttatgc tgcagatcag tttgagccca
2821 aggcatccat gaaacattac aggaaaatta ttgacagcaa tggtttcccg ggcccagaaa
2881 ctctggaaag attttgtcca gaagaattca ccgtgtgtac tgagtgcagt ttttttcaca
2941 cccgaaagtc tttactggct ttcatagctt ttctattttt tgcttctatt atttctctct
3001 cccttatatt ttactactcg aagaaaggca gaagaagtta caaatagttc tgaacatttt
3061 tctattcatt cattttgaaa taattatgca gacacatcag ctgttaacca tttgcacctc
3121 taagtgttgt gaaactgtaa atttcataca tttgacttct agaaaacatt tttgtggctt
3181 atgacagagt ttttgaaatg gcataggtg atcgtaaaat attgaataat gcgaatagtg
3241 cctgaatttg ttctcttttt gggtgattaa aaaactgaca ggcactataa tttctgtaac
3301 acactaacaa aagcatgaaa ataggaacc acaccaatgc aacatttgtg cagaaatttg
3361 aatgacaaga ttaggaatat tttcttctgc acccacttct aaatttaatg ttttctgga
3421 agtagtaatt gcaagagttc gaatagaaag ttatgtacca agtaaccatt tctcagctgc
3481 cataataatg cctagtggct tcccctctgt caaatctagt ttcctatgga aaagaagatg
3541 gcagatacag gagagacgac agagggtcct aggctggaat gttcctttcg aaagcaatgc
3601 ttctatcaaa tactagtatt aatttatgta tctggttaat gacatacttg gagagcaaat
3661 tatggaaatg tgtattttat atgattttg aggtcctgtc taaaccctgt gtccctgagg
3721 gatctgtctc actggcatct tgttgagggc cttgcacata ggaaactttt gataagtatc
```

-continued

```
3781 tgcggaaaaa caaacatgaa tcctgtgata ttgggctctt caggaagcat aaagcaattg 3841 tgaaatacag tataccgcag tggctctagg tggaggaaag gaggaaaaag tgcttattat 3901 gtgcaacatt atgattaatc tgattataca ccattttttga gcagatcttg aatgaatga 3961 catgaccttt ccctagagaa taaggatgaa ataatcactc attctatgaa cagtgacact 4021 actttctatt ctttagctgt actgtaattt ctttgagttg atagttttac aaattcttaa 4081 taggttcaaa agcaatctgg tctgaataac actggatttg tttctgtgat ctctgaggtc 4141 tattttatgt ttttgctgct acttctgtgg aagtagcttt gaactagttt tactttgaac 4201 tttcacgctg aaacatgcta gtgatatcta gaaagggcta attaggtctc atcctttaat 4261 gccccttaaa taagtcttgc tgattttcag acagggaagt ctctctatta cactggagct 4321 gttttataga taagtcaata ttgtatcagg caagataaac caatgtcata acaggcattg 4381 ccaacctcac tgacacaggg tcatagtgta taataatata ctgtactata taatatatca 4441 tctttagagg tatgattttt tcatgaaaga taagcttttg gtaatattca ttttaaagtg 4501 gacttattaa aattggatgc tagagaatca agtttatttt atgtatatat ttttctgatt 4561 ataagagtaa tatatgttca ttgtaaaaat ttttaaaaca cagaaactat atgcaaagaa 4621 aaaataaaaa ttatctataa tctcagaacc cagaaatagc cactattaac atttcctacg 4681 tattttattt tacatagatc atattgtata tagttagtat ctttattaat ttttattatg 4741 aaactttcct ttgtcattat tagtcttcaa aagcatgatt tttaatagtt gttgagtatt 4801 ccaccacagg aatgtatcac aacttaaccg ttcccgtttg ttagactagt ttcttattaa 4861 tgttgatgaa tgttgtttaa aaataatttt gttgctacat ttactttaat ttccttgact 4921 gtaaagagaa gtaattttgc tccttgataa agtattatat taataataaa tctgcctgca 4981 acttttttgcc ttctttcata atc
```

Klotho amino acid sequence (NP_004786)

(SEQ ID NO: 2)

```
  1 MPASAPPRRP RPPPPSLSLL LVLLGLGGRR LRAEPGDGAQ TWARFSRPPA PEAAGLFQGT

61 FPDGFLWAVG SAAYQTEGGW QQHGKGASIW DTFTHHPLAP PGDSRNASLP LGAPSPLQPA

121 TGDVASDSYN NVFRDTEALR ELGVTHYRFS ISWARVLPNG SAGVPNREGL RYYRRLLERL

181 RELGVQPVVT LYHWDLPQRL QDAYGGWANR ALADHFRDYA ELCFRHFGGQ VKYWITIDNP

241 YVVAWHGYAT GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP DFTESEKKFI

361 KGTADFFALC FGPTLSFQLL DPHMKFRQLE SPNLRQLLSW IDLEFNHPQI FIVENGWFVS

421 GTTKRDDAKY MYYLKKFIME TLKAIKLDGV DVIGYTAWSL MDGFEWHRGY SIRRGLFYVD

481 FLSQDKMLLP KSSALFYQKL IEKNGFPPLP ENQPLEGTFP CDFAWGVVDN YIQVDTTLSQ

541 FTDLNVYLWD VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL LARQGAWENP

661 YTALAFAEYA RLCFQELGHH VKLWITMNEP YTRNMTYSAG HNLLKAHALA WHVYNEKFRH

721 AQNGKISIAL QADWIEPACP FSQKDKEVAE RVLEFDIGWL AEPIFGSGDY PWVMRDWLNQ

781 RNNFLLPYFT EDEKKLIQGT FDFLALSHYT TILVDSEKED PIKYNDYLEV QEMTDITWLN

841 SPSQVAVVPW GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS NGFPGPETLE

961 RFCPEEFTVC TECSFFHTRK SLLAFIAFLF FASIISLSLI FYYSKKGRRS YK
```

-continued beta-Klotho nucleic acid sequence (NM_175737)
Protein coding region: 98-3232

(SEQ ID NO: 3)

```
   1 atcctcagtc tcccagttca agctaatcat tgacagagct ttacaatcac aagcttttac
  61 tgaagctttg ataagacagt ccagcagttg gtggcaaatg aagccaggct gtgcggcagg
 121 atctccaggg aatgaatgga ttttcttcag cactgatgaa ataaccacac gctataggaa
 181 tacaatgtcc aacgggggat tgcaaagatc tgtcatcctg tcagcactta ttctgctacg
 241 agctgttact ggattctctg gagatggaag agctatatgg tctaaaaatc ctaattttac
 301 tccggtaaat gaaagtcagc tgtttctcta tgacactttc cctaaaaact ttttctgggg
 361 tattgggact ggagcattgc aagtggaagg gagttggaag aaggatggaa aaggaccttc
 421 tatatgggat catttcatcc acacacacct taaaaatgtc agcagcacga atggttccag
 481 tgacagttat atttttctgg aaaaagactt atcagccctg gattttatag gagtttcttt
 541 ttatcaattt tcaatttcct ggccaaggct ttccccgat ggaatagtaa cagttgccaa
 601 cgcaaaaggt ctgcagtact acagtactct tctggacgct ctagtgctta gaaacattga
 661 acctatagtt actttatacc actgggattt gcctttggca ctacaagaaa aatatgggg
 721 gtggaaaaat gataccataa tagatatctt caatgactat gccacatact gtttccagat
 781 gtttgggac cgtgtcaaat attggattac aattcacaac ccatatctag tggcttggca
 841 tgggtatggg acaggtatgc atgcccctgg agagaaggga aatttagcag ctgtctacac
 901 tgtgggacac aacttgatca aggctcactc gaaagtttgg cataactaca cacacattt
 961 ccgcccacat cagaagggtt ggttatcgat cacgttggga tctcattgga tcgagccaaa
1021 ccggtcggaa acacgatgg atatattcaa atgtcaacaa tccatggttt ctgtgcttgg
1081 atggtttgcc aaccctatcc atgggatgg cgactatcca gaggggatga aagaagtt
1141 gttctccgtt ctacccattt tctctgaagc agagaagcat gagatgagag cacagctga
1201 tttctttgcc ttttcttttg gacccaacaa cttcaagccc ctaaacacca tggctaaaat
1261 gggacaaaat gtttcactta atttaagaga agcgctgaac tggattaaac tggaatacaa
1321 caaccctcga atcttgattg ctgagaatgg ctggttcaca gacagtcgtg tgaaaacaga
1381 agacaccacg gccatctaca tgatgaagaa tttcctcagc caggtgcttc aagcaataag
1441 gttagatgaa atacgagtgt ttggttatac tgcctggtct ctcctggatg gctttgaatg
1501 gcaggatgct tacaccatcc gccgaggatt attttatgtg gattttaaca gtaaacagaa
1561 agagcggaaa cctaagtctt cagcacacta ctacaaacag atcatacgag aaaatggttt
1621 ttctttaaaa gagtccacgc cagatgtgca gggccagttt ccctgtgact ctcctgggg
1681 tgtcactgaa tctgttctta gcccgagtc tgtggcttcg tccccacagt tcagcgatcc
1741 tcatctgtac gtgtggaacg ccactggcaa cagactgttg caccgagtgg aaggggtgag
1801 gctgaaaaca cgacccgctc aatgcacaga ttttgtaaac atcaaaaac aacttgagat
1861 gttggcaaga atgaaagtca cccactaccg gtttgctctg gattgggcct cggtccttcc
1921 cactggcaac ctgtccgcgg tgaaccgaca ggccctgagg tactacaggt gcgtggtcag
1981 tgagggctg aagcttggca tctccgcgat ggtcaccctg tattatccga cccacgccca
2041 cctaggcctc cccgagcctc tgttgcatgc cgacggggtgg ctgaacccat cgacggccga
2101 ggccttccag gcctacgctg ggctgtgctt ccaggagctg ggggacctgg tgaagctctg
2161 gatcaccatc aacgagccta accggctaag tgacatctac aaccgctctg caacgacac
2221 ctacggggcg cgcacaacc tgctggtggc ccacgccctg gctggcgcc tctacgaccg
2281 gcagttcagg ccctcacagc gcggggccgt gtcgctgtcg ctgcacgcgg actgggcgga
```

-continued

```
2341 acccgccaac ccctatgctg actcgcactg gagggcggcc gagcgcttcc tgcagttcga
2401 gatcgcctgg ttcgccgagc cgctcttcaa gaccggggac taccccgcgg ccatgaggga
2461 atacattgcc tccaagcacc gacggggggct ttccagctcg ccctgccgc gcctcaccga
2521 ggccgaaagg aggctgctca agggcacggt cgacttctgc gcgctcaacc acttcaccac
2581 taggttcgtg atgcacgagc agctggccgg cagccgctac gactcggaca gggacatcca
2641 gtttctgcag gacatcaccc gcctgagctc cccacgcgc ctggctgtga ttccctgggg
2701 ggtgcgcaag ctgctgcggt gggtccggag gaactacggc gacatggaca tttacatcac
2761 cgccagtggc atcgacgacc aggctctgga ggatgaccgg ctccggaagt actacctagg
2821 gaagtacctt caggaggtgc tgaaagcata cctgattgat aaagtcagaa tcaaaggcta
2881 ttatgcattc aaactggctg aagagaaatc taaacccaga tttggattct tcacatctga
2941 ttttaaagct aaatcctcaa tacaattta caacaaagtg atcagcagca ggggcttccc
3001 ttttgagaac agtagttcta gatgcagtca gacccaagaa aatacagagt gcactgtctg
3061 cttattcctt gtgcagaaga aaccactgat attcctgggt tgttgcttct tctccaccct
3121 ggttctactc ttatcaattg ccatttttca aaggcagaag agaagaaagt tttggaaagc
3181 aaaaaactta caacacatac cattaaagaa aggcaagaga gttgttagct aaactgatct
3241 gtctgcatga tagacagttt aaaaattcat cccagttcc
``` beta-Klotho amino acid sequence (NP_783864)
(SEQ ID NO: 4)

```
  1 mkpgcaagsp gnewiffstd eittryrntm sngglqrsvi lsalillrav tgfsgdgrai
 61 wsknpnftpv nesqlflydt fpknffwgig tgalqvegsw kkdgkgpsiw dhfihthlkn
121 vsstngssds yiflekdlsa ldfigvsfyq fsiswprlfp dgivtvanak glqyystlld
181 alvlrniepi vtlyhwdlpl alqekyggwk ndtiidifnd yatycfqmfg drvkywitih
241 npylvawhgy gtgmhapgek gnlaavytvg hnlikahskv whnynthfrp hqkgwlsitl
301 gshwiepnrs entmdifkcq qsmvsvlgwf anpihgdgdy pegmrkklfs vlpifseaek
361 hemrgtadff afsfgpnnfk pintmakmgq nvslnlreal nwikleynnp riliaengwf
421 tdsrvktedt taiymmknfl sqvlqairld eirvfgytaw slldgfewqd aytirrglfy
481 vdfnskqker kpkssahyyk qiirengfsl kestpdvqgq fpcdfswgvt esvlkpesva
541 sspqfsdphl yvwnatgnrl lhrvegvrlk trpaqctdfv nikkqlemla rmkvthyrfa
601 ldwasvlptg nlsavnrqal ryyrcvvseg lklgisamvt lyypthahlg lpepllhadg
661 wlnpstaeaf qayaglcfqe lgdlvklwit inepnrlsdi ynrsgndtyg aahnllvaha
721 lawrlydrqf rpsqrgaysl slhadwaepa npyadshwra aerflqfela wfaeplfktg
781 dypaamreyi askhrrglss salprlteae rrllkgtvdf calnhfttrf vmheqlagsr
841 ydsdrdiqfl qditrlsspt rlavipwgvr kllrwvrrny gdmdiyitas giddqaledd
901 rlrkyylgky lqevlkayll dkvrikgyya fklaeekskp rfgfftsdfk akssiqfynk
961 vissrgfpfe nsssrcsqtq entectvclf lvqkkplifl gccffstivl llsialfqrq
1021 krrkfwkakn lqhiplkkgk rvvs
```

Human Klotho domain 1 (KL-D1) amino acid sequence
(SEQ ID NO: 5)

```
 58                                                               qgt
 61 fpdgflwavg saayqteggw qqhgkgasiw dtfthhplap pgdsrnaslp lgapsplqpa
121 tgdvasdsyn nvfrdtealr elgvthyrfs iswarvlpng sagvpnregl ryyrrllerl
181 relgvqpvvt lyhwdlpqrl qdayggwanr aladhfrdya elcfrhfggq vkywitidnp
```

```
241 yvvawhgyat grlapgirgs prlgylvahn lllahakvwh lyntsfrptq ggqvsialss 301 hwinprrmtd hsikecqksl dfvlgwfakp vfidgdypes mknnlssilp dfteselckkfi
```
(corrections) 
```
301 hwinprrmtd hsikecqksl dfvlgwfakp vfidgdypes mknnlssilp dfteseklcfi
```

```
301 hwinprrmtd hsikecqksl dfvlgwfakp vfidgdypes mknnlssilp dftesekkfi 361 kgtadffalc fgptlsfqll dphmkfrqle spnlrqllsw idlefnhpqi fivengwfvs 421 gttkrddaky myylkkfime tlkaikldgv dvigytawsl mdgfewhrgy sirrglfyvd 481 flsqdkmllp kssalfyqkl iekngf
```

Human Klotho domain 2 (KL-D2) amino acid sequence
(SEQ ID NO: 6)
```
517                                   gtfp cdfawgvvdn yiqvdttlsq 541 ftdlnvylwd vhhskrlikv dgvvtkkrks ycvdfaaiqp qiallqemhv thfrfsldwa 601 lilplgnqsq vnhtilqyyr cmaselvrvn itpvvalwqp mapnqglprl larqgawenp 661 ytalafaeya rlcfqelghh vklwitmnep ytrnmtysag hnllkahala whvynekfrh 721 aqngkisial qadwiepacp fsqkdkevae rvlefdigwl aepifgsgdy pwvmrdwlnq 781 rnnfllpyft edekkliqgt fdflalshyt tilvdseked pikyndylev qemtditwln 841 spsqvavvpw glrkvlnwlk fkygdlpmyi isngiddglh aeddqlrvyy mqnyinealk 901 ahildginlc gyfaysfndr taprfglyry aadqfepkas mkhyrkiids ngf
```

Klotho extracellular domain (without signal peptide) amino acid sequence
(SEQ ID NO: 7)
```
 28                                 epgdgaq twarfsrppa peaaglfqgt 61 fpdgflwavg saayqteggw qqhgkgasiw dtfthhplap pgdsrnaslp lgapsplqpa 121 tgdvasdsyn nvfrdtealr elgvthyrfs iswarvlpng sagvpnregl ryyrrllerl 181 relgvqpvvt lyhwdlpqrl qdayggwanr aladhfrdya elcfrhfggq vkywitidnp 241 yvvawhgyat grlapgirgs prlgylvahn lllahakvwh lyntsfrptq ggqvsialss 301 hwinprrmtd hsikecqksl dfvlgwfakp vfidgdypes mknnlssilp dftesekkfi 361 kgtadffalc fgptlsfqll dphmkfrqle spnlrqllsw idlefnhpqi fivengwfvs 421 gttkrddaky myylkkfime tlkaikldgv dvigytawsl mdgfewhrgy sirrglfyvd 481 flsqdkmllp kssalfyqkl iekngfpplp enqplegtfp cdfawgvvdn yiqvdttlsq 541 ftdlnvylwd vhhskrlikv dgvvtkkrks ycvdfaaiqp qiallqemhv thfrfsldwa 601 lilplgnqsq vnhtilqyyr cmaselvrvn itpvvalwqp mapnqglprl larqgawenp 661 ytalafaeya rlcfqelghh vklwitmnep ytrnmtysag hnllkahala whvynekfrh 721 aqngkisial qadwiepacp fsqkdkevae rvlefdigwl aepifgsgdy pwvmrdwlnq 781 rnnfllpyft edekkliqgt fdflalshyt tilvdseked pikyndylev qemtditwln 841 spsqvavvpw glrkvlnwlk fkygdlpmyi isngiddglh aeddqlrvyy mqnyinealk 901 ahildginlc gyfaysfndr taprfglyry aadqfepkas mkhyrkiids ngfpgpetle 961 rfcpeeftvc tecsffhtrk sl
```

Klotho signal peptide amino acid sequence
(SEQ ID NO: 8)
```
  1 mpasapprrp rppppslsll lvllglggrr lra
```

IgG signal peptide amino acid sequence
(SEQ ID NO: 9)
```
  1 msvltqvlal lllwltgtrc rrlra
```

(Gly4 Ser)3 polypeptide linker nucleic acid sequence
(SEQ ID NO: 10)
```
  1 ggaggtggag gttcaggagg tggaggttca ggaggtggag gttca
```

(Gly4 Ser)3 polypeptide linker amino acid sequence
(SEQ ID NO: 11)
```
  1 GGGGSGGGGS GGGGS
```

-continued (Gly₄ Ser) polypeptide linker amino acid sequence
(SEQ ID NO: 12)
  1 GGGGS (Gly) polypeptide linker amino acid sequence
(SEQ ID NO: 13)
  1 G (Gly Gly) polypeptide linker amino acid sequence
(SEQ ID NO: 14)
  1 GG (Gly Ser) polypeptide linker amino acid sequence
(SEQ ID NO: 15)
  1 GS (Gly₂ Ser) polypeptide linker amino acid sequence
(SEQ ID NO: 16)
  1 GGS (Ala) polypeptide linker amino acid sequence
(SEQ ID NO: 17)
  1 A (Ala Ala) polypeptide linker amino acid sequence
(SEQ ID NO: 18)
  1 AA Klotho signal peptide-Klotho extracellular domain-FGF23 (R179Q) amino acid sequence
(SEQ ID NO: 19)
```
   1 MPASAPPRRP RPPPPSLSLL LVLLGLGGRR LRAEPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGTFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFTVC TECSFFHTRK SLGSGGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN THAGGTGPEG CRPFAKFI*
```

IgG signal peptide-Klotho extracellular domain-FGF23 (R179Q) amino acid sequence (SEQ ID NO: 20)

```
  1 MSVLTQVLAL LLLWLTGLGG RRLRAEPGDG AQTWARFSRP PAPEAAGLFQ
 51 GTFPDGFLWA VGSAAYQTEG GWQQHGKGAS IWDTFTHHPL APPGDSRNAS
101 LPLGAPSPLQ PATGDVASDS YNNVFRDTEA LRELGVTHYR FSISWARVLP
151 NGSAGVPNRE GLRYYRRLLE RLRELGVQPV VTLYHWDLPQ RLQDAYGGWA
201 NRALADHFRD YAELCFRHFG GQVKYWITID NPYVVAWHGY ATGRLAPGIR
251 GSPRLGYLVA HNLLLAHAKV WHLYNTSFRP TQGGQVSIAL SSHWINPRRM
301 TDHSIKECQK SLDFVLGWFA KPVFIDGDYP ESMKNNLSSI LPDFTESEKK
351 FIKGTADFFA LCFGPTLSFQ LLDPHMKFRQ LESPNLRQLL SWIDLEFNHP
401 QIFIVENGWF VSGTTKRDDA KYMYYLKKFI METLKAIKLD GVDVIGYTAW
451 SLMDGFEWHR GYSIRRGLFY VDFLSQDKML LPKSSALFYQ KLIEKNGFPP
501 LPENQPLEGT FPCDFAWGVV DNYIQVDTTL SQFTDLNVYL WDVHHSKRLI
551 KVDGVVTKKR KSYCVDFAAI QPQIALLQEM HVTHFRFSLD WALILPLGNQ
601 SQVNHTILQY YRCMASELVR VNITPVVALW QPMAPNQGLP RLLARQGAWE
651 NPYTALAFAE YARLCFQELG HHVKLWITMN EPYTRNMTYS AGHNLLKAHA
701 LAWHVYNEKF RHAQNGKISI ALQADWIEPA CPFSQKDKEV AERVLEFDIG
751 WLAEPIFGSG DYPWVMRDWL NQRNNFLLPY FTEDEKKLIQ GTFDFLALSH
801 YTTILVDSEK EDPIKYNDYL EVQEMTDITW LNSPSQVAVV PWGLRKVLNW
851 LKFKYGDLPM YIISNGIDDG LHAEDDQLRV YYMQNYINEA LKAHILDGIN
901 LCGYFAYSFN DRTAPRFGLY RYAADQFEPK ASMKHYRKII DSNGFPGPET
951 LERFCPEEFT VCTECSFFHT RKSLGSGGGG SGGGGSGGGG SLKYPNASPL
1001 LGSSWGGLIH LYTATARNSY HLQIHKNGHV DGAPHQTIYS ALMIRSEDAG
1051 FVVITGVMSR RYLCMDFRGN IFGSHYFDPE NCRFQHQTLE NGYDVYHSPQ
1101 YHFLVSLGRA KRAFLPGMNP PPYSQFLSRR NEIPLIHFNT PIPRRHTQSA
1151 EDDSERDPLN VLKPRARMTP APASCSQELP SAEDNSPMAS DPLGVVRGGR
1201 VNTHAGGTGP EGCRPFAKFI *
```

KL-D1-FGF23 (R179Q) amino acid sequence (SEQ ID NO: 21)

```
  1 MPASAPPRRP RPPPPSLSLL LVLLGLGGRR LRAEPGDGAQ TWARFSRPPA
 51 PEAAGLFQGT FPDGFLWAVG SAAYQTEGGW QQHGKGASIW DTFTHHPLAP
101 PGDSRNASLP LGAPSPLQPA TGDVASDSYN NVFRDTEALR ELGVTHYRFS
151 ISWARVLPNG SAGVPNREGL RYYRRLLERL RELGVQPVVT LYHWDLPQRL
201 QDAYGGWANR ALADHFRDYA ELCFRHFGGQ VKYWITIDNP YVVAWHGYAT
251 GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP
351 DFTESEKKFI KGTADFFALC FGPTLSFQLL DPHMKFRQLE SPNLRQLLSW
401 IDLEFNHPQI FIVENGWFVS GTTKRDDAKY MYYLKKFIME TLKAIKLDGV
451 DVIGYTAWSL MDGFEWHRGY SIRRGLFYVD FLSQDKMLLP KSSALFYQKL
501 IEKNGFPPLP ENQPLEGSGG GGSGGGGSGG GGSLKYPNAS PLLGSSWGGL
551 IHLYTATARN SYHLQIHKNG HVDGAPHQTI YSALMIRSED AGFVVITGVM
601 SRRYLCMDFR GNIFGSHYFD PENCRFQHQT LENGYDVYHS PQYHFLVSLG
```

```
651 RAKRAFLPGM NPPPYSQFLS RRNEIPLIHF NTPIPRRHTQ SAEDDSERDP

701 LNVLKPRARM TPAPASCSQE LPSAEDNSPM ASDPLGVVRG GRVNTHAGGT

751 GPEGCRPFAK FI*
```

KL-D2-FGF23 (R179Q) amino acid sequence (SEQ ID NO: 22)

```
  1 MPASAPPRRP RPPPPSLSLL LVLLGLGGRR LPLPENQPLE GTFPCDFAWG

51 VVDNYIQVDT TLSQFTDLNV YLWDVHHSKR LIKVDGVVTK KRKSYCVDFA

101 AIQPQIALLQ EMHVTHFRFS LDWALILPLG NQSQVNHTIL QYYRCMASEL

151 VRVNITPVVA LWQPMAPNQG LPRLLARQGA WENPYTALAF AEYARLCFQE

201 LGHHVKLWIT MNEPYTRNMT YSAGHNLLKA HALAWHVYNE KFRHAQNGKI

251 SIALQADWIE PACPFSQKDK EVAERVLEFD IGWLAEPIFG SGDYPWVMRD

301 WLNQRNNFLL PYFTEDEKKL IQGTFDFLAL SHYTTILVDS EKEDPIKYND

351 YLEVQEMTDI TWLNSPSQVA VVPWGLRKVL NWLKFKYGDL PMYIISNGID

401 DGLHAEDDQL RVYYMQNYIN EALKAHILDG INLCGYFAYS FNDRTAPRFG

451 LYRYAADQFE PKASMKHYRK IIDSNGFPGP ETLERFCPEE FTVCTECSFF

501 HTRKSLGSGG GGSGGGGSGG GGSLKYPNAS PLLGSSWGGL IHLYTATARN

551 SYHLQIHKNG HVDGAPHQTI YSALMIRSED AGFVVITGVM SRRYLCMDFR

601 GNIFGSHYFD PENCRFQHQT LENGYDVYHS PQYHFLVSLG RAKRAFLPGM

651 NPPPYSQFLS RRNEIPLIHF NTPIPRRHTQ SAEDDSERDP LNVLKPRARM

701 TPAPASCSQE LPSAEDNSPM ASDPLGVVRG GRVNTHAGGT GPEGCRPFAK

751 FI*
```

(KL-D1)$_2$-FGF23 (R179Q) amino acid sequence (SEQ ID NO: 23)

```
  1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGSGT FPDGFLWAVG SAAYQTEGGW QQHGKGASIW

551 DTFTHHPLAP PGDSRNASLP LGAPSPLQPA TGDVASDSYN NVFRDTEALR

601 ELGVTHYRFS ISWARVLPNG SAGVPNREGL RYYRRLLERL RELGVQPVVT

651 LYHWDLPQRL QDAYGGWANR ALADHFRDYA ELCFRHFGGQ VKYWITIDNP

701 YVVAWHGYAT GRLAPGIRGS PRLGYLVAHN LLLAHAKVWH LYNTSFRPTQ

751 GGQVSIALSS HWINPRRMTD HSIKECQKSL DFVLGWFAKP VFIDGDYPES

801 MKNNLSSILP DFTESEKKFI KGTADFFALC FGPTLSFQLL DPHMKFRQLE

851 SPNLRQLLSW IDLEFNHPQI FIVENGWFVS GTTKRDDAKY MYYLKKFIME

901 TLKAIKLDGV DVIGYTAWSL MDGFEWHRGY SIRRGLFYVD FLSQDKMLLP
```

```
 951 KSSALFYQKL IEKNGFPEFG SGGGGSGGGG SGGGGSLKYP NASPLLGSSW

1001 GGLIHLYTAT ARNSYHLQIH KNGHVDGAPH QTIYSALMIR SEDAGFVVIT

1051 GVMSRRYLCM DFRGNIFGSH YFDPENCRFQ HQTLENGYDV YHSPQYHFLV

1101 SLGRAKRAFL PGMNPPPYSQ FLSRRNEIPL IHFNTPIPRR HTQSAEDDSE

1151 RDPLNVLKPR ARMTPAPASC SQELPSAEDN SPMASDPLGV VRGGRVNTHA

1201 GGTGPEGCRP FAKFI*
```

(KL-D2)$_2$-FGF23 (R179Q) amino acid sequence (SEQ ID NO: 24)

```
   1 MPASAPPRRP RPPPPSLSLL LVLLGLGGRR LPLPENQPLE GTFPCDFAWG

51 VVDNYIQVDT TLSQFTDLNV YLWDVHHSKR LIKVDGVVTK KRKSYCVDFA

101 AIQPQIALLQ EMHVTHFRFS LDWALILPLG NQSQVNHTIL QYYRCMASEL

151 VRVNITPVVA LWQPMAPNQG LPRLLARQGA WENPYTALAF AEYARLCFQE

201 LGHHVKLWIT MNEPYTRNMT YSAGHNLLKA HALAWHVYNE KFRHAQNGKI

251 SIALQADWIE PACPFSQKDK EVAERVLEFD IGWLAEPIFG SGDYPWVMRD

301 WLNQRNNFLL PYFTEDEKKL IQGTFDFLAL SHYTTILVDS EKEDPIKYND

351 YLEVQEMTDI TWLNSPSQVA VVPWGLRKVL NWLKFKYGDL PMYIISNGID

401 DGLHAEDDQL RVYYMQNYIN EALKAHILDG INLCGYFAYS FNDRTAPRFG

451 LYRYAADQFE PKASMKHYRK IIDSNGFPGP ETLERFCPEE FTVCTECSFF

501 HTRKSLGTFP CDFAWGVVDN YIQVDTTLSQ FTDLNVYLWD VHHSKRLIKV

551 DGVVTKKRKS YCVDFAAIQP QIALLQEMHV THFRFSLDWA LILPLGNQSQ

601 VNHTILQYYR CMASELVRVN ITPVVALWQP MAPNQGLPRL LARQGAWENP

651 YTALAFAEYA RLCFQELGHH VKLWITMNEP YTRNMTYSAG HNLLKAHALA

701 WHVYNEKFRH AQNGKISIAL QADWIEPACP FSQKDKEVAE RVLEFDIGWL

751 AEPIFGSGDY PWVMRDWLNQ RNNFLLPYFT EDEKKLIQGT FDFLALSHYT

801 TILVDSEKED PIKYNDYLEV QEMTDITWLN SPSQVAVVPW GLRKVLNWLK

851 FKYGDLPMYI ISNGIDDGLH AEDDQLRVYY MQNYINEALK AHILDGINLC

901 GYFAYSFNDR TAPRFGLYRY AADQFEPKAS MKHYRKIIDS NGFGSGGGGS

951 GGGGSGGGGS LKYPNASPLL GSSWGGLIHL YTATARNSYH LQIHKNGHVD

1001 GAPHQTIYSA LMIRSEDAGF VVITGVMSRR YLCMDFRGNI FGSHYFDPEN

1051 CRFQHQTLEN GYDVYHSPQY HFLVSLGRAK RAFLPGMNPP PYSQFLSRRN

1101 EIPLIHFNTP IPRRHTQSAE DDSERDPLNV LKPRARMTPA PASCSQELPS

1151 AEDNSPMASD PLGVVRGGRV NTHAGGTGPE GCRPFAKFI*
```

FGF23 (R179Q)-Klotho extracellular domain amino acid sequence (SEQ ID NO: 25)

```
   1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGSGGGGSGG GGSGGGGSLK EPGDGAQTWA RFSRPPAPEA AGLFQGTFPD

301 GFLWAVGSAA YQTEGGWQQH GKGASIWDTF THHPLAPPGD SRNASLPLGA

351 PSPLQPATGD VASDSYNNVF RDTEALRELG VTHYRFSISW ARVLPNGSAG

401 VPNREGLRYY RRLLERLREL GVQPVVTLYH WDLPQRLQDA YGGWANRALA
```

```
451 DHFRDYAELC FRHFGGQVKY WITIDNPYVV AWHGYATGRL APGIRGSPRL

501 GYLVAHNLLL AHAKVWHLYN TSFRPTQGGQ VSIALSSHWI NPRRMTDHSI

551 KECQKSLDFV LGWFAKPVFI DGDYPESMKN NLSSILPDFT ESEKKFIKGT

601 ADFFALCFGP TLSFQLLDPH MKFRQLESPN LRQLLSWIDL EFNHPQIFIV

651 ENGWFVSGTT KRDDAKYMYY LKKFIMETLK AIKLDGVDVI GYTAWSLMDG

701 FEWHRGYSIR RGLFYVDFLS QDKMLLPKSS ALFYQKLIEK NGFPPLPENQ

751 PLEGTFPCDF AWGVVDNYIQ VDTTLSQFTD LNVYLWDVHH SKRLIKVDGV

801 VTKKRKSYCV DFAAIQPQIA LLQEMHVTHF RFSLDWALIL PLGNQSQVNH

851 TILQYYRCMA SELVRVNITP VVALWQPMAP NQGLPRLLAR QGAWENPYTA

901 LAFAEYARLC FQELGHHVKL WITMNEPYTR NMTYSAGHNL LKAHALAWHV

951 YNEKFRHAQN GKISIALQAD WIEPACPFSQ KDKEVAERVL EFDIGWLAEP

1001 IFGSGDYPWV MRDWLNQRNN FLLPYFTEDE KKLIQGTFDF LALSHYTTIL

1051 VDSEKEDPIK YNDYLEVQEM TDITWLNSPS QVAVVPWGLR KVLNWLKFKY

1101 GDLPMYIISN GIDDGLHAED DQLRVYYMQN YINEALKAHI LDGINLCGYF

1151 AYSFNDRTAP RFGLYRYAAD QFEPKASMKH YRKIIDSNGF PGPETLERFC

1201 PEEFTVCTEC SFFHTRKSL*
```

FGF23 (R179Q)-KL-D1 amino acid sequence                    (SEQ ID NO: 26)

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IQGTFPDGFL WAVGSAAYQT EGGWQQHGKG ASIWDTFTHH PLAPPGDSRN

301 ASLPLGAPSP LQPATGDVAS DSYNNVFRDT EALRELGVTH YRFSISWARV

351 LPNGSAGVPN REGLRYYRRL LERLRELGVQ PVVTLYHWDL PQRLQDAYGG

401 WANRALADHF RDYAELCFRH FGGQKYWIT IDNPYVVAWH GYATGRLAPG

451 IRGSPRLGYL VAHNLLLAHA KVWHLYNTSF RPTQGGQVSI ALSSHWINPR

501 RMTDHSIKEC QKSLDFVLGW FAKPVFIDGD YPESMKNNLS SILPDFTESE

551 KKFIKGTADF ALCFGPTLS FQLLDPHMKF RQLESPNLRQ LLSWIDLEFN

601 HPQIFIVENG WFVSGTTKRD DAKYMYYLKK FIMETLKAIK LDGVDVIGYT

651 AWSLMDGFEW HRGYSIRRGL FYVDFLSQDK MLLPKSSALF YQKLIEKNGF

652 *
```

FGF23 (R179Q)-KL-D2 amino acid sequence                    (SEQ ID NO: 27)

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGTFPCDFAW GVVDNYIQVD TTLSQFTDLN VYLWDVHHSK RLIKVDGVVT

301 KKRKSYCVDF AAIQPQIALL QEMHVTHFRF SLDWALILPL GNQSQVNHTI
```

```
351 LQYYRCMASE LVRVNITPVV ALWQPMAPNQ GLPRLLARQG AWENPYTALA

401 FAEYARLCFQ ELGHHVKLWI TMNEPYTRNM TYSAGHNLLK AHALAWHVYN

451 EKFRHAQNGK ISIALQADWI EPACPFSQKD KEVAERVLEF DIGWLAEPIF

501 GSGDYPWVMR DWLNQRNNFL LPYFTEDEKK LIQGTFDFLA LSHYTTILVD

551 SEKEDPIKYN DYLEVQEMTD ITWLNSPSQV AVVPWGLRKV LNWLKFKYGD

601 LPMYIISNGI DDGLHAEDDQ LRVYYMQNYI NEALKAHILD GINLCGYFAY

651 SFNDRTAPRF GLYRYAADQF EPKASMKHYR KIIDSNGF*
```
FGF23 (R179Q)-(KL-D1)₂ amino acid sequence                       (SEQ ID NO: 28)
```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IQGTFPDGFL WAVGSAAYQT EGGWQQHGKG ASIWDTFTHH PLAPPGDSRN

301 ASLPLGAPSP LQPATGDVAS DSYNNVFRDT EALRELGVTH YRFSISWARV

351 LPNGSAGVPN REGLRYYRRL LERLRELGVQ PVVTLYHWDL PQRLQDAYGG

401 WANRALADHF RDYAELCFRH FGGQVKYWIT IDNPYVVAWH GYATGRLAPG

451 IRGSPRLGYL VAHNLLLAHA KVWHLYNTSF RPTQGGQVSI ALSSHWINPR

501 RMTDHSIKEC QKSLDFVLGW FAKPVFIDGD YPESMKNNLS SILPDFTESE

551 KKFIKGTADF FALCFGPTLS FQLLDPHMKF RQLESPNLRQ LLSWIDLEFN

601 HPQIFIVENG WFVSGTTKRD DAKYMYYLKK FIMETLKAIK LDGVDVIGYT

651 AWSLMDGFEW HRGYSIRRGL FYVDFLSQDK MLLPKSSALF YQKLIEKNGF

701 QGTFPDGFLW AVGSAAYQTE GGWQQHGKGA SIWDTFTHHP LAPPGDSRNA

751 SLPLGAPSPL QPATGDVASD SYNNVFRDTE ALRELGVTHY RFSISWARVL

801 PNGSAGVPNR EGLRYYRRLL ERLRELGVQP VVTLYHWDLP QRLQDAYGGW

851 ANRALADHFR DYAELCFRHF GGQVKYWITI DNPYVVAWHG YATGRLAPGI

901 RGSPRLGYLV AHNLLLAHAK VWHLYNTSFR PTQGGQVSIA LSSHWINPRR

951 MTDHSIKECQ KSLDFVLGWF AKPVFIDGDY PESMKNNLSS ILPDFTESEK

1001 KFIKGTADFF ALCFGPTLSF QLLDPHMKFR QLESPNLRQL LSWIDLEFNH

1051 PQIFIVENGW FVSGTTKRDD AKYMYYLKKF IMETLKAIKL DGVDVIGYTA

1101 WSLMDGFEWH RGYSIRRGLF YVDFLSQDKM LLPKSSALFY QKLIEKNGF*
```
FGF23 (R179Q) -(KL-D2)₂ amino acid sequence                      (SEQ ID NO: 29)
```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGTFPCDFAW GVVDNYIQVD TTLSQFTDLN VYLWDVHHSK RLIKVDGVVT

301 KKRKSYCVDF AAIQPQIALL QEMHVTHFRF SLDWALILPL GNQSQVNHTI

351 LQYYRCMASE LVRVNITPVV ALWQPMAPNQ GLPRLLARQG AWENPYTALA

401 FAEYARLCFQ ELGHHVKLWI TMNEPYTRNM TYSAGHNLLK AHALAWHVYN
```

-continued

```
 451 EKFRHAQNGK ISIALQADWI EPACPFSQKD KEVAERVLEF DIGWLAEPIF

501 GSGDYPWVMR DWLNQRNNFL LPYFTEDEKK LIQGTFDFLA LSHYTTILVD

551 SEKEDPIKYN DYLEVQEMTD ITWLNSPSQV AVVPWGLRKV LNWLKFKYGD

601 LPMYIISNGI DDGLHAEDDQ LRVYYMQNYI NEALKAHILD GINLCGYFAY

651 SFNDRTAPRF GLYRYAADQF EPKASMKHYR KIIDSNGFGT FPCDFAWGVV

701 DNYIQVDTTL SQFTDLNVYL WDVHHSKRLI KVDGVVTKKR KSYCVDFAAI

751 QPQIALLQEM HVTHFRFSLD WALILPLGNQ SQVNHTILQY YRCMASELVR

801 VNITPVVALW QPMAPNQGLP RLLARQGAWE NPYTALAFAE YARLCFQELG

851 HHVKLWITMN EPYTRNMTYS AGHNLLKAHA LAWHVYNEKF RHAQNGKISI

901 ALQADWIEPA CPFSQKDKEV AERVLEFDIG WLAEPIFGSG DYPWVMRDWL

951 NQRNNFLLPY FTEDEKKLIQ GTFDFLALSH YTTILVDSEK EDPIKYNDYL

1001 EVQEMTDITW LNSPSQVAVV PWGLRKVLNW LKFKYGDLPM YIISNGIDDG

1051 LHAEDDQLRV YYMQNYINEA LKAHILDGIN LCGYFAYSFN DRTAPRFGLY

1101 RYAADQFEPK ASMKHYRKII DSNGF*
```

FGF19 nucleic acid sequence (NM_005117)
Protein coding region (464-1114)
(SEQ ID NO: 30)

```
   1 gctcccagcc aagaacctcg ggccgctgc gcggtgggga ggagttcccc gaaacccggc 61 cgctaagcga ggcctcctcc tcccgcagat ccgaacggcc tgggcggggt caccccggct 121 gggacaagaa gccgccgcct gcctgcccgg gccggggag ggggctgggg ctggggccgg 181 aggcggggtg tgagtgggtg tgtgcggggg cggaggctt gatgcaatcc cgataagaaa 241 tgctcgggtc tcttgggcac ctacccgtgg ggcccgtaag gcgctactat ataaggctgc 301 cggcccggag ccgccgcgcc gtcagagcag gagcgctgcg tccaggatct agggccacga 361 ccatcccaac ccggcactca cagccccgca gcgcatcccg gtcgccgccc agcctcccgc 421 accccccatcg ccggagctgc gccgagagcc cagggaggt gccatgcgga gcgggtgtgt 481 ggtggtccac gtatggatcc tggccggcct ctggctggcc gtggccgggc gccccctcgc 541 cttctcggac gcggggcccc acgtgcacta cggctggggc gacccatcc gcctgcggca 601 cctgtacacc tccggccccc acgggctctc cagctgcttc ctgcgcatcc gtgccgacgg 661 cgtcgtggac tgcgcgcggg gccagagcgc gcacagtttg ctggagatca aggcagtcgc 721 tctgcggacc gtggccatca agggcgtgca cagcgtgcgg tacctctgca tgggcgccga 781 cggcaagatg cagggctgc ttcagtactc ggaggaagac tgtgctttcg aggaggagat 841 ccgcccagat ggctacaatg tgtaccgatc cgagaagcac cgcctcccgg tctccctgag 901 cagtgccaaa cagcggcagc tgtacaagaa cagaggcttt cttccactct ctcatttcct 961 gcccatgctg cccatggtcc cagaggagcc tgaggacctc aggggccact ggaatctga 1021 catgttctct tcgcccctgg agaccgacag catggacccca tttgggcttg tcaccggact 1081 ggaggccgtg aggagtccca gctttgagaa gtaactgaga ccatgcccgg gcctcttcac 1141 tgctgccagg ggctgtggta cctgcagcgt ggggacgtg cttctacaag aacagtcctg 1201 agtccacgtt ctgtttagct ttaggaagaa acatctagaa gttgtacata ttcagagttt 1261 tccattggca gtgccagttt ctagccaata gacttgtctg atcataacat tgtaagcctg 1321 tagcttgccc agctgctgcc tgggccccca ttctgctccc tcgaggttgc tggacaagct 1381 gctgcactgt ctcagttctg cttgaatacc tccatcgatg gggaactcac ttcctttgga 1441 aaaattctta tgtcaagctg aaattctcta atttttctc atcacttccc caggagcagc
```

```
1501 cagaagacag gcagtagttt taatttcagg aacaggtgat ccactctgta aaacagcagg 1561 taaatttcac tcaaccccat gtgggaattg atctatatct ctacttccag ggaccatttg 1621 cccttcccaa atccctccag gccagaactg actggagcag gcatggccca ccaggcttca 1681 ggagtagggg aagcctggag ccccactcca gccctgggac aacttgagaa ttccccctga 1741 ggccagttct gtcatggatg ctgtcctgag aataacttgc tgtcccggtg tcacctgctt 1801 ccatctccca gcccaccagc cctctgccca cctcacatgc ctccccatgg attggggcct 1861 cccaggcccc ccaccttatg tcaacctgca cttcttgttc aaaaatcagg aaaagaaaag 1921 atttgaagac cccaagtctt gtcaataact tgctgtgtgg aagcagcggg ggaagaccta 1981 gaaccctttc cccagcactt ggttttccaa catgatattt atgagtaatt tatttgata 2041 tgtacatctc ttattttctt acattattta tgcccccaaa ttatatttat gtatgtaagt 2101 gaggtttgtt ttgtatatta aaatggagtt tgtttgtaaa aaaaaaaaaa aaaaaaa
```

FGF19 amino acid sequence (NP_005108)

(SEQ ID NO: 31)

```
  1 MRSGCVVVHV WILAGLWLAV AGRPLAFSDA GPHVHYGWGD PIRLRHLYTS GPHGLSSCFL

61 RIRADGVVDC ARGQSAHSLL EIKAVALRTV AIKGVHSVRY LCMGADGKMQ GLLQYSEEDC

121 AFEEEIRPDG YNVYRSEKHR LPVSLSSAKQ RQLYKNRGFL PLSHFLPMLP MVPEEPEDLR

181 GHLESDMFSS PLETDSMDPF GLVTGLEAVR SPSFEK
```

FGF21 nucleic acid sequence (NM_019113)
Protein coding region 151-780

(SEQ ID NO: 32)

```
  1 CTGTCAGCTG AGGATCCAGC CGAAAGAGGA GCCAGGCACT CAGGCCACCTG AGTCTACTC

61 ACCTGGACAA CTGGAATCTG GCACCAATTC TAAACCACTC AGCTTCTCCGA GCTCACACC

121 CCGGAGATCA CCTGAGGACC CGAGCCATTG ATGGACTCGG ACGAGACCGGG TTCGAGCAC

181 TCAGGACTGT GGGTTTCTGT GCTGGCTGGT CTTCTGCTGG GAGCCTGCCAG GCACACCCC

241 ATCCCTGACT CCAGTCCTCT CCTGCAATTC GGGGGCCAAG TCCGGCAGCGG TACCTCTAC

301 ACAGATGATG CCCAGCAGAC AGAAGCCCAC CTGGAGATCA GGGAGGATGG GACGGTGGGG

361 GGCGCTGCTG ACCAGAGCCC CGAAAGTCTC CTGCAGCTGA AAGCCTTGAAG CCGGGAGTT

421 ATTCAAATCT TGGGAGTCAA GACATCCAGG TTCCTGTGCC AGCGGCCAGAT GGGGCCCTG

481 TATGGATCGC TCCACTTTGA CCCTGAGGCC TGCAGCTTCC GGGAGCTGCTT CTTGAGGAC

541 GGATACAATG TTTACCAGTC CGAAGCCCAC GGCCTCCCGC TGCACCTGCCA GGGAACAAG

601 TCCCCACACC GGGACCCTGC ACCCCGAGGA CCAGCTCGCT TCCTGCCACTA CCAGGCCTG

661 CCCCCCGCAC TCCCGGAGCC ACCCGGAATC CTGGCCCCCC AGCCCCCCGAT GTGGGCTCC

721 TCGGACCCTC TGAGCATGGT GGGACCTTCC CAGGGCCGAA GCCCCAGCTAC GCTTCCTGA

781 AGCCAGAGGC TGTTTACTAT GACATCTCCT CTTTATTTAT TAGGTTATTTA TCTTATTTA

841 TTTTTTTATT TTTCTTACTT GAGATAATAA AGAGTTCCAG AGGAGAAAAA AAAAAAAA

901 AAAAAAAAA AAAAAAAAA AAAAAAAAA AAAAAAAA
```

FGF21 amino acid sequence (NP_061986)

(SEQ ID NO: 33)

```
  1 MDSDETGFEH SGLWVSVLAG LLLGACQAHP IPDSSPLLQF GGQVRQRYLYTDDAQQTEAH

61 LEIREDGTVG GAADQSPESL LQLKALKPGV IQILGVKTSR FLCQRPDGALYGSLHFDPEA

121 CSFRELLLED GYNVYQSEAH GLPLHLPGNK SPHRDPAPRG PARFLPLPGLPPALPEPPGI

181 LAPQPPDVGS SDPLSMVGPS QGRSPSYAS
```

FGF23 nucleic acid sequence (NM_020638)
Protein coding region 147-902

(SEQ ID NO: 34)

```
   1 cggcaaaaag gagggaatcc agtctaggat cctcacacca gctacttgca agggagaagg
  61 aaaaggccag taaggcctgg gccaggagag tcccgacagg agtgtcaggt ttcaatctca
 121 gcaccagcca ctcagagcag ggcacgatgt tgggggcccg cctcaggctc tgggtctgtg
 181 ccttgtgcag cgtctgcagc atgagcgtcc tcagagccta tcccaatgcc tccccactgc
 241 tcggtccag ctggggtggc ctgatccacc tgtacacagc cacagccagg aacagctacc
 301 acctgcagat ccacaagaat ggccatgtgg atggcgcacc ccatcagacc atctacagtg
 361 ccctgatgat cagatcagag gatgctggct tgtggtgat acaggtgtg atgagcagaa
 421 gataccctg catggatttc agaggcaaca ttttttggatc acactatttc gacccggaga
 481 actgcaggtt ccaacaccag acgctggaaa acgggtacga cgtctaccac tctcctcagt
 541 atcacttcct ggtcagtctg ggccgggcga agagagcctt cctgccaggc atgaacccac
 601 ccccgtactc ccagttcctg tcccggagga acgagatccc cctaattcac ttcaacaccc
 661 ccatacccacg gcggcacacc cggagcgccg aggacgactc ggagcgggac cccctgaacg
 721 tgctgaagcc ccgggccccgg atgacccccgg ccccggcctc ctgttcacag gagctcccga
 781 gcgccgagga caacagcccg atggccagtg acccattagg ggtggtcagg ggcggtcgag
 841 tgaacacgac cgctggggga acgggcccgg aaggctgccg ccccttcgcc aagttcatct
 901 agggtcgctg gaagggcacc ctctttaacc catccctcag caaacgcagc tcttcccaag
 961 gaccaggtcc cttgacgttc cgaggatggg aaaggtgaca gggcatgta tggaatttgc
1021 tgcttctctg gggtcccttc acaggaggt cctgtgagaa ccaacctttg aggcccaagt
1081 catgggtttt caccgccttc ctcactccat atagaacacc tttcccaata ggaaaccccca
1141 acaggtaaac tagaaatttc cccttcatga aggtagagag aaggggtctc tcccaacata
1201 tttctcttcc ttgtgcctct cctctttatc acttttaagc ataaaaaaaa aaaaaaaaaa
1261 aaaaaaaaaa aaaagcagtg ggttcctgag ctcaagactt tgaaggtgta gggaagagga
1321 aatcggagat cccagaagct tctccactgc cctatgcatt tatgttagat gccccgatcc
1381 cactggcatt tgagtgtgca aaccttgaca ttaacagctg aatggggcaa gttgatgaaa
1441 acactacttt caagccttcg ttcttccttg agcatctctg gggaagagct gtcaaaagac
1501 tggtggtagg ctggtgaaaa cttgacagct agacttgatg cttgctgaaa tgaggcagga
1561 atcataatag aaaactcagc ctccctacag ggtgagcacc ttctgtctcg ctgtctccct
1621 ctgtgcagcc acagccagag ggcccagaat ggccccactc tgttcccaag cagttcatga
1681 tacagcctca cctttttggcc ccatctctgg ttttttgaaaa tttggtctaa ggaataaata
1741 gcttttacac tggctcacga aaatctgccc tgctagaatt tgcttttcaa aatgaaaata
1801 aattccaact ctcctaagag gcatttaatt aaggctctac ttccaggttg agtaggaatc
1861 cattctgaac aaactacaaa aatgtgactg ggaagggggc tttgagagac tgggactgct
1921 ctgggttagg ttttctgtgg actgaaaaat cgtgtccttt tctctaaatg aagtggcatc
1981 aaggactcag ggggaaagaa atcaggggac atgttataga agttatgaaa agacaaccac
2041 atggtcaggc tcttgtctgt ggtctctagg gctctgcagc agcagtggct cttcgattag
2101 ttaaaactct cctaggctga cacatctggg tctcaatccc cttggaaatt cttggtgcat
2161 taaatgaagc cttaccccat tactgcggtt cttcctgtaa gggggctcca ttttcctccc
2221 tctctttaaa tgaccaccta aaggacagta tattaacaag caaagtcgat tcaacaacag
2281 cttcttccca gtcactttt ttttttctcac tgccatcaca tactaacctt atactttgat
```

-continued

```
2341 ctattctttt tggttatgag agaaatgttg ggcaactgtt tttacctgat ggttttaagc 2401 tgaacttgaa ggactggttc ctattctgaa acagtaaaac tatgtataat agtatatagc 2461 catgcatggc aaatatttta atatttctgt tttcatttcc tgttggaaat attatcctgc 2521 ataatagcta ttggaggctc ctcagtgaaa gatcccaaaa ggattttggt ggaaaactag 2581 ttgtaatctc acaaactcaa cactaccatc aggggttttc tttatggcaa agccaaaata 2641 gctcctacaa tttcttatat ccctcgtcat gtggcagtat ttatttattt atttggaagt 2701 ttgcctatcc ttctatattt atagatattt ataaaaatgt aaccccttttt tcctttcttc 2761 tgtttaaaat aaaaataaaa tttatctcag cttctgttag cttatcctct ttgtagtact 2821 acttaaaagc atgtcggaat ataagaataa aaaggattat gggagggaa cattagggaa 2881 atccagagaa ggcaaaattg aaaaaaagat tttagaattt taaaattttc aaagatttct 2941 tccattcata aggagactca atgattttaa ttgatctaga cagaattatt taagttttat 3001 caatattgga tttctggt
```

FGF23 amino acid sequence (NP_065689)
(SEQ ID NO: 35)
```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

FGF23 (R179Q) amino acid sequence
(SEQ ID NO: 36)
```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTQS

181 AEDDSERDPL NVLKPRARMT PAPASCSQEL PSAEDNSPMA SDPLGVVRGG RVNTHAGGTG

241 PEGCRPFAKF I
```

Human beta-Klotho domain 1 (b-KL-D1) amino acid sequence
(SEQ ID NO: 37)
```
 77                 ydt fpknffwgig tgalqvegsw kkdgkgpsiw dhfihthlkn 121 vsstngssds yiflekdlsa ldfigvsfyq fsiswprlfp dgivtvanak glqyystlld 181 alvlrniepi vtlyhwdlpl alqekyggwk ndtiidifnd yatycfqmfg drvkywitih 241 npylvawhgy gtgmhapgek gnlaavytvg hnlikahskv whnynthfrp hqkgwlsitl 301 gshwiepnrs entmdifkcq qsmvsvlgwf anpihgdgdy pegmrkklfs vlpifseaek 361 hemrgtadff afsfgpnnfk plntmakmgq nvslnlreal nwikleynnp riliaengwf 421 tdsrvktedt taiymmknfl sqvlqairld eirvfgytaw slldgfewqd aytirrglfy 481 vdfnskqker kpkssahyyk qiirengf
```

Human beta-Klotho domain 2 (b-KL-D2) amino acid sequence
(SEQ ID NO: 38)
```
571                       trpaqctdfv nikkqlemla rmkvthyrfa 601 ldwasvlptg nlsavnrqal ryyrcvvseg lklgisamvt lyypthahlg lpepllhadg 661 wlnpstaeaf qayaglcfqe lgdlvklwit inepnrlsdi ynrsgndtyg aahnllvaha 721 lawrlydrqf rpsqrgavsl slhadwaepa npyadshwra aerflqfela wfaeplfktg 781 dypaamreyi askhrrglss salprlteae rrllkgtvdf calnhfttrf vmheqlagsr 841 ydsdrdiqfl qditrlsspt rlavipwgvr kllrwvrrny gdmdiyitas giddqaledd
```

-continued
```
901 rlrkyylgky lqevlkayli dkvrikgyya fklaeekskp rfgffsdfk akssiqfynk 961 vissrgf
```

Beta-Klotho extracellular domain (without signal peptide) amino acid sequence
(SEQ ID NO: 39)
```
 52                                                            gfsgdgrai 61 wsknpnftpv nesqlflydt fpknffwgig tgalqvegsw kkdgkgpsiw dhfihthlkn 121 vsstngssds yifleklkdlsa ldfigvsfyq fsiswprlfp dgivtvanak glqyystlld 181 alvlrniepi vtlyhwdlpl alqekyggwk ndtiidifnd yatycfqmfg drvkywitih 241 npylvawhgy gtgmhapgek gnlaavytvg hnlikahskv whnynthfrp hqkgwlsitl 301 gshwiepnrs entmdifkcq qsmvsvlgwf anpihgdgdy pegmrkklfs vlpifseaek 361 hemrgtadff afsfgpnnfk plntmakmgq nvslnlreal nwikleynnp riliaengwf 421 tdsrvktedt taiymmknfl sqvlgairld eirvfgytaw slldgfewqd aytirrglfy 481 vdfnskqker kpkssahyyk qiirengfsl kestpdvqgq fpcdfswgvt esvlkpesva 541 sspqfsdphl yvwnatgnrl lhrvegvrlk trpaqctdfv nikkqlemla rmkvthyrfa 601 ldwasvlptg nlsavnrqal ryyrcvvseg lklgisamvt lyypthahlg lpeplihadg 661 wlnpstaeaf qayaglcfqe lgdlvklwit inepnrlsdi ynrsgndtyg aahnllvaha 721 lawrlydrqf rpsqrgavsl slhadwaepa npyadshwra aerflqfeia wfaeplfktg 781 dypaamreyi askhrrglss salprlteae rrllkgtvdf calnhfttrf vmheqlagsr 841 ydsdrdiqfl qditrlsspt rlavipwgvr kllrwvrrny gdmdiyitas giddqaledd 901 rlrkyylgky lqevlkayli dkvrikgyya fklaeekskp rfgffsdfk akssiqfynk 961 vissrgfpfe nsssrcsqtq entectvclf lvqkkpl
``` sKlotho without signal peptide - FGF23 amino acid sequence (without signal peptide)
(SEQ ID NO: 40)
```
                                         EPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS
```

```
 951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTRSAED DSERDPLNVL KPRARMTPAP ASCSQELPSA EDNSPMASDP

1201 LGVVRGGRVN THAGGTGPEG CRPFAKFI*
``` sKlotho without signal peptide-FGF23 (R179Q) (without signal peptide) amino acid sequence (SEQ ID NO: 41)

```
     EPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTQSAED DSERDPLNVL KPRARMTPAP ASCSQELPSA EDNSPMASDP

1201 LGVVRGGRVN THAGGTGPEG CRPFAKFI*
```

FGF23 without signal peptide (SEQ ID NO: 42)

```
                YPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

-continued

FGF23(R179Q) without signal peptide (SEQ ID NO: 43)

```
                        YPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
121 ENGYDVYHSP QYHFLVSLGR AKRAFLPGMN PPPYSQFLSR RNEIPLIHFN TPIPRRHTQS
181 AEDDSERDPL NVLKPRARMT PAPASCSQEL PSAEDNSPMA SDPLGVVRGG RVNTHAGGTG
241 PEGCRPFAKF I
``` sKlotho with Klotho signal peptide (SEQ ID NO: 44)

```
  1 MPASAPPRRP RPPPPSLSLL LVLLGLGGRR LRAEPGDGAQ TWARFSRPPA
 51 PEAAGLFQGT FPDGFLWAVG SAAYQTEGGW QQHGKGASIW DTFTHHPLAP
101 PGDSRNASLP LGAPSPLQPA TGDVASDSYN NVFRDTEALR ELGVTHYRFS
151 ISWARVLPNG SAGVPNREGL RYYRRLLERL RELGVQPVVT LYHWDLPQRL
201 QDAYGGWANR ALADHFRDYA ELCFRHFGGQ VKYWITIDNP YVVAWHGYAT
251 GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP
351 DFTESEKKFI KGTADFFALC FGPTLSFQLL DPHMKFRQLE SPNLRQLLSW
401 IDLEFNHPQI FIVENGWFVS GTTKRDDAKY MYYLKKFIME TLKAIKLDGV
451 DVIGYTAWSL MDGFEWHRGY SIRRGLFYVD FLSQDKMLLP KSSALFYQKL
501 IEKNGFPPLP ENQPLEGTFP CDFAWGVVDN YIQVDTTLSQ FTDLNVYLWD
551 VHHSKRLIKV DGVVTKKRKS YCVDFAAIQP QIALLQEMHV THFRFSLDWA
601 LILPLGNQSQ VNHTILQYYR CMASELVRVN ITPVVALWQP MAPNQGLPRL
651 LARQGAWENP YTALAFAEYA RLCFQELGHH VKLWITMNEP YTRNMTYSAG
701 HNLLKAHALA WHVYNEKFRH AQNGKISIAL QADWIEPACP FSQKDKEVAE
751 RVLEFDIGWL AEPIFGSGDY PWVMRDWLNQ RNNFLLPYFT EDEKKLIQGT
801 FDFLALSHYT TILVDSEKED PIKYNDYLEV QEMTDITWLN SPSQVAVVPW
851 GLRKVLNWLK FKYGDLPMYI ISNGIDDGLH AEDDQLRVYY MQNYINEALK
901 AHILDGINLC GYFAYSFNDR TAPRFGLYRY AADQFEPKAS MKHYRKIIDS
951 NGFPGPETLE RFCPEEFTVC TECSFFHTRK SL
``` sKlotho with IgG Signal peptide (SEQ ID NO: 45)

```
  1 MSVLTQVLAL LLLWLTGLGG RRLRAEPGDG AQTWARFSRP PAPEAAGLFQ
 51 GTFPDGFLWA VGSAAYQTEG GWQQHGKGAS IWDTFTHHPL APPGDSRNAS
101 LPLGAPSPLQ PATGDVASDS YNNVFRDTEA LRELGVTHYR FSISWARVLP
151 NGSAGVPNRE GLRYYRRLLE RLRELGVQPV VTLYHWDLPQ RLQDAYGGWA
201 NRALADHFRD YAELCFRHFG GQVKYWITID NPYVVAWHGY ATGRLAPGIR
251 GSPRLGYLVA HNLLLAHAKV WHLYNTSFRP TQGGQVSIAL SSHWINPRRM
301 TDHSIKECQK SLDFVLGWFA KPVFIDGDYP ESMKNNLSSI LPDFTESEKK
351 FIKGTADFFA LCFGPTLSFQ LLDPHMKFRQ LESPNLRQLL SWIDLEFNHP
401 QIFIVENGWF VSGTTKRDDA KYMYYLKKFI METLKAIKLD GVDVIGYTAW
451 SLMDGFEWHR GYSIRRGLFY VDFLSQDKML LPKSSALFYQ KLIEKNGFPP
501 LPENQPLEGT FPCDFAWGVV DNYIQVDTTL SQFTDLNVYL WDVHHSKRLI
551 KVDGVVTKKR KSYCVDFAAI QPQIALLQEM HVTHFRFSLD WALILPLGNQ
```

```
601 SQVNHTILQY YRCMASELVR VNITPVVALW QPMAPNQGLP RLLARQGAWE

651 NPYTALAFAE YARLCFQELG HHVKLWITMN EPYTRNMTYS AGHNLLKAHA

701 LAWHVYNEKF RHAQNGKISI ALQADWIEPA CPFSQKDKEV AERVLEFDIG

751 WLAEPIFGSG DYPWVMRDWL NQRNNFLLPY FTEDEKKLIQ GTFDFLALSH

801 YTTILVDSEK EDPIKYNDYL EVQEMTDITW LNSPSQVAVV PWGLRKVLNW

851 LKFKYGDLPM YIISNGIDDG LHAEDDQLRV YYMQNYINEA LKAHILDGIN

901 LCGYFAYSFN DRTAPRFGLY RYAADQFEPK ASMKHYRKII DSNGFPGPET

951 LERFCPEEFT VCTECSFFHT RKSL*
``` sKlotho-FGF23-FcLALA v1

(SEQ ID NO: 46)
```
   1 ATGCCCGCCA GCGCCCCGCC GCGCCGCCCG CGGCCGCCGC CGCCGTCGCT GTCGCTGCTG

61 CTGGTGCTGC TGGGCCTGGG CGGCCGCCGC CTGCGTGCGG AGCCGGGCGA CGGCGCGCAG

121 ACCTGGGCCC GTTTCTCGCG GCCTCCTGCC CCCGAGGCCG CGGGCCTCTT CCAGGGCACC

181 TTCCCCGACG GCTTCCTCTG GGCCGTGGGC AGCGCCGCCT ACCAGACCGA GGGCGGCTGG

241 CAGCAGCACG GCAAGGGTGC GTCCATCTGG GATACGTTCA CCCACCACCC CCTGGCACCC

301 CCGGGAGACT CCCGGAACGC CAGTCTGCCG TTGGGCGCCC CGTCGCCGCT GCAGCCCGCC

361 ACCGGGGACG TAGCCAGCGA CAGCTACAAC AACGTCTTCC GCGACACGGA GGCGCTGCGC

421 GAGCTCGGGG TCACTCACTA CCGCTTCTCC ATCTCGTGGG CGCGAGTGCT CCCCAATGGC

481 AGCGCGGGCG TCCCCAACCG CGAGGGGCTG CGCTACTACC GGCGCCTGCT GGAGCGGCTG

541 CGGGAGCTGG GCGTGCAGCC CGTGGTCACC CTGTACCACT GGGACCTGCC CCAGCGCCTG

601 CAGGACGCCT ACGGCGGCTG GGCCAACCGC GCCCTGGCCG ACCACTTCAG GGATTACGCG

661 GAGCTCTGCT TCCGCCACTT CGGCGGTCAG GTCAAGTACT GGATCACCAT CGACAACCCC

721 TACGTGGTGG CCTGGCACGG CTACGCCACC GGGCGCCTGG CCCCCGGCAT CCGGGGCAGC

781 CCGCGGCTCG GGTACCTGGT GGCGCACAAC CTCCTCCTGG CTCATGCCAA AGTCTGGCAT

841 CTCTACAATA CTTCTTTCCG TCCCACTCAG GGAGGTCAGG TGTCCATTGC CCTAAGCTCT

901 CACTGGATCA ATCCTCGAAG AATGACCGAC CACAGCATCA AAGAATGTCA AAAATCTCTG

961 GACTTTGTAC TAGGTTGGTT TGCCAAACCC GTATTTATTG ATGGTGACTA TCCCGAGAGC

1021 ATGAAGAATA ACCTTTCATC TATTCTGCCT GATTTTACTG AATCTGAGAA AAGTTCATC

1081 AAAGGAACTG CTGACTTTTT TGCTCTTTGC TTTGGACCCA CCTTGAGTTT CAACTTTTG

1141 GACCCTCACA TGAAGTTCCG CCAATTGGAA TCTCCCAACC TGAGGCAACT GCTTTCCTGG

1201 ATTGACTTG AATTTAACCA TCCTCAAATA TTTATTGTGG AAAATGGCTG GTTTGTCTCA

1261 GGGACCACCA AGAGAGATGA TGCCAAATAT ATGTATTACC TCAAAAAGTT CATCATGGAA

1321 ACCTTAAAAG CCATCAAGCT GGATGGGGTG GATGTCATCG GTATACCGC ATGGTCCCTC

1381 ATGGATGGTT TCGAGTGGCA CAGAGGTTAC AGCATCAGGC GTGGACTCTT CTATGTTGAC

1441 TTTCTAAGCC AGGACAAGAT GTTGTTGCCA AAGTCTTCAG CCTGTTCTA CCAAAAGCTG

1501 ATAGAGAAAA ATGGCTTCCC TCCTTTACCT GAAAATCAGC CCCTAGAAGG ACATTTCCC

1561 TGTGACTTTG CTTGGGGAGT TGTTGACAAC TACATTCAAG TAGATACCAC TCTGTCTCAG

1621 TTTACCGACC TGAATGTTTA CCTGTGGGAT GTCCACCACA GTAAAAGGCT TATTAAAGTG

1681 GATGGGGTTG TGACCAAGAA GAGGAAATCC TACTGTGTTG ACTTTGCTGC CATCCAGCCC

1741 CAGATCGCTT TACTCCAGGA AATGCACGTT ACACATTTTC GCTTCTCCCT GGACTGGGCC

1801 CTGATTCTCC CTCTGGGTAA CCAGTCCCAG GTGAACCACA CCATCCTGCA GTACTATCGC

1861 TGCATGGCCA GCGAGCTTGT CCGTGTCAAC ATCACCCCAG TGGTGGCCCT GTGGCAGCCT
```

```
-continued
1921 ATGGCCCCGA ACCAAGGACT GCCGCGCCTC CTGGCCAGGC AGGGCGCCTG GGAGAACCCC
1981 TACACTGCCC TGGCCTTTGC AGAGTATGCC CGACTGTGCT TTCAAGAGCT CGGCCATCAC
2041 GTCAAGCTTT GGATAACGAT GAATGAGCCG TATACAAGGA ATATGACATA CAGTGCTGGC
2101 CACAACCTTC TGAAGGCCCA TGCCCTGGCT TGGCATGTGT ACAATGAAAA GTTTAGGCAT
2161 GCTCAGAATG GGAAAATATC CATAGCCTTG CAGGCTGATT GGATAGAACC TGCCTGCCCT
2221 TTCTCCCAAA AGGACAAAGA GGTGGCCGAG AGAGTTTTGG AATTTGACAT TGGCTGGCTG
2281 GCTGAGCCCA TTTTCGGCTC TGGAGATTAT CCATGGGTGA TGAGGGACTG GCTGAACCAA
2341 AGAAACAATT TTCTTCTTCC TTATTTCACT GAAGATGAAA AAAAGCTAAT CCAGGGTACC
2401 TTTGACTTTT TGGCTTTAAG CCATTATACC ACCATCCTTG TAGACTCAGA AAAGAAGAT
2461 CCAATAAAAT ACAATGATTA CCTAGAAGTG CAAGAAATGA CCGACATCAC GTGGCTCAAC
2521 TCCCCCAGTC AGGTGGCGGT AGTGCCCTGG GGGTTGCGCA AAGTGCTGAA CTGGCTGAAG
2581 TTCAAGTACG GAGACCTCCC CATGTACATA ATATCCAACG GAATCGATGA CGGGCTGCAT
2641 GCTGAGGACG ACCAGCTGAG GGTGTATTAT ATGCAGAATT ACATAAACGA AGCTCTCAAA
2701 GCCCACATAC TGGATGGTAT CAATCTTTGC GGATACTTTG CTTATTCGTT TAACGACCGC
2761 ACAGCTCCGA GGTTTGGCCT CTATCGTTAT GCTGCAGATC AGTTTGAGCC CAAGGCATCC
2821 ATGAAACATT ACAGGAAAAT TATTGACAGC AATGGTTTCC CGGGCCCAGA AACTCTGGAA
2881 AGATTTTGTC CAGAAGAATT CACCGTGTGT ACTGAGTGCA GTTTTTTCA CACCCGAAAG
2941 TCTTTAGGAT CCGGAGGTGG AGGTTCAGGA GGTGGAGGTT CAGGAGGTGG AGGTTCACTT
3001 AAGTATCCCA ATGCCTCCCC ACTGCTCGGC TCCAGCTGGG GTGGCCTGAT CCACCTGTAC
3061 ACAGCCACAG CCAGGAACAG CTACCACCTG CAGATCCACA AGAATGGCCA TGTGGATGGC
3121 GCACCCCATC AGACCATCTA CAGTGCCCTG ATGATCAGAT CAGAGGATGC TGGCTTTGTG
3181 GTGATTACAG GTGTGATGAG CAGAAGATAC CTCTGCATGG ATTTCAGAGG CAACATTTTT
3241 GGATCACACT ATTTCGACCC GGAGAACTGC AGGTTCCAAC ACCAGACGCT GGAAAACGGG
3301 TACGACGTCT ACCACTCTCC TCAGTATCAC TTCCTGGTCA GTCTGGGCCG GGCGAAGAGA
3361 GCCTTCCTGC CAGGCATGAA CCCACCCCCG TACTCCCAGT CCTGTCCCG GAGGAACGAG
3421 ATCCCCCTAA TTCACTTCAA CACCCCCATA CCACGGCGGC ACACCCAGAG CGCCGAGGAC
3481 GACTCGGAGC GGGACCCCCT GAACGTGCTG AAGCCCCGGG CCCGGATGAC CCCGGCCCCG
3541 GCCTCCTGTT CACAGGAGCT CCCGAGCGCC GAGGACAACA GCCCGATGGC CAGTGACCCA
3601 TTAGGGGTGG TCAGGGGCGG TCGAGTGAAC ACGCACGCTG GGGAACGGG CCCGGAAGGC
3661 TGCCGCCCCT TCGCCAAGTT CATCGGAGGT GGAGGTTCAA AAACCCACAC GTGTCCTCCT
3721 TGTCCTGCCC CAGAAGCAGC AGGTGGTCCA TCAGTTTTTC TTTTCCCTCC CAAACCCAAG
3781 GATACGCTGA TGATCTCTCG CACGCCTGAG GTGACATGCG TCGTAGTAGA CGTGAGCCAC
3841 GAAGATCCCG AGGTGAAGTT CAATTGGTAT GTGGACGGAG TAGAAGTGCA TAACGCGAAA
3901 ACTAAGCCGC GCGAGGAACA ATATAACAGT ACTTACAGGG TGGTATCCGT GCTCACAGTC
3961 CTGCACCAGG ACTGGCTGAA CGGTAAGGAA TACAAGTGCA AAGTAAGCAA CAAGGCACTT
4021 CCCGCGCCTA TTGAGAAAAC AATCTCCAAG GCGAAGGGAC AACCAAGAGA ACCTCAGGTT
4081 TACACTCTCC CGCCTTCCAG GGAAGAGATG ACCAAAAATC AAGTTTCCCT GACTTGCCTC
4141 GTCAAAGGAT TCTACCCTTC CGACATTGCT GTTGAATGGG AAAGCAATGG ACAACCAGAG
4201 AACAACTACA AGACAACACC CCCGGTGCTG GATAGTGACG GATCTTTCTT TCTCTACTCA
4261 AAGCTGACCG TGGATAAGTC CAGGTGGCAG CAGGGAAACG TGTTTTCCTG CTCTGTCATG
```

-continued

4321 CATGAAGCGC TGCATAATCA CTATACCCAG AAGTCTCTGA GCTTGAGCCC AGGCAAGTAA sKlotho-FGF23-FcLALA v1

(SEQ ID NO: 47)

```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTQSAED DSERDPLNVL KPRARMTPAP ASCSQELPSA EDNSPMASDP

1201 LGVVRGGRVN THAGGTGPEG CRPFAKFIGG GGSKTHTCPP CPAPEAAGGP

1251 SVFLFPPKPK DTLMISRTPE VTCVVVDVSH EDPEVKFNWY VDGVEVHNAK

1301 TKPREEQYNS TYRVVSVLTV LHQDWLNGKE YKCKVSNKAL PAPIEKTISK

1351 AKGQPREPQV YTLPPSREEM TKNQVSLTCL VKGFYPSDIA VEWESNGQPE

1401 NNYKTTPPVL DSDGSFFLYS KLTVDKSRWQ QGNVFSCSVM HEALHNHYTQ

1451 KSLSLSPGK*
``` sKlotho-FGF23-FcLALA v2

(SEQ ID NO: 48)

```
   1 ATGCCCGCCA GCGCCCCGCC GCGCCGCCCG CGGCCGCCGC CGCCGTCGCT GTCGCTGCTG

61 CTGGTGCTGC TGGGCCTGGG CGGCCGCCGC CTGCGTGCGG AGCCGGGCGA CGGCGCGCAG

121 ACCTGGGCCC GTTTCTCGCG GCCTCCTGCC CCCGAGGCCG CGGGCCTCTT CCAGGGCACC

181 TTCCCCGACG GCTTCCTCTG GGCCGTGGGC AGCGCCGCCT ACCAGACCGA GGGCGGCTGG

241 CAGCAGCACG GCAAGGGTGC GTCCATCTGG GATACGTTCA CCCACCACCC CCTGGCACCC

301 CCGGGAGACT CCCGGAACGC CAGTCTGCCG TTGGGCGCCC CGTCGCCGCT GCAGCCCGCC

361 ACCGGGGACG TAGCCAGCGA CAGCTACAAC AACGTCTTCC GCGACACGGA GGCGCTGCGC

421 GAGCTCGGGG TCACTCACTA CCGCTTCTCC ATCTCGTGGG CGCGAGTGCT CCCCAATGGC
```

```
 481 AGCGCGGGCG TCCCCAACCG CGAGGGGCTG CGCTACTACC GGCGCCTGCT GGAGCGGCTG

541 CGGGAGCTGG GCGTGCAGCC CGTGGTCACC CTGTACCACT GGGACCTGCC CCAGCGCCTG

601 CAGGACGCCT ACGGCGGCTG GGCCAACCGC GCCCTGGCCG ACCACTTCAG GGATTACGCG

661 GAGCTCTGCT TCCGCCACTT CGGCGGTCAG GTCAAGTACT GGATCACCAT CGACAACCCC

721 TACGTGGTGG CCTGGCACGG CTACGCCACC GGGCGCCTGG CCCCCGGCAT CCGGGGCAGC

781 CCGCGGCTCG GGTACCTGGT GGCGCACAAC CTCCTCCTGG CTCATGCCAA AGTCTGGCAT

841 CTCTACAATA CTTCTTTCCG TCCCACTCAG GGAGGTCAGG TGTCCATTGC CCTAAGCTCT

901 CACTGGATCA ATCCTCGAAG AATGACCGAC CACAGCATCA AGAATGTCA AAATCTCTG

961 GACTTTGTAC TAGGTTGGTT TGCCAAACCC GTATTTATTG ATGGTGACTA TCCCGAGAGC

1021 ATGAAGAATA ACCTTTCATC TATTCTGCCT GATTTTACTG AATCTGAGAA AAGTTCATC

1081 AAAGGAACTG CTGACTTTTT TGCTCTTTGC TTTGGACCCA CCTTGAGTTT CAACTTTTG

1141 GACCCTCACA TGAAGTTCCG CCAATTGGAA TCTCCCAACC TGAGGCAACT GCTTCCTGG

1201 ATTGACCTTG AATTTAACCA TCCTCAAATA TTTATTGTGG AAAATGGCTG GTTTGTCTCA

1261 GGGACCACCA AGAGAGATGA TGCCAAATAT ATGTATTACC TCAAAAAGTT CATCATGGAA

1321 ACCTTAAAAG CCATCAAGCT GGATGGGGTG GATGTCATCG GGTATACCGC ATGGTCCCTC

1381 ATGGATGGTT TCGAGTGGCA CAGAGGTTAC AGCATCAGGC GTGGACTCTT CTATGTTGAC

1441 TTTCTAAGCC AGGACAAGAT GTTGTTGCCA AAGTCTTCAG CCTTGTTCTA CCAAAAGCTG

1501 ATAGAGAAAA ATGGCTTCCC TCCTTTACCT GAAAATCAGC CCTAGAAGG GACATTTCCC

1561 TGTGACTTTG CTTGGGGAGT TGTTGACAAC TACATTCAAG TAGATACCAC TCTGTCTCAG

1621 TTTACCGACC TGAATGTTTA CCTGTGGGAT GTCCACCACA GTAAAAGGCT TATTAAAGTG

1681 GATGGGGTTG TGACCAAGAA GAGGAAATCC TACTGTGTTG ACTTTGCTGC CATCCAGCCC

1741 CAGATCGCTT TACTCCAGGA AATGCACGTT ACACATTTTC GCTTCTCCCT GGACTGGGCC

1801 CTGATTCTCC CTCTGGGTAA CCAGTCCCAG GTGAACCACA CCATCCTGCA GTACTATCGC

1861 TGCATGGCCA GCGAGCTTGT CCGTGTCAAC ATCACCCCAG TGGTGGCCCT GTGGCAGCCT

1921 ATGGCCCCGA ACCAAGGACT GCCGCGCCTC CTGGCCAGGC AGGGCGCCTG GGAGAACCCC

1981 TACACTGCCC TGGCCTTTGC AGAGTATGCC CGACTGTGCT TTCAAGAGCT CGGCCATCAC

2041 GTCAAGCTTT GGATAACGAT GAATGAGCCG TATACAAGGA ATATGACATA CAGTGCTGGC

2101 CACAACCTTC TGAAGGCCCA TGCCCTGGCT TGGCATGTGT ACAATGAAAA GTTTAGGCAT

2161 GCTCAGAATG GGAAAATATC CATAGCCTTG CAGGCTGATT GGATAGAACC TGCCTGCCCT

2221 TTCTCCCAAA AGGACAAAGA GGTGGCCGAG AGAGTTTTGG AATTTGACAT TGGCTGGCTG

2281 GCTGAGCCCA TTTTCGGCTC TGGAGATTAT CCATGGGTGA TGAGGGACTG GCTGAACCAA

2341 AGAAACAATT TTCTTCTTCC TTATTTCACT GAAGATGAAA AAAGCTAAT CCAGGGTACC

2401 TTTGACTTTT TGGCTTTAAG CCATTATACC ACCATCCTTG TAGACTCAGA AAAGAAGAT

2461 CCAATAAAAT ACAATGATTA CCTAGAAGTG CAAGAAATGA CCGACATCAC GTGGCTCAAC

2521 TCCCCCAGTC AGGTGGCGGT AGTGCCCTGG GGGTTGCGCA AAGTGCTGAA CTGGCTGAAG

2581 TTCAAGTACG GAGACCTCCC CATGTACATA ATATCCAACG GAATCGATGA CGGGCTGCAT

2641 GCTGAGGACG ACCAGCTGAG GGTGTATTAT ATGCAGAATT ACATAAACGA AGCTCTCAAA

2701 GCCCACATAC TGGATGGTAT CAATCTTTGC GGATACTTTG CTTATTCGTT TAACGACCGC

2761 ACAGCTCCGA GGTTTGGCCT CTATCGTTAT GCTGCAGATC AGTTTGAGCC CAAGGCATCC

2821 ATGAAACATT ACAGGAAAAT TATTGACAGC AATGGTTTCC CGGGCCCAGA AACTCTGGAA
```

-continued

```
2881 AGATTTTGTC CAGAAGAATT CACCGTGTGT ACTGAGTGCA GTTTTTTTCA CACCCGAAAG

2941 TCTTTAGGAT CCGGAGGTGG AGGTTCAGGA GGTGGAGGTT CAGGAGGTGG AGGTTCACTT

3001 AAGTATCCCA ATGCCTCCCC ACTGCTCGGC TCCAGCTGGG GTGGCCTGAT CCACCTGTAC

3061 ACAGCCACAG CCAGGAACAG CTACCACCTG CAGATCCACA AGAATGGCCA TGTGGATGGC

3121 GCACCCCATC AGACCATCTA CAGTGCCCTG ATGATCAGAT CAGAGGATGC TGGCTTTGTG

3181 GTGATTACAG TGTGTGATGAG CAGAAGATAC CTCTGCATGG ATTTCAGAGG CAACATTTTT

3241 GGATCACACT ATTTCGACCC GGAGAACTGC AGGTTCCAAC ACCAGACGCT GGAAAACGGG

3301 TACGACGTCT ACCACTCTCC TCAGTATCAC TTCCTGGTCA GTCTGGGCCG GGCGAAGAGA

3361 GCCTTCCTGC AGGCATGAA CCCACCCCCG TACTCCCAGT TCCTGTCCCG GAGGAACGAG

3421 ATCCCCCTAA TTCACTTCAA CACCCCCATA CCACGGCGGC ACACCCAGAG CGCCGAGGAC

3481 GACTCGGAGC GGGACCCCCT GAACGTGCTG AAGCCCCGGG CCCGGATGAC CCCGGCCCCG

3541 GCCTCCTGTT CACAGGAGCT CCCGAGCGCC GAGGACAACA GCCCGATGGC CAGTGACCCA

3601 TTAGGGGTGG TCAGGGCGG TCGAGTGAAC ACGCACGCTG GGGGAACGGG CCCGGAAGGC

3661 TGCCGCCCCT TCGCCAAGTT CATCGGAGGT GGAGGTTCAG CCCCAGAAGC AGCAGGTGGT

3721 CCATCAGTTT TTCTTTTCCC TCCCAAACCC AAGGATACGC TGATGATCTC TCGCACGCCT

3781 GAGGTGACAT GCGTCGTAGT AGACGTGAGC CACGAAGATC CCGAGGTGAA GTTCAATTGG

3841 TATGTGGACG GAGTAGAAGT GCATAACGCG AAAACTAAGC CGCGCGAGGA ACAATATAAC

3901 AGTACTTACA GGGTGGTATC CGTGCTCACA GTCCTGCACC AGGACTGGCT GAACGGTAAG

3961 GAATACAAGT GCAAAGTAAG CAACAAGGCA CTTCCCGCGC CTATTGAGAA ACAATCTCC

4021 AAGGCGAAGG GACAACCAAG AGAACCTCAG GTTTACACTC TCCCGCCTTC CAGGGAAGAG

4081 ATGACCAAAA ATCAAGTTTC CCTGACTTGC CTCGTCAAAG GATTCTACCC TTCCGACATT

4141 GCTGTTGAAT GGGAAAGCAA TGGACAACCA GAGAACAACT ACAAGACAAC ACCCCCGGTG

4201 CTGGATAGTG ACGGATCTTT CTTTCTCTAC TCAAAGCTGA CCGTGGATAA GTCCAGGTGG

4261 CAGCAGGGAA ACGTGTTTTC CTGCTCTGTC ATGCATGAAG CGCTGCATAA TCACTATACC

4321 CAGAAGTCTC TGAGCTTGAG CCCAGGCAAG TAA
``` sKlotho-FGF23-FcLALA v2  (SEQ ID NO: 49)

```
  1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE
```

-continued

```
 751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTQSAED DSERDPLNVL KPRARMTPAP ASCSQELPSA EDNSPMASDP

1201 LGVVRGGRVN THAGGTGPEG CRPFAKFIGG GGSAPEAAGG PSVFLFPPKP

1251 KDTLMISRTP EVTCVVVDVS HEDPEVKFNW YVDGVEVHNA KTKPREEQYN

1301 STYRVVSVLT VLHQDWLNGK EYKCKVSNKA LPAPIEKTIS KAKGQPREPQ

1351 VYTLPPSREE MTKNQVSLTC LVKGFYPSDI AVEWESNGQP ENNYKTTPPV

1401 LDSDGSFFLY SKLTVDKSRW QQGNVFSCSV MHEALHNHYT QKSLSLSPGK

1451 *
```

FGF23-FcLALA v1

(SEQ ID NO: 50)

```
   1 ATGTTGGGGG CCCGCCTCAG GCTCTGGGTC TGTGCCTTGT GCAGCGTCTG CAGCATGAGC

61 GTCCTCAGAG CCTATCCCAA TGCCTCCCCA CTGCTCGGCT CCAGCTGGGG TGGCCTGATC

121 CACCTGTACA CAGCCACAGC CAGGAACAGC TACCACCTGC AGATCCACAA GAATGGCCAT

181 GTGGATGGCG CACCCCATCA GACCATCTAC AGTGCCCTGA TGATCAGATC AGAGGATGCT

241 GGCTTTGTGG TGATTACAGG TGTGATGAGC AGAAGATACC TCTGCATGGA TTTCAGAGGC

301 AACATTTTTG GATCACACTA TTTCGACCCG GAGAACTGCA GGTTCCAACA CCAGACGCTG

361 GAAAACGGGT ACGACGTCTA CCACTCTCCT CAGTATCACT TCCTGGTCAG TCTGGGCCGG

421 GCGAAGAGAG CCTTCCTGCC AGGCATGAAC CCACCCCCGT ACTCCCAGTT CCTGTCCCGG

481 AGGAACGAGA TCCCCCTAAT TCACTTCAAC ACCCCCATAC CACGGCGGCA CACCCAGAGC

541 GCCGAGGACG ACTCGGAGCG GGACCCCCTG AACGTGCTGA AGCCCCGGGC CCGGATGACC

601 CCGGCCCCGG CCTCCTGTTC ACAGGAGCTC CCGAGCGCCG AGGACAACAG CCCGATGGCC

661 AGTGACCCAT TAGGGGTGGT CAGGGGCGGT CGAGTGAACA CGCACGCTGG GGGAACGGGC

721 CCGGAAGGCT GCCGCCCCTT CGCCAAGTTC ATCGGAGGTG GAGGTTCAAA AACCCACACG

781 TGTCCTCCTT GTCCTGCCCC AGAAGCAGCA GGTGGTCCAT CAGTTTTTCT TTTCCCTCCC

841 AAACCCAAGG ATACGCTGAT GATCTCTCGC ACGCCTGAGG TGACATGCGT CGTAGTAGAC

901 GTGAGCCACG AAGATCCCGA GGTGAAGTTC AATTGGTATG TGGACGGAGT AGAAGTGCAT

961 AACGCGAAAA CTAAGCCGCG CGAGGAACAA TATAACAGTA CTTACAGGGT GGTATCCGTG

1021 CTCACAGTCC TGCACCAGGA CTGGCTGAAC GGTAAGGAAT ACAAGTGCAA AGTAAGCAAC

1081 AAGGCACTTC CCGCGCCTAT TGAGAAAACA ATCTCCAAGG CGAAGGGACA CCAAGAGAA

1141 CCTCAGGTTT ACACTCTCCC GCCTTCCAGG GAAGAGATGA CCAAAAATCA GTTTCCCTG

1201 ACTTGCCTCG TCAAAGGATT CTACCCTTCC GACATTGCTG TTGAATGGGA AAGCAATGGA

1261 CAACCAGAGA ACAACTACAA GACAACACCC CCGGTGCTGG ATAGTGACGG ATCTTTCTTT

1321 CTCTACTCAA AGCTGACCGT GGATAAGTCC AGGTGGCAGC AGGGAAACGT GTTTTCCTGC
```

-continued

```
1381 TCTGTCATGC ATGAAGCGCT GCATAATCAC TATACCCAGA AGTCTCTGAG CTTGAGCCCA

1441 GGCAAGTAA
```

FGF23(R179Q)-FcLALAv1

(SEQ ID NO: 51)

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*
```

FGF23-FcLALA v2

(SEQ ID NO: 52)

```
  1 ATGTTGGGGG CCCGCCTCAG GCTCTGGGTC TGTGCCTTGT GCAGCGTCTG CAGCATGAGC

61 GTCCTCAGAG CCTATCCCAA TGCCTCCCCA CTGCTCGGCT CCAGCTGGGG TGGCCTGATC

121 CACCTGTACA CAGCCACAGC CAGGAACAGC TACCACCTGC AGATCCACAA GAATGGCCAT

181 GTGGATGGCG CACCCCATCA GACCATCTAC AGTGCCCTGA TGATCAGATC AGAGGATGCT

241 GGCTTTGTGG TGATTACAGG TGTGATGAGC AGAAGATACC TCTGCATGGA TTTCAGAGGC

301 AACATTTTTG GATCACACTA TTTCGACCCG GAGAACTGCA GGTTCCAACA CCAGACGCTG

361 GAAAACGGGT ACGACGTCTA CCACTCTCCT CAGTATCACT TCCTGGTCAG TCTGGGCCGG

421 GCGAAGAGAG CCTTCCTGCC AGGCATGAAC CCACCCCCGT ACTCCCAGTT CCTGTCCCGG

481 AGGAACGAGA TCCCCCTAAT TCACTTCAAC ACCCCCATAC CACGGCGGCA CACCCAGAGC

541 GCCGAGGACG ACTCGGAGCG GGACCCCCTG AACGTGCTGA AGCCCCGGGC CCGGATGACC

601 CCGGCCCCGG CCTCCTGTTC ACAGGAGCTC CCGAGCGCCG AGGACAACAG CCCGATGGCC

661 AGTGACCCAT TAGGGGTGGT CAGGGGCGGT CGAGTGAACA CGCACGCTGG GGGAACGGGC

721 CCGGAAGGCT GCCGCCCCTT CGCCAAGTTC ATCGGAGGTG GAGGTTCAGC CCCAGAAGCA

781 GCAGGTGGTC CATCAGTTTT TCTTTTCCCT CCCAAACCCA AGGATACGCT GATGATCTCT

841 CGCACGCCTG AGGTGACATG CGTCGTAGTA GACGTGAGCC ACGAAGATCC CGAGGTGAAG

901 TTCAATTGGT ATGTGGACGG AGTAGAAGTG CATAACGCGA AAACTAAGCC GCGCGAGGAA

961 CAATATAACA GTACTTACAG GGTGGTATCC GTGCTCACAG TCCTGCACCA GGACTGGCTG

1021 AACGGTAAGG AATACAAGTG CAAAGTAAGC AACAAGGCAC TTCCCGCGCC TATTGAGAAA

1081 ACAATCTCCA AGGCGAAGGG ACAACCAAGA GAACCTCAGG TTTACACTCT CCCGCCTTCC

1141 AGGGAAGAGA TGACCAAAAA TCAAGTTTCC CTGACTTGCC TCGTCAAAGG ATTCTACCCT

1201 TCCGACATTG CTGTTGAATG GGAAAGCAAT GGACAACCAG AGAACAACTA CAAGACAACA

1261 CCCCCGGTGC TGGATAGTGA CGGATCTTTC TTTCTCTACT CAAAGCTGAC CGTGGATAAG

1321 TCCAGGTGGC AGCAGGGAAA CGTGTTTTCC TGCTCTGTCA TGCATGAAGC GCTGCATAAT

1381 CACTATACCC AGAAGTCTCT GAGCTTGAGC CCAGGCAAGT AA
```

FGF23(R179Q)-FcLALAv2                                                    (SEQ ID NO: 53)

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

---

What is claimed is:

1. A functionally active fusion polypeptide, wherein the sequence of the fusion polypeptide comprises the sequence of SEQ ID NO: 49.

2. A pharmaceutical composition comprising the fusion polypeptide of claim 1 and a pharmaceutically acceptable carrier.

3. A nucleic acid comprising a sequence that encodes a functionally active fusion polypeptide, wherein the sequence of the fusion polypeptide comprises the sequence of SEQ ID NO: 49.

4. A host cell containing the nucleic acid of claim 3.

5. A vector comprising the nucleic acid of claim 3.

6. A method for activating Egr-1 in an individual, comprising the step of:
 administering to the individual a therapeutically effective dose of a pharmaceutical composition comprising a functionally active fusion polypeptide, wherein the sequence of the fusion polypeptide comprises the sequence of SEQ ID NO: 49.

7. The method of claim 6, wherein the individual is in need of a treatment for an agerelated condition selected from the group consisting of sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

8. The method of claim 7, wherein the age-related condition is muscle wasting.

9. The method of claim 6, wherein the individual is in need of a treatment for a metabolic disorder selected from the group consisting of Type II Diabetes, Metabolic Syndrome, hyperglycemia, and obesity.

10. The method of claim 6, wherein the individual is in need of a treatment for hyperphosphatemia or calcinosis.

11. The method of claim 6, wherein the individual is in need of a treatment for chronic renal disease or chronic renal failure.

12. The method of claim 6, wherein the individual is in need of a treatment for cancer.

13. The method of claim 12, wherein the cancer is breast cancer.

14. The method of claim 6, wherein the individual is in need of a treatment for muscle atrophy.

15. A functionally active fusion polypeptide, wherein the sequence of the fusion polypeptide consists of the sequence of SEQ ID NO: 49.

16. A pharmaceutical composition comprising the fusion polypeptide of claim 15 and a pharmaceutically acceptable carrier.

17. A nucleic acid comprising a sequence that encodes a functionally active fusion polypeptide, wherein the sequence of the fusion polypeptide consists of the sequence of SEQ ID NO: 49.

* * * * *